(12) United States Patent
Inukai et al.

(10) Patent No.: US 6,472,384 B1
(45) Date of Patent: Oct. 29, 2002

(54) ANTIMICROBIAL COMPOUNDS

(75) Inventors: Masatoshi Inukai, Matsudo; Masakatsu Kaneko, Yokohama; Toshio Takatsu, Nishitokyo; Hitoshi Hotoda, Urawa; Masatoshi Arai, Nishitokyo; Shunichi Miyakoshi, Hachioji; Masaaki Kizuka, Tsuchiura; Yasumasa Ogawa, Iwaki, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/757,393

(22) Filed: Jan. 9, 2001

Related U.S. Application Data

(63) Continuation of application No. PCT/JP99/03718, filed on Jul. 9, 1999.

(30) Foreign Application Priority Data

Jul. 9, 1998 (JP) ............................................ 10-194285
Sep. 24, 1998 (JP) ............................................ 10-269445

(51) Int. Cl.⁷ .................... A61K 31/553; A61K 31/505; C07D 515/00; C07D 239/02; C07D 401/00
(52) U.S. Cl. .................. 514/211.03; 514/269; 540/488; 544/209; 544/310
(58) Field of Search ............................ 514/211.03, 269; 540/488; 544/309, 310

(56) References Cited

FOREIGN PATENT DOCUMENTS

| JP | 60-259190 A | 12/1985 |
|---|---|---|
| JP | 5-148293 A | 6/1993 |

OTHER PUBLICATIONS

H. Yamaguchi et al, Capuramycin, A New Nucleoside Antibiotic Taxonomy, Fermentation, Isolation and Characterization, *The Journal of Antibiotics*, vol. 39, No. 8, pp. 1047–1053 (1986).

H. Seto et al, "The Structure of a New Nucleoside Antibiotic, Capuramycin", *Tetrahedron Letters*, vol. 29, No. 19, pp. 2342–2346 (1988).

H. Seto, "Structural Studies of Natural Products by New NMR Techniques", *Pure and Applied Chemistry*, vol. 61, No. 3, pp. 365–368 (1989).

S. Knapp et al, "Synthesis of Capuramycin", *Journal of Organic Chemistry*, vol. 59, No. 2, pp. 281–283 (1994).

*Primary Examiner*—Mukund J. Shah
*Assistant Examiner*—Tamthom N. Truong
(74) *Attorney, Agent, or Firm*—Frishauf, Holtz, Goodman & Chick, P.C.

(57) ABSTRACT

The present invention relates to ester, ether and N-alkylcarbamoyl derivatives of compound (Ia) and pharmaceutically acceptable salts thereof. These compounds exhibit excellent antibacterial activity and are useful for the treatment or prevention of bacterial infections.

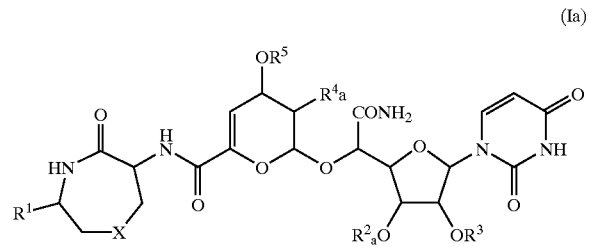

(Ia)

(wherein $R^1$ is a hydrogen atom or a methyl group; $R^2_a$ is a hydrogen atom, a protecting group for a hydroxy group, or a methyl group; $R^3$ is a hydrogen atom or a protecting group for a hydroxy group; $R^4_a$ is a hydrogen atom, a hydroxy group or a protected hydroxy group; $R^5$ is a hydrogen atom or a protecting group for a hydroxy group; and X is a methylene group or a sulfur atom). The invention also includes compounds which are related to the aforeidentified compounds.

93 Claims, No Drawings

ANTIMICROBIAL COMPOUNDS

This application is a continuation application of International Application PCT/JP99/003718 (not published in English) filed Jul. 9, 1999.

The present invention relates to a compound of formula (I), (XI), (XII), (XIII), (XIV), (XV) or (XVI) and a derivative of a compound of formula (Ia) which have excellent antibiotic activity or a pharmaceutically acceptable salt thereof.

FIELD OF THE INVENTION

The present invention is also a pharmaceutical composition comprising a compound described above as an active ingredient effective to treat or prevent infectious diseases.

The present invention includes a use of a compound described above in order to prepare a medicament effective to treat or prevent infectious diseases.

The present invention is concerned with a method effective to treat or prevent infectious diseases in warm-blooded animals comprising administering a pharmacologically effective amount of a compound described above to them.

The present invention includes a microorganism capable of producing a compound of formula (I), (XI), (XII), (XIV), (XV) or (XVI).

The present invention also includes a process for preparing a compound of formula (I), (XI), (XII), (XIV), (XV) or (XVI) using the said microorganism.

BACKGROUND OF THE INVENTION

A β-lactam antibiotic, an amino-glycoside, isoniazid or rifampicin has been conventionally used in treatment or prophylaxis of microbial infections including tubercule bacillus. Recently there have been a lot of bacteria resistant to these antibiotics. It is desirable to develop new compounds which are different type antimicrobial agents from conventional ones.

On the other hand it has been known that capuramycin having a formula shown below exhibits anti-tubercule bacillus activity (J. Antibiotics. 29. (8). 1047–1053 (1986)).

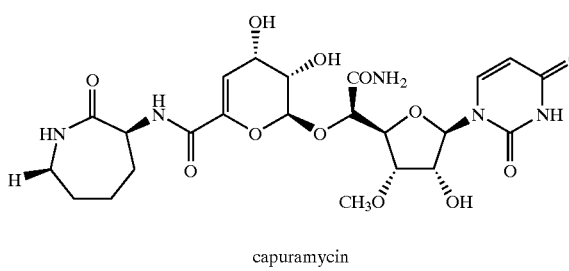

capuramycin

We found new compounds of formula (I), (XI), (XII), (XIV), (XV) or (XVI). which do not show any cross resistance to conventional medicaments, in the cultivation products of a microorganism. We prepared the derivatives of compounds described above and capuramycin. We studied the physiological activity of these derivatives for several years and found that these derivatives exhibit excellent antibiotic activity.

The compounds of the present invention can provide a method effective to treat and prevent infection diseases including ones arising from bacteria resistant to the conventional antibiotics. Compounds of formula (I), (XI), (XII), (XIV), (XV) or (XVI) are also useful starting materials for preparation of the compounds of the present invention having excellent antibiotic activity.

DISCLOSURE OF THE INVENTION

The present invention includes a compound of formula (I)

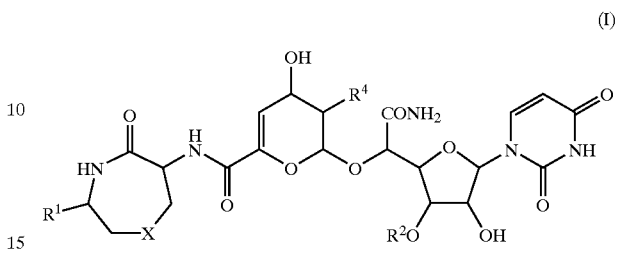

(wherein
$R^1$ is a methyl group, $R^2$ is a methyl group, $R^4$ is a hydroxy group, and X is a methylene group;
$R^1$ is a methyl group, $R^2$ is a hydrogen atom, $R^4$ is a hydroxy group, and X is a methylene group;
$R^1$ is a methyl group, $R^2$ is a methyl group, $R^4$ is a hydrogen atom, and X is a methylene group;
$R^1$ is a hydrogen atom, $R^2$ is a hydrogen atom, $R^4$ is a hydroxy group, and X is a methylene group; or
$R^1$ is a methyl group, $R^2$ is a methyl group, $R^4$ is a hydroxy group, and X is a sulfur atom) or a pharmaceutically acceptable salt thereof; or
a pharmaceutically acceptable ester, ether or N-alkylcarbamoyl derivative of a compound of formula (Ia)

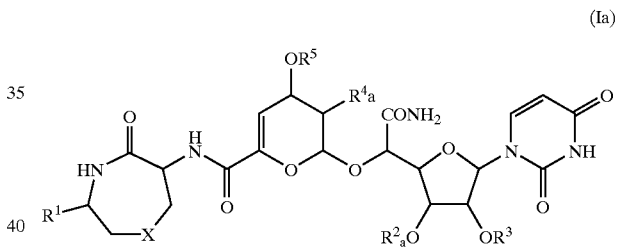

(wherein $R^1$ is a hydrogen atom or a methyl group, $R^2_a$ is a hydrogen atom, a protecting group for a hydroxy group, or a methyl group, $R^3$ is a hydrogen atom or a protecting group for a hydroxy group, $R^4_a$ is a hydrogen atom, a hydroxy group or a protected hydroxy group, $R^5$ is a hydrogen atom or a protecting group for a hydroxy group, and X is a methylene group or a sulfur atom,
with the proviso that
when
X is a sulfur atom,
$R^1$ is a methyl group, $R^2_a$ is a methyl group, and $R^4_a$ is a hydroxy group or a protected hydroxy group;
when
X is a methylene group, $R^1$ is a methyl group, and $R^2_a$ is a hydrogen atom,
$R^4_a$ is a hydroxy group or a protected hydroxy group; or
when
X is a methylene group and $R^1$ is a hydrogen atom, $R^2_a$ is a methyl group and $R^4_a$ is a hydroxy group or protected hydroxy group);
or a pharmaceutically acceptable salt thereof.

the term "N-alkylcarbamoyl" as used hereinafter in the specification includes N-alkylcarbamoyl, N-alkenylcarbamoyl and N-alkynylcarbamoyl.

The present invention is also a pharmaceutical composition comprising a compound described above as an active ingredient effective to treat or prevent infectious diseases.

The present invention includes the use of a compound described above in order to prepare a medicament effective to treat or prevent infectious diseases.

The present invention is concerned with a method effective to treat or prevent infectious diseases in warm-blooded animals comprising administering a pharmacologically effective amount of a compound described above to them.

The present invention includes a microorganism capable of producing a compound of formula (I).

The present invention also includes a process for preparing a compound of formula (I) using the said microorganism.

In the above formulae, the protecting group of "protecting group for a hydroxy group" and "protected hydroxy group" of $R^2_a$ and the like can be removed by a chemical procedure such as hydrogenolysis, hydrolysis, electrolysis or photolysis (hereinafter referred to as a general protecting group) or can be removed by biological method such as hydrolysis in vivo (with the proviso that it is not an ester residue group such as an acyl group). "The protecting group which can be removed by biological method such as hydrolysis in vivo" can be cleaved by biologically method such as hydrolysis in the human body to give a corresponding free acid or a salt thereof. Whether a compound has a protecting group removed in vivo is determined by detection of a corresponding parent compound or a pharmaceutically acceptable salt thereof in the body fluid of a rat or mouse to which it is administered by intravenous injection.

A general protecting group is selected from the group consisting of:

"tetrahydropyranyl and tetrahydrothiopyranyl group" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl;

"tetrahydrofuranyl and tetrahydrothiofuranyl group" such as tetrahydrofuran-2-yl and tetrahydrothiofuran-2-yl;

"tri(lower alkyl)silyl group (hereinafter a lower alkyl moiety represents a group selected from the group consisting of $C_1$–$C_6$ alkyl group such as the methyl, ethyl, propyl, isopropyl, butyl, isobutyl, tert-butyl, pentyl and hexyl group) such as the trimethylsilyl, triethylsilyl, isopropyldimethylsilyl, tert-butyldimethylsilyl, diisopropylmethylsilyl, di(tert-butyl)methylsilyl and triisopropylsilyl group;

"silyl group substituted with one or two aryl groups and two or one lower alkyl groups" such as diphenylmethylsilyl, diphenylbutylsilyl, diphenylisopropylsilyl, and diisopropylphenylsilyl;

"lower alkoxymethyl group" (hereinafter an alkoxy moiety represents a group selected from the group consisting of $C_1$–$C_6$ alkoxy group such as methoxy, ethoxy, propoxy, isopropoxy, butoxy, isobutoxy, tert-butoxy, pentyloxy and hexyloxy), such as methoxymethyl, 1,1-dimethyl-1-methoxymethyl, ethoxymethyl, propoxymethyl, isopropoxymethyl, butoxymethyl and tert-butoxymethyl;

"lower alkoxy-lower alkoxylmethyl group" such as the 2-methoxyethoxymethyl group;

"halogeno-lower-alkoxymethyl group" such as the 2,2,2-trichloroethoxymethyl and bis(2-chloroethoxy)methyl group;

"substituted ethyl group", for example an ethyl group substituted with a lower alkoxy group such as the 1-ethoxyethyl or 1-(isopropoxy)ethyl group, and for example a halogenoethyl group such as the 2,2,2-trichloroethyl group;

"aralkyl group" (aryl moiety is selected from the group consisting of $C_6$–$C_{14}$ aryl group such as phenyl, naphthyl, biphenyl, anthryl and phenanthryl group), for example a lower alkyl group substituted with 1 to 3 aryl groups such as benzyl, α-naphthyl, β-naphthyl, diphenylmethyl, triphenylmethyl, α-naphthyldiphenylmethyl and 9-anthrylmethyl, and for example a lower alkyl group substituted with 1 to 3 aryl groups, which are substituted with lower alkyl, lower alkoxy, nitro, halogen or cyano group, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl group;

"alkoxycarbonyl group", for example lower alkoxycarbonyl group such as methoxycarbonyl, ethoxycarbonyl, tert-butoxycarbonyl and isobutoxycarbonyl, and for example lower alkoxycarbonyl group substituted with halogen or tri(lower alkyl)silyl group such as 2,2,2-trichloroethoxycarbonyl and 2-trimethylsilylethoxycarbonyl;

"alkenyloxycarbonyl group" (said alkenyl moiety is a $C_2$–$C_6$ alkenyl group) such as the vinyloxycarbonyl and allyloxycarbonyl group; and "aralkyloxycarbonyl group in which the aryl ring is optionally substituted with one or two lower alkoxy or nitro groups" such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl group.

A preferable "general protecting group of hydroxy group" is the tetrahydropyranyl, tetrahydrothiopyranyl, silyl, aralkyl or aralkyloxycarbonyl group.

A more preferable "general protecting group of hydroxy group" is the tetrahydropyran-2-yl, 4-methoxytetrahydropyran-4-yl, tetrahydrothiopyran-2-yl, trimethylsilyl, triethylsilyl, tert-butyldimethylsilyl, di(tert-butyl)methylsilyl, diphenylmethylsilyl, benzyl, diphenylmethyl, triphenylmethyl, 4-methylbenzyl, 4-methoxybenzyl, 2-nitrobenzyl, 4-nitrobenzyl, 4-chlorobenzyl, benzyloxycarbonyl, 4-methoxybenzyloxycarbonyl, 2-nitrobenzyloxycarbonyl or 4-nitrobenzyloxycarbonyl group.

A most preferable "general protecting group of hydroxy group" is the trimethylsilyl, tert-butyldimethylsilyl, triphenylmethyl, benzyl or 4-methoxybenzyl group.

A hydroxy protecting group which can be removed by biological method such as hydrolysis in vivo is selected from the group consisting of "1-aliphatic acyloxy-lower alkyl group" (hereinafter, acyl moiety is selected from the group consisting of $C_1$–$C_{10}$ straight or branched chain alkanoyl group) such as formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl;

"1-(aliphatic-acylthio)-(lower alkyl)group" such as formylthiomethyl, acetylthiomethyl, dimethylaminoacetylthiomethyl, propionylthiomethyl, butyrylthiomethyl, pivaloylthiomethyl, valerylthiomethyl, isovalerylthiomethyl, hexanoylthiomethyl, 1-formylthioethyl, 1-acetylthioethyl, 1-propionylthioethyl, 1-butyrylthioethyl, 1-pivaloylthioethyl, 1-valerylthioethyl, 1-isovalerylthioethyl, 1-hexanoylthioethyl, 1-formylthiopropyl, 1-acetylthiopropyl, 1-propionylthiopropyl, 1-butyrylthiopropyl, 1-pivaloylthiopropyl, 1-valerylthiopropyl, 1-isovalerylthiopropyl, 1-hexanoylthiopropyl, 1-acetylthiobutyl, 1-propionylthiobutyl, 1-butyrylthiobutyl, 1-pivaloylthiobutyl, 1-acetylthiopentyl, 1-propionylthiopentyl, 1-butyrylthiopentyl, 1-pivaloylthiopentyl and 1-pivaloylthiohexyl;

"1-(cycloalkylcarbonyloxy)-(lower alkyl) group" such as the cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl group, "(1-aromatic acyloxy)-(lower alkyl) group (the aromatic acyl moiety is selected from the group consisting of $C_6$–$C_{10}$ arylcarbonyl groups)" such as the benzoyloxymethyl group;

"1-(lower alkoxycarbonyloxy)-(lower alkyl) group" such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(tert-butoxycarbonyloxy)ethyl, 1-(pentyloxycarbonyloxy)ethyl, 1-(hexyloxycarbonyloxy)ethyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(iosobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl;

"1-(cycloalkyloxycarbonyloxy)-(lower alkyl) group" such as cyclopentyloxycarbonyloxymethyl, cyclohexyloxycarbonyloxymethyl, 1-(cyclopentyloxycarbonyloxy)ethyl, 1-(cyclohexyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclopentyloxycarbonyloxy)pentyl, (cyclopentyloxycarbonyloxy)pentyl, 1-(cyclohexyloxycarbonyloxy)pentyl, 1-(cyclopentyloxycarbonyloxy)hexyl and 1-(cyclohexyloxycarbonyloxy)hexyl;

"phthalidyl group" such as the phthalidyl, dimethylphthalidyl and dimethoxyphthalidyl group;

"oxodioxolenylmethyl group" such as (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen4-yl )methyl, (5-propyl-2-oxo-1,3-dioxolen-4-yl)methyl, (5-isopropyl-2-oxo-1,3-dioxolen-4-yl )methyl and (5-butyl-2-oxo-1,3-dioxolen-4-yl)methyl;

"carbamoyl group";

"carbamoyl group substituted with one or two lower alkyl groups";

"lower alkyl-dithioethyl group" such as methyldithioethyl, ethyldithioethyl, propyldithioethyl, butyldithioethyl, pentyldithioethyl and hexyldithioethyl group; and "1-(acyloxy)alkyloxycarbonyl group" such as the pivaloyloxymethyloxycarbonyl group.

A preferable "hydroxy protecting group which can be removed by biological method such as hydrolysis in vivo" is selected from the group consisting of a 1-(aliphatic acyloxy)-(lower alkyl) group, a 1-(cycloalkylcarbonyloxy)-(lower alkyl) group, a 1-(lower alkoxycarbonyloxy)-(lower alkyl) group, a 1-(cycloalkyloxycarbonyloxy)-(lower alkyl) group, a phthalidyl and an oxodioxolenylmethyl group.

A more preferable "hydroxy protecting group which can be removed by biological method such as hydrolysis in vivo" is selected from the group consisting of acetoxymethyl, propionyloxymethyl, butyryloxymethyl, pivaloyloxymethyl, valeryloxymethyl, 1-acetoxyethyl, butyryloxyethyl, 1-pivaloyloxyethyl, cyclopentylcarbonyloxymethyl, cyclohexylcarbonyloxymethyl, 1-cyclopentylcarbonyloxyethyl, 1-cyclohexylcarbonyloxyethyl, methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-(methoxycarbonyloxy)ethyl, 1-(ethoxycarbonyloxy)ethyl, 1-(isopropoxycarbonyloxy)ethyl, cyclopentyloxycarbonyloxymethyl, cyclohexyloxycarbonyloxymethyl, 1-(cyclopentyloxycarbonyloxy)ethyl, 1-(cyclohexyloxycarbonyloxy)ethyl, phthalidyl, (5-phenyl-2-oxo-1,3-dioxolen4-yl)methyl, [5-(4-methylphenyl)-2-oxo-1,3-dioxolen-4-yl]methyl, (5-methyl-2-oxo-1,3-dioxolen-4-yl)methyl and (5-ethyl-2-oxo-1,3-dioxolen-4-yl) methyl group.

A most preferable "hydroxy protecting group which can be removed by biological method such as hydrolysis in vivo" is selected from the group consisting of acetoxymethyl, propionyloxymethyl, butyrvloxymethyl, pivaloyloxymethyl, valeryloxymethyl, cyclopentylcarbonyloxymethyl, cyclohexylcarbonyloxymethyl, methoxycarbonyloxymethyl, ethoxycarbonyloxymethyl, propoxycarbonyloxymethyl, isopropoxycarbonyloxymethyl, butoxycarbonyioxymethyl, isobutoxycarbonyloxymethyl, cyclopentyloxycarbonyloxymethyl, cyclohexyloxycarbonyloxymethyl, (5-phenyl-2-oxo-1,3-dioxolen-4-yl )methyl. [5-(4-methylphenyl)-2-oxo-1,3-dioxolen-4-yl]methyl, (5-methyl-2-oxo-1,3-dioxolen-4-yl) methyl and (5-ethyl-2-oxo-1,3-dioxolen-4-yl )methyl group.

The term "pharmaceutically acceptable ester, ether and N-alkylcarbamoyl derivatives" refers to a derivative that is a useful medicament without significant toxicity.

The ester residue of ester derivatives is selected from the group consisting of "carbonyl and oxycarbonyl group to which a straight or branched chain $C_1$–$C_{21}$ alkyl group is attached", in which said alkyl group is selected from the group consisting of methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl. 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, 3,7,11,15-tetramethylhexadecyl and henicosyl groups;

"carbonyl and oxycarbonyl group to which a straight or branched chain $C_2$–$C_{21}$ alkenyl or alkynyl group is attached", in which said alkenyl or alkynyl group is selected from the group consisting of ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl, cis-8-heptadecenyl, cis, cis-8,11-heptadecadienyl, cis, cis, cis-8,11,14-heptadecatrienyl, cis-10-nonadecenyl, and cis-12-icosenyl;

"carbonyl and oxycarbonyl group to which a straight or branched chain $C_2$–$C_{21}$ alkenyl or alkynyl group is attached", in which said alkenyl or alkynyl group is selected from the group consisting of ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl;

"carbonyl and oxycarbonyl group to which straight or branched chain $C_1$–$C_{21}$ alkyl group which has one or more substituents selected from the group consisting of lower alkoxy, halogen (hereinafter for example fluorine, chlorine, bromine and iodine, preferably fluorine and chlorine) and nitro groups is attached", in which said substituted alkyl group is selected from the group consisting of methoxymethyl, ethoxymethyl, methoxyethyl, ethoxyethyl, trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl, 2,2-dibromoethyl, nitromethyl, dinitromethyl, 1-nitroethyl, 2-nitroethyl and 1,2-dinitroethyl;

"carbonyl and oxycarbonyl group to which a ($C_6$–$C_{10}$ aryl)-($C_1$–$C_{21}$) alkyl group wherein said aryl moiety optionally has one or more substituents selected from the group consisting of lower alkyl, lower alkoxy, halo and nitro groups is attached", in which said arylalkyl group is selected from the group consisting of benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthvlbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl;

"carbonyl and oxycarbonyl group to which a $C_6$–$C_{10}$ aryl group which optionally has one or more substituents selected from the group consisting of lower alkyl, lower alkoxy halo and nitro groups is attached", in which said aryl group is selected from the group consisting of phenyl, naphthyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3,5-difluorophenyl, 2,5-difluorophenyl, 2,6-difluorophenyl, 2,4-difluorophenyl, 3,5-dibromophenyl, 2,5-dibromophenyl 2,6-dichlorophenyl, 2,4-dichlorophenyl, 2,3,6-trifluorophenyl, 2,3,4-trifluorophenyl, 3,4,5-trifluorophenyl, 2,5,6-trifluorophenyl, 2,4,6-trifluorophenyl, 2,3,6-tribromophenyl, 2,3,4-tribromophenyl, 3,4,5-tribromophenyl, 2,5,6-trichlorophenyl, 2,4,6-trichlorophenyl, 1-fluoro-2-naphthyl, 2-fluoro-1-naphthyl, 3-fluoro-1-naphthyl, 1-chloro-2-naphthyl, 2-chloro-1-naphthyl, 3-bromo-1-naphthyl, 3,8-difluoro-1-naphthyl, 2,3-difluoro-1-naphthyl, 4,8-difluoro-1-naphthyl, 5,6-difluoro-1-naphthyl, 3,8-dichloro-1-naphthyl, 2,3-dichloro-1-naphthyl, 4,8-dibromo-1-naphthyl, 5,6-dibromo-1-naphthyl, 2,3,6-trifluoro-1-naphthyl, 2,3,4-trifluoro-1-naphthyl, 3,4,5-trifluoro-1-naphthyl, 4,5,6-trifluoro-1-naphthyl, 2,4,8-trifluoro-1-naphthyl, 2-methylphenyl, 3-methylphenyl, 4-methylphenyl, 2-ethylphenyl, 3-propylphenyl, 4-ethylphenyl, 2-butylphenyl, 3-pentylphenyl, 4-pentylphenyl, 3,5-dimethylphenyl, 2,5-dimethylphenyl, 2,6-dimethylphenyl, 2,4-dimethylphenyl, 3,5-dibutylphenyl, 2,5-dipentylphenyl, 2,6-dipropylmethylphenyl, 2,4-dipropylphenyl, 2,3,6-trimethylphenyl, 2,3,4-trimethylphenyl, 3,4,5-trimethylphenyl, 2,5,6-trimethylphenyl, 2,4,6-trimethylphenyl, 2,3,6-tributylphenyl, 2,3,4-tripentylphenyl, 3,4,5-tributylphenyl, 2,5,6-tripropylmethylphenyl, 2,4,6-tripropylphenyl, 1-methyl-2-naphthyl, 2-methyl-1-naphthyl, 3-methyl-1-naphthyl, 1-ethyl-2-naphthyl, 2-propyl-1-naphthyl, 3-butyl-1-naphthyl, 3,8-dimethyl-1-naphthyl, 2,3-dimethyl-1-naphthyl, 4,8-dimethyl-1-naphthyl, 5,6-dimethyl-1-naphthyl, 3,8-diethyl-1-naphthyl, 2,3-dipropyl-1-naphthyl, 4,8-dipentyl-1-naphthyl, 5,6-dibutyl-1-naphthyl, 2,3,6-trimethyl-1-naphthyl, 2,3,4-trimethyl-1-naphthyl, 3,4,5-trimethyl-1-naphthyl, 4,5,6-trimethyl-1-naphthyl, 2,4,8-trimethyl-1-naphthyl, 2-methoxyphenyl, 3-methoxyphenyl, 4-methoxyphenyl, 2-ethoxyphenyl, 3-propoxphenyl, 4-ethoxyphenyl, 2-butoxyphenyl, 3-pentyloxyphenyl, 4-pentyloxyphenyl, 3,5-dimethoxyphenyl, 2,5-dimethoxyphenyl, 2,6-dimethoxyphenyl, 2,4-dimethoxyphenyl, 3,5-dibutoxyphenyl, 2,5-dipentyloxyphenyl, 2,6-dipropoxymethoxphenyl, 2,4-dipropoxyphenyl, 2,3,6-trimethoxyphenyl, 2,3,4-trimethoxyphenyl, 3,4,5-trimethoxyphenyl, 5,6-trimethoxyphenyl, 2,4,6-trimethoxyphenyl, 2,3,6-tributoxyphenyl, 2,3,4-tripentyloxyphenyl, 3,4,5-tributoxyphenyl, 2,5,6-tripropoxyphenyl, 2,4,6-tripropoxyphenyl, 1-methoxy-2-naphthyl, 2-methoxy-1-naphthyl, 3-methoxy-1-naphthyl, 1-ethoxy-2-naphthyl, 2-propoxy-1-naphthyl, 3-butoxy-1-naphthyl, 3,8-dimethoxy-1-naphthyl, 2,3-dimethoxy-1-naphthyl, 4,8-dimethoxy-1-naphthyl 5,6-dimethoxy-1-naphthyl, 3,8-diethoxy-1-naphthyl, 2,3-dipropoxy-1-naphthyl, 4,8-dipentyloxy-1-naphthyl, 5,6-dibutoxy-1-naphthyl, 2,3,6-trimethoxy-1-naphthyl, 2,3,4-trimethoxy-1-naphthyl, 3,4,5-trimethoxy-1-naphthyl, 4,5,6-trimethoxy-1-naphthyl, 2,4,8-trimethoxy-1-naphthyl, 2-nitrophenyl, 3-nitrophenyl, 4-nitrophenyl, 3,5-dinitrophenyl, 2,5-dinitrophenyl 2,6-dinitrophenyl, 2,4-dinitrophenyl, 2,3,6-trinitrophenyl, 2,3,4-trinitrophenyl, 3,4,5-trinitrophenyl, 2,5,6-trinitrophenyl, 2,4,6-trinitrophenyl, 1-nitro-2-naphthyl, 2-nitro-1-naphthyl, 3-nitro-1-naphthyl, 3,8-dinitro-1-naphthyl, 2,3-dinitro-1-naphthyl, 4,8-dinitro-1-naphthyl, 5.6-dinitro-1-naphthyl. 2,3,6-trinitro-1-naphthyl, 2,3,4-trinitro-1-naphthyl, 3,4,5-trinitro-1-naphthyl, 4,5,6-trinitro-1-naphthyl and 2,4,8-trinitro-1-naphthyl;

"carboxy $(C_1–C_{10})$alkylcarbonyl group" such as succinoyl, glutaroyl, and adipoyl;

"residue of salt of a phosphate diester which independently has two lower alkyl groups"; and "residue forming ester of amino acid which is optionally protected with a tert-butyloxycarbonyl, benzyloxycarbonyl or trityl group" such as glycine, alanine, valine, leucine, isoleucine, phenylalanine, proline, tryptophan, glutamine and glutamic acid.

A preferable ester residue of ester derivatives is $R^6CO—$ or $R^6OCO—$ group wherein $R^6$ is selected from the group consisting of hydrogen; a $C_1–C_{21}$ alkyl group; a $C_2–C_{21}$ alkenyl or alkynyl group having 1 to 3 double or triple bonds; a $C_1–C_{21}$ alkyl group substituted with 1 to 4 substituents selected from the group consisting of lower alkoxy, halo and nitro groups; a $C_1–C_{21}$ alkyl group substituted with 1 to 3 $C_6–C_{10}$ aryl groups which are optionally substituted with 1 to 4 substituents selected from the group consisting of lower alkyl, lower alkoxy, halo and nitro groups; and a $C_6–C_{10}$ aryl group which is optionally substituted with 1 to 4 substituents selected from the group consisting of lower alkyl, lower alkoxy, halo, and nitro groups.

A more preferable ester residue of ester derivatives is $R^6CO—$ or $R^6OCO—$ group wherein $R^6$ is selected from the group consisting of hydrogen; a $C_1–C_{21}$ alkyl group; a $C_2–C_{21}$ alkenyl group having 1 to 3 double bonds; a $C_2–C_6$ alkynyl group having one triple bond; a $C_1–C_6$ alkyl group substituted with 1 to 4 substituents selected from the group consisting of $C_1–C_4$ alkoxy, halo and nitro groups; a $C_1–C_6$ alkyl group substituted with 1 to 3 $C_6–C_{10}$ aryl groups which are optionally substituted with 1 to 3 substituents selected from the group consisting of $C_1–C_4$ alkyl, $C_1–C_4$ alkoxy, halo and nitro groups; and a $C_6–C_{10}$ aryl group which is optionally substituted with 1 to 3 substituents selected from the group consisting of C1–C4 alkyl, C1–C4 alkoxy, halo and nitro groups.

A more preferable ester residue of ester derivatives is $R^6CO—$ or $R^6OCO—$ group wherein $R^6$ is selected from the group consisting of a $C_1–C_{21}$ alkyl group; a $C_6–C_{20}$ alkenyl group having 1 to 3 double bonds; a $C_2–C_6$ alkynyl group having one triple bond; a $C_1–C_6$ alkyl group substituted with one substituent selected from the group consisting of $C_1–C_4$ alkoxy and nitro groups; a $C_1–C_6$ alkyl group substituted with 1 to 3 substituents selected from the group consisting of halogen; a $C_1–C_4$ alkyl group substituted with 1 to 3 phenyl or naphthyl groups which are optionally substituted with 1 to 3 substituents selected from the group consisting of $C_1–C_4$ alkyl, $C_1–C_4$ alkoxy, halo and nitro groups; and a phenyl or naphthyl group which is optionally substituted with 1 to 3 substituents selected from the group consisting of $C_1–C_4$ alkyl, $C_1–C_4$ alkoxy, halo and nitro groups.

A more preferable ester residue of ester derivatives is $R^6CO—$ or $R^6OCO—$ group wherein $R^6$ is selected from the group consisting of a $C_6–C_{20}$ alkyl group; a $C_{10}–C_{20}$ alkenyl group having 1 to 3 double bonds; a $C_3–C_5$ alkynyl group having one triple bond; a $C_1–C_4$ alkyl group substituted with one substituent selected from the group consisting of $C_1–C_4$ alkoxy and nitro groups: a $C_1–C_4$ alkyl group substituted with 1 to 3 substituents selected from the group consisting of fluoro and chloro groups: a $C_1–C_4$ alkyl group substituted with 1 to 3 phenyl groups which are optionally substituted with 1 or 2 substituents selected from the group consisting of $C_1–C_2$ alkyl, $C_1–C_4$ alkoxy, fluoro and chloro groups; and a phenyl group which is optionally substituted with 1 to 3 substituents selected from the group consisting of $C_1–C_2$ alkyl, $C_1–C_4$ alkoxy, fluoro and chloro groups.

A more preferable ester residue of ester derivatives is $R^6CO—$ or $R^6OCO—$ group wherein $R^6$ is selected from the group consisting of a $C_6–C_{20}$ alkyl group, a $C_{10}–C_{20}$ alkenyl group having 1 to 3 double bonds, a $C_3–C_5$ alkynyl group having one triple bond; a $C_1–C_4$ alkyl group substituted with one substituent selected from the group consisting of $C_1–C_4$ alkoxy, fluoro, chloro and nitro groups; a $C_1–C_4$ alkyl group substituted with 1 to 3 phenyl groups which are optionally substituted with 1 or 2 substituents selected from the group consisting of $C_1–C_2$ alkyl, $C_1–C_4$ alkoxy, fluoro and chloro groups; and a phenyl group which is optionally substituted with 1 to 3 substituents selected from the group consisting of $C_1–C_2$ alkyl $C_1–C_4$ alkoxy, fluoro and chloro groups.

A still more preferable ester residue of ester derivatives is $R^6CO—$ or $R^6OCO—$ group wherein $R^6$ is selected from the group consisting of a $C_6–C_{20}$ alkyl group; a $C_{10}–C_{20}$ alkenyl group having 1 to 3 double bonds; a $C_3–C_5$ alkynyl group having one triple bond; a $C_1–C_4$ alkyl group substituted with one substituent selected from the group consisting of $C_1–C_4$ alkoxy groups, and a $C_1–C_4$ alkyl group substituted with 1 or 2 phenyl groups which are optionally substituted with 1 or 2 substituents selected from the group consisting of $C_1–C_2$ alkyl, $C_1–C_4$ alkoxy, fluoro and chloro groups.

A most preferable ester residue of ester derivatives is $R^6CO—$ or $R^6OCO—$ group wherein $R^6$ is selected from the group consisting of a $C_6–C_{20}$ alkyl group and a $C_{10}–C_{20}$ alkenyl group having 1 to 3 double bonds.

An ether residue of ether derivatives is selected from the group consisting of

"straight or branched chain $C_1–C_{21}$ alkyl group" such as the methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, 3,7,11,15-tetramethylhexadecyl and henicosyl groups;

"straight or branched chain $C_2$–$C_{21}$ alkenyl or alkynyl group" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl, cis-8-heptadecenyl, cis, cis-8,11-heptadecadienyl, cis, cis, cis-8,11,14-heptadecatrienyl, cis-10-nonadecenyl, cis-12-icosenyl, ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl;

"straight or branched chain $C_1$–$C_{21}$ alkyl group which has one or more substituents selected from the group consisting of lower alkoxy, halogen (hereinafter for example fluorine, chlorine, bromine and iodine, preferably fluorine and chlorine) and nitro groups" such as methoxymethyl, ethoxymethyl, methoxyethyl, ethoxyethyl, trifluoromethyl, tnchloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl, 2,2-dibromoethyl, nitromethyl, dinitromethyl, 1-nitroethyl, 2-nitroethyl and 1,2-dinitroethyl;

"($C_6$–$C_{10}$)aryl-($C_1$–$C_{21}$)alkyl group wherein said aryl moiety optionally has one or more substituents selected from the group consisting of lower alkyl, lower alkoxy, halo and nitro group" such as benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl. 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentvl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl; and "$C_6$–$C_{10}$aryl group which optionally has one or more substituents selected from the group consisting of lower alkyl, lower alkoxy, halo and nitro groups" such as phenyl, naphthyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3,5-difluorophenyl, 2,5-difluorophenyl, 2,6-difluorophenyl, 2,4-difluorophenyl, 3,5-dibromophenyl, 2,5-dibromophenyl, 2,6-dichlorophenyl, 2,4-dichlorophenyl, 2,3,6-trifluorophenyl, 2,3,4-trifluorophenyl, 3,4,5-trifluorophenyl, 2,5,6-trifluorophenyl, 2,4,6-trifluorophenyl, 2,3,6-tribromophenyl, 2,3,4-tribromophenyl, 3,4,5-tribromophenyl, 2,5,6-trichlorophenyl, 2,4,6-trichlorophenyl, 1-fluoro-2-naphthyl, 2-fluoro-1-naphthyl, 3-fluoro-1-naphthyl, 1-chloro-2-naphthyl, 2-chloro-1-naphthyl, 3-bromo-1-naphthyl, 3,8-difluoro-1-naphthyl, 2,3-difluoro-1-naphthyl, 4,8-difluoro-1-naphthyl, 5,6-difluoro-1-naphthyl, 3,8-dichloro-1-naphthyl, 2,3-dichloro-1-naphthyl, 4,8-dibromo-1-naphthyl, 5,6-dibromo-1-naphthyl, 2,3,6-trifluoro-1-naphthyl, 2,3,4-trifluoro-1-naphthyl, 3,4,5-trifluoro-1-naphthyl, 4,5,6-trifluoro-1-naphthyl, 2,4,8-trifluoro-1-naphthyl, 2-methylphenyl, 3-methylphenyl, 4-methylphenyl, 2-ethylphenyl, 3-propylphenyl, 4-ethylphenyl, 2-butylphenyl, 3-pentylphenyl, 4-pentylphenyl, 3,5-dimethylphenyl, 2,5-dimethylphenyl, 2,6-dimethylphenyl, 2,4-dimethylphenyl, 3,5-dibutylphenyl, 2,5-dipentylphenyl, 2,6-dipropylmethylphenyl, 2,4-dipropylphenyl, 2,3,6-trimethylphenyl, 2,3,4-trimethylphenyl, 3,4,5-trimethylphenyl, 2,5,6-trimethylphenyl, 2,4,6-trimethylphenyl, 2,3,6-tributyiphenyl, 2,3,4-tripentylphenyl, 3,4,5-tributylphenyl, 2,5,6-tripropylmethylphenyl, 2,4,6-tripropylphenyl, 1-methyl-2-naphthyl, 2-methyl-1-naphthyl, 3-methyl-1-naphthyl, 1-ethyl-2-naphthyl, 2-propyl-1-naphthyl, 3-butyl-1-naphthyl, 3,8-dimethyl-1-naphthyl, 2,3-dimethyl-1-naphthyl, 4,8-dimethyl-1-naphthyl, 5,6-dimethyl-1-naphthyl, 3,8-diethyl-1-naphthyl, 2,3-dipropyl-1-naphthyl, 4,8-dipentyl-1-naphthyl, 5,6-dibutyl-1-naphthyl, 2,3,6-trimethyl-1-naphthyl, 2,3,4-trimethyl-1-naphthyl, 3,4,5-trimethyl-1-naphthyl, 4,5,6-trimethyl-1-naphthyl, 2,4,8-trimethyl-1-naphthyl, 2-methoxyphenyl, 3-methoxyphenyl, 4-methoxyphenyl, 2-ethoxyphenyl, 3-propoxyphenyl, 4-ethoxyphenyl, 2-butoxyphenyl, 3-pentoxyphenyl, 4-pentyloxyphenyl, 3,5-dimethoxyphenyl, 2,5-dimethoxyphenyl, 2,6-dimethoxyphenyl, 2,4-dimethoxyphenyl, 3,5-dibutoxyphenyl, 2,5-dipentyloxyphenyl, 2,6-dipropoxymethoxyphenyl, 2,4-dipropoxyphenyl, 2,3,6-trimethoxyphenyl, 2,3,4-trimethoxyphenyl, 3,4,5-trimethoxyphenyl, 2,5,6-trimethoxyphenyl, 2,4,6-trimethoxyphenyl, 2,3,6-tributoxyphenyl, 2,3,4-tripentyloxyphenyl, 3,4,5-tributoxyphenyl, 2,5,6-tripropoxyphenyl, 2,4,6-tripropoxyphenyl, 1-methoxy-2-naphthyl, 2-methoxy-1-naphthyl, 3-methoxy-1-naphthyl, 1-ethoxy-2-naphthyl, 2-propoxy-1-naphthyl, 3-butoxy-1-naphthyl, 3,8-dimethoxy-1-naphthyl, 2,3-dimethoxy-1-naphthyl, 4,8-dimethoxy-1-naphthyl, 5,6-dimethoxy-1-naphthyl, 3,8-diethoxy-1-naphthyl, 2,3-dipropoxy-1-naphthyl, 4,8-dipentyloxy-1-naphthyl, 5,6-dibutoxy-1-naphthyls 2,3,6-trimethoxy-1-naphthyl, 2,3,4-trimethoxy-1-naphthyl, 3,4,5-trimethoxy-1-naphthyl, 4,5,6-trimethoxy-1-naphthyl, 2,4,8-trimethoxy-1-naphthyl, 2-nitrophenyl, 3-nitrophenyl, 4-nitrophenyl, 3,5-dinitrophenyl, 2,5-dinitrophenyl, 2,6-dinitrophenyl, 2,4-dinitrophenyl, 2,3,6-trinitrophenyl, 2,3,4-trinitrophenyl, 3,4,5-trinitrophenyl, 2,5,6-trinitrophenyl, 2,4,6-trinitrophenyl, 1-nitro-2-naphthyl, 2-nitro-1-naphthyl, 3-nitro-1-naphthyl, 3,8- dinitro-1-naphthyl, 2,3-dinitro-1-naphthyl, 4,8-dinitro-1-naphthyl, 5,6-dinitro-1-naphthyl, 2,3,6-trinitro-1-naphthyl, 2,3,4-trinitro-1-naphthyl, 3,4,5-trinitro-1-naphthyl, 4,5,6-trinitro-1-naphthyl and 2,4,8-trinitro-1-naphthyl. A preferable ether residue of ether derivatives is selected from the group consisting of a $C_1$–$C_{21}$ alkyl group; a $C_2$–$C_{21}$ alkenyl or alkynyl group having 1 to 3 double or triple bonds; a $C_1$–$C_2$a alkyl group which has 1 to 4 substituents selected from the group consisting of lower alkoxy, halo and nitro groups; a $C_1$–$C_{21}$ alkyl group which has 1 to 3 $C_6$–$C_{10}$ aryl groups which are optionally substituted with 1 to 4 substituents selected from the group consisting of lower alkyl. lower alkoxy, halo and nitro groups; and a $C_6$–$C_{10}$ aryl group which is optionally substituted with 1 to 4 substituents selected from the group consisting of lower alkyl, lower alkoxy, halo and nitro groups.

A more preferable ether residue of ether derivatives is selected from the group consisting of a $C_1$–$C_{21}$ alkyl group; a $C_2$–$C_{21}$ alkenyl group having 1 to 3 double bonds; a $C_2$–$C_6$ alkynyl group having one triple bond; a $C_1$–$C_6$ alkyl group which has 1 to 4 substituents selected from the group consisting of $C_1$–$C_4$ alkoxy, halogen and nitro groups; a $C_1$–$C_6$ alkyl group which has 1 to 3 $C_6$–$C_{10}$ aryl groups which are optionally substituted with 1 to 3 substituents selected from the group consisting of $C_1$–$C_4$ alkyl, $C_1$–$C_4$ alkoxy, halo and nitro groups; and a $C_6$–$C_{10}$ aryl group which is optionally substituted with 1 to 3 substituents selected from the group consisting of $C_1$–$C_4$ alkyl, $C_1$–$C_4$ alkoxy, halo and nitro groups.

A more preferable ether residue of ether derivatives is selected from the group consisting of a $C_1$–$C_{21}$ alkyl group; a $C_6$–$C_{20}$ alkenyl group having 1 to 3 double bonds; a $C_2$–$C_6$ alkynyl group having one triple bond; a $C_1$–$C_6$ alkyl group which has one substituent selected from the group consisting of $C_1$–$C_4$ alkoxy and nitro groups; a $C_1$–$C_6$ alkyl group which has 1 to 3 substituents selected from the group consisting of halo groups; a $C_1$–$C_4$ alkyl group which has 1 to 3 phenyl or naphthyl groups which are optionally substituted with 1 to 3 substituents selected from the group consisting of $C_1$–$C_4$ alkyl, $C_1$–$C_4$ alkoxy, halo and nitro groups; and a phenyl or naphthyl group which is optionally substituted with 1 to 3 substituents selected from the group consisting of $C_1$–$C_4$ alkyl, $C_1$–$C_4$ alkoxy, halo and nitro groups.

A more preferable ether residue of ether derivatives is selected from the group consisting of a $C_6$–$C_{20}$ alkyl group; a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy and nitro group; a $C_1$–$C_4$ alkyl group which has 1 to 3 substituents selected from the group consisting of fluoro and chloro groups; a $C_1$–$C_4$ alkyl group which has 1 to 3 phenyl groups which are optionally substituted with 1 or 2 substituents selected from the group consisting of $C_1$–$C_2$ alkyl, $C_1$–$C_4$ alkoxy, fluoro and chloro group; and a phenyl group which is optionally substituted with 1 to 3 substituents selected from the group consisting of $C_1$–$C_2$ alkyl, $C_1$–$C_4$ alkoxy. fluoro and chloro groups.

A more preferable ether residue of ether derivatives is selected from the group consisting of a $C_6$–$C_{20}$ alkyl group: a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy, fluoro, chloro and nitro groups; a $C_1$–$C_4$ alkyl group which has 1 to 3 phenyl groups which are optionally substituted with 1 or 2 substituents selected from the group consisting of $C_1$–$C_2$ alkyl, $C_1$–$C_4$ alkoxy, fluoro and chloro groups; and a phenyl group which is optionally substituted with 1 to 3 substituents selected from the group consisting of $C_1$–$C_2$ alkyl, $C_1$–$C_4$alkoxy, fluoro and chloro groups.

A still more preferable ether residue of ether derivative is selected from the group consisting of a $C_6$–$C_{20}$ alkyl group: a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy groups; and a $C_1$–$C_4$ alkyl group which has 1 or 2 phenyl groups optionally substituted with 1 or 2 substituents selected from the group consisting of $C_1$–$C_2$ alkydl $C_1$–$C_4$ alkoxy, fluoro and chloro groups.

A most preferable ether residue of ether derivatives is selected from the group consisting of a $C_6$–$C_{20}$ alkyl group and a $C_{10}$–$C_{20}$ alkenyl group having 1 to 3 double bonds.

An alkyl residue of N-alkylcarbamoyl derivatives is selected from the group consisting of "straight or branched chain $C_1$–$C_{21}$ alkyl group" such as methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, 3,7,11,15-tetramethylhexadecyl and henicosyl groups;

"straight or branched chain $C_2$–$C_{21}$ alkenyl or alkynyl group" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl, cis-8-heptadecenyl, cis, cis-8,11-heptadecadienyl, cis, cis, cis-8,11,14-heptadecatrienyl, cis-10-nonadecenyl, cis-12-icosenyl, ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl;

"straight or branched chain $C_1$–$C_{21}$ alkyl group which has substituents selected from the group consisting of alkoxy. halogen (hereinafter example fluorine, chlorine, bromine and iodine, preferably fluorine and chlorine) and nitro" such as methoxymethyl, ethoxymethyl, methoxyethyl, ethoxyethyl, trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl, 2,2-dibromoethyl, nitromethyl, dinitromethyl, 1-nitroethyl, 2-nitroethyl and 1,2-dinitroethyl; and "$(C_6-C_{10})$aryl-$(C_1-C_{21})$alkyl group wherein said aryl moiety optionally has substituent selected from the group consisting of lower alkyl, lower alkoxy, halogen and nitro groups" such as benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl.

A preferable alkyl residue of N-alkylcarbamoyl derivatives is selected from the group consisting of a $C_1-C_{21}$ alkyl group; a $C_2-C_{21}$ alkenyl or alkynyl group having 1 to 3 double or triple bonds; a $C_1-C_{21}$ alkyl group which has one or more substituents selected from the group consisting of lower alkoxy, halo and nitro groups; and a $C_1-C_{21}$ alkyl group which has 1 to 3 $C_6-C_{10}$ aryl groups which are optionally substituted with 1 to 4 substituents selected from the group consisting of lower alkyl, lower alkoxy, halo and nitro groups.

A more preferable alkyl residue of N-alkylcarbamoyl derivatives is selected from the group consisting of a $C_1-C_{21}$ alkyl group; a $C_2-C_{21}$ alkenyl group having 1 to 3 double bonds; a $C_2-C_6$ alkynyl group having one triple bond; a $C_1-C_6$ alkyl group which has 1 to 4 substituents selected from the group consisting of $C_1-C_4$ alkoxy, halogen and nitro groups; and a $C_1-C_6$ alkyl group which has 1 to 3 $C_6-C_{10}$ aryl groups which are optionally substituted with 1 to 3 substituents selected from the group consisting of $C_1-C_4$ alkyl, $C_1-C_4$ alkoxy, halo and nitro groups.

A more preferable alkyl residue of N-alkylcarbamoyl derivatives is selected from the group consisting of a $C_1-C_{21}$ alkyl group; a $C_6-C_{20}$ alkenyl group having 1 to 3 double bonds; a $C_2-C_6$ alkynyl group having one triple bond; a $C_1-C_6$ alkyl group which has one substituent selected from the group consisting of $C_1-C_4$ alkoxy and nitro groups; a $C_1-C_6$ alkyl group which has 1 to 3 substituents selected from the group consisting of halo group; and a $C_1-C_4$ alkyl group which has 1 to 3 phenyl or naphthyl groups which are optionally substituted with 1 to 3 substituents selected from the group consisting of $C_1-C_4$ alkyl, $C_1-C_4$ alkoxy, halo and nitro groups.

A more preferable alkyl residue of N-alkylcarbamoyl derivatives is selected from the group consisting of a $C_6-C_{20}$ alkyl group; a $C_{10}-C_{20}$ alkenyl group having 1 to 3 double bonds; a $C_3-C_5$ alkynyl group having one triple bond: a $C_1-C_4$ alkyl group which has one substituent selected from the group consisting of $C_1-C_4$ alkoxy and nitro groups; a $C_1-C_4$ alkyl group which has 1 to 3 substituents selected from the group consisting of fluoro and chloro groups; and a $C_1-C_4$ alkyl group which has 1 to 3 phenyl groups which are optionally substituted with 1 to 2 substituents selected from the group consisting of $C_1-C_2$ alkyl, $C_1-C_4$ alkoxy, fluoro and chloro groups.

A more preferable alkyl residue of N-alkylcarbamoyl derivatives is selected from the group consisting of a $C_6-C_{10}$ alkyl group, a $C_{10}-C_{20}$ alkenyl group having 1 to 3 double bonds; a $C_3-C_5$ alkynyl group having one triple bond; a $C_1-C_4$ alkyl group which has one substituent selected from the group consisting of $C_1-C_4$ alkoxy. fluoro, chloro and nitro groups, and a $C_1-C_4$ alkyl group which has 1 to 3 phenyl groups which are optionally substituted with 1 to 2 substituents selected from the group consisting of $C_1-C_2$ alkyl, $C_1-C_4$ alkoxy, fluoro and chloro groups.

A still more preferable alkyl residue of N-alkylcarbamoyl derivative is selected from the group consisting of a $C_6-C_{20}$ alkyl group; a $C_{10}-C_{20}$ alkenyl group having 1 to 3 double bonds; a $C_3-C_5$ alkynyl group having one triple bond; a $C_1-C_4$ alkyl group which has one substituent selected from the group consisting of $C_1-C_4$ alkoxy groups; and a $C_1-C_4$ alkyl group which has 1 to 2 phenyl groups optionally substituted with 1 to 2 substituents selected from the group consisting of $C_1-C_2$ alkyl, $C_1-C_4$ alkoxy, fluoro and chloro groups.

A most preferable alkyl residue of N-alkylcarbamoyl derivatives is selected from the group consisting of a $C_6-C_{20}$ alkyl group and a $C_{10}-C_{20}$ alkenyl group having 1 to 3 double bonds.

In compound (Ia), there are several functional groups to which the hydroxy protecting group, and the ester, ether and alkyl residues can be attached. Therefore a plurality of protecting groups and residues can independently exist by optional combination of these protecting groups and residues.

A preferable pharmaceutically acceptable ester derivative of (Ia) is a derivative which has one or two of the ester residues at $R^2$, $R^3$ and/or $R^5$. A more preferable ester derivative is a derivative which has one or two of the ester residues at $R^3$ and/or $R^5$. A still more preferable ester derivative is a derivative which has one of the ester residues at $R^3$ or $R^5$. A most preferable ester derivative is a derivative which has one of the ester residue at $R^3$.

A preferable pharmaceutically acceptable ether derivative of (Ia) is a derivative which has one or two of the ether residues at $R^2$, $R^3$ and/or $R^5$. A more preferable ether derivative is a derivative which has one or two of the ether residues at $R^3$ and/or $R^5$. A still more preferable ether derivative is a derivative which has one of the ether residues at $R^3$ or $R^5$. A most preferable ether derivative is a derivative which has one of the ether residues at $R^3$.

A preferable pharmaceutically acceptable N-alkylcarbamoyl derivative is a derivative having one of the alkyl residues.

The term "pharmaceutically acceptable salt" refers to a salt that is a useful medicament without significant toxicity.

Where compound (I), (Ia), and pharmaceutically acceptable ester, ether and N-alkyl derivatives of compound (Ia) have a basic group such as an amino group these compounds can be converted into an acid addition salt by a conventional treatment with an acid. Such acid addition salts include inorganic acid salts such as hydrochloride, hydrobromide, sulfate and phosphate; organic acid salts such as acetate, benzoate, oxalate. maleate, fumarate, tartrate and citrate; and sulfonic acid salts such as methanesulfonate, benzenesulfonate and p-toluenesulfonate.

Where compound (I) and pharmaceutically acceptable ester, ether and N-alkyl derivatives of compound (Ia) have an acidic group such as a carboxy group, these compounds can be converted into a base addition salt by a conventional treatment with a base. Such base addition salts include alkali metal salts such as sodium, potassium and lithium salts; alkaline earth metal salts such as calcium and magnesium salts; metal salts such as aluminium, iron, zinc, copper, nickel and cobalt salts; and quaternary ammonium salts such as ammonium salt.

When compound (I) and pharmaceutically acceptable derivative of compound (Ia) are allowed to stand in the atmosphere, these compounds may take up water to form a hydrate. The present invention includes such hydrates. Compound (I) and pharmaceutically acceptable derivative of compound (Ia) may absorb a solvent to form a solvate. The present invention includes such solvates.

Compound (I) and pharmaceutically acceptable derivative of compound (Ia) have several asymmetric carbons and therefore they can exist as several stereoisomers such as enantiomers and diastereomers in which each carbon has R or S configuration. The compound of the present invention encompasses individual enantiomers and diastereomers and mixtures of these stereoisomers in all proportions.

A preferable configuration of the compound of the present invention is shown below:

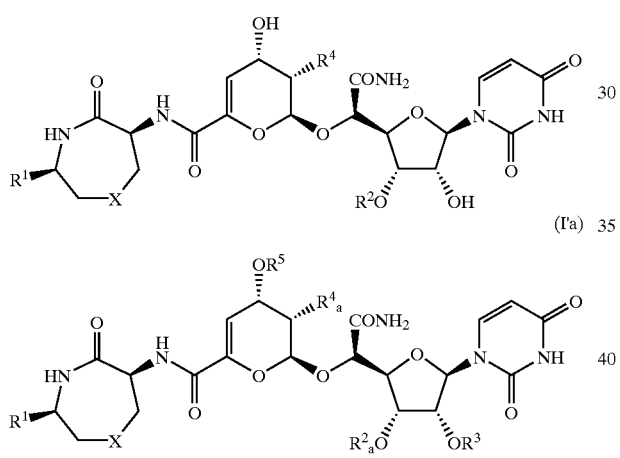

A preferable compound (I) is selected from the following compounds:
(1) a compound (I) wherein $R^2$ is a methyl group,
(2) a compound (I) wherein $R^4$ is a hydroxy group,
(3) a compound (I) wherein X is a methylene group;
   or a compound wherein $R^2$, $R^4$ and X is selected in optional combination of (1), (2) and (3), for example:
(4) a compound (I) wherein $R^4$ is a hydroxy group and X is a methylene group, and
(5) a compound (I) wherein $R^2$ is a methyl group, $R^4$ is a hydroxy group and X is a methylene group.

A preferable compound of formula (Ia) is selected from the following compounds:
(i) a compound (Ia) wherein the protecting group for a hydroxy group is selected from the group consisting of "tetrahydropyranyl or tetrahydrothiopyranyl group", "silyl group", "aralkyl group", "aralkyloxycarbonyl group", "1-(aliphatic acyloxy)-(lower alkyl) group", "1-(cycloalkylcarbonyloxy)-(lower alkyl) group", "1-(lower alkoxycarbonyloxy)-(lower alkyl) group", "1-(cycloalkyloxycarbonyloxy)-(lower alkyl) group", "phthalidyl" and "oxodioxolenylmethyl group".

(ii) a compound (Ia) wherein the protecting group for a hydroxy group is selected from the group consisting of tetrahydropyran-2-yl, 4-methoxytetrahydropyran-4-yl, tetrahydrothiopyran-2-yl, trimethylsilyl, triethylsilyl, tert-butyldimethylsilyl, di(tert-butyl)methylsilyl, diphenylmethylsilyl, benzyl, diphenylmethyl, triphenylmethyl, 4-methylbenzyl, 4-methoxybenzyl, 2-nitrobenzyl, 4-nitrobenzyl, 4-chlorobenzyl, benzyloxycarbonyl, 4-methoxybenzyloxycarbonyl, 2-nitrobenzyloxycarbonyl, 4-nitrobenzyloxycarbonyl, acetoxymethyl, propionyloxymethyl, butyryloxymethyl, pivaloyloxymethyl, valeryloxymethyl, 1-acetoxyethyl, butyryloxyethyl, 1-pivaloyloxyethyl, cyclopentylcarbonyloxymethyl, cyclohexylcarbonyloxymethyl, 1-cyclopentylcarbonyloxyethyl, 1-cyclohexylcarbonyloxyethyl, methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-(methoxycarbonyloxy)ethyl, 1-(ethoxycarbonyloxy)ethyl, 1-(isopropoxycarbonyloxy)ethyl, cyclopentyloxycarbonyloxymethyl, cyclohexyloxycarbonyloxymethyl, 1-(cyclopentyloxycarbonyloxy)ethyl, 1-(cyclohexyloxycarbonyloxy)ethyl, phthalidyl, (5-phenyl-2-oxo-1,3-dioxolen-4-yl)methyl, [5-(4-methylphenyl)-2-oxo-1,3-dioxolen-4-yl]methyl, (5-methyl-2-oxo-1,3-dioxolen-4-yl)methyl and (5-ethyl-2-oxo-1,3-dioxolen-4-yl)methyl group.

(iii) a compound (Ia) wherein the protecting group of hydroxy group is selected from the group consisting of trimethylsilyl, tert-butyldimethylsilyl, triphenylmethyl, benzyl, 4-methoxybenzyl, acetoxymethyl, propionyloxymethyl, butyryloxymethyl, pivaloyloxymethyl, valeryloxymethyl, cyclopentylcarbonyloxymethyl, cyclohexylcarbonyloxymethyl, methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, cyclopentyloxycarbonyloxymethyl, cyclohexyloxycarbonyloxymethyl, (5-phenyl-2-oxo-1,3-dioxolen-4-yl)methyl, [5-(4-methylphenyl)-2-oxo-1,3-dioxolen-4-yl]methyl, (5-methyl-2-oxo-1,3-dioxolen-4-yl)methyl and (5-ethyl-2-oxo-1,3-dioxolen-4-yl)methyl group.

A preferable ester derivative of compound (Ia) is selected from the following compounds:
(iv) an ester derivative of compound (Ia) wherein the ester residue is $R^6CO-$ or $R^6OCO-$ group in which $R^6$ is selected from the group consisting of hydrogen; a $C_1-C_{21}$ alkyl group; a $C_2-C_{21}$ alkenyl or alkynyl group having 1 to 3 double or triple bonds; a $C_1-C_{21}$ alkyl group substituted with 1 to 4 substituents selected from the group consisting of lower alkoxy, halo and nitro groups; a $C_1-C_{21}$ alkyl group substituted with 1 to 3 $C_6-C_{10}$ aryl groups which are optionally substituted with 1 to 4 substituents selected from the group consisting of lower alkyl, lower alkoxy, halo and nitro groups; and a $C_6-C_{10}$ aryl group which is optionally substituted with 1 to 4 substituents selected from the group consisting of lower alkyl, lower alkoxy, halo and nitro groups.

(v) an ester derivative of compound (Ia) wherein the ester residue is $R^6CO-$ or $R^6OCO-$ group in which $R^6$ is selected from the group consisting of hydrogen; a $C_1-C_{21}$ alkyl group; a $C_2-C_{21}$ alkenyl group having 1 to 3 double bonds; a $C_2-C_6$ alkynyl group having one triple bond; a $C_1-C_6$ alkyl group substituted with 1 to 4 substituents selected from the group consisting of $C_1-C_4$ alkoxy, halo and nitro groups; a $C_1-C_6$ alkyl group substituted with 1 to 3 $C_6-C_{10}$ aryl groups which are optionally substituted with 1 to 3 substituents selected from the group consisting of $C_1-C_4$ alkyl, $C_1-C_4$ alkoxy, halo and nitro groups; and a $C_6-C_{10}$ aryl group which is optionally substituted with 1 to 3 substituents selected from the group consisting of $C_1-C_4$ alkyl $C_1-C_4$ alkoxy, halo and nitro groups.

(vi) an ester derivative of compound (Ia) wherein the ester residue is $R^6CO-$ or $R^6OCO-$ group in which $R^6$ is selected from the group consisting of a $C_1-C_2$, alkyl group; a $C_6-C_{20}$ alkenyl group having 1 to 3 double bonds; a $C_2-C_6$ alkynyl group having one triple bond; a $C_1-C_6$ alkyl group substituted with one substituent selected from the group consisting of $C_1-C_4$ alkoxy and nitro groups; a $C_1-C_6$ alkyl group substituted with 1 to 3 substituents selected from the group consisting of halogen; a $C_1-C_4$ alkyl group substituted with 1 to 3 phenyl or naphthyl groups which are optionally substituted with 1 to 3 substituents selected from the group consisting of $C_1-C_4$ alkyl, $C_1-C_4$ alkoxy, halo and nitro groups; and a phenyl or naphthyl group which is optionally substituted with 1 to 3 substituents selected from the group consisting of $C_1-C_4$ alkyl, $C_1-C_4$ alkoxy, halo and nitro groups.

(vii) an ester derivative of compound (Ia) wherein the ester residue is $R^6CO-$ or $R^6OCO-$ group in which $R^6$ is selected from the group consisting of $C_6-C_{20}$ alkyl group; a $C_{10}-C_{20}$ alkenyl group having 1 to 3 double bonds; a $C_3-C_5$ alkynyl group having one triple bond; a $C_1-C_4$ alkyl group substituted with one substituent selected from the group consisting of $C_1-C_4$ alkoxy, and nitro groups: a $C_1-C_4$ alkyl group substituted with 1 to 3 substituents selected from the group consisting of fluoro and chloro groups; a $C_1-C_4$ alkyl group substituted with 1 to 3 phenyl groups which are optionally substituted with 1 or 2 substituents selected from the group consisting of $C_1-C_2$ alkyl, $C_1-C_4$ alkoxy, fluoro, and chloro groups; and a phenyl group which is optionally substituted with 1 to 3 substituents selected from the group consisting of $C_1-C_2$ alkyl, $C_1-C_4$ alkoxy, fluoro and chloro groups.

(viii) an ester derivative of compound (Ia) wherein the ester residue is $R^6CO-$ or $R^6OCO-$ group in which $R^6$ is selected from the group consisting of a $C_6-C_{20}$ alkyl group; a $C_{10}-C_{20}$ alkenyl group having 1 to 3 double bonds; a $C_3-C_5$ alkynyl group having one triple bond; a $C_1-C_4$ alkyl group substituted with one substituent selected from the group consisting of $C_1-C_4$ alkoxy, fluoro, chloro and nitro groups a $C_1-C_4$ alkyl group substituted with 1 to 3 phenyl groups which are optionally substituted with 1 or 2 substituents selected from the group consisting of $C_1-C_2$ alkyl, $C_1-C_4$ alkoxy, fluoro, and chloro groups; and a phenyl group which is optionally substituted with 1 to 3 substituents selected from the group consisting of $C_1-C_2$ alkyl, $C_1-C_4$ alkoxy, fluoro and chloro groups.

(ix) an ester derivative of compound (Ia) wherein the ester residue is $R^6CO-$ or $R^6OCO-$ group in which $R^6$ is selected from the group consisting of a $C_6-C_{20}$ alkyl group; a $C_{10}-C_{20}$ alkenyl group having 1 to 3 double bonds; a $C_3-C_5$ alkynyl group having one triple bond; a $C_1-C_4$ alkyl group substituted with one substituent selected from the group consisting of $C_1-C_4$ alkoxy groups; and a $C_1-C_4$ alkyl group substituted with 1 to 2 phenyl groups which are optionally substituted with 1 or 2 substituents selected from the group consisting of $C_1-C_2$ alkyl, $C_1-C_4$ alkoxy, fluoro and chloro groups.

(x) an ester derivative of compound (Ia) wherein the ester residue is $R^6CO-$ or $R^6OCO-$ group in which $R^6$ is selected from the group consisting of a $C_6-C_{20}$ alkyl group; and a $C_{10}-C_{20}$ alkenyl group having 1 to 3 double bonds.

A preferable ether derivative of compound (Ia) is selected from following compounds:

(xi) an ether derivative of compound (Ia) wherein the ether residue is selected from the group consisting of a $C_1-C_{21}$ alkyl group; a $C_2-C_{21}$ alkenyl or alkynyl group having 1 to 3 double or triple bonds; a $C_1-C_{21}$ alkyl group which has 1 to 3 substituents selected from the group consisting of lower alkoxy, halo and nitro groups; a $C_1-C_{21}$ alkyl group which has 1 to 3 $C_6-C_{10}$ aryl groups which are optionally substituted with 1 to 4 substituents selected from the group consisting of lower alkyl, lower alkoxy, halo and nitro groups; and a $C_6-C_{10}$ aryl group which is optionally substituted with 1 to 4 is substituents selected from the group consisting of lower alkyl, lower alkoxy, halo and nitro groups.

(xii) an ether derivative of compound (Ia) wherein the ether residue is selected from the group consisting of a $C_1-C_{21}$ alkyl group; a $C_2-C_{21}$ alkenyl group having 1 to 3 double bonds; a $C_2-C_6$ alkynyl group having one triple bond; a $C_1-C_6$ alkyl group which has 1 to 4 substituents selected from the group consisting of $C_1-C_4$ alkoxy, halo and nitro group; a $C_1-C_6$ alkyl group which has 1 to 3 $C_6-C_{10}$ aryl groups which is optionally substituted with 1 to 3 substituents selected from the group consisting of $C_1-C_4$ alkyl, $C_1-C_4$ alkoxy, halo and nitro groups; and a $C_6-C_{10}$ aryl group which are optionally substituted with 1 to 3 substituents selected from the group consisting of $C_1-C_4$ alkyl, $C_1-C_4$ alkoxy, halo and nitro groups.

(xiii) an ether derivative of compound (Ia) wherein the ether residue is selected from the group consisting of a $C_1-C_{21}$ alkyl group; $C_6-C_{20}$ alkenyl group having 1 to 3 double bonds; a $C_2-C_6$ alkynyl group having one triple bond; a $C_1-C_6$ alkyl group which has one substituent selected from the group consisting of $C_1-C_4$ alkoxy and nitro groups; $C_1-C_6$ alkyl group which has 1 to 3 substituents selected from the group consisting of halo group; a $C_1-C_4$ alkyl group which has 1 to 3 phenyl or naphthyl groups which are optionally substituted with 1 to 3 substituents selected from the group consisting of $C_1-C_4$ alkyl, $C_1-C_4$ alkoxy, halogen and nitro groups; and a phenyl or naphthyl group which is optionally substituted with 1 to 3 substituents selected from the group consisting of $C_1-C_4$ alkyl, $C_1-C_4$ alkoxy, halo and nitro groups.

(xiv) an ether derivative of compound (Ia) wherein the ether residue is selected from the group consisting of a $C_6-C_{20}$ alkyl group a $C_{10}-C_{20}$ alkenyl group having 1 to 3 double bonds; a $C_3-C_5$ alkynyl group having one triple bond; a $C_1-C_4$ alkyl group which has one substituent selected from the group consisting of $C_1$–$C_4$ alkoxy and nitro groups; a $C_1$–$C_4$ alkyl group which has 1 to 3 substituents selected from the group consisting of fluoro and chloro groups; a $C_1$–$C_4$ alkyl group which has 1 to 3 phenyl groups which are optionally substituted with 1 or 2 substituents selected from the group consisting of $C_1$–$C_2$ alkyl, $C_1$–$C_4$ alkoxy, fluoro and chloro groups; and a phenyl group which is optionally substituted with 1 to 3 substituents selected from the group consisting of $C_1$–$C_2$ alkyl, $C_1$–$C_4$ alkoxy, fluoro and chloro groups.

(xv) an ether derivative of compound (Ia) wherein the ether residue is selected from the group consisting of a $C_6$–$C_{20}$ alkyl group; a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy, fluoro, chloro, and nitro groups; a $C_1$–$C_4$ alkyl group which has 1 to 3 phenyl groups which are optionally substituted with 1 or 2 substituents selected from the group consisting of $C_1$–$C_2$ alkyl, $C_1$–$C_4$ alkoxy, fluoro and chloro groups, and a phenyl group which is optionally substituted with 1 to 3 substituents selected from the group consisting of $C_1$–$C_2$ alkyl, $C_1$–$C_4$ alkoxy, fluoro and chloro groups.

(xvi) an ether derivative of compound (Ia) wherein the ether residue is selected from the group consisting of a $C_6$–$C_{20}$ alkyl group; a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy group; and a $C_1$–$C_4$ alkyl group which has 1 or 2 phenyl groups optionally substituted with 1 or 2 substituents selected from the group consisting of $C_1$–$C_4$ alkyl. $C_1$–$C_4$ alkoxy, fluoro and chloro groups.

(xvii) an ether derivative of compound (Ia) wherein the ether residue is selected from the group consisting of a $C_6$–$C_{20}$ alkyl group and a $C_{10}$–$C_{20}$ alkenyl group having 1 to 3 double bonds.

A preferable N-alkylcarbamoyl derivative of compound (Ia) is selected from the following compounds:

(xviii) an N-alkylcarbamoyl derivative of compound (Ia) wherein the alkyl residue of the N-alkylcarbamoyl derivative is selected from the group consisting of a $C_1$–$C_{21}$ alkyl group; a $C_2$–$C_{21}$ alkenyl or alkynyl group having 1 to 3 double or triple bonds; a $C_1$–$C_{21}$ alkyl group which has 1 to 4 substituents selected from the group consisting of lower alkoxy, halo and nitro groups; and a $C_1$–$C_{21}$ alkyl group which has 1 to 3 $C_6$–$C_{10}$ aryl groups which are optionally substituted with 1 to 4 substituents selected from the group consisting of lower alkyl, lower alkoxy, halo and nitro groups.

(xix) an N-alkylcarbamoyl derivative of compound (Ia) wherein the alkyl residue is selected from the group consisting of a $C_1$–$C_{21}$ alkyl group; a $C_2$–$C_{21}$ alkenyl group having 1 to 3 double bonds; a $C_2$–$C_6$ alkynyl group having one triple bond; a $C_1$–$C_6$ alkyl group which has 1 to 4 substituents selected from the group consisting of $C_1$–$C_4$ alkoxy, halo and nitro groups; and a $C_1$–$C_6$ alkyl group which has 1 to 3 $C_6$–$C_{10}$ aryl groups which are optionally substituted with 1 to 3 substituents selected from the group consisting of $C_1$–$C_4$ alkyl, $C_1$–$C_4$ alkoxy, halo and nitro group.

(xx) an N-alkylcarbamoyl derivative of compound (Ia) wherein the alkyl residue is selected from the group consisting of a $C_1$–$C_{21}$ alkyl group; a $C_6$–$C_{20}$ alkenyl group having 1 to 3 double bonds; a $C_2$–$C_6$ alkynyl group having one triple bond; a $C_1$–$C_6$ alkyl group which has one substituent selected from the group consisting of $C_1$–$C_4$ alkoxy and nitro groups; a $C_1$–$C_6$ alkyl group which has 1 to 3 substituents selected from the group consisting of halo groups; and a $C_1$–$C_4$ alkyl group which has 1 to 3 phenyl or naphthyl groups which are optionally substituted with 1 to 3 substituents selected from the group consisting of $C_1$–$C_4$ alkyl, $C_1$–$C_4$ alkoxy, halo and nitro groups.

(xxi) an N-alkylcarbamoyl derivative of compound (Ia) wherein the alkyl residue is selected from the group consisting of a $C_6$–$C_{20}$ alkyl group; a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy and nitro groups; a $C_1$–$C_4$ alkyl group which has 1 to 3 substituents selected from the group consisting of fluoro and chloro groups; and a $C_1$–$C_4$ alkyl group which has 1 to 3 phenyl groups which are optionally substituted with 1 or 2 substituents selected from the group consisting of $C_1$–$C_2$ alkyl, $C_1$–$C_4$ alkoxy, fluoro and chloro groups.

(xxii) an N-alkylcarbamoyl derivative of compound (Ia) wherein the alkyl residue is selected from the group consisting of a $C_6$–$C_{20}$ alkyl group; a $C_{10}C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy, fluoro, chloro and nitro groups; and a $C_1$–$C_4$ alkyl group which has 1 to 3 phenyl groups which are optionally substituted with 1 or 2 substituents selected from the group consisting of $C_1$–$C_2$ alkyl, $C_1$–$C_4$ alkoxy, fluoro and chloro groups.

(xxiii) an N-alkylcarbamoyl derivative of compound (Ia) wherein the alkyl residue is selected from the group consisting of $C_6$–$C_{20}$ alkyl group; a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy groups; and $C_1$–$C_4$ alkyl group which has 1 or 2 phenyl groups optionally substituted with 1 or 2 substituents selected from the group consisting of $C_1$–$C_2$ alkyl $C_1$–$C_4$ alkoxy, fluoro and chloro groups.

(xxiv) an N-alkylcarbamoyl derivative of compound (Ia) wherein the alkyl residue is selected from the group consisting of a $C_6$–$C_{20}$ alkyl group and a $C_{10}$–$C_{20}$ alkenyl group having 1 to 3 double bonds.

A more preferable compound (Ia) is selected from group (i) to (iii); group (iv) to (x); group (xi) to (xvii); group (xviii) to (xxiv) in optional combination of these groups, for example:

(xxv) a compound (Ia) wherein the protecting group for a hydroxy group is (i) and the ester residue is (iv).

(xxvi) a compound (Ia) wherein the protecting group for a hydroxy group is (ii) and the ester residue is (v).

(xxvii) a compound (Ia) wherein the protecting group for a hydroxy group is (iii) and the ester residue is (vi).

(xxviii) a compound (Ia) wherein the protecting group for a hydroxy group is (i) and the ether residue is (xi).

(xxix) a compound (Ia) wherein the protecting group for a hydroxy group is (ii) and the ester residue is (xii).

(xxx) a compound (Ia) wherein the protecting group for a hydroxy group is (iii) and the ether residue is (xiii).

(xxxi) a compound (Ia) wherein the protecting group for a hydroxy group is (i) and the alkyl residue is (xviii).

(xxxii) a compound (Ia) wherein the protecting group for a hydroxy group is (ii) and the alkyl residue is (xix).

(xxxiii) a compound (Ia) wherein the protecting group for a hydroxy group is (iii) and the residue is (xx).

The following Tables 1 and 2 are intended to illustrate typical compounds (I) and (Ia) of the present invention and are not intended to limit the scope of this invention.

TABLE 1

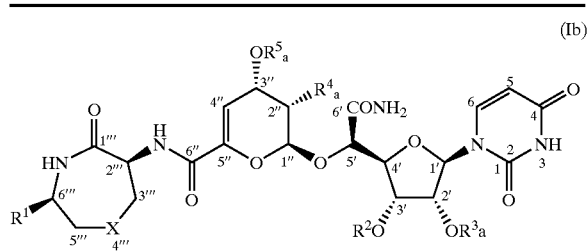
(Ib)

| Exemp. comp. No. | X | $R^1$ | $R^2$ | $R^3_a$ | $R^4_a$ | $R^5_a$ |
|---|---|---|---|---|---|---|
| 1 | $CH_2$ | Me | Me | H | OH | H |
| 2 | $CH_2$ | Me | H | H | OH | H |
| 3 | $CH_2$ | Me | Me | H | H | H |
| 4 | $CH_2$ | Me | Me | A7 | OH | H |
| 5 | $CH_2$ | Me | Me | A8 | OH | H |
| 6 | $CH_2$ | Me | Me | A9 | OH | H |
| 7 | $CH_2$ | Me | Me | A10 | OH | H |
| 8 | $CH_2$ | Me | Me | A12 | OH | H |
| 9 | $CH_2$ | Me | Me | A14 | OH | H |
| 10 | $CH_2$ | Me | Me | A15 | OH | H |
| 11 | $CH_2$ | Me | Me | A16 | OH | H |
| 12 | $CH_2$ | Me | Me | A17 | OH | H |
| 13 | $CH_2$ | Me | Me | A18 | OH | H |
| 14 | $CH_2$ | Me | Me | A20 | OH | H |
| 15 | $CH_2$ | Me | Me | A22 | OH | H |
| 16 | $CH_2$ | Me | Me | OLE | OH | H |
| 17 | $CH_2$ | Me | Me | LE | OH | H |
| 18 | $CH_2$ | Me | Me | LEN | OH | H |
| 19 | $CH_2$ | Me | Me | CES | OH | H |
| 20 | $CH_2$ | Me | Me | CDS | OH | H |
| 21 | $CH_2$ | Me | Me | DPP | OH | H |
| 22 | $CH_2$ | Me | Me | TMPP | OH | H |
| 23 | $CH_2$ | Me | Me | NPP | OH | H |
| 24 | $CH_2$ | Me | Me | MPP | OH | H |
| 25 | $CH_2$ | Me | Me | CP | OH | H |
| 26 | $CH_2$ | Me | Me | ND | OH | H |
| 27 | $CH_2$ | Me | Me | TCN | OH | H |
| 28 | $CH_2$ | Me | Me | MP | OH | H |
| 29 | $CH_2$ | Me | Me | CPA | OH | H |
| 30 | $CH_2$ | Me | Me | BZ | OH | H |
| 31 | $CH_2$ | Me | Me | NBZ | OH | H |
| 32 | $CH_2$ | Me | Me | CB | OH | H |
| 33 | $CH_2$ | Me | Me | MB | OH | H |
| 34 | $CH_2$ | Me | Me | EB | OH | H |
| 35 | $CH_2$ | Me | Me | MO | OH | H |
| 36 | $CH_2$ | Me | Me | MD | OH | H |
| 37 | $CH_2$ | Me | Me | MDD | OH | H |
| 38 | $CH_2$ | Me | Me | MTD | OH | H |
| 39 | $CH_2$ | Me | Me | MHD | OH | H |
| 40 | $CH_2$ | Me | Me | DMO | OH | H |
| 41 | $CH_2$ | Me | Me | DMD | OH | H |
| 42 | $CH_2$ | Me | Me | DMDD | OH | H |
| 43 | $CH_2$ | Me | Me | DMTD | OH | H |
| 44 | $CH_2$ | Me | Me | DMHD | OH | H |
| 45 | $CH_2$ | H | H | H | OH | H |
| 46 | $CH_2$ | H | Me | A7 | OH | H |
| 47 | $CH_2$ | H | Me | A8 | OH | H |
| 48 | $CH_2$ | H | Me | A9 | OH | H |
| 49 | $CH_2$ | H | Me | A10 | OH | H |
| 50 | $CH_2$ | H | Me | A12 | OH | H |

TABLE 1-continued

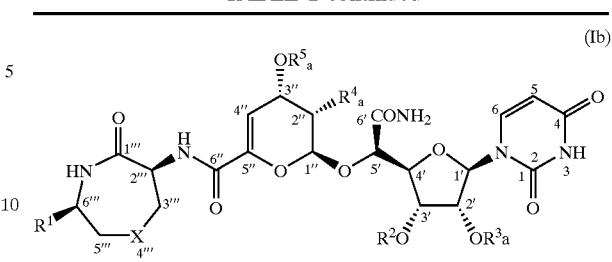
(Ib)

| Exemp. comp. No. | X | $R^1$ | $R^2$ | $R^3_a$ | $R^4_a$ | $R^5_a$ |
|---|---|---|---|---|---|---|
| 51 | $CH_2$ | H | Me | A14 | OH | H |
| 52 | $CH_2$ | H | Me | A15 | OH | H |
| 53 | $CH_2$ | H | Me | A16 | OH | H |
| 54 | $CH_2$ | H | Me | A17 | OH | H |
| 55 | $CH_2$ | H | Me | A18 | OH | H |
| 56 | $CH_2$ | H | Me | A20 | OH | H |
| 57 | $CH_2$ | H | Me | A22 | OH | H |
| 58 | $CH_2$ | H | Me | OLE | OH | H |
| 59 | $CH_2$ | H | Me | LE | OH | H |
| 60 | $CH_2$ | H | Me | LEN | OH | H |
| 61 | $CH_2$ | H | Me | CES | OH | H |
| 62 | $CH_2$ | H | Me | CDS | OH | H |
| 63 | $CH_2$ | H | Me | DPP | OH | H |
| 64 | $CH_2$ | H | Me | TMPP | OH | H |
| 65 | $CH_2$ | H | Me | NPP | OH | H |
| 66 | $CH_2$ | H | Me | MPP | OH | H |
| 67 | $CH_2$ | H | Me | CP | OH | H |
| 68 | $CH_2$ | H | Me | ND | OH | H |
| 69 | $CH_2$ | H | Me | TCN | OH | H |
| 70 | $CH_2$ | H | Me | MP | OH | H |
| 71 | $CH_2$ | H | Me | CPA | OH | H |
| 72 | $CH_2$ | H | Me | BZ | OH | H |
| 73 | $CH_2$ | H | Me | NBZ | OH | H |
| 74 | $CH_2$ | H | Me | CB | OH | H |
| 75 | $CH_2$ | H | Me | MB | OH | H |
| 76 | $CH_2$ | H | Me | EB | OH | H |
| 77 | $CH_2$ | H | Me | MO | OH | H |
| 78 | $CH_2$ | H | Me | MD | OH | H |
| 79 | $CH_2$ | H | Me | MDD | OH | H |
| 80 | $CH_2$ | H | Me | MTD | OH | H |
| 81 | $CH_2$ | H | Me | MHD | OH | H |
| 82 | $CH_2$ | H | Me | DMO | OH | H |
| 83 | $CH_2$ | H | Me | DMD | OH | H |
| 84 | $CH_2$ | H | Me | DMDD | OH | H |
| 85 | $CH_2$ | H | Me | DMTD | OH | H |
| 86 | $CH_2$ | H | Me | DMHD | OH | H |
| 87 | $CH_2$ | Me | Me | H | OH | A7 |
| 88 | $CH_2$ | Me | Me | H | OH | A8 |
| 89 | $CH_2$ | Me | Me | H | OH | A9 |
| 90 | $CH_2$ | Me | Me | H | OH | A10 |
| 91 | $CH_2$ | Me | Me | H | OH | A12 |
| 92 | $CH_2$ | Me | Me | H | OH | A14 |
| 93 | $CH_2$ | Me | Me | H | OH | A15 |
| 94 | $CH_2$ | Me | Me | H | OH | A16 |
| 95 | $CH_2$ | Me | Me | H | OH | A17 |
| 96 | $CH_2$ | Me | Me | H | OH | A18 |
| 97 | $CH_2$ | Me | Me | H | OH | A20 |
| 98 | $CH_2$ | Me | Me | H | OH | A22 |
| 99 | $CH_2$ | Me | Me | H | OH | OLE |
| 100 | $CH_2$ | Me | Me | H | OH | LE |
| 101 | $CH_2$ | Me | Me | H | OH | LEN |
| 102 | $CH_2$ | Me | Me | H | OH | CES |
| 103 | $CH_2$ | Me | Me | H | OH | CDS |
| 104 | $CH_2$ | Me | Me | H | OH | DPP |
| 105 | $CH_2$ | Me | Me | H | OH | TMPP |
| 106 | $CH_2$ | Me | Me | H | OH | NPP |
| 107 | $CH_2$ | Me | Me | H | OH | MPP |
| 108 | $CH_2$ | Me | Me | H | OH | CP |
| 109 | $CH_2$ | Me | Me | H | OH | ND |
| 110 | $CH_2$ | Me | Me | H | OH | TCN |
| 111 | $CH_2$ | Me | Me | H | OH | MP |
| 112 | $CH_2$ | Me | Me | H | OH | CPA |

TABLE 1-continued

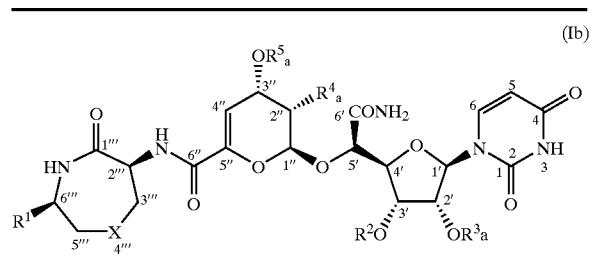

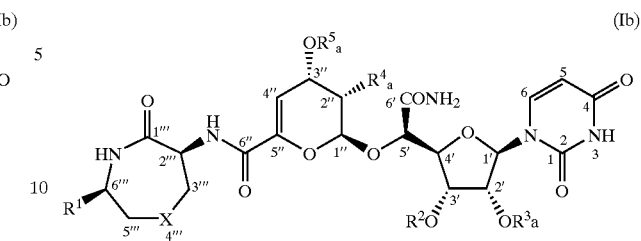

| Exemp. comp. No. | X | $R^1$ | $R^2$ | $R^3_a$ | $R^4_a$ | $R^5_a$ |
|---|---|---|---|---|---|---|
| 113 | $CH_2$ | Me | Me | H | OH | BZ |
| 114 | $CH_2$ | Me | Me | H | OH | NBZ |
| 115 | $CH_2$ | Me | Me | H | OH | CB |
| 116 | $CH_2$ | Me | Me | H | OH | MB |
| 117 | $CH_2$ | Me | Me | H | OH | EB |
| 118 | $CH_2$ | Me | Me | H | OH | MO |
| 119 | $CH_2$ | Me | Me | H | OH | MD |
| 120 | $CH_2$ | Me | Me | H | OH | MDD |
| 121 | $CH_2$ | Me | Me | H | OH | MTD |
| 122 | $CH_2$ | Me | Me | H | OH | MHD |
| 123 | $CH_2$ | Me | Me | H | OH | DMO |
| 124 | $CH_2$ | Me | Me | H | OH | DMD |
| 125 | $CH_2$ | Me | Me | H | OH | DMDD |
| 126 | $CH_2$ | Me | Me | H | OH | DMTD |
| 127 | $CH_2$ | Me | Me | H | OH | DMHD |
| 128 | $CH_2$ | H | Me | H | OH | A7 |
| 129 | $CH_2$ | H | Me | H | OH | A8 |
| 130 | $CH_2$ | H | Me | H | OH | A9 |
| 131 | $CH_2$ | H | Me | H | OH | A10 |
| 132 | $CH_2$ | H | Me | H | OH | A12 |
| 133 | $CH_2$ | H | Me | H | OH | A14 |
| 134 | $CH_2$ | H | Me | H | OH | A15 |
| 135 | $CH_2$ | H | Me | H | OH | A16 |
| 136 | $CH_2$ | H | Me | H | OH | A17 |
| 137 | $CH_2$ | H | Me | H | OH | A18 |
| 138 | $CH_2$ | H | Me | H | OH | A20 |
| 139 | $CH_2$ | H | Me | H | OH | A22 |
| 140 | $CH_2$ | H | Me | H | OH | OLE |
| 141 | $CH_2$ | H | Me | H | OH | LE |
| 142 | $CH_2$ | H | Me | H | OH | LEN |
| 143 | $CH_2$ | H | Me | H | OH | CES |
| 144 | $CH_2$ | H | Me | H | OH | CDS |
| 145 | $CH_2$ | H | Me | H | OH | DPP |
| 146 | $CH_2$ | H | Me | H | OH | TMPP |
| 147 | $CH_2$ | H | Me | H | OH | NPP |
| 148 | $CH_2$ | H | Me | H | OH | MPP |
| 149 | $CH_2$ | H | Me | H | OH | CP |
| 150 | $CH_2$ | H | Me | H | OH | ND |
| 151 | $CH_2$ | H | Me | H | OH | TCN |
| 152 | $CH_2$ | H | Me | H | OH | MP |
| 153 | $CH_2$ | H | Me | H | OH | CPA |
| 154 | $CH_2$ | H | Me | H | OH | BZ |
| 155 | $CH_2$ | H | Me | H | OH | NBZ |
| 156 | $CH_2$ | H | Me | H | OH | CB |
| 157 | $CH_2$ | H | Me | H | OH | MB |
| 158 | $CH_2$ | H | Me | H | OH | EB |
| 159 | $CH_2$ | H | Me | H | OH | MO |
| 160 | $CH_2$ | H | Me | H | OH | MD |
| 161 | $CH_2$ | H | Me | H | OH | MDD |
| 162 | $CH_2$ | H | Me | H | OH | MTD |
| 163 | $CH_2$ | H | Me | H | OH | MHD |
| 164 | $CH_2$ | H | Me | H | OH | DMO |
| 165 | $CH_2$ | H | Me | H | OH | DMD |
| 166 | $CH_2$ | H | Me | H | OH | DMDD |
| 167 | $CH_2$ | H | Me | H | OH | DMTD |
| 168 | $CH_2$ | H | Me | H | OH | DMHD |
| 169 | $CH_2$ | Me | Me | A7 | H | H |
| 170 | $CH_2$ | Me | Me | A8 | H | H |
| 171 | $CH_2$ | Me | Me | A9 | H | H |
| 172 | $CH_2$ | Me | Me | A10 | H | H |
| 173 | $CH_2$ | Me | Me | A12 | H | H |
| 174 | $CH_2$ | Me | Me | A14 | H | H |
| 175 | $CH_2$ | Me | Me | A15 | H | H |
| 176 | $CH_2$ | Me | Me | A16 | H | H |
| 177 | $CH_2$ | Me | Me | A17 | H | H |
| 178 | $CH_2$ | Me | Me | A18 | H | H |
| 179 | $CH_2$ | Me | Me | A20 | H | H |
| 180 | $CH_2$ | Me | Me | A22 | H | H |
| 181 | $CH_2$ | Me | Me | OLE | H | H |
| 182 | $CH_2$ | Me | Me | LE | H | H |
| 183 | $CH_2$ | Me | Me | LEN | H | H |
| 184 | $CH_2$ | Me | Me | CES | H | H |
| 185 | $CH_2$ | Me | Me | CDS | H | H |
| 186 | $CH_2$ | Me | Me | DPP | H | H |
| 187 | $CH_2$ | Me | Me | TMPP | H | H |
| 188 | $CH_2$ | Me | Me | NPP | H | H |
| 189 | $CH_2$ | Me | Me | MPP | H | H |
| 190 | $CH_2$ | Me | Me | CP | H | H |
| 191 | $CH_2$ | Me | Me | ND | H | H |
| 192 | $CH_2$ | Me | Me | TCN | H | H |
| 193 | $CH_2$ | Me | Me | MP | H | H |
| 194 | $CH_2$ | Me | Me | CPA | H | H |
| 195 | $CH_2$ | Me | Me | BZ | H | H |
| 196 | $CH_2$ | Me | Me | NBZ | H | H |
| 197 | $CH_2$ | Me | Me | CB | H | H |
| 198 | $CH_2$ | Me | Me | MB | H | H |
| 199 | $CH_2$ | Me | Me | EB | H | H |
| 200 | $CH_2$ | Me | Me | MO | H | H |
| 201 | $CH_2$ | Me | Me | MD | H | H |
| 202 | $CH_2$ | Me | Me | MDD | H | H |
| 203 | $CH_2$ | Me | Me | MTD | H | H |
| 204 | $CH_2$ | Me | Me | MHD | H | H |
| 205 | $CH_2$ | Me | Me | DMO | H | H |
| 206 | $CH_2$ | Me | Me | DMD | H | H |
| 207 | $CH_2$ | Me | Me | DMDD | H | H |
| 208 | $CH_2$ | Me | Me | DMTD | H | H |
| 209 | $CH_2$ | Me | Me | DMHD | H | H |
| 210 | $CH_2$ | Me | Me | H | H | A7 |
| 211 | $CH_2$ | Me | Me | H | H | A8 |
| 212 | $CH_2$ | Me | Me | H | H | A9 |
| 213 | $CH_2$ | Me | Me | H | H | A10 |
| 214 | $CH_2$ | Me | Me | H | H | A12 |
| 215 | $CH_2$ | Me | Me | H | H | A14 |
| 216 | $CH_2$ | Me | Me | H | H | A15 |
| 217 | $CH_2$ | Me | Me | H | H | A16 |
| 218 | $CH_2$ | Me | Me | H | H | A17 |
| 219 | $CH_2$ | Me | Me | H | H | A18 |
| 220 | $CH_2$ | Me | Me | H | H | A20 |
| 221 | $CH_2$ | Me | Me | H | H | A22 |
| 222 | $CH_2$ | Me | Me | H | H | OLE |
| 223 | $CH_2$ | Me | Me | H | H | LE |
| 224 | $CH_2$ | Me | Me | H | H | LEN |
| 225 | $CH_2$ | Me | Me | H | H | CES |
| 226 | $CH_2$ | Me | Me | H | H | CDS |
| 227 | $CH_2$ | Me | Me | H | H | DPP |
| 228 | $CH_2$ | Me | Me | H | H | TMPP |
| 229 | $CH_2$ | Me | Me | H | H | NPP |
| 230 | $CH_2$ | Me | Me | H | H | MPP |
| 231 | $CH_2$ | Me | Me | H | H | CP |
| 232 | $CH_2$ | Me | Me | H | H | ND |
| 233 | $CH_2$ | Me | Me | H | H | TCN |
| 234 | $CH_2$ | Me | Me | H | H | MP |
| 235 | $CH_2$ | Me | Me | H | H | CPA |
| 236 | $CH_2$ | Me | Me | H | H | BZ |

TABLE 1-continued

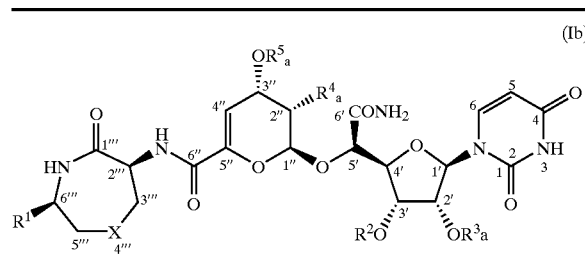

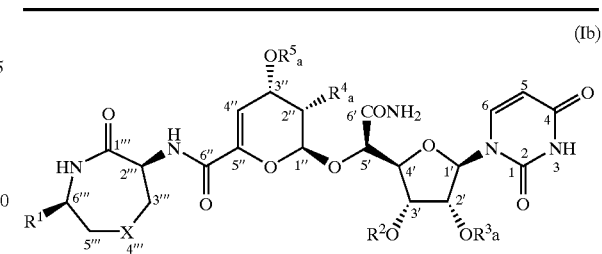

| Exemp. comp. No. | X | R¹ | R² | R³ₐ | R⁴ₐ | R⁵ₐ |
|---|---|---|---|---|---|---|
| 237 | CH₂ | Me | Me | H | H | NBZ |
| 238 | CH₂ | Me | Me | H | H | CB |
| 239 | CH₂ | Me | Me | H | H | MB |
| 240 | CH₂ | Me | Me | H | H | EB |
| 241 | CH₂ | Me | Me | H | H | MO |
| 242 | CH₂ | Me | Me | H | H | MD |
| 243 | CH₂ | Me | Me | H | H | MDD |
| 244 | CH₂ | Me | Me | H | H | MTD |
| 245 | CH₂ | Me | Me | H | H | MHD |
| 246 | CH₂ | Me | Me | H | H | DMO |
| 247 | CH₂ | Me | Me | H | H | DMD |
| 248 | CH₂ | Me | Me | H | H | DMDD |
| 249 | CH₂ | Me | Me | H | H | DMTD |
| 250 | CH₂ | Me | Me | H | H | DMHD |
| 251 | CH₂ | Me | Me | H | AO7 | A7 |
| 252 | CH₂ | Me | Me | H | AO8 | A8 |
| 253 | CH₂ | Me | Me | H | AO9 | A9 |
| 254 | CH₂ | Me | Me | H | AO10 | A10 |
| 255 | CH₂ | Me | Me | H | AO12 | A12 |
| 256 | CH₂ | Me | Me | H | AO14 | A14 |
| 257 | CH₂ | Me | Me | H | AO15 | A15 |
| 258 | CH₂ | Me | Me | H | AO16 | A16 |
| 259 | CH₂ | Me | Me | H | AO17 | A17 |
| 260 | CH₂ | Me | Me | H | AO18 | A18 |
| 261 | CH₂ | Me | Me | H | OLEO | OLE |
| 262 | CH₂ | Me | Me | H | LEO | LE |
| 263 | CH₂ | Me | Me | H | LENO | LEN |
| 264 | CH₂ | Me | Me | H | CESO | CES |
| 265 | CH₂ | Me | Me | H | CDSO | CDS |
| 266 | CH₂ | Me | Me | H | DPPO | DPP |
| 267 | CH₂ | Me | Me | H | TMPPO | TMPP |
| 268 | CH₂ | Me | Me | H | NPPO | NPP |
| 269 | CH₂ | Me | Me | H | MPPO | MPP |
| 270 | CH₂ | Me | Me | H | CPO | CP |
| 271 | CH₂ | Me | Me | H | NDO | ND |
| 272 | CH₂ | Me | Me | H | TCNO | TCN |
| 273 | CH₂ | Me | Me | H | MPO | MP |
| 274 | CH₂ | Me | Me | H | CPAO | CPA |
| 275 | CH₂ | Me | Me | H | BZO | BZ |
| 276 | CH₂ | Me | Me | H | NBZO | NBZ |
| 277 | CH₂ | Me | Me | H | CBO | CB |
| 278 | CH₂ | Me | Me | H | MBO | MB |
| 279 | CH₂ | Me | Me | H | EBO | EB |
| 280 | CH₂ | H | Me | H | AO7 | A7 |
| 281 | CH₂ | H | Me | H | AO8 | A8 |
| 282 | CH₂ | H | Me | H | AO9 | A9 |
| 283 | CH₂ | H | Me | H | AO10 | A10 |
| 284 | CH₂ | H | Me | H | AO12 | A12 |
| 285 | CH₂ | H | Me | H | AO14 | A14 |
| 286 | CH₂ | H | Me | H | AO15 | A15 |
| 287 | CH₂ | H | Me | H | AO16 | A16 |
| 288 | CH₂ | H | Me | H | AO17 | A17 |
| 289 | CH₂ | H | Me | H | AO18 | A18 |
| 290 | CH₂ | H | Me | H | OLEO | OLE |
| 291 | CH₂ | H | Me | H | LEO | LE |
| 292 | CH₂ | H | Me | H | LENO | LEN |
| 293 | CH₂ | H | Me | H | CESO | CES |
| 294 | CH₂ | H | Me | H | CDSO | CDS |
| 295 | CH₂ | H | Me | H | DPPO | DPP |
| 296 | CH₂ | H | Me | H | TMPPO | TMPP |
| 297 | CH₂ | H | Me | H | NPPO | NPP |
| 298 | CH₂ | H | Me | H | MPPO | MPP |
| 299 | CH₂ | H | Me | H | CPO | CP |
| 300 | CH₂ | H | Me | H | NDO | ND |
| 301 | CH₂ | H | Me | H | TCNO | TCN |
| 302 | CH₂ | H | Me | H | MPO | MP |
| 303 | CH₂ | H | Me | H | CPAO | CPA |
| 304 | CH₂ | H | Me | H | BZO | BZ |
| 305 | CH₂ | H | Me | H | NBZO | NBZ |
| 306 | CH₂ | H | Me | H | CBO | CB |
| 307 | CH₂ | H | Me | H | MBO | MB |
| 308 | CH₂ | H | Me | H | EBO | EB |
| 309 | CH₂ | Me | Me | A7 | OH | A7 |
| 310 | CH₂ | Me | Me | A8 | OH | A8 |
| 311 | CH₂ | Me | Me | A9 | OH | A9 |
| 312 | CH₂ | Me | Me | A10 | OH | A10 |
| 313 | CH₂ | Me | Me | A12 | OH | A12 |
| 314 | CH₂ | Me | Me | A14 | OH | A14 |
| 315 | CH₂ | Me | Me | A15 | OH | A15 |
| 316 | CH₂ | Me | Me | A16 | OH | A16 |
| 317 | CH₂ | Me | Me | A17 | OH | A17 |
| 318 | CH₂ | Me | Me | A18 | OH | A18 |
| 319 | CH₂ | Me | Me | OLE | OH | OLE |
| 320 | CH₂ | Me | Me | LE | OH | LE |
| 321 | CH₂ | Me | Me | LEN | OH | LEN |
| 322 | CH₂ | Me | Me | CES | OH | CES |
| 323 | CH₂ | Me | Me | CDS | OH | CDS |
| 324 | CH₂ | Me | Me | DPP | OH | DPP |
| 325 | CH₂ | Me | Me | TMPP | OH | TMPP |
| 326 | CH₂ | Me | Me | NPP | OH | NPP |
| 327 | CH₂ | Me | Me | MPP | OH | MPP |
| 328 | CH₂ | Me | Me | CP | OH | CP |
| 329 | CH₂ | Me | Me | ND | OH | ND |
| 330 | CH₂ | Me | Me | TCN | OH | TCN |
| 331 | CH₂ | Me | Me | MP | OH | MP |
| 332 | CH₂ | Me | Me | CPA | OH | CPA |
| 333 | CH₂ | Me | Me | BZ | OH | BZ |
| 334 | CH₂ | Me | Me | NBZ | OH | NBZ |
| 335 | CH₂ | Me | Me | CB | OH | CB |
| 336 | CH₂ | Me | Me | MB | OH | MB |
| 337 | CH₂ | Me | Me | EB | OH | EB |
| 338 | CH₂ | H | Me | A7 | OH | A7 |
| 339 | CH₂ | H | Me | A8 | OH | A8 |
| 340 | CH₂ | H | Me | A9 | OH | A9 |
| 341 | CH₂ | H | Me | A10 | OH | A10 |
| 342 | CH₂ | H | Me | A12 | OH | A12 |
| 343 | CH₂ | H | Me | A14 | OH | A14 |
| 344 | CH₂ | H | Me | A15 | OH | A15 |
| 345 | CH₂ | H | Me | A16 | OH | A16 |
| 346 | CH₂ | H | Me | A17 | OH | A17 |
| 347 | CH₂ | H | Me | A18 | OH | A18 |
| 348 | CH₂ | H | Me | OLE | OH | OLE |
| 349 | CH₂ | H | Me | LE | OH | LE |
| 350 | CH₂ | H | Me | LEN | OH | LEN |
| 351 | CH₂ | H | Me | CES | OH | CES |
| 352 | CH₂ | H | Me | CDS | OH | CDS |
| 353 | CH₂ | H | Me | DPP | OH | DPP |
| 354 | CH₂ | H | Me | TMPP | OH | TMPP |
| 355 | CH₂ | H | Me | NPP | OH | NPP |
| 356 | CH₂ | H | Me | MPP | OH | MPP |
| 357 | CH₂ | H | Me | CP | OH | CP |
| 358 | CH₂ | H | Me | ND | OH | ND |
| 359 | CH₂ | H | Me | TCN | OH | TCN |
| 360 | CH₂ | H | Me | MP | OH | MP |

TABLE 1-continued

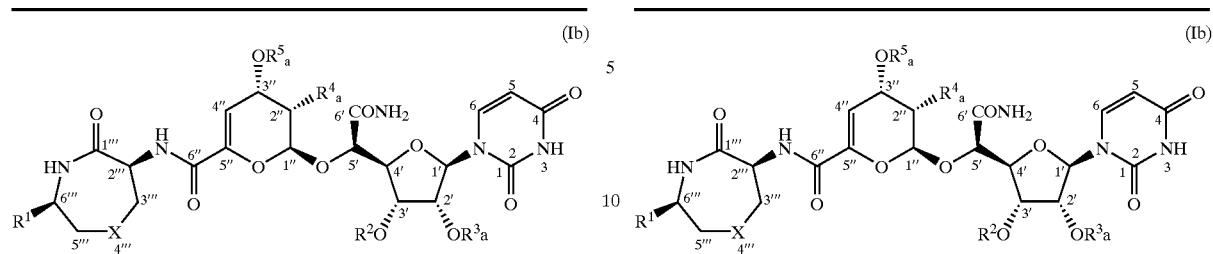

(Ib)

| Exemp. comp. No. | X | R¹ | R² | R³$_a$ | R⁴$_a$ | R⁵$_a$ |
|---|---|---|---|---|---|---|
| 361 | CH₂ | H | Me | CPA | OH | CPA |
| 362 | CH₂ | H | Me | BZ | OH | BZ |
| 363 | CH₂ | H | Me | NBZ | OH | NBZ |
| 364 | CH₂ | H | Me | CB | OH | CB |
| 365 | CH₂ | H | Me | MB | OH | MB |
| 366 | CH₂ | H | Me | EB | OH | EB |
| 367 | CH₂ | Me | Me | A7 | H | A7 |
| 368 | CH₂ | Me | Me | A8 | H | A8 |
| 369 | CH₂ | Me | Me | A9 | H | A9 |
| 370 | CH₂ | Me | Me | A10 | H | A10 |
| 371 | CH₂ | Me | Me | A12 | H | A12 |
| 372 | CH₂ | Me | Me | A14 | H | A14 |
| 373 | CH₂ | Me | Me | A15 | H | A15 |
| 374 | CH₂ | Me | Me | A16 | H | A16 |
| 375 | CH₂ | Me | Me | A17 | H | A17 |
| 376 | CH₂ | Me | Me | A18 | H | A18 |
| 377 | CH₂ | Me | Me | OLE | H | OLE |
| 378 | CH₂ | Me | Me | LE | H | LE |
| 379 | CH₂ | Me | Me | LEN | H | LEN |
| 380 | CH₂ | Me | Me | CES | H | CES |
| 381 | CH₂ | Me | Me | CDS | H | CDS |
| 382 | CH₂ | Me | Me | DPP | H | DPP |
| 383 | CH₂ | Me | Me | TMPP | H | TMPP |
| 384 | CH₂ | Me | Me | NPP | H | NPP |
| 385 | CH₂ | Me | Me | MPP | H | MPP |
| 386 | CH₂ | Me | Me | CP | H | CP |
| 387 | CH₂ | Me | Me | ND | H | ND |
| 388 | CH₂ | Me | Me | TCN | H | TCN |
| 389 | CH₂ | Me | Me | MP | H | MP |
| 390 | CH₂ | Me | Me | CPA | H | CPA |
| 391 | CH₂ | Me | Me | BZ | H | BZ |
| 392 | CH₂ | Me | Me | NBZ | H | NBZ |
| 393 | CH₂ | Me | Me | CB | H | CB |
| 394 | CH₂ | Me | Me | MB | H | MB |
| 395 | CH₂ | Me | Me | EB | H | EB |
| 396 | S | Me | Me | H | OH | H |
| 397 | S | Me | Me | A7 | OH | H |
| 398 | S | Me | Me | A8 | OH | H |
| 399 | S | Me | Me | A9 | OH | H |
| 400 | S | Me | Me | A10 | OH | H |
| 401 | S | Me | Me | A12 | OH | H |
| 402 | S | Me | Me | A14 | OH | H |
| 403 | S | Me | Me | A15 | OH | H |
| 404 | S | Me | Me | A16 | OH | H |
| 405 | S | Me | Me | A17 | OH | H |
| 406 | S | Me | Me | A18 | OH | H |
| 407 | S | Me | Me | A20 | OH | H |
| 408 | S | Me | Me | A22 | OH | H |
| 409 | S | Me | Me | OLE | OH | H |
| 410 | S | Me | Me | LE | OH | H |
| 411 | S | Me | Me | LEN | OH | H |
| 412 | S | Me | Me | CES | OH | H |
| 413 | S | Me | Me | CDS | OH | H |
| 414 | S | Me | Me | DPP | OH | H |
| 415 | S | Me | Me | TMPP | OH | H |
| 416 | S | Me | Me | NPP | OH | H |
| 417 | S | Me | Me | MPP | OH | H |
| 418 | S | Me | Me | CP | OH | H |
| 419 | S | Me | Me | ND | OH | H |
| 420 | S | Me | Me | TCN | OH | H |
| 421 | S | Me | Me | MP | OH | H |
| 422 | S | Me | Me | CPA | OH | H |
| 423 | S | Me | Me | BZ | OH | H |
| 424 | S | Me | Me | NBZ | OH | H |
| 425 | S | Me | Me | CB | OH | H |
| 426 | S | Me | Me | MB | OH | H |
| 427 | S | Me | Me | EB | OH | H |
| 428 | S | Me | Me | MO | OH | H |
| 429 | S | Me | Me | MD | OH | H |
| 430 | S | Me | Me | MDD | OH | H |
| 431 | S | Me | Me | MTD | OH | H |
| 432 | S | Me | Me | MHD | OH | H |
| 433 | S | Me | Me | DMO | OH | H |
| 434 | S | Me | Me | DMD | OH | H |
| 435 | S | Me | Me | DMDD | OH | H |
| 436 | S | Me | Me | DMTD | OH | H |
| 437 | S | Me | Me | DMHD | OH | H |
| 438 | S | Me | Me | H | OH | A7 |
| 439 | S | Me | Me | H | OH | A8 |
| 440 | S | Me | Me | H | OH | A9 |
| 441 | S | Me | Me | H | OH | A10 |
| 442 | S | Me | Me | H | OH | A12 |
| 443 | S | Me | Me | H | OH | A14 |
| 444 | S | Me | Me | H | OH | A15 |
| 445 | S | Me | Me | H | OH | A16 |
| 446 | S | Me | Me | H | OH | A17 |
| 447 | S | Me | Me | H | OH | A18 |
| 448 | S | Me | Me | H | OH | A20 |
| 449 | S | Me | Me | H | OH | A22 |
| 450 | S | Me | Me | H | OH | OLE |
| 451 | S | Me | Me | H | OH | LE |
| 452 | S | Me | Me | H | OH | LEN |
| 453 | S | Me | Me | H | OH | CES |
| 454 | S | Me | Me | H | OH | CDS |
| 455 | S | Me | Me | H | OH | DPP |
| 456 | S | Me | Me | H | OH | TMPP |
| 457 | S | Me | Me | H | OH | NPP |
| 458 | S | Me | Me | H | OH | MPP |
| 459 | S | Me | Me | H | OH | CP |
| 460 | S | Me | Me | H | OH | ND |
| 461 | S | Me | Me | H | OH | TCN |
| 462 | S | Me | Me | H | OH | MP |
| 463 | S | Me | Me | H | OH | CPA |
| 464 | S | Me | Me | H | OH | BZ |
| 465 | S | Me | Me | H | OH | NBZ |
| 466 | S | Me | Me | H | OH | CB |
| 467 | S | Me | Me | H | OH | MB |
| 468 | S | Me | Me | H | OH | EB |
| 469 | S | Me | Me | H | OH | MO |
| 470 | S | Me | Me | H | OH | MD |
| 471 | S | Me | Me | H | OH | MDD |
| 472 | S | Me | Me | H | OH | MTD |
| 473 | S | Me | Me | H | OH | MHD |
| 474 | S | Me | Me | H | OH | DMO |
| 475 | S | Me | Me | H | OH | DMD |
| 476 | S | Me | Me | H | OH | DMDD |
| 477 | S | Me | Me | H | OH | DMTD |
| 478 | S | Me | Me | H | OH | DMHD |
| 479 | S | Me | Me | H | AO7 | A7 |
| 480 | S | Me | Me | H | AO8 | A8 |
| 481 | S | Me | Me | H | AO9 | A9 |
| 482 | S | Me | Me | H | AO10 | A10 |
| 483 | S | Me | Me | H | AO12 | A12 |
| 484 | S | Me | Me | H | AO14 | A14 |

TABLE 1-continued

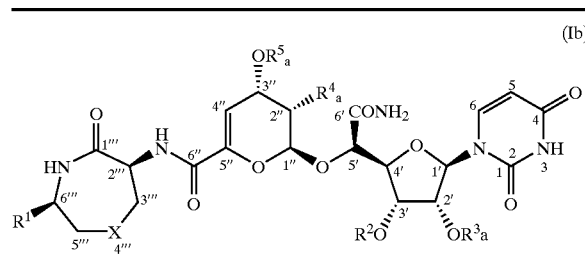

(Ib)

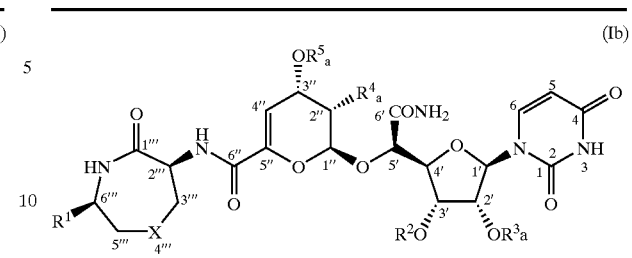

(Ib)

| Exemp. comp. No. | X | R¹ | R² | R³$_a$ | R⁴$_a$ | R⁵$_a$ |
|---|---|---|---|---|---|---|
| 485 | S | Me | Me | H | AO15 | A15 |
| 486 | S | Me | Me | H | AO16 | A16 |
| 487 | S | Me | Me | H | AO17 | A17 |
| 488 | S | Me | Me | H | AO18 | A18 |
| 489 | S | Me | Me | H | OLEO | OLE |
| 490 | S | Me | Me | H | LEO | LE |
| 491 | S | Me | Me | H | LENO | LEN |
| 492 | S | Me | Me | H | CESO | CES |
| 493 | S | Me | Me | H | CDSO | CDS |
| 494 | S | Me | Me | H | DPPO | DPP |
| 495 | S | Me | Me | H | TMPPO | TMPP |
| 496 | S | Me | Me | H | NPPO | NPP |
| 497 | S | Me | Me | H | MPPO | MPP |
| 498 | S | Me | Me | H | CPO | CP |
| 499 | S | Me | Me | H | NDO | ND |
| 500 | S | Me | Me | H | TCNO | TCN |
| 501 | S | Me | Me | H | MPO | MP |
| 502 | S | Me | Me | H | CPAO | CPA |
| 503 | S | Me | Me | H | BZO | BZ |
| 504 | S | Me | Me | H | NBZO | NBZ |
| 505 | S | Me | Me | H | CBO | CB |
| 506 | S | Me | Me | H | MBO | MB |
| 507 | S | Me | Me | H | EBO | EB |
| 508 | S | Me | Me | A7 | OH | A7 |
| 509 | S | Me | Me | A8 | OH | A8 |
| 510 | S | Me | Me | A9 | OH | A9 |
| 511 | S | Me | Me | A10 | OH | A10 |
| 512 | S | Me | Me | A12 | OH | A12 |
| 513 | S | Me | Me | A14 | OH | A14 |
| 514 | S | Me | Me | A15 | OH | A15 |
| 515 | S | Me | Me | A16 | OH | A16 |
| 516 | S | Me | Me | A17 | OH | A17 |
| 517 | S | Me | Me | A18 | OH | A18 |
| 518 | S | Me | Me | OLE | OH | OLE |
| 519 | S | Me | Me | LE | OH | LE |
| 520 | S | Me | Me | LEN | OH | LEN |
| 521 | S | Me | Me | CES | OH | CES |
| 522 | S | Me | Me | CDS | OH | CDS |
| 523 | S | Me | Me | DPP | OH | DPP |
| 524 | S | Me | Me | TMPP | OH | TMPP |
| 525 | S | Me | Me | NPP | OH | NPP |
| 526 | S | Me | Me | MPP | OH | MPP |
| 527 | S | Me | Me | CP | OH | CP |
| 528 | S | Me | Me | ND | OH | ND |
| 529 | S | Me | Me | TCN | OH | TCN |
| 530 | S | Me | Me | MP | OH | MP |
| 531 | S | Me | Me | CPA | OH | CPA |
| 532 | S | Me | Me | BZ | OH | BZ |
| 533 | S | Me | Me | NBZ | OH | NBZ |
| 534 | S | Me | Me | CB | OH | CB |
| 535 | S | Me | Me | MB | OH | MB |
| 536 | S | Me | Me | EB | OH | EB |
| 537 | CH$_2$ | Me | Me | C6OC | OH | H |
| 538 | CH$_2$ | Me | Me | C7OC | OH | H |
| 539 | CH$_2$ | Me | Me | C8OC | OH | H |
| 540 | CH$_2$ | Me | Me | C9OC | OH | H |
| 541 | CH$_2$ | Me | Me | C10OC | OH | H |
| 542 | CH$_2$ | Me | Me | C11OC | OH | H |
| 543 | CH$_2$ | Me | Me | C12OC | OH | H |
| 544 | CH$_2$ | Me | Me | MMA10 | OH | H |
| 545 | CH$_2$ | Me | Me | MMA12 | OH | H |
| 546 | CH$_2$ | Me | Me | MMA14 | OH | H |
| 547 | CH$_2$ | Me | Me | DMA10 | OH | H |
| 548 | CH$_2$ | Me | Me | DMA12 | OH | H |
| 549 | CH$_2$ | Me | Me | DMA14 | OH | H |
| 550 | CH$_2$ | Me | Me | H | OH | C6OC |
| 551 | CH$_2$ | Me | Me | H | OH | C7OC |
| 552 | CH$_2$ | Me | Me | H | OH | C8OC |
| 553 | CH$_2$ | Me | Me | H | OH | C9OC |
| 554 | CH$_2$ | Me | Me | H | OH | C10OC |
| 555 | CH$_2$ | Me | Me | H | OH | C11OC |
| 556 | CH$_2$ | Me | Me | H | OH | C12OC |
| 557 | CH$_2$ | Me | Me | H | OH | MMA10 |
| 558 | CH$_2$ | Me | Me | H | OH | MMA12 |
| 559 | CH$_2$ | Me | Me | H | OH | MMA14 |
| 560 | CH$_2$ | Me | Me | H | OH | DMA10 |
| 561 | CH$_2$ | Me | Me | H | OH | DMA12 |
| 562 | CH$_2$ | Me | Me | H | OH | DMA14 |
| 563 | CH$_2$ | H | Me | C6OC | OH | H |
| 564 | CH$_2$ | H | Me | C7OC | OH | H |
| 565 | CH$_2$ | H | Me | C8OC | OH | H |
| 566 | CH$_2$ | H | Me | C9OC | OH | H |
| 567 | CH$_2$ | H | Me | C10OC | OH | H |
| 568 | CH$_2$ | H | Me | C11OC | OH | H |
| 569 | CH$_2$ | H | Me | C12OC | OH | H |
| 570 | CH$_2$ | H | Me | MMA10 | OH | H |
| 571 | CH$_2$ | H | Me | MMA12 | OH | H |
| 572 | CH$_2$ | H | Me | MMA14 | OH | H |
| 573 | CH$_2$ | H | Me | DMA10 | OH | H |
| 574 | CH$_2$ | H | Me | DMA12 | OH | H |
| 575 | CH$_2$ | H | Me | DMA14 | OH | H |
| 576 | CH$_2$ | H | Me | H | OH | C6OC |
| 577 | CH$_2$ | H | Me | H | OH | C7OC |
| 578 | CH$_2$ | H | Me | H | OH | C8OC |
| 579 | CH$_2$ | H | Me | H | OH | C9OC |
| 580 | CH$_2$ | H | Me | H | OH | C10OC |
| 581 | CH$_2$ | H | Me | H | OH | C11OC |
| 582 | CH$_2$ | H | Me | H | OH | C12OC |
| 583 | CH$_2$ | H | Me | H | OH | MMA10 |
| 584 | CH$_2$ | H | Me | H | OH | MMA12 |
| 585 | CH$_2$ | H | Me | H | OH | MMA14 |
| 586 | CH$_2$ | H | Me | H | OH | DMA10 |
| 587 | CH$_2$ | H | Me | H | OH | DMA12 |
| 588 | CH$_2$ | H | Me | H | OH | DMA14 |
| 589 | CH$_2$ | Me | Me | C5 | OH | H |
| 590 | CH$_2$ | Me | Me | C6 | OH | H |
| 591 | CH$_2$ | Me | Me | C7 | OH | H |
| 592 | CH$_2$ | Me | Me | C8 | OH | H |
| 593 | CH$_2$ | Me | Me | C9 | OH | H |
| 594 | CH$_2$ | Me | Me | C10 | OH | H |
| 595 | CH$_2$ | Me | Me | C11 | OH | H |
| 596 | CH$_2$ | Me | Me | C12 | OH | H |
| 597 | CH$_2$ | Me | Me | C13 | OH | H |
| 598 | CH$_2$ | Me | Me | C14 | OH | H |
| 599 | CH$_2$ | Me | Me | C15 | OH | H |
| 600 | CH$_2$ | Me | Me | C16 | OH | H |
| 601 | CH$_2$ | Me | Me | C6 | OH | A7 |
| 602 | CH$_2$ | Me | Me | C6 | OH | A8 |
| 603 | CH$_2$ | Me | Me | C6 | OH | A9 |
| 604 | CH$_2$ | Me | Me | C6 | OH | A10 |
| 605 | CH$_2$ | Me | Me | C6 | OH | A12 |
| 606 | CH$_2$ | Me | Me | C6 | OH | A14 |
| 607 | CH$_2$ | Me | Me | C6 | OH | A15 |
| 608 | CH$_2$ | Me | Me | C6 | OH | A16 |

TABLE 1-continued

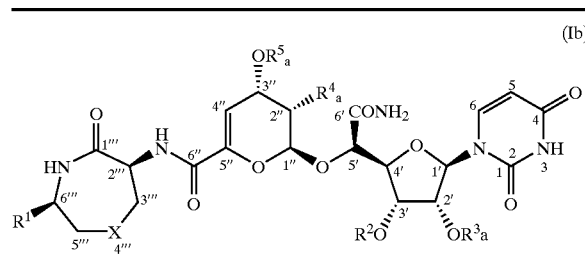

(Ib)

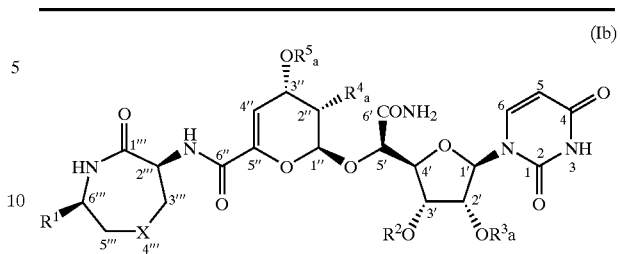

(Ib)

| Exemp. comp. No. | X | $R^1$ | $R^2$ | $R^3_a$ | $R^4_a$ | $R^5_a$ | Exemp. comp. No. | X | $R^1$ | $R^2$ | $R^3_a$ | $R^4_a$ | $R^5_a$ |
|---|---|---|---|---|---|---|---|---|---|---|---|---|---|
| 609 | $CH_2$ | Me | Me | C6 | OH | A17 | 671 | $CH_2$ | Me | Me | C10 | OH | C11OC |
| 610 | $CH_2$ | Me | Me | C6 | OH | A18 | 672 | $CH_2$ | Me | Me | C10 | OH | C12OC |
| 611 | $CH_2$ | Me | Me | C6 | OH | OLE | 673 | $CH_2$ | Me | Me | C10 | OH | MMA10 |
| 612 | $CH_2$ | Me | Me | C6 | OH | LE | 674 | $CH_2$ | Me | Me | C10 | OH | MMA12 |
| 613 | $CH_2$ | Me | Me | C6 | OH | LEN | 675 | $CH_2$ | Me | Me | C10 | OH | MMA14 |
| 614 | $CH_2$ | Me | Me | C6 | OH | C6OC | 676 | $CH_2$ | Me | Me | C10 | OH | DMA10 |
| 615 | $CH_2$ | Me | Me | C6 | OH | C7OC | 677 | $CH_2$ | Me | Me | C10 | OH | DMA12 |
| 616 | $CH_2$ | Me | Me | C6 | OH | C8OC | 678 | $CH_2$ | Me | Me | C10 | OH | DMA14 |
| 617 | $CH_2$ | Me | Me | C6 | OH | C9OC | 679 | $CH_2$ | Me | Me | C12 | OH | A7 |
| 618 | $CH_2$ | Me | Me | C6 | OH | C10OC | 680 | $CH_2$ | Me | Me | C12 | OH | A8 |
| 619 | $CH_2$ | Me | Me | C6 | OH | C11OC | 681 | $CH_2$ | Me | Me | C12 | OH | A9 |
| 620 | $CH_2$ | Me | Me | C6 | OH | C12OC | 682 | $CH_2$ | Me | Me | C12 | OH | A10 |
| 621 | $CH_2$ | Me | Me | C6 | OH | MMA10 | 683 | $CH_2$ | Me | Me | C12 | OH | A12 |
| 622 | $CH_2$ | Me | Me | C6 | OH | MMA12 | 684 | $CH_2$ | Me | Me | C12 | OH | A14 |
| 623 | $CH_2$ | Me | Me | C6 | OH | MMA14 | 685 | $CH_2$ | Me | Me | C12 | OH | A15 |
| 624 | $CH_2$ | Me | Me | C6 | OH | DMA10 | 686 | $CH_2$ | Me | Me | C12 | OH | A16 |
| 625 | $CH_2$ | Me | Me | C6 | OH | DMA12 | 687 | $CH_2$ | Me | Me | C12 | OH | A17 |
| 626 | $CH_2$ | Me | Me | C6 | OH | DMA14 | 688 | $CH_2$ | Me | Me | C12 | OH | A18 |
| 627 | $CH_2$ | Me | Me | C8 | OH | A7 | 689 | $CH_2$ | Me | Me | C12 | OH | OLE |
| 628 | $CH_2$ | Me | Me | C8 | OH | A8 | 690 | $CH_2$ | Me | Me | C12 | OH | LE |
| 629 | $CH_2$ | Me | Me | C8 | OH | A9 | 691 | $CH_2$ | Me | Me | C12 | OH | LEN |
| 630 | $CH_2$ | Me | Me | C8 | OH | A10 | 692 | $CH_2$ | Me | Me | C12 | OH | C6OC |
| 631 | $CH_2$ | Me | Me | C8 | OH | A12 | 693 | $CH_2$ | Me | Me | C12 | OH | C7OC |
| 632 | $CH_2$ | Me | Me | C8 | OH | A14 | 694 | $CH_2$ | Me | Me | C12 | OH | C8OC |
| 633 | $CH_2$ | Me | Me | C8 | OH | A15 | 695 | $CH_2$ | Me | Me | C12 | OH | C9OC |
| 634 | $CH_2$ | Me | Me | C8 | OH | A16 | 696 | $CH_2$ | Me | Me | C12 | OH | C10OC |
| 635 | $CH_2$ | Me | Me | C8 | OH | A17 | 697 | $CH_2$ | Me | Me | C12 | OH | C11OC |
| 636 | $CH_2$ | Me | Me | C8 | OH | A18 | 698 | $CH_2$ | Me | Me | C12 | OH | C12OC |
| 637 | $CH_2$ | Me | Me | C8 | OH | OLE | 699 | $CH_2$ | Me | Me | C12 | OH | MMA10 |
| 638 | $CH_2$ | Me | Me | C8 | OH | LE | 700 | $CH_2$ | Me | Me | C12 | OH | MMA12 |
| 639 | $CH_2$ | Me | Me | C8 | OH | LEN | 701 | $CH_2$ | Me | Me | C12 | OH | MMA14 |
| 640 | $CH_2$ | Me | Me | C8 | OH | C6OC | 702 | $CH_2$ | Me | Me | C12 | OH | DMA10 |
| 641 | $CH_2$ | Me | Me | C8 | OH | C7OC | 703 | $CH_2$ | Me | Me | C12 | OH | DMA12 |
| 642 | $CH_2$ | Me | Me | C8 | OH | C8OC | 704 | $CH_2$ | Me | Me | C12 | OH | DMA14 |
| 643 | $CH_2$ | Me | Me | C8 | OH | C9OC | 705 | $CH_2$ | H | Me | C5 | OH | H |
| 644 | $CH_2$ | Me | Me | C8 | OH | C10OC | 706 | $CH_2$ | H | Me | C6 | OH | H |
| 645 | $CH_2$ | Me | Me | C8 | OH | C11OC | 707 | $CH_2$ | H | Me | C7 | OH | H |
| 646 | $CH_2$ | Me | Me | C8 | OH | C12OC | 708 | $CH_2$ | H | Me | C8 | OH | H |
| 647 | $CH_2$ | Me | Me | C8 | OH | MMA10 | 709 | $CH_2$ | H | Me | C9 | OH | H |
| 648 | $CH_2$ | Me | Me | C8 | OH | MMA12 | 710 | $CH_2$ | H | Me | C10 | OH | H |
| 649 | $CH_2$ | Me | Me | C8 | OH | MMA14 | 711 | $CH_2$ | H | Me | C11 | OH | H |
| 650 | $CH_2$ | Me | Me | C8 | OH | DMA10 | 712 | $CH_2$ | H | Me | C12 | OH | H |
| 651 | $CH_2$ | Me | Me | C8 | OH | DMA12 | 713 | $CH_2$ | H | Me | C13 | OH | H |
| 652 | $CH_2$ | Me | Me | C8 | OH | DMA14 | 714 | $CH_2$ | H | Me | C14 | OH | H |
| 653 | $CH_2$ | Me | Me | C10 | OH | A7 | 715 | $CH_2$ | H | Me | C15 | OH | H |
| 654 | $CH_2$ | Me | Me | C10 | OH | A8 | 716 | $CH_2$ | H | Me | C16 | OH | H |
| 655 | $CH_2$ | Me | Me | C10 | OH | A9 | 717 | $CH_2$ | H | Me | C6 | OH | A7 |
| 656 | $CH_2$ | Me | Me | C10 | OH | A10 | 718 | $CH_2$ | H | Me | C6 | OH | A8 |
| 657 | $CH_2$ | Me | Me | C10 | OH | A12 | 719 | $CH_2$ | H | Me | C6 | OH | A9 |
| 658 | $CH_2$ | Me | Me | C10 | OH | A14 | 720 | $CH_2$ | H | Me | C6 | OH | A10 |
| 659 | $CH_2$ | Me | Me | C10 | OH | A15 | 721 | $CH_2$ | H | Me | C6 | OH | A12 |
| 660 | $CH_2$ | Me | Me | C10 | OH | A16 | 722 | $CH_2$ | H | Me | C6 | OH | A14 |
| 661 | $CH_2$ | Me | Me | C10 | OH | A17 | 723 | $CH_2$ | H | Me | C6 | OH | A15 |
| 662 | $CH_2$ | Me | Me | C10 | OH | A18 | 724 | $CH_2$ | H | Me | C6 | OH | A16 |
| 663 | $CH_2$ | Me | Me | C10 | OH | OLE | 725 | $CH_2$ | H | Me | C6 | OH | A17 |
| 664 | $CH_2$ | Me | Me | C10 | OH | LE | 726 | $CH_2$ | H | Me | C6 | OH | A18 |
| 665 | $CH_2$ | Me | Me | C10 | OH | LEN | 727 | $CH_2$ | H | Me | C6 | OH | OLE |
| 666 | $CH_2$ | Me | Me | C10 | OH | C6OC | 728 | $CH_2$ | H | Me | C6 | OH | LE |
| 667 | $CH_2$ | Me | Me | C10 | OH | C7OC | 729 | $CH_2$ | H | Me | C6 | OH | LEN |
| 668 | $CH_2$ | Me | Me | C10 | OH | C8OC | 730 | $CH_2$ | H | Me | C6 | OH | C6OC |
| 669 | $CH_2$ | Me | Me | C10 | OH | C9OC | 731 | $CH_2$ | H | Me | C6 | OH | C7OC |
| 670 | $CH_2$ | Me | Me | C10 | OH | C10OC | 732 | $CH_2$ | H | Me | C6 | OH | C8OC |

TABLE 1-continued

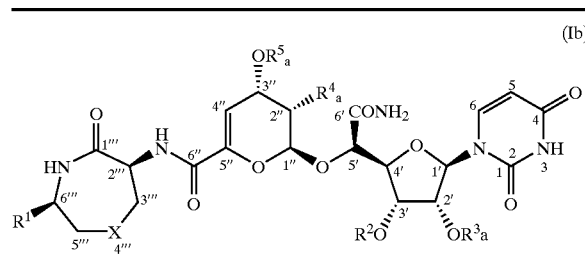

(Ib)

| Exemp. comp. No. | X | $R^1$ | $R^2$ | $R^3_a$ | $R^4_a$ | $R^5_a$ |
|---|---|---|---|---|---|---|
| 733 | $CH_2$ | H | Me | C6 | OH | C9OC |
| 734 | $CH_2$ | H | Me | C6 | OH | C10OC |
| 735 | $CH_2$ | H | Me | C6 | OH | C11OC |
| 736 | $CH_2$ | H | Me | C6 | OH | C12OC |
| 737 | $CH_2$ | H | Me | C6 | OH | MMA10 |
| 738 | $CH_2$ | H | Me | C6 | OH | MMA12 |
| 739 | $CH_2$ | H | Me | C6 | OH | MMA14 |
| 740 | $CH_2$ | H | Me | C6 | OH | DMA10 |
| 741 | $CH_2$ | H | Me | C6 | OH | DMA12 |
| 742 | $CH_2$ | H | Me | C6 | OH | DMA14 |
| 743 | $CH_2$ | H | Me | C8 | OH | A7 |
| 744 | $CH_2$ | H | Me | C8 | OH | A8 |
| 745 | $CH_2$ | H | Me | C8 | OH | A9 |
| 746 | $CH_2$ | H | Me | C8 | OH | A10 |
| 747 | $CH_2$ | H | Me | C8 | OH | A12 |
| 748 | $CH_2$ | H | Me | C8 | OH | A14 |
| 749 | $CH_2$ | H | Me | C8 | OH | A15 |
| 750 | $CH_2$ | H | Me | C8 | OH | A16 |
| 751 | $CH_2$ | H | Me | C8 | OH | A17 |
| 752 | $CH_2$ | H | Me | C8 | OH | A18 |
| 753 | $CH_2$ | H | Me | C8 | OH | OLE |
| 754 | $CH_2$ | H | Me | C8 | OH | LE |
| 755 | $CH_2$ | H | Me | C8 | OH | LEN |
| 756 | $CH_2$ | H | Me | C8 | OH | C6OC |
| 757 | $CH_2$ | H | Me | C8 | OH | C7OC |
| 758 | $CH_2$ | H | Me | C8 | OH | C8OC |
| 759 | $CH_2$ | H | Me | C8 | OH | C9OC |
| 760 | $CH_2$ | H | Me | C8 | OH | C10OC |
| 761 | $CH_2$ | H | Me | C8 | OH | C11OC |
| 762 | $CH_2$ | H | Me | C8 | OH | C12OC |
| 763 | $CH_2$ | H | Me | C8 | OH | MMA10 |
| 764 | $CH_2$ | H | Me | C8 | OH | MMA12 |
| 765 | $CH_2$ | H | Me | C8 | OH | MMA14 |
| 766 | $CH_2$ | H | Me | C8 | OH | DMA10 |
| 767 | $CH_2$ | H | Me | C8 | OH | DMA12 |
| 768 | $CH_2$ | H | Me | C8 | OH | DMA14 |
| 769 | $CH_2$ | H | Me | C10 | OH | A7 |
| 770 | $CH_2$ | H | Me | C10 | OH | A8 |
| 771 | $CH_2$ | H | Me | C10 | OH | A9 |
| 772 | $CH_2$ | H | Me | C10 | OH | A10 |
| 773 | $CH_2$ | H | Me | C10 | OH | A12 |
| 774 | $CH_2$ | H | Me | C10 | OH | A14 |
| 775 | $CH_2$ | H | Me | C10 | OH | A15 |
| 776 | $CH_2$ | H | Me | C10 | OH | A16 |
| 777 | $CH_2$ | H | Me | C10 | OH | A17 |
| 778 | $CH_2$ | H | Me | C10 | OH | A18 |
| 779 | $CH_2$ | H | Me | C10 | OH | OLE |
| 780 | $CH_2$ | H | Me | C10 | OH | LE |
| 781 | $CH_2$ | H | Me | C10 | OH | LEN |
| 782 | $CH_2$ | H | Me | C10 | OH | C6OC |
| 783 | $CH_2$ | H | Me | C10 | OH | C7OC |
| 784 | $CH_2$ | H | Me | C10 | OH | C8OC |
| 785 | $CH_2$ | H | Me | C10 | OH | C9OC |
| 786 | $CH_2$ | H | Me | C10 | OH | C10OC |
| 787 | $CH_2$ | H | Me | C10 | OH | C11OC |
| 788 | $CH_2$ | H | Me | C10 | OH | C12OC |
| 789 | $CH_2$ | H | Me | C10 | OH | MMA10 |
| 790 | $CH_2$ | H | Me | C10 | OH | MMA12 |
| 791 | $CH_2$ | H | Me | C10 | OH | MMA14 |
| 792 | $CH_2$ | H | Me | C10 | OH | DMA10 |
| 793 | $CH_2$ | H | Me | C10 | OH | DMA12 |
| 794 | $CH_2$ | H | Me | C10 | OH | DMA14 |

TABLE 1-continued

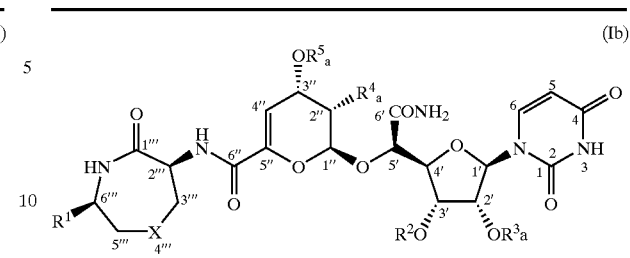

(Ib)

| Exemp. comp. No. | X | $R^1$ | $R^2$ | $R^3_a$ | $R^4_a$ | $R^5_a$ |
|---|---|---|---|---|---|---|
| 795 | $CH_2$ | H | Me | C12 | OH | A7 |
| 796 | $CH_2$ | H | Me | C12 | OH | A8 |
| 797 | $CH_2$ | H | Me | C12 | OH | A9 |
| 798 | $CH_2$ | H | Me | C12 | OH | A10 |
| 799 | $CH_2$ | H | Me | C12 | OH | A12 |
| 800 | $CH_2$ | H | Me | C12 | OH | A14 |
| 801 | $CH_2$ | H | Me | C12 | OH | A15 |
| 802 | $CH_2$ | H | Me | C12 | OH | A16 |
| 803 | $CH_2$ | H | Me | C12 | OH | A17 |
| 804 | $CH_2$ | H | Me | C12 | OH | A18 |
| 805 | $CH_2$ | H | Me | C12 | OH | OLE |
| 806 | $CH_2$ | H | Me | C12 | OH | LE |
| 807 | $CH_2$ | H | Me | C12 | OH | LEN |
| 808 | $CH_2$ | H | Me | C12 | OH | C6OC |
| 809 | $CH_2$ | H | Me | C12 | OH | C7OC |
| 810 | $CH_2$ | H | Me | C12 | OH | C8OC |
| 811 | $CH_2$ | H | Me | C12 | OH | C9OC |
| 812 | $CH_2$ | H | Me | C12 | OH | C10OC |
| 813 | $CH_2$ | H | Me | C12 | OH | C11OC |
| 814 | $CH_2$ | H | Me | C12 | OH | C12OC |
| 815 | $CH_2$ | H | Me | C12 | OH | MMA10 |
| 816 | $CH_2$ | H | Me | C12 | OH | MMA12 |
| 817 | $CH_2$ | H | Me | C12 | OH | MMA14 |
| 818 | $CH_2$ | H | Me | C12 | OH | DMA10 |
| 819 | $CH_2$ | H | Me | C12 | OH | DMA12 |
| 820 | $CH_2$ | H | Me | C12 | OH | DMA14 |

TABLE 2

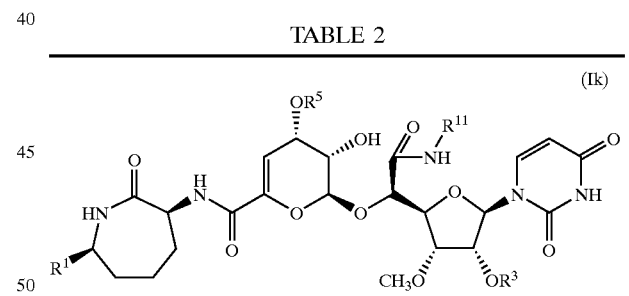

(Ik)

| Exemp. Comp. No. | R1 | R11 | R3 | R5 |
|---|---|---|---|---|
| 891 | Me | Me | H | H |
| 892 | Me | Me | A7 | H |
| 893 | Me | Me | A8 | H |
| 894 | Me | Me | A9 | H |
| 895 | Me | Me | A10 | H |
| 896 | Me | Me | A12 | H |
| 897 | Me | Me | A14 | H |
| 898 | Me | Me | A15 | H |
| 899 | Me | Me | A16 | H |
| 900 | Me | Me | A17 | H |
| 901 | Me | Me | A18 | H |
| 902 | Me | Me | C6OC | H |
| 903 | Me | Me | C7OC | H |
| 904 | Me | Me | C8OC | H |
| 905 | Me | Me | C9OC | H |

TABLE 2-continued (Ik)

| Exemp. Comp. No. | R1 | R11 | R3 | R5 |
|---|---|---|---|---|
| 906 | Me | Me | C10OC | H |
| 907 | Me | Me | C11OC | H |
| 908 | Me | Me | C12OC | H |
| 909 | Me | Me | MMA10 | H |
| 910 | Me | Me | DMA10 | H |
| 911 | Me | Me | C5 | H |
| 912 | Me | Me | C6 | H |
| 913 | Me | Me | C7 | H |
| 914 | Me | Me | C8 | H |
| 915 | Me | Me | C9 | H |
| 916 | Me | Me | C10 | H |
| 917 | Me | Me | C11 | H |
| 918 | Me | Me | C12 | H |
| 919 | Me | Me | C13 | H |
| 920 | Me | Me | C14 | H |
| 921 | Me | Me | H | A6 |
| 922 | Me | Me | H | A7 |
| 923 | Me | Me | H | A8 |
| 924 | Me | Me | H | A9 |
| 925 | Me | Me | H | A10 |
| 926 | Me | Me | H | A11 |
| 927 | Me | Me | H | A12 |
| 928 | Me | Me | H | A13 |
| 929 | Me | Me | H | A14 |
| 930 | Me | Me | H | A15 |
| 931 | Me | Me | H | A16 |
| 932 | Me | Me | H | A17 |
| 933 | Me | Me | H | A18 |
| 934 | Me | Me | H | C6OC |
| 935 | Me | Me | H | C7OC |
| 936 | Me | Me | H | C8OC |
| 937 | Me | Me | H | C9OC |
| 938 | Me | Me | H | C10OC |
| 939 | Me | Me | H | C11OC |
| 940 | Me | Me | H | C12OC |
| 941 | Me | C2 | H | H |
| 942 | Me | C2 | A7 | H |
| 943 | Me | C2 | A8 | H |
| 944 | Me | C2 | A9 | H |
| 945 | Me | C2 | A10 | H |
| 946 | Me | C2 | A12 | H |
| 947 | Me | C2 | A14 | H |
| 948 | Me | C2 | A15 | H |
| 949 | Me | C2 | A16 | H |
| 950 | Me | C2 | A17 | H |
| 951 | Me | C2 | A18 | H |
| 952 | Me | C2 | C6OC | H |
| 953 | Me | C2 | C7OC | H |
| 954 | Me | C2 | C8OC | H |
| 955 | Me | C2 | C9OC | H |
| 956 | Me | C2 | C10OC | H |
| 957 | Me | C2 | C11OC | H |
| 958 | Me | C2 | C12OC | H |
| 959 | Me | C2 | MMA10 | H |
| 960 | Me | C2 | DMA10 | H |
| 961 | Me | C2 | C5 | H |
| 962 | Me | C2 | C6 | H |
| 963 | Me | C2 | C7 | H |
| 964 | Me | C2 | C8 | H |
| 965 | Me | C2 | C9 | H |
| 966 | Me | C2 | C10 | H |
| 967 | Me | C2 | C11 | H |
| 968 | Me | C2 | C12 | H |
| 969 | Me | C2 | C13 | H |
| 970 | Me | C2 | C14 | H |
| 971 | Me | C2 | H | A6 |
| 972 | Me | C2 | H | A7 |
| 973 | Me | C2 | H | A8 |
| 974 | Me | C2 | H | A9 |
| 975 | Me | C2 | H | A10 |
| 976 | Me | C2 | H | A11 |
| 977 | Me | C2 | H | A12 |
| 978 | Me | C2 | H | A13 |
| 979 | Me | C2 | H | A14 |
| 980 | Me | C2 | H | A15 |
| 981 | Me | C2 | H | A16 |
| 982 | Me | C2 | H | A17 |
| 983 | Me | C2 | H | A18 |
| 984 | Me | C2 | H | C6OC |
| 985 | Me | C2 | H | C7OC |
| 986 | Me | C2 | H | C8OC |
| 987 | Me | C2 | H | C9OC |
| 988 | Me | C2 | H | C10OC |
| 989 | Me | C2 | H | C11OC |
| 990 | Me | C2 | H | C12OC |
| 991 | Me | C3 | H | H |
| 992 | Me | C3 | A7 | H |
| 993 | Me | C3 | A8 | H |
| 994 | Me | C3 | A9 | H |
| 995 | Me | C3 | A10 | H |
| 996 | Me | C3 | A12 | H |
| 997 | Me | C3 | A14 | H |
| 998 | Me | C3 | A15 | H |
| 999 | Me | C3 | A16 | H |
| 1000 | Me | C3 | A17 | H |
| 1001 | Me | C3 | A18 | H |
| 1002 | Me | C3 | C6OC | H |
| 1003 | Me | C3 | C7OC | H |
| 1004 | Me | C3 | C8OC | H |
| 1005 | Me | C3 | C9OC | H |
| 1006 | Me | C3 | C10OC | H |
| 1007 | Me | C3 | C11OC | H |
| 1008 | Me | C3 | C12OC | H |
| 1009 | Me | C3 | MMA10 | H |
| 1010 | Me | C3 | DMA10 | H |
| 1011 | Me | C3 | C5 | H |
| 1012 | Me | C3 | C6 | H |
| 1013 | Me | C3 | C7 | H |
| 1014 | Me | C3 | C8 | H |
| 1015 | Me | C3 | C9 | H |
| 1016 | Me | C3 | C10 | H |
| 1017 | Me | C3 | C11 | H |
| 1018 | Me | C3 | C12 | H |
| 1019 | Me | C3 | C13 | H |
| 1020 | Me | C3 | C14 | H |
| 1021 | Me | C3 | H | A6 |
| 1022 | Me | C3 | H | A7 |
| 1023 | Me | C3 | H | A8 |
| 1024 | Me | C3 | H | A9 |
| 1025 | Me | C3 | H | A10 |
| 1026 | Me | C3 | H | A11 |
| 1027 | Me | C3 | H | A12 |
| 1028 | Me | C3 | H | A13 |
| 1029 | Me | C3 | H | A14 |
| 1030 | Me | C3 | H | A15 |
| 1031 | Me | C3 | H | A16 |

TABLE 2-continued (Ik)

| Exemp. Comp. No. | R1 | R11 | R3 | R5 |
|---|---|---|---|---|
| 1032 | Me | C3 | H | A17 |
| 1033 | Me | C3 | H | A18 |
| 1034 | Me | C3 | H | C6OC |
| 1035 | Me | C3 | H | C7OC |
| 1036 | Me | C3 | H | C8OC |
| 1037 | Me | C3 | H | C9OC |
| 1038 | Me | C3 | H | C10OC |
| 1039 | Me | C3 | H | C11OC |
| 1040 | Me | C3 | H | C12OC |
| 1041 | Me | C6 | H | H |
| 1042 | Me | C6 | A7 | H |
| 1043 | Me | C6 | A8 | H |
| 1044 | Me | C6 | A9 | H |
| 1045 | Me | C6 | A10 | H |
| 1046 | Me | C6 | A12 | H |
| 1047 | Me | C6 | A14 | H |
| 1048 | Me | C6 | A15 | H |
| 1049 | Me | C6 | A16 | H |
| 1050 | Me | C6 | A17 | H |
| 1051 | Me | C6 | A18 | H |
| 1052 | Me | C6 | C6OC | H |
| 1053 | Me | C6 | C7OC | H |
| 1054 | Me | C6 | C8OC | H |
| 1055 | Me | C6 | C9OC | H |
| 1056 | Me | C6 | C10OC | H |
| 1057 | Me | C6 | C11OC | H |
| 1058 | Me | C6 | C12OC | H |
| 1059 | Me | C6 | MMA10 | H |
| 1060 | Me | C6 | DMA10 | H |
| 1061 | Me | C6 | C5 | H |
| 1062 | Me | C6 | C6 | H |
| 1063 | Me | C6 | C7 | H |
| 1064 | Me | C6 | C8 | H |
| 1065 | Me | C6 | C9 | H |
| 1066 | Me | C6 | C10 | H |
| 1067 | Me | C6 | C11 | H |
| 1068 | Me | C6 | C12 | H |
| 1069 | Me | C6 | C13 | H |
| 1070 | Me | C6 | C14 | H |
| 1071 | Me | C6 | H | A6 |
| 1072 | Me | C6 | H | A7 |
| 1073 | Me | C6 | H | A8 |
| 1074 | Me | C6 | H | A9 |
| 1075 | Me | C6 | H | A10 |
| 1076 | Me | C6 | H | A11 |
| 1077 | Me | C6 | H | A12 |
| 1078 | Me | C6 | H | A13 |
| 1079 | Me | C6 | H | A14 |
| 1080 | Me | C6 | H | A15 |
| 1081 | Me | C6 | H | A16 |
| 1082 | Me | C6 | H | A17 |
| 1083 | Me | C6 | H | A18 |
| 1084 | Me | C6 | H | C6OC |
| 1085 | Me | C6 | H | C7OC |
| 1086 | Me | C6 | H | C8OC |
| 1087 | Me | C6 | H | C9OC |
| 1088 | Me | C6 | H | C10OC |
| 1089 | Me | C6 | H | C11OC |
| 1090 | Me | C6 | H | C12OC |
| 1091 | Me | C12 | H | H |
| 1092 | Me | C12 | A7 | H |
| 1093 | Me | C12 | A8 | H |
| 1094 | Me | C12 | A9 | H |
| 1095 | Me | C12 | A10 | H |
| 1096 | Me | C12 | A12 | H |
| 1097 | Me | C12 | A14 | H |
| 1098 | Me | C12 | A15 | H |
| 1099 | Me | C12 | A16 | H |
| 1100 | Me | C12 | A17 | H |
| 1101 | Me | C12 | A18 | H |
| 1102 | Me | C12 | C6OC | H |
| 1103 | Me | C12 | C7OC | H |
| 1104 | Me | C12 | C8OC | H |
| 1105 | Me | C12 | C9OC | H |
| 1106 | Me | C12 | C10OC | H |
| 1107 | Me | C12 | C11OC | H |
| 1108 | Me | C12 | C12OC | H |
| 1109 | Me | C12 | MMA10 | H |
| 1110 | Me | C12 | DMA10 | H |
| 1111 | Me | C12 | C5 | H |
| 1112 | Me | C12 | C6 | H |
| 1113 | Me | C12 | C7 | H |
| 1114 | Me | C12 | C8 | H |
| 1115 | Me | C12 | C9 | M |
| 1116 | Me | C12 | C10 | H |
| 1117 | Me | C12 | C11 | H |
| 1118 | Me | C12 | C12 | H |
| 1119 | Me | C12 | C13 | H |
| 1120 | Me | C12 | C14 | H |
| 1121 | Me | C12 | H | A6 |
| 1122 | Me | C12 | H | A7 |
| 1123 | Me | C12 | H | A8 |
| 1124 | Me | C12 | H | A9 |
| 1125 | Me | C12 | H | A10 |
| 1126 | Me | C12 | H | A11 |
| 1127 | Me | C12 | H | A12 |
| 1128 | Me | C12 | H | A13 |
| 1129 | Me | C12 | H | A14 |
| 1130 | Me | C12 | H | A15 |
| 1131 | Me | C12 | H | A16 |
| 1132 | Me | C12 | H | A17 |
| 1133 | Me | C12 | H | A18 |
| 1134 | Me | C12 | H | C6OC |
| 1135 | Me | C12 | H | C7OC |
| 1136 | Me | C12 | H | C8OC |
| 1137 | Me | C12 | H | C9OC |
| 1138 | Me | C12 | H | C10OC |
| 1139 | Me | C12 | H | C11OC |
| 1140 | Me | C12 | H | C12OC |
| 1141 | H | Me | H | H |
| 1142 | H | Me | A7 | H |
| 1143 | H | Me | A8 | H |
| 1144 | H | Me | A9 | H |
| 1145 | H | Me | A10 | H |
| 1146 | N | Me | A12 | H |
| 1147 | H | Me | A14 | H |
| 1148 | H | Me | A15 | H |
| 1149 | H | Me | A16 | H |
| 1150 | H | Me | A17 | H |
| 1151 | H | Me | A18 | H |
| 1152 | H | Me | C6OC | H |
| 1153 | H | Me | C7OC | H |
| 1154 | H | Me | C8OC | H |
| 1155 | H | Me | C9OC | H |
| 1156 | H | Me | C10OC | H |
| 1157 | H | Me | C11OC | H |

TABLE 2-continued (Ik)

| Exemp. Comp. No. | R1 | R11 | R3 | R5 |
|---|---|---|---|---|
| 1158 | H | Me | C12OC | H |
| 1159 | H | Me | MMA10 | H |
| 1160 | H | Me | DMA10 | H |
| 1161 | H | Me | C5 | H |
| 1162 | H | Me | C6 | H |
| 1163 | H | Me | C7 | H |
| 1164 | H | Me | C8 | H |
| 1165 | H | Me | C9 | H |
| 1166 | H | Me | C10 | H |
| 1167 | H | Me | C11 | H |
| 1168 | H | Me | C12 | H |
| 1169 | H | Me | C13 | H |
| 1170 | H | Me | C14 | H |
| 1171 | H | Me | H | A6 |
| 1172 | H | Me | H | A7 |
| 1173 | H | Me | H | A8 |
| 1174 | H | Me | H | A9 |
| 1175 | H | Me | H | A10 |
| 1176 | H | Me | H | A11 |
| 1177 | H | Me | H | A12 |
| 1178 | H | Me | H | A13 |
| 1179 | H | Me | H | A14 |
| 1180 | H | Me | H | A15 |
| 1181 | H | Me | H | A16 |
| 1182 | H | Me | H | A17 |
| 1183 | H | Me | H | A18 |
| 1184 | H | Me | H | C6OC |
| 1185 | H | Me | H | C7OC |
| 1186 | H | Me | H | C8OC |
| 1187 | H | Me | H | C9OC |
| 1188 | H | Me | H | C10OC |
| 1189 | H | Me | H | C11OC |
| 1190 | H | Me | H | C12OC |
| 1191 | H | C2 | H | H |
| 1192 | H | C2 | A7 | H |
| 1193 | H | C2 | A8 | H |
| 1194 | H | C2 | A9 | H |
| 1195 | H | C2 | A10 | H |
| 1196 | H | C2 | A12 | H |
| 1197 | H | C2 | A14 | H |
| 1198 | H | C2 | A15 | H |
| 1199 | H | C2 | A16 | H |
| 1200 | H | C2 | A17 | H |
| 1201 | H | C2 | A18 | H |
| 1202 | H | C2 | C6OC | H |
| 1203 | H | C2 | C7OC | H |
| 1204 | H | C2 | C8OC | H |
| 1205 | H | C2 | C9OC | H |
| 1206 | H | C2 | C10OC | H |
| 1207 | H | C2 | C11OC | H |
| 1208 | H | C2 | C12OC | H |
| 1209 | H | C2 | MMA10 | H |
| 1210 | H | C2 | DMA10 | H |
| 1211 | H | C2 | C5 | H |
| 1212 | H | C2 | C6 | H |
| 1213 | H | C2 | C7 | H |
| 1214 | H | C2 | C8 | H |
| 1215 | H | C2 | C9 | H |
| 1216 | H | C2 | C10 | H |
| 1217 | H | C2 | C11 | H |
| 1218 | H | C2 | C12 | H |
| 1219 | H | C2 | C13 | H |
| 1220 | H | C2 | C14 | H |
| 1221 | H | C2 | H | A6 |
| 1222 | H | C2 | H | A7 |
| 1223 | H | C2 | H | A8 |
| 1224 | H | C2 | H | A9 |
| 1225 | H | C2 | H | A10 |
| 1226 | H | C2 | H | A11 |
| 1227 | H | C2 | H | A12 |
| 1228 | H | C2 | H | A13 |
| 1229 | H | C2 | H | A14 |
| 1230 | H | C2 | H | A15 |
| 1231 | H | C2 | H | A16 |
| 1232 | H | C2 | H | A17 |
| 1233 | H | C2 | H | A18 |
| 1234 | H | C2 | H | C6OC |
| 1235 | H | C2 | H | C7OC |
| 1236 | H | C2 | H | C8OC |
| 1237 | H | C2 | H | C9OC |
| 1238 | H | C2 | H | C10OC |
| 1239 | H | C2 | H | C11OC |
| 1240 | H | C2 | H | C12OC |
| 1241 | H | C3 | H | H |
| 1242 | H | C3 | A7 | H |
| 1243 | H | C3 | A8 | H |
| 1244 | H | C3 | A9 | H |
| 1245 | H | C3 | A10 | H |
| 1246 | H | C3 | A12 | H |
| 1247 | H | C3 | A14 | H |
| 1248 | H | C3 | A15 | H |
| 1249 | H | C3 | A16 | H |
| 1250 | H | C3 | A17 | H |
| 1251 | H | C3 | A18 | H |
| 1252 | H | C3 | C6OC | H |
| 1253 | H | C3 | C7OC | H |
| 1254 | H | C3 | C8OC | H |
| 1255 | H | C3 | C9OC | H |
| 1256 | H | C3 | C10OC | H |
| 1257 | H | C3 | C11OC | H |
| 1258 | H | C3 | C12OC | H |
| 1259 | H | C3 | MMA10 | H |
| 1260 | H | C3 | DMA10 | H |
| 1261 | H | C3 | C5 | H |
| 1262 | H | C3 | C6 | H |
| 1263 | H | C3 | C7 | H |
| 1264 | H | C3 | C8 | H |
| 1265 | H | C3 | C9 | H |
| 1266 | H | C3 | C10 | H |
| 1267 | H | C3 | C11 | H |
| 1268 | H | C3 | C12 | H |
| 1269 | H | C3 | C13 | H |
| 1270 | H | C3 | C14 | H |
| 1271 | H | C3 | H | A6 |
| 1272 | H | C3 | H | A7 |
| 1273 | H | C3 | H | A8 |
| 1274 | H | C3 | H | A9 |
| 1275 | H | C3 | H | A10 |
| 1276 | H | C3 | H | A11 |
| 1277 | H | C3 | H | A12 |
| 1278 | H | C3 | H | A13 |
| 1279 | H | C3 | H | A14 |
| 1280 | H | C3 | H | A15 |
| 1281 | H | C3 | H | A16 |
| 1282 | H | C3 | H | A17 |
| 1283 | H | C3 | H | A18 |

TABLE 2-continued (Ik)

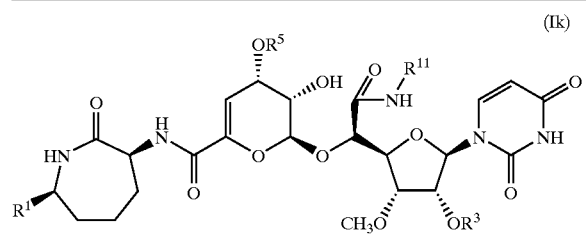

| Exemp. Comp. No. | R1 | R11 | R3 | R5 |
|---|---|---|---|---|
| 1284 | H | C3 | H | C6OC |
| 1285 | H | C3 | H | C7OC |
| 1286 | H | C3 | H | C8OC |
| 1287 | H | C3 | H | C9OC |
| 1288 | H | C3 | H | C10OC |
| 1289 | H | C3 | H | C11OC |
| 1290 | H | C3 | H | C12OC |
| 1291 | H | C6 | H | H |
| 1292 | H | C6 | A7 | H |
| 1293 | H | C6 | A8 | H |
| 1294 | H | C6 | A9 | H |
| 1295 | H | C6 | A10 | H |
| 1296 | H | C6 | A12 | H |
| 1297 | H | C6 | A14 | H |
| 1298 | H | C6 | A15 | H |
| 1299 | H | C6 | A16 | H |
| 1300 | H | C6 | A17 | H |
| 1301 | H | C6 | A18 | H |
| 1302 | H | C6 | C6OC | H |
| 1303 | H | C6 | C7OC | H |
| 1304 | H | C6 | C8OC | H |
| 1305 | H | C6 | C9OC | H |
| 1306 | H | C6 | C10OC | H |
| 1307 | H | C6 | C11OC | H |
| 1308 | H | C6 | C12OC | H |
| 1309 | H | C6 | MMA10 | H |
| 1310 | H | C6 | DMA10 | H |
| 1311 | H | C6 | C5 | H |
| 1312 | H | C6 | C6 | H |
| 1313 | H | C6 | C7 | H |
| 1314 | H | C6 | C8 | H |
| 1315 | H | C6 | C9 | H |
| 1316 | H | C6 | C10 | H |
| 1317 | H | C6 | C11 | H |
| 1318 | H | C6 | C12 | H |
| 1319 | H | C6 | C13 | H |
| 1320 | H | C6 | C14 | H |
| 1321 | H | C6 | H | A6 |
| 1322 | H | C6 | H | A7 |
| 1323 | H | C6 | H | A8 |
| 1324 | H | C6 | H | A9 |
| 1325 | H | C6 | H | A10 |
| 1326 | H | C6 | H | A11 |
| 1327 | R | C6 | H | A12 |
| 1328 | H | C6 | H | A13 |
| 1329 | H | C6 | H | A14 |
| 1330 | H | C6 | H | A15 |
| 1331 | H | C6 | H | A16 |
| 1332 | H | C6 | H | A17 |
| 1333 | H | C6 | H | A18 |
| 1334 | H | C6 | H | C6OC |
| 1335 | H | C6 | H | C7OC |
| 1336 | H | C6 | H | C8OC |
| 1337 | H | C6 | H | C9OC |
| 1338 | H | C6 | H | C10OC |
| 1339 | H | C6 | H | C11OC |
| 1340 | H | C6 | H | C12OC |
| 1341 | H | C12 | H | H |
| 1342 | H | C12 | A7 | H |
| 1343 | H | C12 | A8 | H |
| 1344 | H | C12 | A9 | H |
| 1345 | H | C12 | A10 | H |
| 1346 | H | C12 | A12 | H |

TABLE 2-continued (Ik)

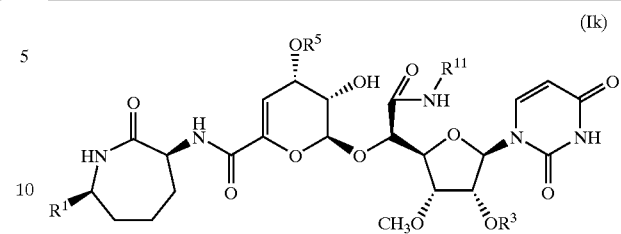

| Exemp. Comp. No. | R1 | R11 | R3 | R5 |
|---|---|---|---|---|
| 1347 | H | C12 | A14 | H |
| 1348 | H | C12 | A15 | H |
| 1349 | H | C12 | A16 | H |
| 1350 | H | C12 | A17 | H |
| 1351 | H | C12 | A18 | H |
| 1352 | H | C12 | C6OC | H |
| 1353 | H | C12 | C7OC | H |
| 1354 | H | C12 | C8OC | H |
| 1355 | H | C12 | C9OC | H |
| 1356 | H | C12 | C10OC | H |
| 1357 | H | C12 | C11OC | H |
| 1358 | H | C12 | C12OC | H |
| 1359 | H | C12 | MMA10 | H |
| 1360 | H | C12 | DMA10 | H |
| 1361 | H | C12 | C5 | H |
| 1362 | H | C12 | C6 | H |
| 1363 | H | C12 | C7 | H |
| 1364 | H | C12 | C8 | H |
| 1365 | H | C12 | C9 | H |
| 1366 | H | C12 | C10 | H |
| 1367 | H | C12 | C11 | H |
| 1368 | H | C12 | C12 | H |
| 1369 | H | C12 | C13 | H |
| 1370 | H | C12 | C14 | H |
| 1371 | H | C12 | H | A6 |
| 1372 | H | C12 | H | A7 |
| 1373 | H | C12 | H | A8 |
| 1374 | H | C12 | H | A9 |
| 1375 | H | C12 | H | A10 |
| 1376 | H | C12 | H | A11 |
| 1377 | H | C12 | H | A12 |
| 1378 | H | C12 | H | A13 |
| 1379 | H | C12 | H | A14 |
| 1380 | H | C12 | H | A15 |
| 1381 | H | C12 | H | A16 |
| 1382 | H | C12 | H | A17 |
| 1383 | H | C12 | H | A18 |
| 1384 | H | C12 | H | C6OC |
| 1385 | H | C12 | H | C7OC |
| 1386 | H | C12 | H | C8OC |
| 1387 | H | C12 | H | C9OC |
| 1388 | H | C12 | H | C10OC |
| 1389 | H | C12 | H | C11OC |
| 1390 | H | C12 | H | C12OC |
| 1391 | Me | C4 | H | H |
| 1392 | Me | C5 | H | H |
| 1393 | Me | C7 | H | H |
| 1394 | Me | C8 | H | H |
| 1395 | Me | C9 | H | R |
| 1396 | Me | C10 | H | H |
| 1397 | Me | C11 | H | H |
| 1398 | Me | C13 | H | H |
| 1399 | Me | C14 | H | H |
| 1400 | Me | C15 | H | H |
| 1401 | Me | C16 | H | H |
| 1402 | H | C4 | H | H |
| 1403 | H | C5 | H | H |
| 1404 | H | C7 | H | H |
| 1405 | H | C8 | H | H |
| 1406 | H | C9 | H | H |
| 1407 | H | C10 | H | H |
| 1408 | H | C11 | H | H |
| 1409 | H | C13 | H | H |

TABLE 2-continued (Ik)

[Structure showing compound formula (Ik) with OR5, OH, R11, NH, CH3O, OR3, and related groups]

| Exemp. Comp. No. | R1 | R11 | R3 | R5 |
|---|---|---|---|---|
| 1410 | H | C14 | H | H |
| 1411 | H | C15 | H | H |
| 1412 | H | C16 | H | H |

In Tables 1 and 2
Exemp. comp. No. is exemplification compound number,
CH$_2$ is methylene group,
Me is methyl group,
OH is hydroxy group,
A6 is hexanoyl group,
A7 is heptanoyl group,
A8 is octanoyl group,
A9 is nonanoyl group,
A10 is decanoyl group,
A12 is lauroyl group,
A14 is myristoyl group,
A15 is pentadecanoyl group,
A16 is palmitoyl group,
A17 is heptadecanoyl group,
A18 is stearoyl group,
A20 is arachidoyl group,
A22 is behenoyl group,
AO7 is heptanoyloxy group,
AO8 is octanoyloxy group,
AO9 is nonanoyloxy group,
AO10 is decanoyloxy group,
AO12 is lauroyloxy group,
AO14 is myristoyloxy group,
AO15 is pentadecanoyloxy group,
AO16 is palmitoyloxy group,
AO17 is heptadecanoyloxy group,
AO 18 is stearoyloxy group,
AO20 is arachidoyloxy group,
AO22 is behenoyloxy group,
OLE is oleoy group,
LE is linoleoyl group,
LEN is linolenoyl group,
CES is cis-11-eicosenoyl group,
CDS is cis-13-docosenoyl group,
DPP is 3,3-diphenylpropionyl group,
TMPP is 3-(3,4,5-trimethoxyphenyl)propionyl group,
NPP is 2-(4-nitrophenyl)propionyl group,
MPP is 3-(4-methylphenyl)propionyl group,
CP is 3-chloropropionyl group,
ND is 12-nitrodecanoyl group,
TCN is trans-cinnamoyl group,
MP is 3-methoxypropionyl group,
CPA is 4-chlorophenylacetyl group,
BZ is benzoyl group,
NBZ is nitrobenzoyl group,
CB is 3-chlorobenzoyl group,
MB is 2-methoxybenzoyl group,
EB is 4-ethylbenzoyl group,
OLEO is oleoyloxy group,
LEO is linoleoyloxy group,
LENO is linolenoyloxy group,
CESO is cis-11-eicosenoyloxy group,
CDSO is cis-13-docosenoyloxy group,
DPPO is 3,3-diphenylpropionyloxy group,
TMPPO is 3-(3,4,5-trimethoxyphenyl)propionyloxy group,
NPPO is 2-(4-nitrophenyl)propionyloxy group,
MPPO is 3-(4-methylphenyl)propionyloxy group,
CPO is 3-chloropropionyloxy group,
NDO is 12-nitrodecanoyloxy group,
TCNO is trans-cinnamoyloxy group,
MPO is 3-methoxypropionyloxy group,
CPAO is 4-chlorophenylacetyloxy group,
BZO is benzoyloxy group,
NBZO is nitrobenzoyloxy group,
CBO is 3-chlorobenzoyloxy group,
MBO is 2-methoxybenzoyloxy group,
EBO is 4-ethylbenzoyloxy group,
MO is 2-methyloctanoyl group,
MD is 2-methyldecanoyl group,
MDD is 2-methyldodecanoyl group,
MTD is 2-methyltetradecanoyl group,
MHD is 2-methylhexadecanoyl group,
DMO is 2,2-dimethyloctanoyl group,
DMD is 2,2-dimethyldecanoyl group,
DMDD is 2,2-dimethyldodecanoyl group,
DMTD is 2,2-dimethyltetradecanoyl group,
DMHD is 2,2-dimethylhexadecanoyl group,
C2 is ethyl group,
C3 is propyl group,
C4 is butyl group,
C5 is pentyl group,
C6 is hexyl group,
C7 is heptyl group,
C8 is octyl group,
C9 is nonyl group,
C10 is decyl group,
C11 is undecyl group,
C12 is dodecyl group,
C13 is tridecyl group,
C14 is tetradecyl group,
C15 is pentadecyl group,
C16 is hexadecyl group,
C6OC is hexyloxycarbonyl group,
C7OC is heptyloxycarbonyl group,
C8OC is octyloxycarbonyl group,
C9OC is nonyloxycarbonyl group,
C10OC is decyloxycarbonyl group,
C11OC is undecyloxycarbonyl group,
C12OC is dodecyloxycarbonvl group,
MMA10 is 2-methyldecanoyl group,
MMA12 is 2-methyldodecanoyl group,
MMA14 is 2-methyltetradecanoyl group,
DMA10 is 2.2-dimethyldecanoyl group,
DMA12 is 2,2-dimethyldodecanoyl group,
DMA14 is 2,2-dimethyltetradecanoyl group,
In a compound of formula (Ib):
the compound wherein $R^1$ is a methyl group, $R^2$ is a methyl group, $R^3_a$ is a hydrogen atom, $R^4_a$ is a hydroxy group, $R^5_a$ is a hydrogen atom and X is a methylene group represents A-500359A (exemplification compound No. 1);
the compound wherein $R^1$ is a methyl group, $R^2$ is a hydrogen atom, $R^3_a$ is a hydrogen atom, $R^4_a$ is a hydroxy group, $R^5_a$ is a hydrogen atom and X is a methylene group represents A-500359C (exemplification compound No. 2);

the compound wherein $R^1$ is a methyl group, $R^2$ is a methyl group, $R^3_a$ is a hydrogen atom, $R^4_a$ is a hydrogen atom, $R^5_a$ is a hydrogen atom and X is a methylene group represents A-500359D (exemplification compound No. 3);

the compound wherein $R^1$ is a hydrogen atom, $R^2$ is a hydrogen atom, $R^3_a$ is a hydrogen atom, $R^4_a$ is a hydroxy group, $R^5_a$ is a hydrogen atom and X is a methylene group represents A-500359G (exemplification compound No. 45); and the compound wherein $R^1$ is a methyl group, $R^2$ is a methyl group, $R^3_a$ is a hydrogen atom, $R^4_a$ is a hydroxy group, $R^5_a$ is a hydrogen atom and X is a sulfur atom represents A-500359M-2 (exemplification compound No. 396).

In Tables 1 and 2:

preferable compounds include compounds of exemplification compound No. (exemp. comp. No.) 1 to 254, 280 to 283, 309 to 312, 338 to 341, 367 to 370, 396 to 482, 508 to 513, 537 to 588, 592 to 704, 708 to 820, 891 to 910, 914 to 990, 1091 to 1160, 1164 to 1210, 1214 to 1240, 1341 to 1390, 1394 to 1401 and 1405 to 1412;

more preferable compounds include compounds of exemplification compound No. 1 to 3, 7to 11, 45, 49 to 53, 90 to 94, 131 to 135, 172 to 176, 213 to 217, 396, 400 to 404, 537 to 543, 550 to 556, 563 to 569, 576 to 582, 592 to 600, 708 to 716, 891 to 908, 921 to 940, 1091 to 1108, 1121 to 1158,1171 to 1190, 1341 to 1358 and 1371 to 1390;

most preferable compounds include compounds of exemplification compound No. 1 to 3, 7 to 11, 45, 49 to 53, 90 to 94, 131 to 135, 537 to 543, 550 to 556, 563 to 569, 576 to 582, 594, 710, 891, 895, 925, 1091, 1141, 1145, 1175 and 1341;

that is exemp.comp.No.1 represents the compound wherein $R^1$ is a methyl group, $R^2$ is a methyl group, $R^3_a$ is a hydrogen atom, $R^4_a$ is a hydroxy group, $R^5_a$ is a hydrogen atom and X is a methylene group;

exemp.comp.No.2 represents the compound wherein $R^1$ is a methyl group, $R^2$ is a hydrogen atom, $R^3_a$ is a hydrogen atom, $R^4_a$ is a hydroxy group, $R^5_a$ is a hydrogen atom and X is a methylene group;

exemp.comp.No.3 represents the compound wherein $R^1$ is a methyl group, $R^2$ is a methyl group, $R^3_a$ is a hydrogen atom, $R^4_a$ is a hydrogen atom, $R^5_a$ is a hydrogen atom and X is a methylene group:

exemp.comp.No.7 represents the compound wherein $R^1$ is a methyl group, $R^2$ is a methyl group, $R^3_a$ is a decanoyl group, $R^4_a$ is a hydroxy group, $R^5_a$ is a hydrogen atom and X is a methylene group:

exemp.comp.No.8 represents the compound wherein $R^1$ is a methyl group, $R^2$ is a methyl group, $R^3_a$ is a lauroyl group, $R^4_a$ is a hydroxy group. $R^5_a$ is a hydrogen atom and X is a methylene group exemp.comp.No.9 represents the compound wherein $R^1$ is a methyl group, $R^2$ is a methyl group, $R^3_a$ is a myristoyl group, $R^4_a$ is a hydroxy group, $R^5_a$ is a hydrogen atom and X is a methylene group;

exemp.comp.No.10 represents the compound wherein $R^1$ is a methyl group, $R^2$ is a methyl group, $R^3_a$ is a pentadecanoyl group, $R^4_a$ is a hydroxy group, $R^5_a$ is a hydrogen atom and X is a methylene group;

exemp.comp.No.11 represents the compound wherein $R^1$ is a methyl group, $R^2$ is a methyl group, $R^3_a$ is a palmitoyl group, $R^4_a$ is a hydroxy group, $R^5_a$ is a hydrogen atom and X is a methylene group;

exemp.comp.No.45 represents the compound wherein $R^1$ is a hydrogen atom, $R^2$ is a hydrogen atom, $R^3_a$ is a hydrogen atom, $R^4_a$ is a hydroxy group, $R^5_a$ is a hydrogen atom and X is a methylene group;

exemp.comp.No.49 represents the compound wherein $R^1$ is a hydrogen atom, $R^2$ is a methyl group, $R^3_a$ is a decanoyl group, $R^4_a$ is a hydroxy group, $R^5_a$ is a hydrogen atom and X is a methylene group;

exemp.comp.No.50 represents the compound wherein $R^1$ is a hydrogen atom, $R^2$ is a methyl group, $R^3_a$ is a lauroyl group, $R^4_a$ is a hydroxy group, $R^5_a$ is a hydrogen atom and X is a methylene group;

exemp.comp.No.51 represents the compound wherein $R^1$ is a hydrogen atom, $R^2$ is a methyl group, $R^3_a$ is a myristoyl group, $R^4_a$ is a hydroxy group, $R^5_a$ is a hydrogen atom and X is a methylene group, exemp.comp.No.52 represents the compound wherein $R^1$ is a hydrogen atom, $R^2$ is a methyl group, $R^3_a$ is a pentadecanoyl group, $R^4_a$ is a hydroxy group, $R^5_a$ is a hydrogen atom and X is a methylene group;

exemp.comp.No.53 represents the compound wherein $R^1$ is a hydrogen atom, $R^2$ is a methyl group, $R^3_a$ is a palmitoyl group, $R^4_a$ is a hydroxy group, $R^5_a$ is a hydrogen atom and X is a methylene group;

exemp.comp.No.90 represents the compound wherein $R^1$ is a methyl group, $R^2$ is a methyl group, $R^3_a$ is a hydrogen atom, $R^4_a$ is a hydroxy group, $R^5_a$ is a decanoyl group and X is a methylene group;

exemp.comp.No.91 represents the compound wherein $R^1$ is a methyl group, $R^2$ is a methyl group, $R^3_a$ is a hydrogen atom, $R^4_a$ is a hydroxy group, $R^5_a$ is a lauroyl group and X is a methylene group;

exemp.comp.No.92 represents the compound wherein $R^1$ is a methyl group, $R^2$ is a methyl group, $R^3_a$ is a hydrogen atom, $R^4_a$ is a hydroxy group, $R^5_a$ is a myristoyl group and X is a methylene group: exemp.comp.No.93 represents the compound wherein $R^1$ is a methyl group, $R^2$ is a methyl group, $R^3_a$ is a hydrogen atom, $R^4_a$ is a hydroxy group, $R^5_a$ is a pentadecanoyl group and X is a methylene group;

exemp.comp.No.94 represents the compound wherein $R^1$ is a methyl group, $R^2$ is a methyl group, $R^3_a$ is a hydrogen atom, $R^4_a$ is a hydroxy group, $R^5_a$ is a palmitoyl group and X is a methylene group;

exemp.comp.No.131 represents the compound wherein $R^1$ is a hydrogen atom, $R^2$ is a methyl group, $R^3_a$ is a hydrogen atom, $R^4_a$ is a hydroxy group, $R^5_a$ is a decanoyl group and X is a methylene group;

exemp.comp.No.132 represents the compound wherein $R^1$ is a hydrogen atom, $R^2$ is a methyl group, $R^3_a$ is a hydrogen atom, $R^4_a$ is a hydroxy group, $R^5_a$ is a lauroyl group and X is a methylene group;

exemp.comp.No.133 represents the compound wherein $R^1$ is a hydrogen atom, $R^2$ is a methyl group, $R^3_a$ is a hydrogen atom, $R^4_a$ is a hydroxy group, $R^5_a$ is a myristoyl group and X is a methylene group;

exemp.comp.No.134 represents the compound wherein $R^1$ is a hydrogen atom, $R^2$ is a methyl group, $R^3_a$ is a hydrogen atom, $R^4_a$ is a hydroxy group, $R^5_a$ is a pentadecanoyl group and X is a methylene group;

exemp.comp.No.135 represents the compound wherein $R^1$ is a hydrogen atom, $R^2$ is a methyl group, $R^3_a$ is a hydrogen atom, $R^4_a$ is a hydroxy group, $R^5_a$ is a palmitoyl group and X is a methylene group;

exemp.comp.No.537 represents the compound wherein $R^1$ is a methyl group, $R^2$ is a methyl group, $R^3_a$ is a hexyloxycarbonyl group, $R^4_a$ is a hydroxy group, $R^5_a$ is a hydrogen atom and X is a methylene group;

exemp.comp.No.538 represents the compound wherein $R^1$ is a methyl group, $R^2$ is a methyl group, $R^3_a$ is a heptyloxycarbonyl group, $R^4_a$ is a hydroxy group, $R^5_a$ is a hydrogen atom and X is a methylene group;

exemp.comp.No.539 represents the compound wherein $R^1$ is a methyl group, $R^2$ is a methyl group, $R^3_a$ is an octyloxycarbonyl group, $R^4_a$ is a hydroxy group, $R^5_a$ is a hydrogen atom and X is a methylene group;

exemp.comp.No.540 represents the compound wherein $R^1$ is a methyl group, $R^2$ is a methyl group, $R^3_a$ is a nonyloxycarbonyl group, $R^4_a$ is a hydroxy group, $R^5_a$ is a hydrogen atom and X is a methylene group;

exemp.comp.No.541 represents the compound wherein $R^1$ is a methyl group, $R^2$ is a methyl group, $R^3_a$ is a decyloxycarbonyl group, $R^4_a$ is a hydroxy group, $R^5_a$ is a hydrogen atom and X is a methylene group;

exemp.comp.No.542 represents the compound wherein $R^1$ is a methyl group, $R^2$ is a methyl group, $R^3_a$ is an undecyloxycarbonyl group, $R^4_a$ is a hydroxy group, $R^5_a$ is a hydrogen atom and X is a methylene group;

exemp.comp.No.543 represents the compound wherein $R^1$ is a methyl group, $R^2$ is a methyl group, $R^3_a$ is a dodecyloxycarbonyl group, $R^4_a$ is a hydroxy group, $R^5_a$ is a hydrogen atom and X is a methylene group;

exemp.comp.No.550 represents the compound wherein $R^1$ is a methyl group, $R^2$ is a methyl group, $R^3_a$ is a hydrogen atom, $R^4_a$ is a hydroxy group, $R^5_a$ is a hexyloxycarbonyl group and X is a methylene group;

exemp.comp.No.551 represents the compound wherein $R^1$ is a methyl group, $R^2$ is a methyl group, $R^3_a$ is a hydrogen atom. $R^4_a$ is a hydroxy group, $R^5_a$ is a heptyloxycarbonyl group and X is a methylene group;

exemp.comp.No.552 represents the compound wherein $R^1$ is a methyl group, $R^2$ is a methyl group, $R^3_a$ is a hydrogen atom, $R^4_a$ is a hydroxy group, $R^5_a$ is an octyloxycarbonyl group and X is a methylene group;

exemp.comp.No.553 represents the compound wherein $R^1$ is a methyl group, $R^2$ is a methyl group, $R^3_a$ is a hydrogen atom, $R^4_a$ is a hydroxy group, $R^5_a$ is a nonyloxycarbonyl group and X is a methylene group;

exemp.comp.No.554 represents the compound wherein $R^1$ is a methyl group, $R^2$ is a methyl group, $R^3_a$ is a hydrogen atom, $R^4_a$ is a hydroxy group, $R^5_a$ is a decyloxycarbonyl group and X is a methylene group;

exemp.comp.No.555 represents the compound wherein $R^1$ is a methyl group, $R^2$ is a methyl group, $R^3_a$ is a hydrogen atom, $R^4_a$ is a hydroxy group, $R^5_a$ is an undecyloxycarbonyl group and X is a methylene group;

exemp.comp.No.556 represents the compound wherein $R^1$ is a methyl group, $R^2$ is a methyl group, $R^3_a$ is a hydrogen atom, $R^4_a$ is a hydroxy group, $R^5_a$ is a dodecyloxycarbonyl group and X is a methylene group;

exemp.comp.No.563 represents the compound wherein $R^1$ is a hydrogen atom, $R^2$ is a methyl group, $R^3_a$ is a hexyloxycarbonyl group, $R^4_a$ is a hydroxy group, $R^5_a$ is a hydrogen atom and X is a methylene group;

exemp.comp.No.564 represents the compound wherein $R^1$ is a hydrogen atom, $R^2$ is a methyl group, $R^3_a$ is a heptyloxycarbonyl group, $R^4_a$ is a hydroxy group, $R^5_a$ is a hydrogen atom and X is a methylene group;

exemp.comp.No.565 represents the compound wherein $R^1$ is a hydrogen atom, $R^2$ is a methyl group, $R^3_a$ is an octyloxycarbonyl group, $R^4_a$ is a hydroxy group, $R^5_a$ is a hydrogen atom and X is a methylene group;

exemp.comp.No.566 represents the compound wherein $R^1$ is a hydrogen atom, $R^2$ is a methyl group, $R^3_a$ is a nonyloxycarbonyl group, $R^4_a$ is a hydroxy group, $R^5_a$ is a hydrogen atom and X is a methylene group;

exemp.comp.No.567 represents the compound wherein $R^1$ is a hydrogen atom, $R^2$ is a methyl group, $R^3_a$ is a decyloxycarbonyl group, $R^4_a$ is a hydroxy group, $R^5_a$ is a hydrogen atom and X is a methylene group;

exemp.comp.No.568 represents the compound wherein $R^1$ is a hydrogen atom, $R^2$ is a methyl group, $R^3_a$ is an undecyloxycarbonyl group, $R^4_a$ is a hydroxy group, $R^5_a$ is a hydrogen atom and X is a methylene group;

exemp.comp.No.569 represents the compound wherein $R^1$ is a hydrogen atom, $R^2$ is a methyl group, $R^3_a$ is a dodecyloxycarbonyl group, $R^4_a$ is a hydroxy group, $R^5_a$ is a hydrogen atom and X is a methylene group;

exemp.comp.No.576 represents the compound wherein $R^1$ is a hydrogen atom, $R^2$ is a methyl group, $R^3_a$ is a hydrogen atom, $R^4_a$ is a hydroxy group, $R^5_a$ is a hexyloxycarbonyl group and X is a methylene group;

exemp.comp.No.577 represents the compound wherein $R^1$ is a hydrogen atom, $R^2$ is a methyl group, $R^3_a$ is a hydrogen atom, $R^4_a$ is a hydroxy group, $R^5_a$ is a heptyloxycarbonyl group and X is a methylene group;

exemp.comp.No.578 represents the compound wherein $R^1$ is a hydrogen atom, $R^2$ is a methyl group, $R^3_a$ is a hydrogen atom, $R^4_a$ is a hydroxy group, $R^5_a$ is an octyloxycarbonyl group and X is a methylene group;

exemp.comp.No.579 represents the compound wherein $R^1$ is a hydrogen atom, $R^2$ is a methyl group, $R^3_a$ is a hydrogen atom, $R^4_a$ is a hydroxy group, $R^5_a$ is a nonyloxycarbonyl group and X is a methylene group;

exemp.comp.No.580 represents the compound wherein $R^1$ is a hydrogen atom, $R^2$ is a methyl group, $R^3_a$ is a hydrogen atom, $R^4_a$ is a hydroxy group, $R^5_a$ is a decyloxycarbonyl group and X is a methylene group;

exemp.comp.No.581 represents the compound wherein $R^1$ is a hydrogen atom, $R^2$ is a methyl group, $R^3_a$ is a hydrogen atom, $R^4_a$ is a hydroxy group, $R^5_a$ is an undecyloxycarbonyl group and X is a methylene group;

exemp.comp.No.582 represents the compound wherein $R^1$ is a hydrogen atom, $R^2$ is a methyl group, $R^3_a$ is a hydrogen atom, $R^4_a$ is a hydroxy group, $R^5_a$ is a dodecyloxycarbonyl group and X is a methylene group;

exemp.comp.No.594 represents the compound wherein $R^1$ is a methyl group, $R^2$ is a methyl group, $R^3_a$ is a decyl group, $R^4_a$ is a hydroxy group, $R^5_a$ is a hydrogen atom and X is a methylene group;

exemp.comp.No.710 represents the compound wherein $R^1$ is a hydrogen atom, $R^2$ is a methyl group, $R^3_a$ is a decyl group, $R^4_a$ is a hydroxy group, $R^5_a$ is a hydrogen atom and X is a methylene group;

exemp.comp.No.891 represents the compound wherein $R^1$ is a methyl group, $R^{11}$ is a methyl group, $R^3$ is a hydrogen atom, and $R^5$ is a hydrogen atom;

exemp.comp.No.895 represents the compound wherein $R^1$ is a methyl group, $R^{11}$ is a methyl group, $R^3$ is a decanoyl group, and $R^5$ is a hydrogen atom;

exemp.comp.No.925 represents the compound wherein $R^1$ is a methyl group, $R^{11}$ is a methyl group, $R^3$ is a hydrogen atom, and $R^5$ is a decanoyl group;

exemp.comp.No.1091 represents the compound wherein $R^1$ is a methyl group, $R^{11}$ is a dodecyl group, $R^3$ is a hydrogen atom, and $R^5$ is a hydrogen atom;

exemp.comp.No.1141 represents the compound wherein $R^1$ is a hydrogen atom, $R^{11}$ is a methyl group, $R^3$ is a hydrogen atom, and $R^5$ is a hydrogen atom;

exemp.comp.No.1145 represents the compound wherein $R^1$ is a hydrogen atom, $R^{11}$ is a methyl group, $R^3$ is a decanoyl group, and $R^5$ is a hydrogen atom;

exemp.comp.No.1175 represents the compound wherein $R^1$ is a hydrogen atom, $R^{11}$ is a methyl group, $R^3$ is a hydrogen atom, and $R^5$ is a decanoyl group; and exemp.comp.No.1341 represents the compound wherein $R^1$ is a hydrogen atom, $R^{11}$ is a dodecyl group, $R^3$ is a hydrogen atom, and $R^5$ is a hydrogen atom.

Compounds of the present invention represented by the formula (I) or (Ia) can be prepared by the process as described below.

Compounds A-500359A (Exemp. compound No. 1), A-500359C (Exemp. compound No. 2), A-500359D (Exemp. compound No. 3), A-500359G (Exemp. compound No. 45) and A-500359M-2 (Exemp. compound No. 396) of the present invention each represented by the formula (I) are available by culturing a microorganism capable of producing the above described compounds, belonging to the Streptomyces spp. on a suitable medium and then recovering the compound from the cultured broth, *Streptomyces griseus* Strain SANK60196 (which will hereinafter be called "Strain SANK60196"), a preferable microorganism capable of producing Compounds A-500359A, A-500359C, A-500359D, A-500359G or A-500359M-2 has been collected and separated from the soil of Mt. Tsukuba/Ibaraki-ken in a manner known to those skilled in the art.

Mycological properties of Strain SANK60196 are as follows:

1) Morphological Appearance

Strain SANK60196 showed morphological appearance as described below after cultivation at 28° C. for 14 days on a medium specified by International Streptomyces Project (which will hereinafter be abbreviated as "ISP") [refer to Shirling, E. B. and Gottlieb, D., "Int. J. Syst. Bacteriol. 16.313–340 (1996)".] Observation through an optical microscope indicates that substrate mycelia of SANK60196 are favourably grown and branched and show yellowish grey, yellowish brown or pale olive colour, but unlike the strain belonging to Nocardia spp., does not show cleavage or zigzag extension. Aerial mycelia exhibit simple branching. The form of the spore chain is straight or cursed and its chain is formed of 10 to 50 or greater spores. Observation through a scanning electron microscope shows that the spore has an oval shape and it has a smooth surface structure. The spore is 0.6–0.8×0.7–1.2 mm in dimension. The spore is formed only on the aerial mycelia. Formation of sporangia, axial division of aerial cleavage of aerial mycelia and sclerotia are not recognized.

2) Growth Characteristics on Various Culture Media

Growth characteristics of Strain SANK60196 on an agar medium after cultivation at 28° C. for 14 days is as described below in Table 3. In the Table, the composition of the medium attached with ISP No. is the same as specified by ISP. In the item, abbreviations G. AM. R and SP stand for growth, aerial mycelia, reverse colour and soluble pigment, respectively. The colour tone is described in accordance with "Colour Standards. ed. by Japan Colour Laboratory". The indication of the colour tone in parentheses is a colour number in accordance with Munsell colour system. The pale yellow soluble pigment produced in a water-agar medium changes into colourless by 0.05N hydrochloric acid, but shows no change by 0.05N sodium hydroxide.

[Table 3]

Nature of Medium;

Item: characteristics

Yeast extract—malt extract agar (ISP 2);
   G: Excellent, flat, yellowish brown (10YR 5/6)
   AM: Abundantly formed, velvety, pale brown (2.5Y 8/2)
   R: Yellowish brown (10YR 5/8)
   SP: Yellowish brown (10YR 6/8)

Oat meal—agar (ISP 3);
   G: Excellent, flat, yellowish brown (2.5Y 6/6)
   AM: Abundantly formed, velvety, pale yellowish orange (5Y 9/2)
   R: Dark yellow (2.5Y 818)
   SP: Not produced Starch—inorganic salt agar (ISP 4);
   G: Good, flat, yellowish brown (2.5Y 6/4)
   AM: Abundantly formed, velvety, yellowish grey (7.5Y 9/2)
   R: Yellowish brown (2.5Y 6/4)

Glycerin—asparagine agar (ISP 5);
   G: Excellent, flat, pale yellowish brown (2.5Y 7/6)
   AM: Abundantly formed, velvety, yellowish grey (5Y 8/2)
   R: Pale yellowish brown (2.5Y 8/6)
   SP: Not produced Peptone—yeast extract—iron agar (ISP 6);
   G: Excellent, flat, pale olive color (5Y 8/3)
   AM: Slightly produced, velvet), yellowish grey (5Y 9/1)
   R: Pale yellow (5Y 8/6)
   SP: Not produced Tyrosine agar (ISP 7);
   G: Good, flat, grayish yellow brown (2.5Y 5/4)
   AM: Abundantly formed, velvety, light olive grey (7.5Y 8/2)
   R: Yellowish brown (10YR 5/4)
   SP: Grayish yellow brown (2.5Y 4/3)

Sucrose—nitrate agar;
   G: Not so good, flat, pale yellow (5Y 8/6)
   AM: Abundantly formed, velvety, light olive grey (7.5Y 8/2)
   R: Dark yellow (5Y 8/8)
   SP: Pale yellow (5Y 9/6)

Glucose—asparagine agar;
   G: Good, flat, pale yellow (5Y 9/3)
   AM: Not so good, velvety, yellowish grey (5Y 9/1)
   R: Yellowish grey (7.5Y 9/3)
   SP: Not produced Nutrient agar (product of Difco Laboratories);
   G: Good, flat, pale yellowish brown (2.5Y 8/3)
   AM: Good, velvety, yellowish grey (5Y 9/1)

R: Yellowish grey (5Y 9/4)
SP: Not produced
Potato extract—carrot extract agar;
G: Not so good, flat, yellowish grey (7.5Y 9/2)
AM: Not so good, velvet, yellowish grey (5Y 9/2)
R: Yellowish grey (7.5Y 9/3)
SP: Yellowish grey (7.5Y 9/3)
Water agar;
G: Not good, flat, yellowish grey (5Y 9/1)
AM: Not good, velvety, yellowish grey (5ZY 9/1)
R: Yellowish grey (7.5Y 9/4)
SP: Pale yellow (5Y 9/6)

3) Physiological Characteristics

The physiological characteristics of the present strain observed for 2 to 21 days after cultivation at 28° C. are as shown in Table 4. In the table Medium 1 is a yeast extract—malt extract agar medium (ISP 2).

TABLE 4

| | |
|---|---|
| Hydrolysis of starch | positive |
| Liquefaction of gelatin | positive |
| Reduction of nitrates | positive |
| Coagulation of milk | negative |
| Peptonization of milk | positive |
| Formation of melamine-like pigment | positive |
| Substrate decomposition: casein | positive |
| tyrosine | positive |
| xanthine | negative |
| Growth temperature range (Medium 1) | 6 to 35° C. |
| Optimum growth temperature (Medium 1) | 18 to 30° C. |
| Growth in the presence of salt (Medium 1) | 10% |

Utilisation of a carbon source by Strain SANK60196 observed after cultivation at 28° C, for 14 days on a Pridham-Gottlieb agar medium (ISP 9) is as described in Table 5. In the table, "+" means utilisable, while "−" means non-utilisable.

TABLE 5

| | |
|---|---|
| D-glucose | − |
| L-arabinose | − |
| D-xylose | − |
| Inositol | − |
| D-mannitol | + |
| D-fructose | + |
| L-rhamnose | − |
| Sucrose | − |
| Raffinose | − |
| Control | − |

4) Chemotaxonomic Properties

The cell wall of the present strain was investigated in accordance with the method of Hasegawa, et al. [refer to Hasegawa. T., et al., "The Journal of General and Applied Microbiology, 29, 319–322(1983)], resulting in the detection of LL-diaminopimelic acid. The main sugar component in the whole cells of the present strain was investigated in accordance with the method of M. P. Lechevalier [refer to Lechevalier, M. P., "Journal of Laboratory and Clinical Medicine. 71, 934–944(1968)]. As a result, no characteristic component was detected.

The above-described mycological properties have revealed that the present strain belongs to Streptomyces spp. among the actinomycetes. It has been made clear that the present strain is markedly related to *Streptomyces griseus*, as a result of comparison with the microorganism described in the ISP strains by Shirling and Gottlieb [refer to Shirling, E. B. and Gottlieb, D., "International Journal of Systematic Bacteriology, 18, 68–189 and 279–392 (1968); 19, 391–512 (1969); 22, 265–394 (972)"], the microorganism described in "The actinomycetes Vol. 2" written by Waksman [refer to Waksman, S. A., "The actinomycetes 2 (1961)"], with the microorganism described in Bergey's Manual edited by Buchanan and Gibbons [refer to R. E. Buchanan and N. E. Gibbons. "Bergey's Manual of Determinative Bacteriology", 8th edition (1974)], with the microorganism described in "Bergey's Manual of Systematic Bacteriology", edited by Williams [refer to Williams, S. T., et al., "Bergey's Manual of Systematic Bacteriology 4 (1989)"] and with the microorganism described in the recent literature about actinomycetes belonging to Streptomyces spp. It has however been recognized to be different from *Streptomyces griseus*, because it produces a yellowish grey soluble pigment on a glycerin-asparagine agar medium and a pale yellowish brown soluble pigment on a peptone-yeast extract—iron agar medium but produces a soluble pigment neither on a potato extract—carrot extract agar medium nor on a water agar medium; the maximum growth temperature is 40° C.; and it is grown in the presence of 7% of salt.

The present strain having such mycological characteristics is considered to be a novel strain different from *Streptomyces griseus*, but it is impossible to distinguish them based on only the above-described differences. The present inventors therefore identified the present strain as *Streptomyces griseus* SANK60 196.

This strain was internationally deposited with Agency of Industrial Science and Technology, Ministry of International Trade and Industry (1-3, Higashi 1-chome Tsukuba-shi, Ibaraki-ken, 305, JAPAN) as of Feb. 22, 1996, with the accession number of FERM BP-5420.

A description was heretofore made on Strain SANK60196. It is known that various properties of actinomycetes are not fixed but easily change naturally or synthetically. The strain usable in the present invention embraces all of such variants. In other words. the present invention embraces all the strains belonging, to the Streptomyces spp. and capable of producing Compounds A-500359A, A-500359C, A-500359D, A-500359G or A-500359M-2.

Any synthetic or natural medium can be used for cultivation for microorganisms capable of producing Compounds A-500359A, A-500359C, A-500359D, A-500359G or A-500359M-2 of the present invention, insofar as it contains, as needed, a substance selected from carbon sources, nitrogen sources, inorganic ions and organic nutrition sources.

Known carbon sources, nitrogen sources and inorganic salts conventionally employed for cultivation of the strain of the eumycetes or actinomycetes and are utilisable by a microorganism can be used as such nutrition sources.

Specific examples of the carbon source include glucose, fructose, maltose, sucrose, mannitol, glycerol, dextrin, oats, rye, corn starch, potato, corn meal, soybean meal, cotton seed oil, thick malt syrup, theriac, soybean oil, citric acid and tartaric acid. They may be used either singly or in combination. The amount of the carbon source to be added usually varies, but not limited to, within a range of from 1 to 10 wt. %.

As the nitrogen source. a substance containing protein or hydrolyzate thereof can usually be employed. Preferred examples of the nitrogen source include soybean meal, wheat bran, peanut meal, cotton seed meal, casein hydrolyzate, Farmamine, fish meal, corn steep liquor, peptone, meat extract, pressed yeast, dry yeast, yeast extract, malt extract, potato, ammonium sulfate, ammonium nitrate and sodium nitrate. It is preferred to use the nitrogen source either singly or in combination in an amount ranging from 0.2 to 6 wt. % of the amount of the medium.

As the nutrition inorganic salt, ordinarily employed salts from which an ion is available, such as sodium salts, ammonium salts, calcium salts, phosphates, sulfates, chlorides and carbonates can be used. In addition, trace metals such as potassium, calcium, cobalt manganese, iron and magnesium are usable.

For the production of Compound A-500359A, the addition of cobalt or yeast extract is particularly effective.

Upon culturing the microorganism capable of producing Compound A-500359A, A-500359C, A-500359D, A-500359G or A-500359M-2, an inhibitor of antibiotic biosynthesis can be added to produce useful related compounds. Compound A500359M-2 can be produced, for example, by using, as a medium additive, S-(2-aminoethyl)-L-cysteine or salt thereof which is an aspartate kinase inhibitor. The additive can be added to give its final concentration ranging from 1 to 100 mM. Preferably, use of it to give a final concentration of 10 mM permits favorable production of Compound A-500359M-2.

Upon liquid culture, a silicone oil, vegetable oil or surfactant can be added as an antifoamer.

The medium used for the cultivation of Strain SANK 60196 to produce Compound A-500359A, A-500359C, A-500359D, A-500359G or A-500359M-2 preferably has a pH ranging from 5.0 to 8.0.

The temperature which allows Strain SANK60196 to grow ranges from 12 to 36° C. It is preferred to cultivate the strain at 18 to 28° C. in order to produce Compound A-500359A, A-500359C, A-500359D, A-500359G or A-500359M-2, of which 19 to 23° C. is more preferred.

Compound A-500359A, A-500359C, A-500359D, A-500359G or A-500359M-2 is available by aerobic culture of Strain SANK 60196. Ordinarily-employed solid culture, shake culture, and aeration agitation culture can be used as such culturing method.

For small-scale culturing, agitation of the culture for several days at 19 to 23° C. is preferred. Culturing is started by growing a seed culture in a single or two stage process in an Erlenmeyer flask equipped with a baffle (water flow adjusting wall) or an ordinarily-employed Erlenmeyer flask. A carbon source and a nitrogen source can be used in combination as a medium in the seed culture. The flask or seed culture may be shaken at 19 to 23° C. for 5 days or until the seed cultures grow sufficiently in a thermostat incubator. The seed cultures thus grown can be used for inoculation of the second seed culture medium or a production medium. When the seed cultures are used under an intermediate growing step, they are allowed to grow essentially in a similar manner, followed by inoculation of a part of them into a production medium. The flask into which the seed cultures has been inoculated is subjected to culturing with shaking at a constant temperature for several days and after completion of the culturing, the cultured medium in the flask is centrifuged or filtered.

For large-scale cultivation. on the other hand, culturing in a jar fermenter or tank equipped with an agitator and an aeration apparatus is preferred. Prior to culturing in such a container, the culture medium is heated to 125° C. for sterilization. After cooling, the seed cultures which have been allowed to grow in advance by the above-described method are inoculated on the sterilized medium. Then, culturing is carried out with aeration and agitation at 19 to 23° C. This method is suitable for obtaining a large amount of compounds.

Compound A-500359M-2 can be produced by adding, as an aspartate kinase inhibitor, an aqueous solution of S-(2-aminoethyl)-L-cysteine or salt thereof which has been filter sterilized in advance to a sterilized medium at the beginning time of the cultivation or during cultivation.

The production of Compound A-500359A, A-500359C, A-500359D, A-500359G or A-500359M-2 produced can be measured by sampling a portion of the cultured broth and subjecting it to high performance liquid chromatography. The titre of Compound A-500359A, A-500359C, A-500359D, A-500359G or A-5003 59M-2 usually reaches a peak in 3 to 9 days.

After completion of the cultivation, the cell component is separated from the cultured broth by separation with the aid of diatomaceous earth or centrifugation. Compound A-500359A, A-500359C, A-500359D, A-500359G or A-500359M-2 present in the filtrate or supernatant is purified by utilizing its physico-chemical properties with HPLC analytical data as an index. Compound A-500359A, A-500359C, A-500359D, A-500359G or A-500359M-2 present in the filtrate can be purified by using adsorbents singly or in combination, such as activated charcoal (product of Wako Pure Chemicals) and an adsorbing resin such as "Amberlite XAD-2 or XAD-4" (trade name; product of Rohm & Haas), and "Diaion HP-10, HP-20, CHP-20P or HP-50, Sepabeads SP205, SP206 or SP207" (trade name; product of Mitsubishi Chemical). Compound A-500359A, A-500359C, A-500359D, A-500359G or A-500359M-2 in the solution can be separated from impurities by passing a solution containing them through the layer of such adsorbents, or by eluting the adsorbed compounds from the layer with aqueous methanol. aqueous acetone or aqueous normal butanol.

Compounds A-500359A, A-500359C, A-500359D, A-500359G or A-500359M-2 thus obtained can be purified by adsorption column chromatography using an adsorbent such as silica gel, "Florisil" (trade name), or "Cosmosil" (trade name; product of Nacalai Tesque); partition column chromatography using "Sephadex LH-20" (trade name; product of Pharmacia Biotech): gel filtration chromatography using "Toyopearl HW40F" (trade name; product of TOSOH Corp); or high performance liquid chromatography using a normal phase or reversed phase column; or the like.

Compounds A-500359A, A-500359C, A-500359D, A-500359G or A-500359M-2 according to the present invention can be separated and purified by using the above-exemplified separation and purification means singly or in combination as needed, or in some cases, by using one of them in repetition.

Compounds A-500359A, A-500359C, A-500359D, A-500359G and A-500359M-2 of the present invention thus obtained are novel compounds not published in the literature but their antibacterial activity can be determined by a method known to those skilled in the art.

Ester derivatives, ether derivatives and N-alkylcarbamoyl derivatives can each be prepared easily by using any one of the below-described Processes A to F or using them in combination as necessary.

(Process A)

Process A is for the preparation of an ester derivative of Compound (Ia) and by this process, Compound (Ic) wherein $R^2$ is a methyl group can be prepared.

Process A

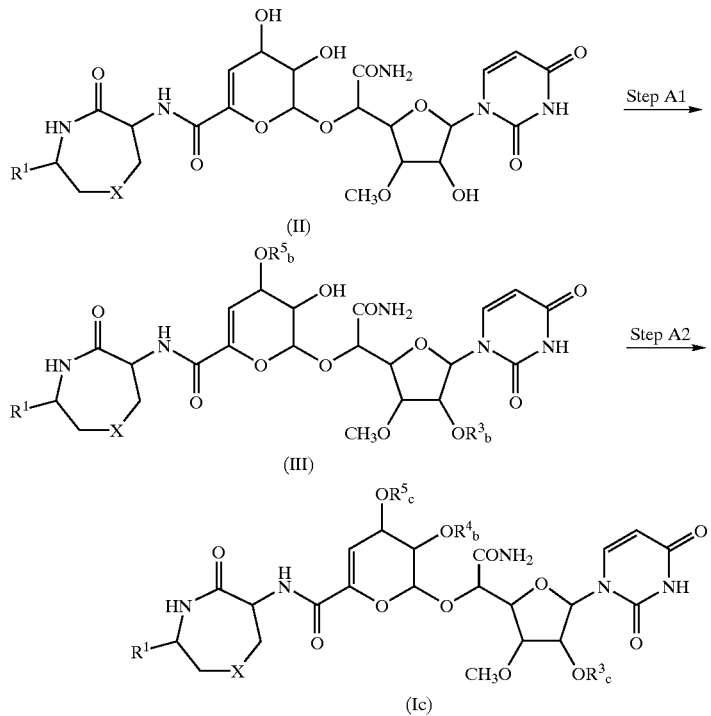

wherein: $R^1$ and X have the same meanings as described above, $R^3{}_b$ represents a hydrogen atom or a hydroxy-protecting group, $R^3{}_c$ represents a hydrogen atom, a hydroxy-protecting group or an ester residue, $R^4{}_b$ represents a hydrogen atom, a hydroxy-protecting group or an ester residue, $R^5{}_b$ represents a hydrogen atom or a hydroxy-protecting group, and $R^5{}_c$ represents a hydrogen atom, a hydroxy-protecting group or an ester residue, with the proviso that $R^3{}_b$ and $R^5{}_b$ do not represent a hydrogen atom at the same time and $R^3{}_c$, $R^4{}_b$ and $R^5{}_c$ do not all represent a hydrogen atom or a hydroxy-protecting group at the same time.

Step A1 is for the preparation of a compound having the formula (III) and it is accomplished by protecting the hydroxy group of the compound of formula (II).

Although the hydroxy-protecting step differs depending on the kind of the protecting group, it is conducted by a process well known in synthetic organic chemistry.

When the hydroxy-protecting group is a "silyl group", "alkoxymethyl group", "substituted ethyl group", "aralkyl group", "alkoxycarbonyl group", "alkenyloxycarbonyl group", "aralkyloxcarbonyl group", "1-(aliphatic acyloxy)-lower alkyl group", "1-(aliphatic acylthio)-lower alkyl group", "1-(cycloalkylcarbonyloxy)-lower alkyl group", "1-(aromatic acyloxy)-lower alkyl group", "1-(lower alkoxycarbonyloxy)-lower alkyl group, "1-(cycloalkyloxycarbonyloxy )-lower alkyl group", "phthalidyl group", "oxodioxolenylmethyl group", "carbamoyl group substituted with 2 lower alkyl groups", "1-(lower alkoxycarbonloxy )-lower alkyl aroup", "lower alkyl-dithioethyl group" or "1-(acyloxy)-alklyloxycarbonyl group", this step is conducted by reacting Compound (II) with a desired hydroxy-protecting group halide in an inert solvent in the presence of a base.

Examples of the hydroxy-protecting, group halide usable in the above reaction include trimethylsilyl chloride triethylsilyl chloride, t-butyldimethylsilyl chloride. t-butyldimethylsilyl bromide, methyldi-t-butylsilyl chloride, methyldi-t-butlsilyl bromide, diphenylmethylsilyl chloride, diphenylmethylsilyl bromide, methoxymethyl chloride, 2-methoxyethoxymethyl chloride, 2.2.2-trichloroethoxymethyl chloride, 1-ethoxyethyl chloride, benzyl chloride, benzyl bromide, α-naphthylmethyl chloride, diphenylmethyl chloride, diphenylmethyl bromide, triphenylmethyl chloride, 4-methylbenzyl chloride, 4-methoxybenzyl chloride, 4-nitrobenzyl chloride, 4-chlorobenzyl chloride, methoxycarbonyl chloride, ethoxycarbonyl chloride, 2,2,2-trichloroethoxycarbonyl chloride, vinyloxycarbonyl chloride, allyloxycarbonyl chloride, benzyloxycarbonyl chloride, benzyloxycarbonyl bromide, 4-methoxybenzyloxycarbonyl chloride, 4-nitrobenzyloxycarbonyl chloride, acetoxymethyl chloride, propionyloxymethyl chloride, butyryloxymethyl chloride, pivaloyloxymethyl chloride, pivaloyloxymethyl bromide, valeryloxymethyl chloride, 1-acetoxyethyl chloride, butyrloxyethyl chloride, 1-pivaloyloxyethyl chloride, cyclopentylcarbonyloxymethyl chloride, cyclohexylcarbonyloxymethyl chloride, 1-cyclopentylcarbonyloxyethyl chloride, 1-cyclohexylcarbonyloxyethyl chloride, methoxycarbonyloxymethyl chloride, methoxycarbonyloxymethyl bromide, ethoxycarbonyloxymethyl chloride, propoxycarbonyloxymethyl chloride, isopropoxycarbonyloxymethyl chloride, butoxycarbonyloxymethyl chloride, isobutoxycarbonyloxymethyl chloride, 1-(methoxycarbonyloxy)ethyl chloride, 1-(methoxycarbonyloxy)ethyl bromide, 1-(ethoxycarbonyloxy)ethyl chloride, 1-(isopropoxycarbonyloxy)ethyl chloride, cyclopentyloxycarbonyloxymethyl chloride, cyclohexyloxycarbonyloxymethyl chloride, 1-(cyclopentyloxycarbonyloxy)ethyl chloride, 1-(cyclohexyloxycarbonyloxy)ethyl chloride, phthalidyl chloride, phthalidyl bromide, (5-phenyl-2-oxo-1, 3-dioxolen-4-yl)methyl chloride, [5-(4-methylphenyl)-2-oxo-1,3-dioxolen-4-yl]methyl chloride, (5-methyl-2-oxo-1, 3-dioxolen-4-yl )methyl chloride, (5-methyl-2-oxo-1,3-dioxolen-4-yl)methyl bromide, (5-ethyl-2-oxo-1,3-dioxolen-4-yl)methyl chloride, dimethylcarbamoyl chloride, diethylcarbamoyl chloride, methyldithioethyl chloride, ethyldithioethyl chloride and pivaloyloxymethyloxycarbonyl chloride, of which triethylsilyl chloride, t-butyldimethylsilyl chloride, t-butyldimethylsilyl bromide, benzyl chloride, benzyl bromide, triphenylmethyl chloride, 4-methoxybenzyl chloride, 2,2,2-trichloroethoxycarbonyl chloride, allyloxycarbonyl chloride, benzyloxycarbonyl chloride, benzyloxycarbonyl bromide, acetoxymethyl chloride and pivaloyloxymethyl chloride are preferred.

Examples of the base include alkali metal hydroxides such as lithium hydroxide, sodium hydroxide and potassium hydroxide, alkali metal carbonates such as lithium carbonate, sodium carbonate and potassium carbonate, alkali metal bicarbonates such as sodium bicarbonate and potassium bicarbonate, alkali metal alkoxides such as lithium methoxide, sodium methoxide, sodium ethoxide and potassium t-butoxide, and organic amines such as triethylamine, tributylamine N-methylmorpholine, pyridine, 4-dimethylaminopyridine, picoline, lutidine, collidine, 1,5-diazabicyclo[4.3.0]-5-nonene and 1,8-diazabicyclo[5.4.0]-7-undecene. Out of these, organic amines are preferred, of which triethylamine, tributylamine, pyridine and lutidine are particularly preferred. Upon use of an organic amine in the liquid form, it also serves as a solvent when used in large excess.

There is no particular limitation on the inert solvent used in the above reaction, provided it is inert to the reaction. Examples include hydrocarbons such as hexane, benzene and toluene, halogenated hydrocarbons such as dichloromethane, chloroform, carbon tetrachloride and 1,2-dichloroethane, ethers such as ether, tetrahydrofuran and dioxane, ketones such as acetone and methyl ethyl ketone, nitriles such as acetonitrile, amides such as N,N-dimethylformamide, N,N-dimethylacetamide, N-methyl-2-pyrrolidone and hexamethylphosphoramide, and sulfoxides such as dimethylsulfoxide; and mixtures thereof. Of these, hydrocarbons and amides are preferred.

Although the reaction temperature differs with the nature of the starting compound (II), the halide and the solvent, it usually ranges from −10° C. to 100° C. (preferably 0 to 50° C.). Although the reaction time differs with the reaction temperature or the like, it ranges from 30 minutes to 5 days (preferably 1 to 3 days).

When the hydroxy-protecting group is a "tetrahydropyranyl or tetrahydrothiopyranyl group" or a "tetrahydrofuranyl or tetrahydrothiofuranyl group", Compound (II) is reacted with a cyclic ether compound such as dihydropyran, 3-bromodihydropyran, 4-methoxydihydropyran, dihydrothiopyran, 4-methoxydihydrothiopyran, dihydrofuran or dihydrothiofuran in an inert solvent in the presence of an acid.

Examples of the acid usable in the above reaction include inorganic acids such as hydrogen chloride, nitric acid, hydrochloric acid and sulfuric acid and organic acids such as acetic acid, trifluoroacetic acid, methanesulfonic acid and p-toluenesulfonic acid, of which hydrogen chloride, hydrochloric acid, sulfuric acid and trifluoroacetic acid are preferred, with hydrogen chloride and hydrochloric acid being particularly preferred.

Examples of the inert solvent usable in the above reaction (which is inert to the reaction) include hydrocarbons such as hexane, benzene and toluene, halogenated hydrocarbons such as dichloromethane, chloroform, carbon tetrachloride and 1,2-dichloroethane, ethers such as ether, tetrahydrofuran and dioxane, ketones such as acetone and methyl ethyl ketone, nitriles such as acetonitrile, arnides such as N,N-dimethylformamide, N,N-dimethylacetamide, N-methyl-2-pyrrolidone and hexamethylphosphoramide, and sulfoxides such as dimethylsulfoxide; and mixtures thereof. Of these, hydrocarbons and ethers are preferred.

Although the reaction temperature differs with the nature of the starting compound (II), the cyclic ether compound and the solvent, it usually ranges from −10° C. to 100° C. (preferably 0 to 50° C.). Although the reaction time differs with the reaction temperature or the like, it usually ranges from 30 minutes to 5 days (preferably 1 to 3 days).

When the hydroxy-protecting group is a "carbamoyl group" or "carbamoyl group substituted with one lower alkyl group". Compound (II) is reacted with an isocyanate or lower alkyl isocyanate such as methyl isocyanate or ethyl isocyanate in an inert solvent in the presence or absence of a base.

Preferred examples of the base usable in the above reaction include the above-exemplified organic amines, with triethylamine, tributylamine, pyridine and lutidine being particularly preferred.

There is no particular limitation on the inert solvent used in the above reaction provided that it is inert to the reaction. Examples include hydrocarbons such as hexane, benzene and toluene, halogenated hydrocarbons such as dichloromethane, chloroform, carbon tetrachloride and 1,2-dichloroethane, ethers such as ether, tetrahydrofuran and dioxane, ketones such as acetone and methyl ethyl ketone, nitrites such as acetonitrile. amides such as N,N-dimethylfornamide, N,N-dimethylacetamide, N-methyl-2-pyrrolidone and hexamethylphosphoramide, and sulfoxides such as dimethylsulfoxide: and mixtures thereof. Of these, hydrocarbons and ethers are preferred.

Although the reaction temperature differs with the nature of the starting compound (II), the cyclic ether compound and the solvent, it usually ranges from −10° C. to 100° C. (preferably 0 to 50° C.). Although the reaction time differs with the reaction temperature or the like. it ranges from 30 minutes to 5 days (preferably 1 to 3 days).

After completion of the reaction, the desired compound in each reaction is collected from the reaction mixture in a manner known to those skilled in the art. The desired compound can be obtained, for example, by filtering off any insoluble matter, as required, and then distilling off the solvent under reduced pressure: or by distilling off the solvent under reduced pressure, adding water to the residue, extracting the mixture with a water immiscible organic solvent such as ethyl acetate, drying over anhydrous magnesium sulfate or the like and then distilling off the solvent. If necessary, the resulting product can be purified further in a manner known to those skilled in the art, for example. by recrystallization, column chromatography or the like.

Step A2 is for the preparation of a compound having the formula (Ic). This step can be accomplished by esterifying Compound (III) and if desired, removing the hydroxy-protecting group from the esterified compound.

Esterification is conducted by reacting Compound (III) with an acid halide or acid anhydride having a desired ester residue in an inert solvent in the presence of a base.

Examples of the acid halide or acid anhydride used in the above reaction include compounds represented by any one of the formulae $R^6CO—Y$, $R^6CO_2CO_2R^9$, $R^6CO—O—COR^6$ and $R^6OCO—Y$ [wherein $R^6$ has the same meaning as described above. Y represents a halogen atom, preferably chlorine or bromine, $R^9$ represents a $C_{1-4}$ alkyl group (preferably ethyl or isopropyl)]; a mixed acid anhydride of formic acid and acetic acid, cyclic acid anhydrides such as succinic acid anhydride, glutaric acid anhydride and adipic acid anhydride: and phosphate ester introducing agents such as compounds represented by the formula $(R^7O)_2PO—Y$ (wherein Y has the same meaning as described above and $R^7$ represents a lower alkyl group), of which the compounds represented by any one of the formulas $R^6CO—Y$, $R^6CO_2CO_2R^9$, $R^6CO—O—COR^6$ and $R^6OCO—Y$ (wherein $R^6$, Y and $R^9$ have the same meanings as described above) are preferred.

Examples of the base usable in the above reaction include alkali metal hydroxides such as lithium hydroxide, sodium hydroxide and potassium hydroxide, alkali metal carbonates such as lithium carbonate, sodium carbonate and potassium carbonate, alkali metal bicarbonates such as sodium bicarbonate and potassium bicarbonate, alkali metal alkoxides such as lithium methoxide, sodium methoxide, sodium ethoxide and potassium t-butoxide, and organic amines such as triethylamine, tributylamine, N-methylmorpholine, pyridine, 4-dimethylaminopyridine, picoline, lutidine, collidine, 1,5-diazabicyclo[4.3.0]-5-nonene and 1,8-diazabicyclo[5.4.0]-7-undecene. Of these, organic amines are preferred, of which triethylamine, tributylamine, pyridine and lutidine are particularly preferred. Upon use of an organic amine in the liquid form, it also serves as a solvent when used in large excess.

When the esterifying reaction is a phosphate ester introducing reaction, it can also be conducted by reacting Compound (III) with a phosphite having a desired ester residue in an inert solvent in the presence of an acid or base, and oxidizing the reaction mixture into the corresponding phosphate ester by an oxidizing agent.

As the phosphite, a compound represented by the formula $(R^7O)_2—P—Z$, wherein $R^7$ represents a $C_{6-20}$ alkyl group and Z represents a halogen atom or a compound represented by the formula $—N(R^8)_2$ (wherein $R^8$ represents a lower $C_{6-20}$ alkyl group)] can be used.

When, in the above formula, Z represents a halogen atom, a base is employed as a catalyst and examples of the base usable are similar to those exemplified above. When Z is not a halogen atom, on the other hand, an acid is used as a catalyst. Any acid can be used, provided that it exhibits acidity as strong as acetic acid. Tetrazole is preferred.

Examples of the oxidizing agent usable in the above reaction include meta-chloroperbenzoic acid, t-butylhydroperoxide and peracetic acid, of which meta-chloroperbenzoic acid is preferred.

There is no particular limitation on the inert solvent usable in the above reaction, provided that it is inert to the reaction. Examples include hydrocarbons such as hexane, benzene and toluene, halogenated hydrocarbons such as dichloromethane, chloroform, carbon tetrachloride and 1,2-dichloroethane, ethers such as ether, tetrahydrofuran and dioxane, ketones such as acetone and methyl ethyl ketone, nitrites such as acetonitrile, amides such as N,N-dimethylformamide, N,N-dimethylacetamide, N-methyl-2-pyrrolidone and hexamethylphosphoramide, and sulfoxides such as dimethylsulfoxide; and mixtures thereof. Of these. hydrocarbons and amides are preferred.

Although the reaction temperature differs with the nature of the starting compound (III), the phosphite and the solvent, it usually ranges from −10° C. to 100° C. (preferably 0 to 50° C.). The reaction time differs with the reaction temperature and the like, but it ranges from 10 minutes to 2 days (preferably 30 minutes to 10 hours).

Esterification can also be conducted by reacting Compound (III) with a carboxylic acid having a desired ester residue in an inert solvent in the presence of a condensing agent.

Examples of the condensing agent usable in the above reaction include carbodiimides such as dicyclohexylcarbodiimide, carbonyl diimidazole and 1-(N, N-dimethylaminopropyl)-3-methylcarbodiimide hydrochloride, of which dicyclohexylcarbodiimide is preferred.

There is no particular limitation on the inert solvent used in the above reaction. provided that it is inert to the reaction. Examples include hydrocarbons such as hexane, benzene and toluene, halogenated hydrocarbons such as dichloromethane, chloroform, carbon tetrachloride and 1,2-dichloroethane. ethers such as ether, tetrahydrofuran and dioxane, ketones such as acetone and methyl ethyl ketone, nitriles such as acetonitrile, amides such as N,N-dimethylformamide, N,N-dimethylacetamide, N-methyl-2-pyrrolidone and hexamethylphosphoramide, and sulfoxides such as dimethylsulfoxide; and mixtures thereof. Of these, hydrocarbons, halogenated hydrocarbons and amides are preferred.

Although the reaction temperature differs with the nature of the starting compound (III), carboxylic acid and solvent. it usually ranges from −10° C. to 100° C. (preferably 0 to 50° C.). The reaction time differs with the reaction temperature or the like, but it usually ranges from 10 minutes to 2 days (preferably 30 minutes to 10 hours).

After completion of the reaction. the desired compound in each reaction is recovered from the reaction mixture in a manner known to those skilled in the art. The desired compound can be obtained, for example, by filtering off any insoluble matter, as necessary, and then distilling off the solvent under reduced pressure; or by distilling off the solvent under reduced pressure, adding water to the residue, extracting the mixture with a water immiscible organic solvent such as ethyl acetate, drying over anhydrous magnesium sulfate or the like and then distilling off the solvent. If necessary, the resulting product can be purified further in a manner known to those skilled in the art, for example, by recrystallization, column chromatography or the like.

Although the desired deprotection of hydroxy-protecting group differs with the kind of protecting group, it is conducted by the process well known in synthetic organic chemistry.

When the hydroxy-protecting group is an "aralkyl group" or "aralkyloxycarbonyl group", deprotection is conducted by contacting the corresponding compound with a reducing agent (including catalytic reduction) or oxidizing agent in an inert solvent.

There is no particular limitation on the inert solvent usable in the removal by catalytic reduction, provided that it is inert to the reaction. Examples include alcohols such as methanol and ethanol, ethers such as diethyl ether, tetrahydrofuran and dioxane, aromatic hydrocarbons such as toluene, benzene and xylene and aliphatic hydrocarbons such as hexane and cyclohexane and esters such as ethyl acetate and propyl acetate and aliphatic acids such as acetic acid, and mixtures of the above-exemplified organic solvent and water, of which alcohols are preferred.

Although there is no particular limitation on the catalyst usable in the above reaction (provided that it is ordinarily employed for catalytic reduction), examples include palladium on carbon. Raney nickel, platinum oxide, platinum black, rhodium-aluminium oxide, triphenylphosphine-rhodium chloride and palladium-barium sulfate, of which palladium on carbon is preferred.

Although there is no particular limitation on the pressure of hydrogen, it usually ranges from 1 to 10 times atmospheric pressure (preferably 1 to 3 times atmospheric pressure).

Although the reaction temperature or reaction time differs with the nature of the starting substance, the solvent and the catalyst, the reaction temperature usually ranges from −20° C. to 100° C. (preferably 0 to 50° C.) and the reaction time usually ranges from 30 minutes to 10 hours (preferably 1 to 5 hours).

There is no particular limitation on the inert solvent usable upon deprotection by an oxidizing agent, provided that it is inert to the reaction. Examples include ketones such as acetone, halogenated hydrocarbons such as methylene chloride, chloroform and carbon tetrachloride, nitriles such as acetonitrile, ethers such as diethyl ether, tetrahydrofuran and dioxane, amides such as dimethylformamide, dimethylacetamide and hexamethylphosphoramide and sulfoxides such as dimethylsulfoxide, and mixed solvents thereof. Preferred are the amides and sulfoxides.

There is no particular limitation imposed on the oxidizing agent usable in the above reaction, provided that it may be employed for oxidization. Examples include alkali metal persulfates such as potassium persulfate and sodium persulfate, ceric ammonium nitrate (CAN) and 2,3-dichloro-5,6-dicyano-p-benzoquinone (DDQ), of which ceric ammonium nitrate (CAN) and 2,3-dichloro-5,6-dicyano-p-benzoquinone (DDQ) are preferred.

Although the reaction temperature and reaction time differs with the nature of the starting substance, the solvent and the catalyst, the reaction temperature usually ranges from −10° C. to 150° C. (preferably 0 to 50° C.) and the reaction time usually ranges from 10 minutes to 24 hours (preferably 30 minutes to 10 hours).

When the hydroxy-protecting group is a t-butyl group, t-butoxycarbonyl group, "alkoxymethyl group", "tetrahydropyranyl or tetahydrothiopyranyl group" or "tetrahydrofuranyl or tetrahydrothiofuranyl group", deprotection is conducted by reacting the corresponding compound with an acid in an inert solvent.

There is no particular limitation on the inert solvent used in the above reaction, provided that it is inert to the reaction. Examples include hydrocarbons such as hexane and benzene, halogenated hydrocarbons such as methylene chloride, chloroform and carbon tetrachloride, esters such as ethyl acetate, ketones such as acetone and methyl ethyl ketone, alcohols such as methanol and ethanol, ethers such as ether, tetrahydrofuran and dioxane; and mixtures thereof with water. Of these, esters, ethers and halogenated hydrocarbons are preferred.

Examples of the acid usable here include inorganic acids such as hydrogen chloride, nitric acid, hydrochloric acid and sulfuric acid, organic acids such as acetic acid, trifluoroacetic acid, methanesulfonic acid and p-toluenesulfonic acid and Lewis acids such as boron trifluoride, of which the inorganic acids and organic acids are preferred and hydrochloric acid, sulfuric acid and trifluoroacetic acid are particularly preferred.

The reaction temperature usually ranges from −10° C. to 100° C. (preferably −5 to 50° C.). Although the reaction time differs with the reaction temperature or the like, it ranges from 5 minutes to 48 hours (preferably 30 minutes to 10 hours).

When the hydroxy-protecting group is a "silyl group", deprotection may be conducted by reacting the corresponding compound with a compound containing a fluoride anion, such as tetrabutylammonium fluoride, in an inert solvent.

There is no particular limitation on the inert solvent used in the above reaction insofar as it is inert to the reaction. Examples include hydrocarbons such as hexane and benzene, halogenated hydrocarbons such as methylene chloride, chloroform and carbon tetrachloride, esters such as ethyl acetate, ketones such as acetone and methyl ethyl ketone, and ethers such as ether, tetrahydrofuran and dioxane; and mixtures thereof with water. Of these, ethers are preferred.

Although there is no particular limitation imposed on the reaction temperature or reaction time, the reaction temperature usually ranges from −10 to 50° C. (preferably 0 to 30° C.) and the reaction time usually ranges from 2 to 24 hours (preferably 10 to 18 hours).

After completion of the reaction, the desired compound in this reaction is separated from the reaction mixture in a manner known to those skilled in the art. The desired compound can be obtained, for example, by neutralizing the reaction mixture as needed, filtering off any insoluble matter, adding a water-immiscible organic solvent such as ethyl acetate to the filtrate, washing the resulting mixture with water and then distilling off the solvent. If necessary, the resulting product can be purified further in a manner known to those skilled in the art, for example, by recrystallization, reprecipitation, column chromatography or the like.

If desired, the hydroxy group of the resulting compound can be esterified or protected.

Esterification of Compound (II) by using 1 to 3 molar equivalents of an esterifying agent can produce a mixture of a compound having 1 to 3 esterified hydroxy groups. By separating the compound from the mixture by column chromatography or the like and then protecting its hydroxy group if desired. Compound (Ic) is also available.
(Process B)

Process B is for the preparation of an ester derivative of Compound (Ia). By this process, Compound (Id), wherein $R^2$ is a methyl group, an —O— ester residue is present at the 2'-position, a hydroxy group or —O— ester residue is present at the 2"-position and a hydroxy group or —O— ester residue is present at the 3"-position can be prepared.
Process B

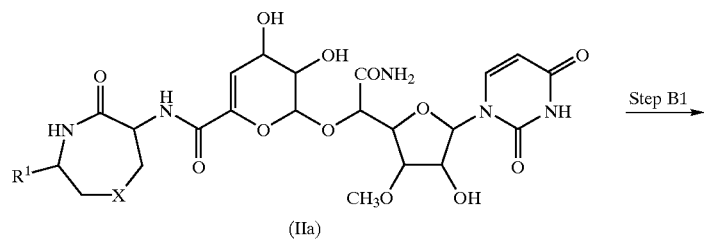

(IIa)

-continued

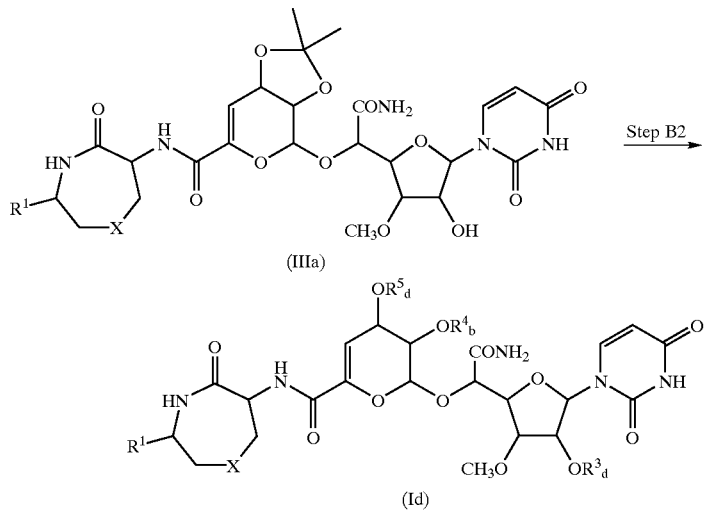

wherein: $R^1$ and X have the same meanings as described above, $R^3_d$ represents an ester residue, $R^4_b$ represents a hydrogen atom or an ester residue and $R^5_d$ represents a hydrogen atom or an ester residue.

Step B1 is a step for preparing a compound of formula (IIIa). This step is conducted by reacting a compound of formula (IIa) with an acetonide agent in an inert solvent in the presence of an acid catalyst.

Examples of the acetonide agent usable in the above reaction include acetone, methoxyisopropene and 2,2-dimethoxypropane, of which acetone and 2,2-dimethoxypropane are preferred.

Examples of the acid catalyst usable in the above reaction include inorganic acids such as hydrogen chloride, nitric acid, hydrochloric acid and sulfuric acid, organic acids such as acetic acid, trifluoroacetic acid, methanesulfonic acid and p-toluenesulfonic acid. Lewis acids such as boron trifluoride and acidic resins such as "Amberlyst 15", of which organic acids and acidic resins are preferred, with p-toluenesulfonic acid and "Amberlyst 15", being more preferred.

The reaction temperature usually ranges from −10 to 100° C. (preferably 0 to 50° C.). Although the reaction time differs with the reaction temperature and the like, it usually ranges from 1 hour to 7 days (preferably 10 hours to 3 days).

After completion of the reaction, the desired compound in this reaction is recovered from the reaction mixture in a manner known to those skilled in the art. The desired compound can be obtained, for example, by neutralizing the reaction mixture as needed, filtering off any insoluble matter, adding a water-immiscible organic solvent such as ethyl acetate to the filtrate, washing the resulting mixture with water and then distilling off the solvent. If necessary, the resulting product can be purified further in a manner known to those skilled in the art, for example, by recrystallization, reprecipitation, column chromatography or the like.

Step B2 is for the preparation of a compound represented by the formula (Id). This step is accomplished by esterifying Compound (IIIa), removing an isopropylidene group from the esterified compound and then esterifying the hydroxy group if desired.

Esterification is conducted as in the corresponding reaction described in Step A2, while the reaction to remove the isopropylidene group is conducted by reacting the corresponding compound with an acid as in Step B1 while using, as an inert solvent, water, an alcohol such as methanol or ethanol or aqueous alcohol.

(Process C)

Process C is for the preparation of an ester derivative of Compound (Ia). By this process, it is possible to prepare Compound (Ie) wherein $R^2$ represents a methyl group, a protected or unprotected hydroxy group or an —O— ester residue is present at the 2"-poisition, and a protected or unprotected hydroxy group or an —O— ester residue is present at the 3"-position.

Process C

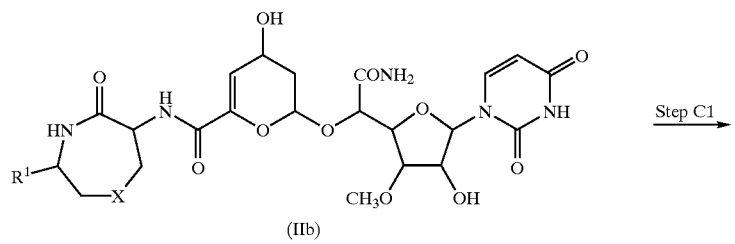

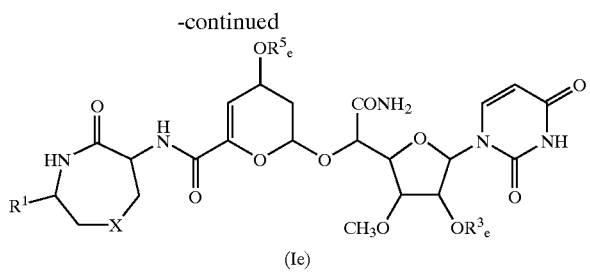

(Ie)

wherein: $R^1$ and X have the same meanings as described above, $R^3_e$ represents a hydrogen atom, a hydroxy-protecting group or an ester residue, and $R^5_e$ represents a hydrogen atom, a hydroxy-protecting group or an ester residue, with the proviso that $R^3_e$ and $R^5_e$ represent neither a hydrogen atom nor a hydroxy-protecting group simultaneously.

Step C1 is a step for preparing Compound (Ie) and this step is accomplished by esterifying the compound of the formula (IIb) and, if desired, protecting the hydroxy group.

Esterification is conducted as in the corresponding reaction described in Step A2. A mixture of monoesters may be obtained by the use of an esterifying agent in an amount of about 1 molar equivalent. This mixture can be easily separated by column chromatography or the like. Use of the esterifying agent in an amount of about 2 molar equivalents yields a diester.

The hydroxy-protecting reaction is conducted in a similar manner to that described in Step A1.

(Process D)

Process D is for the preparation of an ester derivative of Compound (Ia). By this process. Compound (If) having a protected or unprotected hydroxy group or an ester residue at the 2'-position, a protected or unprotected hydroxy group or an ester residue at the 3'-position, a protected or unprotected hydroxy group or an —O— ester residue at the 2"-position and a protected or unprotected hydroxy group or an —O— ester residue at the 3"-position can be prepared.

Process D $R^4_c$ represents a hydrogen atom, a hydroxy-protecting group or an ester residue, and $R^5_f$ represents a hydrogen atom, a hydroxy-protecting group or an ester residue, with the proviso that all of $R^2_a$, $R^3_f$, $R^4_c$ and $R^5_f$ represent neither a hydrogen atom nor a hydroxy-protecting group simultaneously.

Step D1 is a step for the preparation of Compound (If). It can be accomplished by protecting the diol portion of a compound having the formula (IIc) with an isopropylidene group, esterifying the resulting compound, removing the isopropylidene group from the esterified compound and then, esterifying or protecting the hydroxy group if desired.

The protection of the diol portion with an isopropylidene group is conducted in a similar manner to that in Step B1. Use of about 1 molar equivalent yields a mixture of a compound protected at the 2'- and 3'-positions and a compound protected at the 2"- and 3"-positions. The mixture can easily be separated, for example, by column chromatography.

Esterification is conducted in a similar manner to the corresponding reaction in Step A2. Use of an esterifying agent in an amount of about 1 molar equivalent yields a mixture of monoesters. This mixture can easily be separated, for example, by column chromatography. Use of the esterifying agent in an amount of about 2 molar equivalents yields a diester.

The reaction to remove the isopropylidene group is conducted in a similar manner to the corresponding reaction in Step B2.

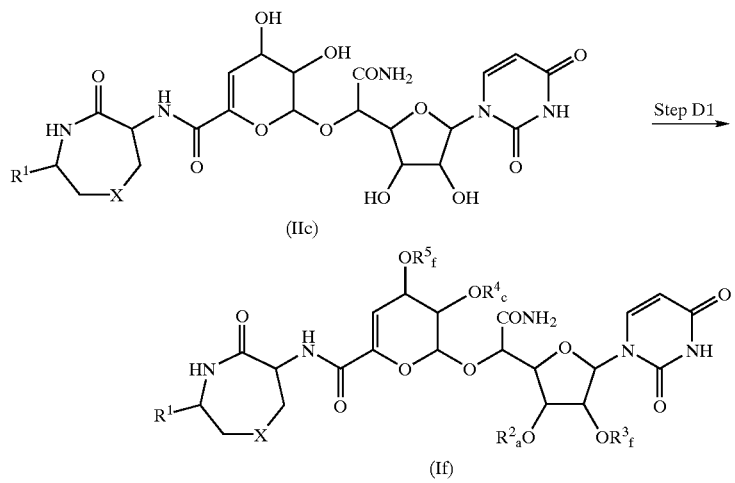

wherein: $R^1$ and X have the same meanings as described above, $R^2_a$ represents a hydrogen atom, a hydroxy-protecting group or an ester residue, $R^3_f$ represents a hydrogen atom, a hydroxy-protecting group or an ester residue, The esterification of the resulting compound, which is conducted as desired, is conducted in a similar manner to the corresponding reaction in Step A2. Use of an esterifying agent in an amount of about 1 molar equivalent yields a mixture of monoesters. This mixture can easily be separated, for example, by column chromatography. Use of the esterifying agent in an amount of about 2 molar equivalents yields a diester. The hydroxy-protecting reaction of the compound thus obtained is conducted in a similar manner to Step A1. Use of a protecting agent in an amount of about 1 molar equivalent yields a mixture of compounds each having one protected hydroxy group. This mixture can easily be separated, for example, by column chromatography. Use of the protecting agent in an amount of about 2 molar equivalents yields a compound having two protected hydroxy groups.

Compound (If) is also available by esterifying the compound of the formula (IIc) with 1 to 4 molar equivalents of an esterifying agent, separating the resulting mixture, for example, by column chromatography and if desired, protecting the hydroxy group.

(Process E)

Process E is for the preparation of an ether derivative of formula (Ig) and (Ih) of Compound (Ia).

Process E

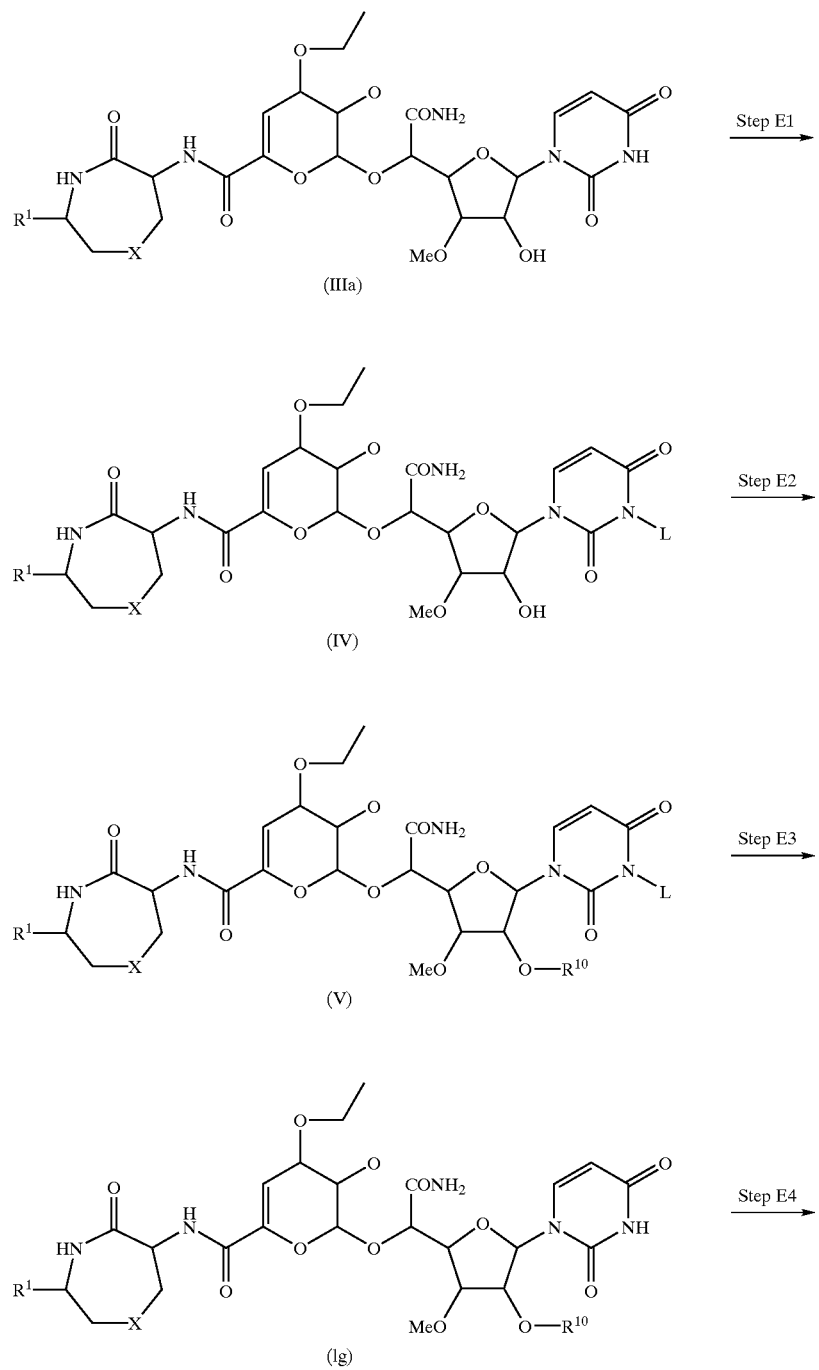

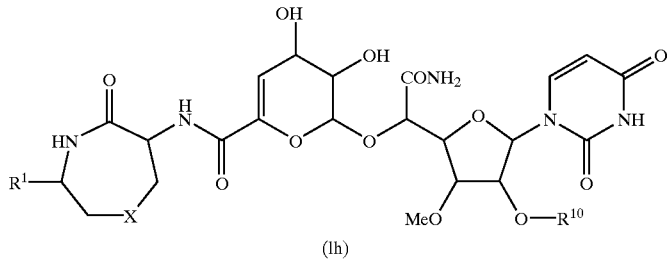

(Ih)

wherein: $R^1$ and X have the same meanings as described above, $R^{10}$ represents the above-described ether residue and L represents a protecting group for the nitrogen atom of the uracil residue.

Step E1 is a step for preparing a compound represented by formula (IV) by reacting a compound of formula (IIIa) with an alkylation protecting reagent represented by the formula LY (wherein L and Y have the same meanings as described above) in an inert solvent in the presence of a base.

Examples of the alkylation protecting reagent (LY) usable in the above reaction include 4-methoxybenzyloxymethyl chloride, pivaloyloxymethyl chloride and acetoxymethyl chloride, of which 4-methoxybenzyloxymethyl chloride is preferred.

Examples of the base usable in the above reaction include tertiary amines such as 1,8-diazabicyclo[5.4.0]undec-7-ene (DBU) and 1,5-diazabicyclo[4.3.0]non-5-ene (DBN) and alkali metal hydrides such as sodium hydride and potassium hydride, of which 1,8-diazabicyclo[5.4.0]undec-7-ene (DBU) is preferred.

Examples of the solvent usable in the above reaction include ethers such as diethyl ether, tetrahydrofuran and dioxane and amides such as N,N-dimethylformamide and N,N-dimethylacetamide, of which N,N-dimethylformamide is preferred.

The reaction temperature usually ranges from −30 to 100° C. (preferably −10 to 30° C.). Although the reaction time differs with the reaction temperature and the like, it usually ranges from 30 minutes to 1 day (preferably 1 hour to 5 hours).

After completion of the reaction. the desired compound in this reaction is recovered from the reaction mixture in a manner known to those skilled in the art. The desired compound can be obtained, for example, by neutralizing the reaction mixture as needed, filtering off any insoluble matter, adding a water-immiscible organic solvent such as ethyl acetate or methylene chloride to the filtrate, washing the resulting mixture with a diluted aqueous solution of hydrochloric acid, an aqueous solution of sodium bicarbonate or saturated saline, drying over anhydrous magnesium sulfate or anhydrous sodium sulfate and then distilling off the solvent. If necessary, the resulting product can be purified further in a manner known to those skilled in the art, for example, recrystallization, reprecipitation, column chromatography or the like.

Step E2 is a step for preparing a compound of the formula (V) by reacting a compound of the formula (IV) with an alkylating agent having a desired ether residue in an inert solvent in the presence of a base.

Examples of the alkylating agent usable in the above reaction include alkyl halides and alkyl triflates, of which an alkyl iodide is preferred.

Examples of the base usable in the above reaction include tertiary amines such as 1,8-diazabicyclo[5.4.0]undec-7-ene (DBU) and 1,5-diazabicyclo[4.3.0]non-5-ene (DBN) and alkali metal hydrides such as sodium hydride and potassium hydride, of which sodium hydride is preferred.

Examples of the solvent usable in the above reaction include ethers such as diethyl ether, tetrahydrofuran and dioxane and amides such as N,N-dimethylformamide and N,N-dimethylacetamide, of which N,N-dimethylformamide is preferred.

The reaction temperature usually ranges from −30 to 100° C. (preferably −10 to 30° C.). Although the reaction time differs with the reaction temperature and the like, it usually ranges from 1 hour to 2 days (preferably 1 hour to 10 hours).

After completion of the reaction, the desired compound in this reaction is recovered from the reaction mixture in a manner known to those skilled in the art. The desired compound can be obtained, for example, by neutralizing the reaction mixture as needed, filtering off any insoluble matter, adding a water-immiscible organic solvent such as ethyl acetate or methylene chloride to the filtrate, washing the resulting mixture with a diluted aqueous solution of hydrochloric acid, an aqueous solution of sodium bicarbonate or saturated saline, drying over anhydrous magnesium sulfate or anhydrous sodium sulfate and then distilling off the solvent. If necessary, the resulting product can be purified further in a manner known to those skilled in the art, for example, recrystallization, reprecipitation, column chromatography or the like.

Step E3 is a step for preparing a compound of the formula (Ig) by reacting a compound of the formula (V) with an agent capable of deprotecting the protected uracil residue in an inert solvent.

When the protecting group contained in the uracil residue in the formula (V) is a 4-methoxybenzyloxymethyl group, examples of the deprotecting agent usable here include 2,3-dichloro-5,6-dicyano-1,4-benzoquinone (DDQ) or cerium (IV) ammonium nitrate (CAN) [preferably 2,3-dichloro-5,6-dicyano-1,4-benzoquinone (DDQ)], while examples of the solvent usable include water, alcohols such as methanol and ethanol, and halogenated hydrocarbons such as methylene chloride and chloroform, and mixtures thereof (preferably a mixed solvent of methylene chloride and water). The reaction temperature usually ranges from 0 to 150° C. (preferably 10 to 100° C.). Although the reaction time differs with the reaction temperature and the like, it usually ranges from 1 hour to 2 days (preferably 1 hour to 10 hours).

When the protecting group contained in the uracil group in the formula (V) is a pivaloyloxymethyl or acetoxymethyl group, examples of the deprotecting agent usable here include alkali metal hydroxides such as sodium hydroxide and potassium hydroxide, alkali metal carbonates such as sodium carbonate and potassium carbonate, aqueous ammonia, and amines such as methylamine and ethylamine (preferably sodium hydroxide or potassium carbonate).

Examples of the solvent include water, alcohols such as methanol and ethanol, ethers such as dioxane and tetrahydrofuran, and mixtures thereof (preferably a mixed solvent of the alcohols and ethers with water). The reaction temperature usually ranges from 0 to 100° C. (preferably 10 to 50° C.). Although the reaction time differs with the reaction temperature and the like. it usually ranges from 10 minutes to 1 day (preferably 1 hour to 10 hours).

After completion of the reaction, the desired compound in the above reaction is recovered from the reaction mixture in a manner known to those skilled in the art. The desired compound can be obtained, for example, by neutralizing the reaction mixture as needed, filtering off any insoluble matter, adding a water-immiscible organic solvent such as ethyl acetate or methylene chloride to the filtrate, washing the resulting mixture with a diluted aqueous solution of hydrochloric acid, an aqueous solution of sodium bicarbonate or saturated saline as needed, drying over anhydrous magnesium sulfate or anhydrous sodium sulfate and then distilling off the solvent. If necessary, the resulting product can be purified further in a manner known to those skilled in the art, for example, by recrystallization, reprecipitation, column chromatography or the like.

Step E4 is a step for preparing a compound of the formula (Ih) by reacting a compound of the formula (Ig) with an acid catalyst in an inert solvent.

Examples of the acid catalyst include inorganic acids such as hydrochloric acid, sulfuric acid and nitric acid, organic acids such as acetic acid, trifluoroacetic acid, trichloroacetic acid, methanesulfonic acid and p-toluenesulfonic acid. Lewis acids such as boron trifluoride and acidic resins such as "Amberlyst 15", of which acetic acid, trifluoroacetic acid, p-toluenesulfonic acid and "Amberlyst 15" are preferred.

Examples of the solvent include water, alcohols such as methanol and ethanol and ethers such as dioxane and tetrahydrofuran, and mixed solvents of the alcohol or ether with water, of which methanol is preferred.

The reaction temperature usually ranges from 0 to 150° C. (preferably 10 to 80° C.). Although the reaction time differs with the reaction temperature and the like, it usually ranges from 1 hour to 2 days (preferable 3 hours to 1 day).

After completion of the reaction, the desired compound in this reaction is recovered from the reaction mixture in a manner known to those skilled in the art. The desired compound can be obtained, for example, by neutralizing the reaction mixture as needed, filtering off any insoluble matter, adding a water-immiscible organic solvent such as ethyl acetate or methylene chloride to the filtrate, washing the resulting mixture with a diluted aqueous solution of hydrochloric acid, an aqueous solution of sodium bicarbonate and saturated saline as needed, and then distilling off the solvent. If necessary, the resulting product can be purified further in a manner known to those skilled in the art, for example, by recrystallization, reprecipitation, or column chromatography.

Compound (Ih) thus obtained can be converted to the corresponding hydroxy-protected compound. ester derivative or N-alkylcarbamoyl derivative by any one of Processes A to D and below-described Process F.

(Process F)

Process F is for the preparation of an N-alkylcarbamoyl derivative of the invention compound (Ia).

Process F

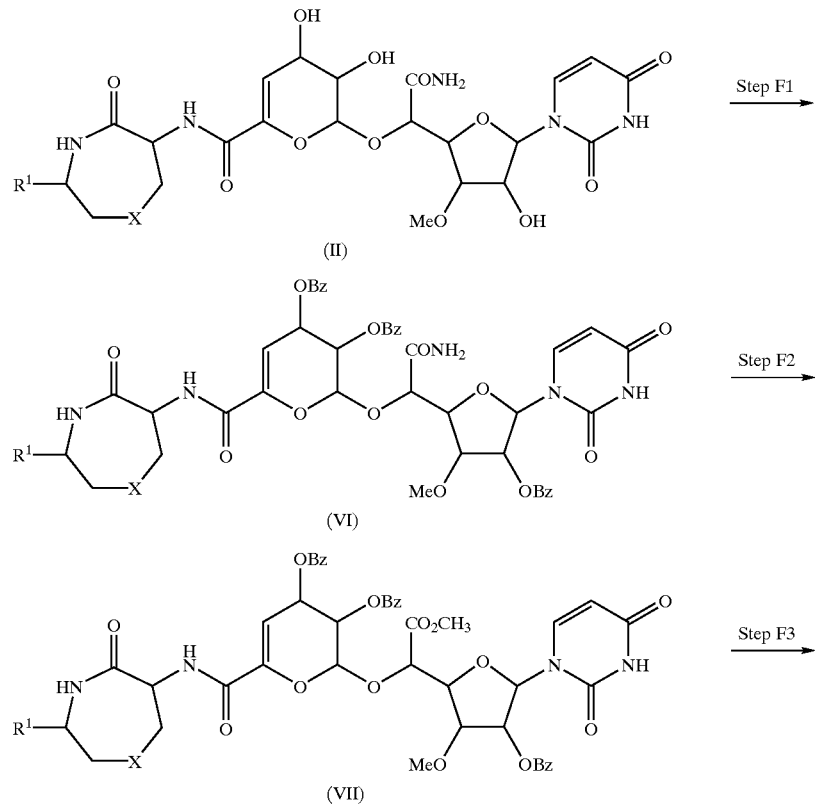

-continued

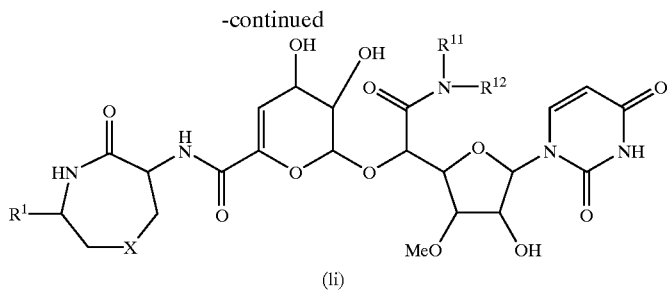

(Ii)

wherein: $R^1$ and X have the same meanings as described above, $R^{11}$ and $R^{12}$ each independently represent the N-alkyl residue of the above-described N-alkyl-carbamoyl group and Bz represents a benzoyl group.

Step F1 is a step for preparing a compound of formula (VI) by reacting a compound of formula (II) with a benzoylating agent in an inert solvent in the presence of a base.

Examples of the benzoylating agent include benzoyl chloride, benzoyl bromide and benzoic anhydride, of which benzoic anhydride is preferred.

Examples of the base usable in the above reaction include organic amines such as triethylamine, 1,8-diazabicyclo[5.4.0]undec-7-ene (DBU), 1,5-diazabicyclo[4.3.0]non-5-ene (DBN), pyridine and 4-dimethylaminopyridine and alkali metal hydrides such as sodium hydride and potassium hydride, of which pyridine and 4-dimethylaminopyridine are preferred.

Examples of the solvent usable in the above reaction include ethers such as diethyl ether, tetrahydrofuran and dioxane, amides such as N,N-dimethylformamide and N,N-dimethylacetamide, halogenated hydrocarbons such as methylene chloride and chloroform, and pyridine, of which pyridine is preferred.

The reaction temperature usually ranges from −30 to 100° C. (preferably −10 to 30° C.). Although the reaction time differs with the reaction temperature and the like, it usually ranges from 30 minutes to 1 day (preferably 1 hour to 10 hours).

After completion of the reaction, the desired compound in this reaction is recovered from the reaction mixture in a manner known to those skilled in the art. The desired compound can be obtained, for example, by neutralizing the reaction mixture if necessary, filtering off any insoluble matter, adding a water-immiscible organic solvent such as ethyl acetate or methylene chloride to the filtrate, washing the resulting mixture with a diluted aqueous solution of hydrochloric acid, an aqueous solution of sodium bicarbonate and saturated saline as needed, drying over anhydrous magnesium sulfate or anhydrous sodium sulfate, and then distilling off the solvent. If necessary, the resulting product can be purified further in a manner known to those skilled in the art, for example, by recrystallization, reprecipitation or column chromatography.

Step F2 is a step for preparing a compound of formula (VII) by reacting a compound of formula (VI) with nitrosylsulfuric acid at 0 to 30° C. in an inert mixed solvent of methylene chloride and water and then reacting diazomethane with the reaction mixture at 0 to 30° C. in methylene chloride.

After completion of the reaction, the desired compound in this reaction is recovered from the reaction mixture in manner known to those skilled in the art. The desired compound can be obtained, for example, by neutralizing the reaction mixture as needed filtering off any insoluble matter, adding a water-immiscible organic solvent such as ethyl acetate or methylene chloride to the filtrate, washing the resulting mixture with a diluted aqueous solution of hydrochloric acid, an aqueous solution of sodium bicarbonate and saturated saline as needed, drying over anhydrous magnesium sulfate or anhydrous sodium sulfate and then distilling off the solvent. If necessary, the resulting product can be purified further in a manner known to those skilled in the art, for example, by recrystallization, reprecipitation or column chromatography.

Step F3 is a step for preparing a compound of the formula (Ii) by reacting a compound of the formula (VII) with an amine in an inert solvent.

Examples of the solvent usable in the above reaction include water, alcohols such as methanol and ethanol and amides such as N,N-dimethylformamide and N,N-dimethylacetamide, of which alcohols are preferred.

The reaction temperature usually ranges from 0 to 100° C. (preferably 10 to 60° C.). Although the reaction time differs with the reaction temperature and the like, it usually ranges from 30 minutes to 1 day (preferably 1 hour to 10 hours).

After completion of the reaction, the desired compound in this reaction is recovered from the reaction mixture in a manner known to those skilled in the art. The desired compound can be obtained, for example, by neutralizing the reaction mixture as needed, filtering off any insoluble matter, adding a water-immiscible organic solvent such as ethyl acetate or methylene chloride to the filtrate, washing the resulting mixture with a diluted aqueous solution of hydrochloric acid, an aqueous solution of sodium bicarbonate and saturated saline as needed, drying over anhydrous magnesium sulfate or anhydrous sodium sulfate and then distilling off the solvent. If necessary, the resulting product can be purified further in a manner known to those skilled in the art, for example, by recrystallization, reprecipitation or column chromatography.

Compound (Ii) thus obtained can be converted to the corresponding hydroxy-protected compound, ester derivative or ether derivative by using any one of the above-described Processes A to E.

The present invention also provides;

(1) Compound A-500359E represented by the following formula (XI):

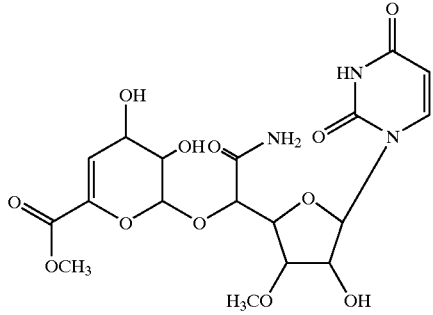

(XI)

or a salt thereof;

(2) Compound A-500359F represented by the following formula (XII):

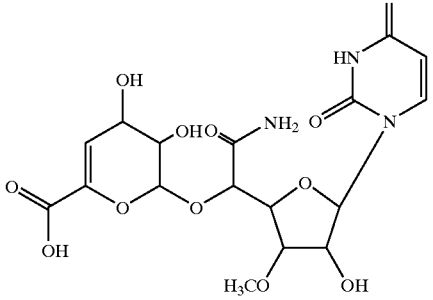

(XII)

or a salt thereof;

(3) Amide derivative of Compound A-500359F represented by the following formula (XIII):

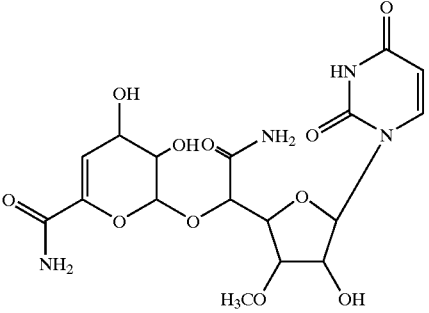

(XIII)

or a salt thereof;

(4) Compound A-500359H represented by the following formula (XIV):

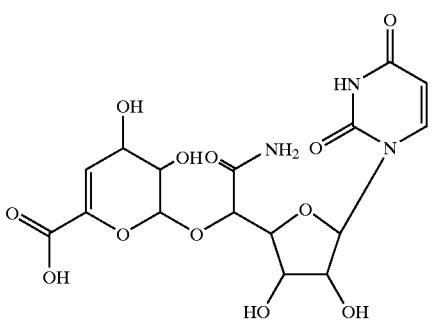

(XIV)

or a salt thereof;

(5) Compound A-500359J represented by the following formula (XV):

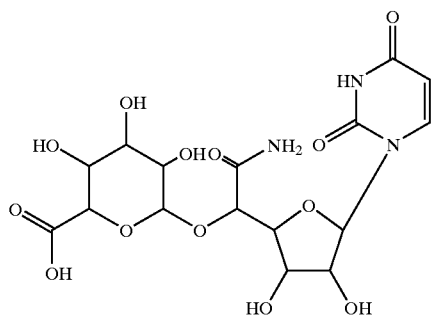

(XV)

or a salt thereof;

(6) Compound A-500359M-3 represented by the following formula (XVI):

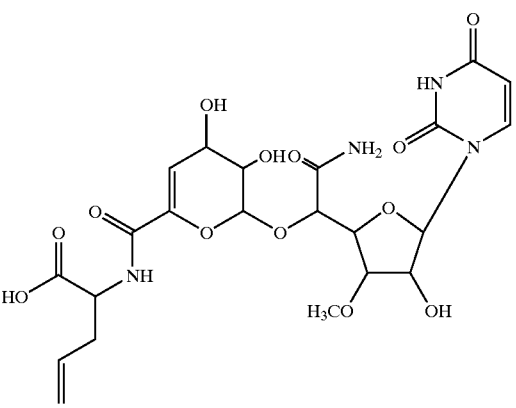

(XVI)

or a salt thereof;

(7) a process for preparing the compound as described in (1), (2), (4) or (5) by cultivating a microorganism capable of producing said compound and belonging to the Streptomyces spp. and recovering the compound from the cultured broth;

(8) a process as described in (7), wherein the microorganism belonging to the Streptomyces spp. and capable of producing the compound is *Streptomyces griseus* SANK60196 (FERM BP-5420) and is capable of producing the compounds as described in (1), (2), (4), or (5);

(9) a microorganism which belongs to the Streptomyces spp. and is capable of producing the compound as described in (1), (2), (4) or (5);

(10) a microorganism as described in (9) which is *Streptomyces griseus* SANK60196 (FERM BP-5420);

(11) a process for preparing the compound as described in (1), (4) or (5) by cultivating a microorganism (which belongs to the Streptomyces spp. and is capable of producing the compound) by using, singly or in combination, S-(2-aminoethyl)-L-cysteine, salts thereof and L-allylglycine as an additive to a medium and collecting the compound as described in (1), (2), (4) or (6) from the cultured broth;

(12) a composition for the treatment or prevention of infectious diseases which contains the compound as described in (1), (2), (3), (4), (5) or (6) or a pharmacologically acceptable salt thereof as an effective ingredient;

(13) use of the compound as described in (1), (2), (3), (4), (5) or (6) or a pharmacologically acceptable salt thereof for the preparation of a medicament for treating or preventing infectious diseases; and

(14) a method of treating or preventing infectious diseases, which comprises administering, to a warm-blooded animal, a pharmacologically effective amount of the compound as described in (1), (2), (3), (4), (5) or (6) or a pharmacologically acceptable salt thereof.

Compounds of the present invention represented by any one of the formulae (XI), (XII), (XIII), (XIV), (XV) and (XVI) are produced in the culture broth of *Streptomyces griseus* Strain SANK60196 which belongs to the Streptomyces spp. and has been separated from the soil collected from Mt. Tsukuba/Igaraki-ken; or produced by microbial conversion in the cultivation process or chemical conversion in the isolation and purification process.

Compound A-500359E of the formula (XI), Compound A-500359F of the formula (XII), Amide derivative of Compound A-500359F of the formula (XIII).

Compound A-500359H of the formula (XIV), Compound A-500359J of the formula (XV) and Compound A-500359M-3 of the formula (XVI) of the present invention each contain asymmetric carbons, and each may therefore exist as various optical isomers. In the present invention, isomers of each of Compound A-500359E, Compound A-500359F, Amide derivative of Compound A-500359F, Compound A-500359H, Compound A-500359J and Compound A-500359M-3 are represented by the same formula, but the present invention embraces all the isomers including racemic compounds and also mixtures thereof. When a stereospecific synthesis process is adopted or an optically active compound is employed as a starting compound, the isomer of each of Compound A-500359E, Compound A-5000359F, Amide derivative of Compound A-500359F, Compound A-500359H, Compound A-500359J and Compound A-500359M-3 may be prepared directly or, if it is prepared in the form of a mixture, each isomer may be obtained in a manner known to those skilled in the art.

Compound A-500359F, Compound A-500359H, Compound A-500359J and Compound A-500359M-3 of the present invention can each be converted into the corresponding salt by a method known to those skilled in the art. The present invention embraces such salts of Compound A-500359F, Compound A-500359H, Compound A-500359J and Compound A-500359M-3. There is no particular restriction on the nature of the salt of any of Compound A-500359F, Compound A-500359H, Compound A-500359J and Compound A-500359M-3, provided that it is medically employed and is pharmacologically acceptable. When the salt of Compound A-500359F, Compound A-500359H, Compound A-500359J or Compound A-500359M-3 is employed for the purpose other than a medicament, for example, employed as an intermediate, no limitation is imposed. Preferred examples of such a salt include alkali metal salts such as a sodium salt, a potassium salt, or a lithium salt, alkaline earth metal salts such as a calcium salt or a magnesium salt, metal salts such as an aluminium salt, an iron salt, a zinc salt, a copper salt, a nickel salt or a cobalt salt, inorganic salts such as an ammonium salt, organic amine salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, a N-benzylphenethylamine salt, a piperazine salt and a tetraamethylammonium salt, or a tris(hydroxymethyl) aminomethane salt, and amino acid salts such as a glycine salt, a lysine salt, an arginine salt, an ornithine salt, or an asparagine salt. More preferred are salts preferably usable as a pharmacologically acceptable salt such as a sodium salt, a potassium salt and an ammonium salt.

Compound A-500359E, Compound A-500359F, Amide derivative of Compound A-500359F, Compound A-500359H, Compound A-500359J and Compound A-500359M-3 of the present invention and salts thereof may each exist as a solvate. For example, when they are allowed to stand in the air or recrystallized, water is adsorbed thereto by absorption or a hydrate may be formed. Such a solvate is also embraced in the present invention.

The present invention also embraces all the compounds, so-called prodrugs, which will be converted into Compound A-500359E, Compound A-500359F, Amide derivative of compound A-500359F, Compound A-500359H, Compound A-500359J or Compound A-500359M-3 by metabolism in vivo.

Compound A-500359E, Compound A-500359F, Compound A-500359H, Compound A-500359J and Compound A-500359M-3 of the present invention which are represented by the formulae (XI), (XII), (XIV), (XV) and (XVI) respectively are available by culturing, in a suitable medium, a microorganism belonging to the Streptomyces spp. and recover from the cultured broth. *Streptomyces griseus* Strain SANK 60196 (which will hereinafter be called "Strain SANK60196"), preferred as the microorganism capable of producing Compound A-500359E, Compound A-500359F, Compound A-500359H, Compound A-500359J and Compound A-500359M-3 are, as described above, collected and isolated from the soil of Ttsukubasan/Ibaraki Prefecture in a conventional manner. Strain SANK60196 has the biological characteristics as described above.

The various characteristics of the actinomycetes belonging to Streptomyces spp. such as Strain SANK60196 are not stable, but as is well known, they easily change naturally or artificially. The strains usable in the present invention include all such variants. The present invention embraces all the strains belonging to the Streptomyces spp. and capable of producing Compound A-500359E, Compound A-500359F, Compound A-500359H, Compound A-500359J or Compound A-500359M-3.

Any synthetic or natural medium is usable as a medium for culturing the microorganism capable of producing Compound A-500359E, Compound A-500359F, Compound A-500359H, Compound A-500359J or Compound A-500359M-3, insofar as it contains a source selected from carbon sources, nitrogen sources, inorganic ions and organic nutrition sources as necessary.

Examples of the nutrition source usable here include knows carbon sources, nitrogen sources and inorganic salts which are conventionally used for the cultivation of a mycotic or actinomycete strain and are utilisable by microorganisms.

Specific examples of the carbon source include glucose, fructose, maltose, sucrose, mannitol, glycerol, dextrin, oats, rye, corn starch, potato, corn meal, soybean meal, cotton seed oil, glutinous malt syrup, syrup, soybean oil, citric acid and tartaric acid. They may be used either singly or in combination. The amount of the carbon source to be added usually varies, but is not limited to, within a range of from 1 to 10 wt. % of the amount of the medium.

A substance containing a protein or a hydrolysate thereof is generally employed as the nitrogen source. Preferred examples of the nitrogen source include soybean meal, wheat bran, peanut meal, cotton seed meal, skimmed milk, casein hydrolysate, Pharmamine (product of Sheffield Chemical), fish meal, corn steep liquor, peptone, meat extract, pressed yeast, dry veast, yeast extract, malt extract, potato, ammonium sulfate, ammonium nitrate and sodium nitrate. It is preferred to use the above-exemplified nitrogen sources either singly or in combination in an amount ranging from 0.2 to 6 wt. % of the amount of the medium.

Any ordinarily employed salt containing an ion such as sodium, ammonium, calcium, phosphate, sulfate, chloride or carbonate can be used as the nutrient inorganic salt. In addition, trace of metals such as potassium, calcium, cobalt, manganese, iron and magnesium are usable.

The addition of cobalt, skimmed milk or yeast extract is particularly effective in the production of Compound A-500359E, Compound A-500359F, Compound A-500359H or Compound A-500359J.

Upon culturing the microorganism, an inhibitor of antibiotic biosynthesis can be added to produce Compound A-500359E, Compound A-500359F and Compound A-500359H, Compound A-500359E, Compound A-500359F and Compound A-500359H can each be produced, for example, by using S-(2-aminoethyl)-L-cysteine or salt thereof which is an aspartate kinase inhibitor singly or in combination with cobalt, skimmed milk and yeast extract, as a medium additive. For example, use of the above-described additive in combination with skimmed milk improves productivity of Compound A-500359E, Compound A-500359F and Compound A-500359H. The additive can be added to give its final concentration ranging from 1 to 100 mM. For the production of Compound A-500359E, Compound A-500359F and Compound A-500359H, the final concentration of 10 mM is preferred.

Use of the above-described additive in combination with an amino acid or salt thereof makes it possible to produce useful compounds related to Compound A-500359F and Compound A-500359H. In particular, by the use in combination with L-allylglycine or a salt thereof. Compound A-500359M-3 (XVI) is available. The L-allylglycine can be added at a final concentration ranging from 1 to 100 mM. At the final concentration of 10 mM. Substance A-500359M-3 can be produced preferably.

Upon liquid culture, an antifoamer such as silicone oil, vegetable oil, surfactant or the like can be used.

The medium for cultivation of Strain SANK60196 to produce Compound A-500359E, Compound A-500359F, Compound A-500359H, or Compound A-500359J preferably has a pH ranging from 5.0 to 8.0.

Although the temperature which allows growth of Strain SANK60196 ranges from 12 to 36° C. the strain is preferably cultured at 18 to 28° C. more preferably 19 to 23° C., in order to produce Compound A-500359E, Compound A-500359F, Compound A-500359H and Compound A-500359J.

By in order to obtain Compound A-500359E, Compound A-500359F, Compound A-500359H, Compound A-500359J and Compound A-500359M-3, an aerobic culture of Strain SANK60196 can be used. Examples of such a cultivation method include ordinarily employed aerobic culture such as solid culture, shaking culture, and aeration agitation culture.

For small-scale cultivation, shake culture for several days at 19 to 23° C. is preferred. Cultivation is started by growing a step of seed culture in a first or second stage process in a baffled Erlenmeyer flask (equipped with a water flow adjusting wall) or an ordinarily-employed Erlenmeyer flask. A carbon source and a nitrogen source can be used in combination as a medium in the seed culture. The seed culture flask may be shaken at 19 to 23° C. for 5 days in a thermostat incubator or shaken until the seed culture grows sufficiently. The seed culture thus grown is used for inoculation on the second seed culture medium or a production medium. When the seed cultures are used under an intermediate growing step, they are allowed to grow in a similar manner, followed by partial inoculation into a production medium. The flask into which the seeds have been inoculated is subjected to culturing with shaking at a constant temperature for several days, and after completion of the cultivation, the cultured medium in the flask is centrifuged or filtered.

For large-scale cultivation, on the other hand, use of a jar fermenter or tank equipped with an agitator and an aeration apparatus is preferred. Prior to cultivation in such a container, a nutrient medium is heated to 121 to 130° C. for sterilization. After cooling, the seed cultures which have been allowed to grow in advance by the above-described method are inoculated on the sterilized medium. Then, cultivation is carried out with aeration and agitation at 19 to 23° C. This method is suitable for preparing a large amount of compounds.

Compound A-500359E, A-500359F or A-500359H can also be produced by adding, as an aspartate kinase inhibitor, an aqueous solution of S-(2-aminoethyl)-L-cysteine or salt thereof which has been previously filter-sterilized in advance to a sterilized medium at the start of, or during, cultivation.

Compound A-500359M-3 can be produced by separately or simultaneously adding aqueous solutions of S-(2-aminoethyl)-L-cysteine or salt thereof, and L-allyl glycine or salt thereof which have been filter sterilized in advance to the sterilized medium at the start of, or during, cultivation.

The product of Compound A-500359E, A-500359F, A-500359H, A-500359J and A-500359M-3 by cultivation can be measured by subjecting a portion of the cultured broth to HPLC analysis. The titre of Compound A-500359E, A-500359F, A-500359H, A-500359J and A-500359M-3 usually reaches a peak in 3 to 15 days.

After completion of the cultivation, the cell component is separated from the cultured broth by filtration with the aid of diatomaceous earth or centrifugation and Compound A-500359E, A-500359F, A-500359H, A-500359J and A-500359M-3 present in the filtrate or supernatant is purified by utilizing their physico-chemical properties with HPLC analytical data as an index. As diatomaceous earth, "Celite 545" (product of Celite Corporation) is preferred. Compound A-500359E, A-500359F, A-500359H, A-500359J and A-50359M-3 present in the filtrate can be purified by using adsorbents singly or in combination, for example, activated charcoal or an adsorbing resin such as "Amberlite XAD-2 or XAD4" (product of Rohm & Haas), and "Diaion HP-10, HP-20, CHP-20P, HP-50 or SP207 (each. product of Mitsubishi Chemical). Compound A-500359E, A-500359F, A-500359H. A-500359J and A-500359M-3 can be separated from impurities by passing a solution containing Compound A-500359E, A-500359F, A-500359H, A-500359J and A-5003 59M-3 through the layer of such an adsorbent as described above, and removing the impurities adsorbed thereto from the solution; or by eluting the adsorbed Compound A-500359E, A-500359F, A-500359H, A-500359J and A-500359M-3 with aqueous methanol, aqueous acetone, aqueous n-butanol, aqueous ammonia, ammonia-containing aqueous methanol or ammonia-containing aqueous acetone. When an ammonia-containing solution is employed as an eluent, the amide derivative of compound A-500359F happens to be produced upon elution from the column or concentration.

Compound A-500359E, Compound A-500359F, the amide derivative of Compound A-500359F, Compound A-500359H, Compound A-500359J and Compound A-500359M-3 thus obtained can be purified by adsorption column chromatography using silica gel, "Florisil", "Cosmosil" (product of Nacalai Tesque), or "Diaion CHP-20P or SP207" (product of Mitsubishi Chemical); gel filtration chromatography with "Sephadex G-10 (product of Pharmacia Biotech) or "Toyopearl HW40F" (product of TOSOH Corporation); anion exchange chromatography with "Dowex 1 or SBR-P" (product of Dow Chemical) or "Diaion PA316" (product of Mitsubishi Chemical); normal phase and reversed phase HPLC; or the like.

Compound A-500359E, Compound A-500359F, the amide derivative of Compound A-500359F, Compound A-500359H, Compound A-500359J and Compound A-500359M-3 of the present invention can be separated and purified by using the above-exemplified separation and purification means singly or in combination as needed, or in some cases, by using one of them in repetition.

Compound A-500359F can be obtained by hydrolysis of Compound A-500359E. For example, hydrolysis is preferably conducted under basic conditions, preferably in aqueous basic solution.

Examples of the basic compound usable for hydrolysis include alkali metal hydroxides and weak acid salts thereof such as sodium hydroxide, potassium hydroxide, lithium hydroxide, sodium acetate, sodium carbonate, potassium carbonate and sodium bicarbonate; alkaline earth metal hydroxides and weak acid salts thereof such as calcium hydroxide, magnesium hydroxide and magnesium acetate; inorganic basic compounds and basic salts thereof such as ammonia; organic amines and basic salts thereof such as t-octylamine, dibenzylamine, morpholine, glucosamine, phenylglycine alkyl ester, ethylenediamine, N-methylglucamine, guanidine, diethylamine, triethylamine, dicyclohexylamine, N,N'-dibenzylethylenediamine. chloroprocaine, procaine, diethanolamine, N-benzylphenethylamine, piperazine, tetramethylammonia and tris(hydroxymethyl)aminomethane. A basic buffer containing an alkali metal ion, an alkaline earth metal ion, an inorganic ion such as ammonia, or an organic amine ion of the above-exemplified basic compounds may also be employed. Among them, alkali metal hydroxides are preferred, of which sodium hydroxide is particularly preferred. In particular, hydrolysis of Compound A-500359E by using sodium hydroxide can easily produce Compound A-500359F.

The concentration of the basic compound used in the above-described reaction preferably ranges from 0.001 to 1N, more preferably 0.3 to 0.1N. The reaction temperature is preferably −20 to 40° C. more preferably 0 to 30° C. The reaction time is preferably 30 seconds to 15 hours, more preferably 30 minutes to 2 hours.

Use of aqueous ammonia as a base produces the amide derivative of Compound A-500359F together with Compound A-500359F, but these compounds can be separated and purified by the above-described method.

The amide derivative of Compound A-500359F may be produced by reacton of Compound A-500359E with ammonia in a solvent.

Examples of the solvent include water and alcohols such as ethanol and methanol, of which water and methanol are preferred.

Gaseous ammonia may be introduced into the solution of the compound, but a solution of ammonia in water or in an alcohol such as methanol or ethanol is usually used. Preferably, an aqueous or methanolic solution is employed.

When aqueous ammonia is employed, its concentration preferably ranges from 0.1 to 1N. more preferably 0.3 to 0.7N. The reaction temperature is preferably —20 to 40° C., more preferably 0 to 30° C. The reaction time is preferably 30 minutes to 15 hours, more preferably 1 to 4 hours.

When aqueous ammonia is used, in addition to the desired amide derivative of Compound A-500359F, Compound A-500359F is produced by the hydrolysis of the ester. These compounds however can be separated and purified by the above-described methods.

The amide derivative of Compound A-500359F can also be produced by reacting Compound A-500359F with a methylating reagent in a solvent, thereby converting it to the methyl ester derivative, that is, Compound A-500359E, and then reacting the resulting compound with ammonia as described above.

Examples of the methylating reagent include diazomethane and dimethylsulfuric acid, of which diazomethane is preferred. The methylating reagent for the conversion of Compound A-500359F to Compound A-500359E is preferably added in an amount of 1 to 5 equivalents, preferably 1.5 to 2 equivalents.

Examples of the solvent usable for the above reaction include water and alcohols such as methanol and ethanol, of which water and methanol are preferred.

The reaction temperature is preferably −20 to 40° C. more preferably 0 to 30° C. The reaction time is preferably 30 minutes to 15 hours. more preferably 1 to 2 hours.

After completion of the reaction. Compound A-500359F, Compound A-500359E, and the amide derivative of Compound A-500359F can be isolated from the reaction mixture by the means selected as needed from those described above in the separation and purification means for Compound A-500359E, Compound A-500359F, the amide derivative of Compound A-500359F, Compound A-500359H, Compound A-500359J and Compound A-50359M-3.

Typical preparation processes for Compound A-500359E, Compound A-500359F, the amide derivative of Compound A-500359F, Compound A-500359H, Compound A-500359J and Compound A-50359M-3 are described hereinabove, but preparation processes are not limited thereto and other processes already known to those skilled in the art may also be employed.

Compound A-500359E, Compound A-500359F, the amide derivative of Compound A-500359F, Compound A-500359H, Compound A-500359J and Compound A-500359M-3 of the present invention thus available are novel compounds which have not been described in the literature. Their growth inhibitory activity against general gram positive bacteria or gram negative bacteria can be determined by the disk assay method using normal agar medium (product of Eiken Chemical) or heart infusion agar medium (product of Difco Laboratories). Growth inhibitory activity against Mycobacteria, gram positive bacteria belonging to the Actinonycetales, can be determined similarly on the above-described medium added further with glycerin.

Typical evaluation methods of biological activity of Compound A-500359E, Compound A-500359F, the amide derivative of Compound A-500359F, Compound A-500359H, Compound A-500359J and Compound A-500359M-3 were described so far, but the evaluation method is not limited thereto, but other evaluation methods already known to those skilled in the art can also be employed.

The compounds of the present invention or pharmacologically acceptable salts thereof may be administered through various routes. Examples include oral administration using tablets, capsules, granules, powders, syrups or the like; and parenteral administration using injections (intravenous, intramuscular or subcutaneous), drops, suppositories or the like. These formulations can be prepared in a conventional manner by adding to a medicament ordinarily employed carriers known in the field of pharmaceutical formulation technique such as an excipient, binder, disintegrator, lubricant, corrigent, adjuvant for solubilization, suspending agent, coating agent, diluent and/ or the like.

For the formation of tablets, various carriers known conventionally in this field can be employed. Examples include excipients such as lactose, sucrose, sodium chloride, glucose, urea starch, calcium carbonate, kaolin, crystalline cellulose and silicic acid; binders such as water, ethanol, propanol, simple syrup, glucose solution, starch solution, gelatin solution, carboxymethyl cellulose, shellac, methyl cellulose, potassium phosphate and polyvinyl pyrrolidone, disintegrants such as dry starch, sodium alginate, agar powder, laminaran powder, sodium bicarbonate, calcium carbonate, polyoxyethylene sorbitan fatty acid ester, sodium lauryl sulfate, stearic monoglyceride, starch and lactose; disintegration suppressants such as sucrose, stearin, cacao butter and hydrogenated oil; absorption facilitators such as quaternary ammonium salts and sodium lauryl sulfate; humectants such as glycerin and starch; adsorbents such as starch lactose, kaolin, bentonite and colloidal silicic acid; and lubricants such as purified talc, stearates, boric acid powder and polyethylene glycol. Tablets can be formed as those having ordinary coating as needed such as sugar coated tablets, gelatin encapsulated tablets, enteric coated tablets, film coated tablets, or double or multiple layer tablets.

For the formation of pills, various carriers conventionally known in this field can be used. Examples include excipients such as glucose, lactose, cacao butter, starch, hardened vegetable oil, kaolin and talc; binders such as gum arabic powder, tragacanth powder, gelatin and ethanol; and disintegrators such as laminaran ajar.

For the formation of suppositories, various carriers conventionally known in this field can be employed. Examples include polyethylene glycol, cacao butter, higher alcohols and esters thereof, gelatin and semi-synthetic glyceride.

For formulation as injections, it is preferred that solutions or suspensions are sterilized and they are made isotonic with the blood. Solutions, emulsions or suspensions can be formed using any diluent conventionally used in this field. Examples include water, ethanol, propylene glycol, ethoxylated isostearyl alcohol, polyoxylated isostearyl alcohol and polyoxyethylene sorbitan esters of fatty acid. It is also possible to incorporate, in a pharmaceutical preparation, salt, glucose or glycerin in an amount sufficient for preparing an isotonic solution, or to add an ordinarily employed adjuvant for solubilization, buffer, soothing agent and/or the like.

If necessary a colourant, preservative, flavor, sweetener or other medicaments may be incorporated.

There is no particular limitation on the content of the compound incorporated as an effective ingredient in the above-described pharmaceutical preparation. It can be chosen suitably from a wide range. In general, it is desired to be contained in an amount of 1 to 70 wt. %, preferably 1 to 30 wt. % in the whole composition.

There is no particular limitation on the administering method of the above-described pharmaceutical preparation and it is determined depending on the dosage form or age, sex or other conditions of a patient to be administered or seriousness of the disease of the patient (human or other mammal). For example, tablets, pills, solutions, suspensions, emulsions, granules or capsules are administered orally. Injections are administered intravenously either singly or as a mixture with an ordinarily employed fluid replacement such as glucose or amino acid. If necessary, they are singly administered intramuscularly, subcutaneously, intracutaneously or intraperitoneally. A suppository is administered rectally.

Although the dose of the pharmaceutical composition differs with the conditions, age and weight of the patient, administration route or dosage form daily dose usually ranges from 2000 mg (preferably 100 mg) as the upper limit to 0.1 mg (preferably 1 mg, more preferably 10 mg) as the lower limit per adult. It can be administered once or in several portions a day according to the conditions.

The present invention will hereinafter be described more specifically by Examples, Tests and Formulation Examples. It should however be borne in mind that the present invention is not limited to or by them. The process for preparing capuramnycin, a known substance, will next be described.

Preparation Example 1

Capuramycin

1) Cultivation of *Streptomyces griseus* Strain SANK 60196 (FERM BP-5420)

Into each of four 2 L Erlenmeyer flasks (seed flasks), each containing 400 ml of a seed culture medium having the below-described composition, were inoculated four loopfuls of Strain SANK 60196 followed by shaking in a rotary shaker at 28° C. and 210 revolutions/min (revolutions per minute: which will hereinafter be abbreviated as "rpm"). Seed culture was thus conducted for 5 days.

Seed culture medium

| | |
|---|---|
| Maltose | 30 g |
| Meat extract | 5 g |
| Polypeptone | 5 g |
| Sodium chloride | 5 g |
| CaCO$_3$ | 3 g |
| Tap water | 1000 ml | pH before sterilization: 7.4

Sterilization: at 121° C. for 30 minutes.

Cultivation was conducted as described below. Described specifically, the seed culture was inoculated at 2% (v/v) into each of four 30 L jar fermenters, each containing 15 L of a sterilized main culture medium having the below-described composition, followed by cultivation with aeration and agitation at 28° C. for 8 days.
Main culture medium

| | |
|---|---|
| Glucose | 30 g |
| Meat extract | 5 g |
| Polypeptone | 5 g |
| Sodium chloride | 5 g |
| $CoCl_2.6H_2O$ | 50 mg |
| $CaCO_3$ | 3 mg |
| Antifoamer ("CB442": product of NOF Corporation) | 50 mg |
| Tap water | 1000 ml | pH before sterilization: 7.4
Sterilization: at 121° C. for 30 minutes
2) Isolation and Purification of Capuramycin After completion of the cultivation, the cultured broth (52 L) obtained above in 1) was filtered with the aid of "Celite 545" (product of Celite Co.) added at 4% (v/v). The filtrate (50 L) was charged on a "Diaion HP-20" column (product of Mitsubishi Chemical; 12 L). The resulting column was washed with 18 L of distilled water and the adsorbed substance was eluted with 50 L of 10% aqueous acetone. The eluate was concentrated by "Evapor" to give 15 L of the concentrate.

Upon purification as described later, the active substance of each fraction was monitored by HPLC under the following conditions.

Column: "Senshu Pak ODS-H-2151" 6φ×150 mm (product of Senshu Scientific Co., Ltd.)
Solvent: 8% acetonitrile—0.04% aqueous trifluoroacetic acid
Flow rate: 1.0 ml/min
Detection: UV 210 nm The resulting concentrate was charged on a "Diaion CHP-20P" column (product of Mitsubishi Chemical: 8 L). The column was washed successively with 16 L each of 10% aqueous methanol and 20% aqueous methanol, followed by stepwise elution of the active substances with 16 L of 30% aqueous methanol and 24 L of 40% aqueous methanol.

On "Diaion CHP-20P" column chromatography, a peak at a retention time of 17.1 minutes upon the above-described HPLC was mainly detected from a 0 to 8 L portion (which will hereinafter be called "Fraction A") of 30% aqueous methanol eluate; peaks at retention times of 13.7 minutes, 17.1 minutes and 22.6 minutes upon the above-described HPLC were detected from a 8 to 16 L portion (which will hereinafter be called "Fraction B") of 30% aqueous methanol eluate; and a peak at a retention time of 22.6 minutes upon the above-described HPLC was detected from a 0 to 12 portion (which will hereinafter be called "Fraction C") of the 40% aqueous methanol eluate. These fractions were concentrated by "Evapor", respectively, whereby 8.5 L of Fraction A, 8.5 L of Fraction B and 12.5 L of Fraction C were obtained, each as a concentrate.

A 16 to 24 L portion (which will hereinafter be called "Fraction D") of the 40% aqueous methanol eluate was concentrated by "Evapor" and lyophilized. whereby 4.7 g of Fraction D was obtained as a crude powdery product.

Fraction B was charged again on a "Diaion CHP-20P" column (1.5 L). After washing the column with 3 L of 10% aqueous methanol, the adsorbed material was eluted stepwise with 3 L each of 20% aqueous methanol, 30% aqueous methanol and 40% aqueous methanol. From a combined fraction (which will hereinafter be called "Fraction E") of the 0.5 to 3 L portion of the 20% aqueous methanol eluate and the 0 to 1 L portion of the 30% aqueous methanol eluate, a peak at a retention time of 17.1 minutes in the above-described HPLC was mainly detected; from a combined fraction (which will hereinafter be called "Fraction F") of the 1 to 3 L portion of the 30% aqueous methanol eluate and the 0 to 0.5 L portion of the 40% aqueous methanol eluate, a peak at a retention time of 13.7 minutes in the above-described HPLC was mainly detected; and from the 0.5 to 3 L portion (which will hereinafter be called "Fraction G") of the 40% aqueous methanol eluate, a peak at a retention time of 22.6 minutes was mainly detected.

Fraction A was combined with Fraction E (the combined one will hereinafter be called "Fraction H"), while Fraction C was combined with Fraction G (the combined one will hereinafter be called "Fraction I"). Fractions F, H and I were concentrated on "Evapor" and lyophilized, respectively, whereby 16.2 g of Fraction H, 33.6 g of Fraction I and 8.6 g of Fraction F were obtained, each as a crude powdery product.

The resulting crude powders product of Fraction H (16.2 g) was dissolved in 250 ml of deionised water. The resulting solution was charged on a "Toyopearl HW-40F" column (product of TOSOH Corporation: 4 L), followed by development with deionised water. As a result of fractionation of the eluate to 75 ml portions each, the active substance having a retention time of 17.1 minutes in the above-described HPLC was eluted in Fraction Nos. 41 to 63. These fractions were collected and concentrated by "Evapor" into 820 ml and the resulting concentrate was lyophilized to give 6.4 g of a crude powdery product.

The crude powdery product thus obtained was dissolved in 400 ml of water. Each of the 80 ml portions of the resulting solution was charged on an HPLC column (YMC-Pack ODS R-3105-20 (100φ×500 mm; product of YMC Co., Ltd.)) equilibrated with a 6% aqueous solution of acetonitrile, followed by column development at a flow rate of 200 ml/min. The ultraviolet absorption of the active substance at 210 nm was detected and a peak eluted at a retention time of 105 to 120 minutes was collected by five fractionation, each in portions of 400 ml.

The resulting fractions were combined and concentrated by "Evapor" into 330 ml, followed by lyophilization, whereby 3.6 g of a substance was obtained in pure form. The substance was identified as capuramycin, a known antibiotic, by structural analysis.

EXAMPLE 1

Preparation of A-500359A (Exemplification (Exemp.) Compound No. 1)

The crude powdery product (33.6 g) of Fraction I obtained in Preparation Example 1 was dissolved in 450 ml of deionised water. The resulting solution was charged on a "Toyopearl HW-40F" column (8 L), followed by elution with deionised water. As a result of fractionation of the eluate into 150 ml portions, the active substance exhibiting a retention time of 22.6 minutes in HPLC was eluted in Fractions Nos. 47 to 73. These fractions were collected, concentrated by "Evapor" into 1.5 L and then lyophilized to give 25 g of a crude powdery product.

The resulting crude powdery product (25 g) was dissolved in 300 ml of deionised water. The resulting solution was charged on a "Cosmosil 140C8-OPN" column (product of Nacalai Tesque; 1.5 L). After washing the column with 3 L of deionised water and 12 L of 1% aqueous acetonitrile, the active compound was eluted with 6 L of 10% aqueous acetonitrile. The eluate was concentrated by "Evapor" into 840 ml and insoluble matter was filtered from the concentrate. The filtrate was lyophilized to give 20 g of Substance A-500359A in pure form. The following data are physico-chemical properties of the resulting substance.
1) Appearance of the substance: white powder
2) Solubility: soluble in water and methanol, insoluble in normal hexane and chloroform
3) Molecular formula: $C_{14}H_{33}N_5O_{12}$
4) Molecular weight: 583 (measured by FAB mass spectrometry)
5) Accurate mass, $[M+H]^+$, as measured by high-resolution FAB mass spectrometry is as follows:
   Found: 584,2189
   Calculated: 584,2205
6) Ultraviolet absorption spectrum: ultraviolet absorption spectrum measured in water exhibits the following maximum absorption:
   257 nm ($\epsilon$ 10,300)
7) Optical rotation: optical rotation measured in methanol exhibits the following value:
   $[\alpha]_D^{20}$: +94.7° (c 1.00, MeOH)
8) Infrared absorption spectrum: Infrared absorption spectrum as measured by the potassium bromide (KBr) disk method exhibits the following maximum absorption:
   3380, 2940, 1690, 1520, 1460, 1430, 1390, 1270, 1110, 1060 $cm^{-1}$.
9) $^1H$ nuclear magnetic resonance spectrum was measured in deuterated methanol with tetramethylsilane as an internal standard. $^1H$ nuclear magnetic resonance spectrum is as follows:
   1.22(3H,d,J=6.7 Hz), 1.29(1H,m), 1.49(1H,m), 1.78(1H,m), 1.87(1H,m), 1.92(1H,m), 2.01 (1H,m), 3.44(3H,s), 3.58 (1H,m), 3.86(1H,br,t,J=4.6 Hz), 3.96 (1H,ddd,J=0.7,4.5,5.7 Hz), 4.30(1H,t,J=5.2 Hz), 4.37(1H,t,J=4.1 Hz), 4.56(1H,dd,J=2.0,11.9 Hz), 4.58(1H,dd,J=2.0,4.3 Hz), 4.67(1H,d,J=2.0 Hz), 5.23(1H,d,J=5.8 Hz), 5.72(1H,d,J=8.1 Hz), 5.88(1H,d,J=5.2 Hz), 6.02(1H,br,dd,J=0.7,3.9 Hz), 7.91(1H,d,J=8.1 Hz) ppm.
10) $^{13}C$ nuclear magnetic resonance spectrum was measured in deuterated methanol with tetramethylsilane as an internal standard. $^{13}C$ nuclear magnetic resonance spectrum is as follows:
   22.2(q), 28.4(t), 32.1(t), 37.9(t), 50.1(d), 53.5(d), 58.8(q), 63.6(d), 68.8(d), 74.6(d), 79.2(d), 81.1(d), 83.6(d), 90.4(d), 101.3(d), 102.9(d), 109.3(d), 142.0(d), 144.4(s), 152.4(s), 161.9(s), 166.1(s), 173.5(s), 175.3(s) ppm.
11) High performance liquid chromatography
   Column: "Senshu Pak ODS-H-2151", 6ϕ×150 mm (product of Senshu Scientific Co., Ltd.)
   Solvent: 8% acetonitrile—water
   Flow rate: 1.0 ml/min
   Detection: UV 210 nm
   Retention time: 20 minutes.

EXAMPLE 2

Preparation of A-500359C (Exemp. Compound No. 2)

The crude powdery product (8.6 g) of Fraction F was dissolved in 500 ml of deionised water. The resulting solution was charged on a "Toyopearl HW-40F" column (8.5 L), which was developed with deionised water. As a result of fractionation of the eluate into 150 ml portions, the active substance exhibiting a retention time of 13.7 minutes in HPLC was eluted in Fraction Nos. 44 to 82. These fractions were collected, concentrated by "Evapor" into 900 ml and lyophilized, whereby 2.2 g of a crude powdery product was obtained.

The resulting crude powdery product (2.2 g) was dissolved in 150 ml of deionised water. The resulting solution was charged on a "Cosmosil 140C18-OPN" column (product of Nacalai Tesque; 1.5 L). After washing the column successively with 3 L of deionised water, 3 L of 0.5% aqueous acetonitrile, 3 L of 1% aqueous acetonitrile and 15 L of 2% aqueous acetonitrile, the active substance was eluted with 10 L of 4% aqueous acetonitrile. The fraction was concentrated by "Evapor" into 500 ml and then lyophilized, whereby 550 g of a crude powdery product was obtained.

The crude powdery product was dissolved in 80 ml of deionised water. The resulting solution was charged on an HPLC column (YMC-Pack ODS R-3105-20 (100ϕ×500 mm; product of YMC)) equilibrated with a 6% aqueous solution of acetonitrile, and the column was developed at a flow rate of 200 ml/min. The ultraviolet absorption of the active fraction at 210 nm was detected and the active fraction eluted at a retention time of from 167 to 180 minutes was collected by fractionation.

The resulting fraction was concentrated into 50 ml by "Evapor", followed by lyophilization, whereby 210 mg of Compound A-500359C was obtained in pure form. The following data are physico-chemical properties of the resulting substance.
1) Appearance of the substance: white powder
2) Solubility: soluble in water, slightly soluble in methanol, insoluble in normal hexane and chloroform
3) Molecular formula: $C_{23}H_{31}N_5O_{12}$
4) Molecular weight: 569 (as measured by FAB mass spectrometry)
5) Accurate mass, $[M+H]^+$, as measured by high-resolution FAB spectrometry is as follows:
   Found: 570,2034
   Calculated: 570,2049
6) Ultraviolet absorption spectrum: ultraviolet absorption spectrum measured in water exhibits the following maximum absorption:
   257 nm ($\epsilon$ 10,700)
7) Optical rotation: optical rotation measured in water exhibits the following value:
   $[\alpha]_D^{20}$: +89° (c 0.44. $H_2O$)
8) Infrared absorption spectrum: Infrared absorption spectrum as measured by the potassium bromide (KBr) disk method exhibits the following absorption maxima:
   3390, 2930, 1690, 1520, 1460, 1430, 1390, 1270, 1110, 1060 $cm^{-1}$.
9) $^1H$ nuclear magnetic resonance spectrum was measured in deuterium oxide with the signal of water as 4.75 ppm. $^1H$ nuclear magnetic resonance spectrum is as follows:
   1.20(3H,d,J=6.7 Hz), 1.29(1H,m), 1.62(1H,m), 1.72(1H,m), 1.75(1H,m), 1.90(1H,m), 1.92(1H,m), 3.65(1H,m), 4.11 (1H,dd,J=5.2,6.3 Hz), 4.15(1H,ddd,J=1.4,4.2,4.3 Hz), 4.18 (1H,dd,J=3.3,5.2 Hz), 4.43(1H,dd,J=2.1,6.3 Hz), 4.49(1H, dd,J=3.0,4.4, Hz), 4.62(1H,dd,J=1.7,10.8 Hz), 4.76(1H,d,J= 2.1 Hz), 5.36(1H,d,J=4.0 Hz), 5.77(1H,d,J=3.3 Hz), 5.84 (1H,d,J=8.1 Hz), 5.98(1H,br,dd,J=1.3,3.0 Hz), 7.72(1H,d,J= 8.1 Hz) ppm.
10) $^{13}C$ nuclear magnetic resonance spectrum was measured in deuterium oxide with 1,4-dioxane (67.4 ppm) as an internal standard. $^{13}C$ nuclear magnetic resonance spectrum is as follows:
   21.0(q), 26.8(t), 29.4(t), 35.4(t), 48.9(d), 52.6(d), 61.9(d), 65.3(d), 69.4(d), 73.8(d), 76.7(d), 83.1(d), 89.7(d), 100.1(d), 101.9(d), 109.1(d), 141.0(d), 141.8(s), 151.6(s), 161.7(s), 166.4(s), 173.5(s), 175.8(s) ppm.

11) High performance liquid chromatography
   Column: "Senshu Pak ODS-H-2151", 6φ+×150 mm (product of Senshu Scientific Co., Ltd.)
   Solvent: 8% acetonitrile—water
   Flow rate: 1.0 ml/min
   Detection: UV 210 nm
   Retention time: 13 minutes.

EXAMPLE 3

Preparation of A-500359D (Exemp. Compound No. 3)

An 800 mg portion of the crude powdery product obtained as Fraction D was dissolved in 10 ml of deionised water. A 500 μl portion of the resulting solution was charged on an HPLC column ("Senshu Pak Pegasil ODS" (20φ×250 mm, product of Senshu Scientific)) which had been equilibrated with a developing solvent containing acetonitrile, methanol and 0.04% aqueous trifluoroacetic acid at 3:21:76, and the column was developed with the same solvent at a rate of 9 ml/min. The ultraviolet absorption of the active fraction at 210 nm was detected and a peak eluted during 35 to 38 minutes was collected by fractionation. The procedure was carried out 20 times to elute the (in portions of 10 ml).

The powder (15 mg) obtained by concentrating the fractions eluted during 35 to 38 minutes and lyophilizing the concentrate was chromatographed again on the same HPLC column and then, concentrated and lyophilized, whereby 7 mg of Compound A-500359D was obtained in pure form.

The following data are the physico-chemical properties of the resulting substance.
1) Appearance of the substance: white powder
2) Solubility: soluble in water and methanol, insoluble in normal hexane and chloroform
3) Molecular formula: $C_{24}H_{33}N_5O_{11}$
4) Molecular weight: 567 (as measured by FAB mass spectrometry)
5) Precise mass, $[M+H]^+$, as measured by high-resolution FAB mass spectrometry is as follows:
   Found: 568,2239
   Calculated: 568,2254
6) Ultraviolet absorption spectrum: ultraviolet absorption spectrum measured in water exhibits the following maximum absorption:
   244 nm (ε 10,000)
7) Optical rotation: optical rotation measured in water exhibits the following value:
   $[\alpha]_D^{20}$: +68° (c 0.69, $H_2O$)
8) Infrared absorption spectrum: Infrared absorption spectrum as measured by the potassium bromide (KBr) disk method exhibits the following absorption maxima:
   3397, 2925, 1683, 1514, 1461, 1432, 1385, 1265, 1205, 1095, 1061 $cm^{-1}$.
9) $^1H$ nuclear magnetic resonance spectrum was measured in deuterium oxide with the signal of water as 4.75 ppm. $^1H$ nuclear magnetic resonance spectrum is as follows:
   1.12(3H,d,J=8.1 Hz), 1.17(1H,m), 1.40(1H,m), 1.67(1H,m), 1.80(1H,m), 1.8(1H,m), 1.90(1H,m), 2.33(1H,m), 3.24 (3H,s), 3.50(1H,m), 3.57(1H,t,J=4.7 Hz), 4.08(1H,t,J=4.8 Hz), 4.37(m),4.40(m), 4.46(1H,br,d,J=10.7 Hz), 4.50(1H,d, J=2.0 Hz), 5.30(1H,br,s), 5.64(1H,d,J=8.1 Hz), 5.73(1H,d, J=4.8 Hz), 5.97(1H,d,J=2.4 Hz), 7.77(1H,d,J=8.1 Hz) ppm.
10) $^{13}C$ nuclear magnetic resonance spectrum was measured in deuterated methanol with the signal of methanol as 49.15 ppm. $^{13}C$ nuclear magnetic resonance spectrum is as follows:
   22.3(q), 28.6(t), 32.3(t), 35.8(d), 38.0(t), 50.2(d), 53.6(d), 58.8(q), 60.7(d), 74.7(d), 77.7(d), 80.9(d), 83.8(d), 90.7(d), 99.5(d), 103.0(d), 112.3(d), 142.0(d), 144.1(d), 152.4(s), 162.4(s), 166.3(s), 173.6(s), 175.5(s) ppm.
11) High performance liquid chromatography
   Column: "Cosmosil 5C18-MS",4.6φ×150 mm (product of Nacalai Tesque)
   Solvent: a 3:21:76 mixture of acetonitrile:methanol:0.04% aqueous trifluoroacetic acid
   Flow rate: 1.0 ml/min
   Detection: UV 210 nm
   Retention time: 9.2 minutes.

EXAMPLE 4

Cultivation of *Streptomyces griseus* Strain SANK 60196 (FERM BP-5420)

Into each of three 2 L Erlenmeyer flasks (seed flasks) each containing 500 ml of a medium having the below-described composition were inoculated, in a sterile condition, four loopfuls of Strain SANK60196, followed by shaking in a rotary shaker at 23° C. and 210 rpm. Seed culture was thus conducted for 5 days.

Seed culture medium

| | |
|---|---|
| Maltose | 30 g |
| Meat extract | 5 g |
| Polypeptone | 5 g |
| Sodium chloride | 5 g |
| $CaCO_3$ | 3 g |
| Antifoamer (CB442) | 50 mg |
| Tap water | 1000 ml | pH before sterilization: 7.4

Sterilization: at 121° C. for 30 minutes

Cultivation was conducted as described below. Described specifically, the seed culture was inoculated at 3% (v/v) into each of two 30 L jar fermenters, each containing 15 L of a sterilized medium having the below-described composition. On Day 1 after the commencement of cultivation at 23° C., filter sterilized S-(2-aminoethyl)-L-cysteine hydrochloride was added to give a final concentration of 8 mM, and cultivation was then carried out with aeration and agitation for 7 days.

Cultivation medium

| | |
|---|---|
| Maltose | 30 g |
| Yeast extract (product of Difco Laboratories) | 5 g |
| Meat extract | 5 g |
| Polypeptone | 5 g |
| Sodium chloride | 5 g |
| Cobalt chloride hexahydrate | 0.5 g |
| $CaCO_3$ | 3 g |
| Antifoamer (CB442) | 50 mg |
| Tap water | 1000 ml | pH before sterilization: 7.4

Sterilization: at 121° C. for 30 minutes

EXAMPLE 5

Preparation of A-500359G (Exemp. Compound No. 45)

After completion of the cultivation, the cultured broth (28 L) obtained in Example 4 was filtered with the aid of "Celite 545".

Upon purification as described later, the active fraction was monitored by the following high performance liquid chromatography (HPLC).

Column: "Senshu Pak ODS-H-2151" 6φ×150 mm (product of Senshu Scientific Co., Ltd.)

Solvent: 8% acetonitrile—0.04% aqueous trifluoroacetic acid

Flow rate: 1.5 ml/min

Detection: UV 210 nm

Retention time: 4.6 minutes

37 L of the resulting filtrate was charged on a "Diaion HP-20" column (5.5 L). After washing the column with 11 L of deionised water, the adsorbed substance was eluted with 11 L of 10% aqueous acetone. The eluate was concentrated to remove acetone. The residue was lyophilized, whereby 40 g of a crude powdery product was obtained.

The resulting crude powdery product was dissolved in 1 L of distilled water and charged on a "Diaion CHP-20P" column (3 L). The column was then washed with 6 L of distilled water, and the adsorbed substance was eluted successively with 6 L of each of 5% aqueous methanol, 10% aqueous methanol and 15% aqueous methanol. The 15% aqueous methanol eluate was concentrated to remove methanol. The residue was lyophilized to give 1.27 g of a powder.

The resulting powder was dissolved in 30 ml of distilled water and the resulting solution was charged on a "Toyopearl HW40F" column (500 ml), followed by elution of the column with distilled water. The eluate was collected by fractionation in portions of 10 ml, each. The active substance having a retention time of 4.6 minutes in the above-described HPLC was eluted in fractions Nos. 41 to 46. The resulting fractions were concentrated and lyophilized to give 134 mg of a powder.

The resulting powder was dissolved in 3 ml of water and a 750 μl portion of the resulting solution was charged on an HPLC column ("Senshu Pak ODS-H-5251" (20 mm×250 mm; product of Senshu Scientific)) equilibrated with 4% aqueous acetonitrile containing 0.04% of aqueous trifluoroacetic acid. The column was developed at a flow rate of 10 ml/min. The ultraviolet absorption of the active substance of 210 nm was detected and a peak eluted during 27 to 30 minutes was collected by fractionation. The process was carried out four times.

These fractions eluted during 27 to 30 minutes were concentrated and lyophilized to afford 20 mg of a powder. The resulting powder was dissolved in 1.6 ml of water and a 800 μl portion of the resulting solution was charged on the above-described HPLC column using instead, as a developing solvent, a 5% aqueous acetonitrile solution containing 0.04% of TFA. The column was developed at a rate of 10 ml/min. The active substance showing ultraviolet absorption at 210 nm was detected and a peak eluted during 19 to 20 minutes was collected again by fractionation. The fractions were concentrated and lyophilized, whereby 14 mg of Compound A-500359G was obtained in pure form. The substance has the following physico-chemical properties:

1) Appearance of the substance: white powder
2) Solubility: soluble in water, slightly soluble in methanol, insoluble in normal hexane and chloroform
3) Molecular formula: $C_{22}H_{29}N_5O_{12}$
4) Molecular weight: 555 (as measured by FAB mass spectrometry)
5) Accurate mass, $[M+H]^+$, as measured by high-resolution FAB mass spectrometry is as follows:
   Found: 556,1891
   Calculated: 556,1890
6) Ultraviolet absorption spectrum: ultraviolet absorption spectrum measured in water exhibits the following maximum absorption:
   257 nm ($\epsilon$ 10,000)
7) Optical rotation: optical rotation measured in water exhibits the following value:
   $[\alpha]_D^{20}$: +109° (c 0.72, $H_2O$)
8) Infrared absorption spectrum: Infrared absorption spectrum as measured by the potassium bromide (KBr) disk method exhibits the following absorption maxima:
   3367, 2931, 1684, 1518, 1482, 1464, 1436, 1408, 1385, 1335, 1272, 1205, 1177, 1114, 1063 $cm^{-1}$.
9) $^1H$ nuclear magnetic resonance spectrum was measured in deuterium oxide with the signal of water as 4.75 ppm. $^1H$ nuclear magnetic resonance spectrum is as follows:
   1.37 (1H, m), 1.65 (1H, m), 1.71 (1H, m), 1.79 (1H, m), 1.92 (1H, m), 1.98 (1H, m), 3.29 (1H,m), 3.36 (1H, m), 4.10 (1H, dd, J=5.0, 6.5 Hz), 4.14 (1H, dt, J=1.5, 4.4 Hz), 4.17 (1H, dd, J=3.2, 5.0 Hz), 4.41 (1H, dd, J=2.1, 6.5 Hz), 4.47 (1H, dd, J=2.9, 4.4 Hz), 4.61 (1H, dd, J=1.8, 11.4 Hz), 4.78 (1H), 5.35 (1H, d, J=4.1 Hz), 5.75 (1H, d, J=3.2 Hz), 5.82 (1H, d, J=8.2 Hz), 5.97 (1H, dd, J=1.5, 2.9 Hz), 7.71 (1H, d, J=8.2 Hz) ppm.
10) $^{13}C$ nuclear magnetic resonance spectrum was measured in deuterium oxide with 1,4-dioxane (67.4 ppm) as an internal standard. $^{13}C$ nuclear magnetic resonance spectrum is as follows:
    28.2 (t), 28.4 (t), 30.5 (t), 42.2 (t), 53.3 (d), 62.7 (d), 66.1 (d), 70.2 (d), 74.5 (d), 77.5 (d), 83.9 (d), 90.5 (d), 100.9 (d), 102.7 (d), 109.9 (d), 141.8 (d), 142.7 (s), 152.2 (s), 162.6 (s), 166.9 (s), 174.3 (s), 177.6 (s) ppm.
11) High performance liquid chromatography:
    Column: "Senshu Pak ODS-H-2151", 6φ×150 mm (product of Senshu Scientific Co., Ltd.)
    Solvent: 8% acetonitrile—0.04% aqueous trifluoroacetic acid
    Flow rate: 1.5 ml/min
    Detection: UV 210 nm
    Retention time: 4.6 minutes

EXAMPLE 6

Cultivation of *Streptomyces griseus* Strain SANK60196 (FERM BP-5420)

Into each of four 2 L Erlenmeyer flasks (seed flasks) each containing 500 ml of a medium having the below-described composition were inoculated, in a sterile condition, four loopfuls of Strain SANK60196, and cultivation was then carried out with shaking in a rotary shaker at 23° C. and 210 rpm. Seed culture was thus conducted for 3 days.

Seed culture medium

| | |
|---|---|
| Maltose | 30 g |
| Meat extract | 5 g |
| Polypeptone | 5 g |
| Sodium chloride | 5 g |
| $CaCO_3$ | 3 g |
| Antifoamer (CB442) | 50 mg |
| Tap water | 1000 ml | pH before sterilization: 7.4

Sterilization: at 121° C. for 30 minutes

The culture was conducted as described below. Described specifically, the seed culture broth was inoculated at 3% (v/v) into each of two 30 L jar fermenters. each containing 15 L of a sterilized medium having the below-described composition. Six hours after commencement of cultivation at 23° C. filter-sterilized S-(2-aminoethyl)-L-cysteine hydrochloride was added to give a final concentration of 10 mM, and cultivation with aeration and agitation was then carried out for 6 days.

Cultivation medium

| | |
|---|---|
| Maltose | 30 g |
| Yeast extract (product of Difco Laboratories) | 5 g |
| Meat extract | 5 g |
| Polypeptone | 5 g |
| Sodium chloride | 5 g |
| CaCO$_3$ | 3 g |
| Antifoamer ("CB442") | 50 mg |
| Tap water | 1000 ml | pH before sterilization: 7.4

Sterilization: at 121° C. for 30 minutes

EXAMPLE 7

Preparation of A-500359 M-2 (Exemp. Compound No. 396)

After completion of cultivation, the cultured broth (30 L) obtained in Example 6 was filtered with the aid of "Celite 545".

Upon purification as described later, the active fraction was monitored by the following high performance liquid chromatography (HPLC) method.

Column: "Senshu Pak ODS-H-2151" 6φ×150 mm (product of Senshu Scientific Co., Ltd.)

Solvent: 8% acetonitrile—0.04% aqueous trifluoroacetic acid

Flow rate: 1.5 ml/min

Detection: UV 210 nm

Retention time: 13.6 minutes

30 L of the resulting filtrate was charged on a "Diaion HP-20" column (6 L). After washing the column with 12 L of deionised water, the adsorbed substance was eluted with 10% aqueous acetone. The fraction eluted in 12 to 24 L was concentrated to remove acetone. The residue was lyophilized, whereby 12 g of a crude powdery product was obtained.

The resulting crude powdery product was dissolved in 650 ml of distilled water. The resulting solution was charged on a "Diaion CHP-20P" column (1 L). The column was then washed with 2 L of distilled water, and the adsorbed substance was eluted with 2 L of 20% aqueous methanol and 4 L of 30% aqueous methanol. The 2 to 4 L portion of the 30% aqueous methanol eluate was concentrated to remove methanol. The residue was lyophilized to yield 2.8 g of a powder.

The resulting powder was dissolved in 50 ml of distilled water and the resulting solution was charged on a "Toyopearl HW40F" column (500 ml), followed by development of the column with distilled water. The eluate was fractionated in portions of 12 ml, each. The active substance having a retention time of 13.6 minutes in the above-described HPLC was eluted in Fraction Nos. 40 to 47. The resulting fractions were concentrated and lyophilized to give 841 mg of a powder.

The resulting powder was dissolved in 23 ml of water and a 1 ml portion of the resulting solution was charged on an HPLC column ("Senshu Pak ODS-H-5251" (20 mm×250 mm; product of Senshu Scientific)) equilibrated with an aqueous solution containing 0.04% trifluoroacetic acid, 4% acetonitrile and 10% methanol. The column was developed at a flow rate of 10 ml/min. The ultraviolet absorption of the active substance of 210 nm was detected and a peak eluted during 23 to 26 minutes was collected by fractionation, the preparation being carried out 23 times.

The fractions eluted during 23 to 26 minutes were concentrated and lyophilized to afford 421 mg of a powder. The resulting powder was dissolved in 40 ml of water again and the resulting solution was charged on the above-described HPLC column using instead, a 7% aqueous acetonitrile solution containing 0.04% of TFA as a developing solvent. The column was developed at a rate of 10 ml/min. The ultraviolet absorption of the active substance of 210 nm was detected and a peak eluted during 33 to 35 minutes was collected again by fractionation, the process being carried out in 40 times. The fractions were concentrated and lyophilized, whereby 190 mg of Substance A-500359 M-2 was obtained in pure form.

The substance has the following physico-chemical properties:

1) Appearance of the substance: white powder
2) Solubility: soluble in water and methanol, insoluble in normal hexane and chloroform
3) Molecular formula: $C_{23}H_{31}N_5O_{12}S$
4) Molecular weight: 601 (as measured by FAB mass spectrometry)
5) Accurate mass, [M+H]$^+$, as measured by high-resolution FAB mass spectrometry is as follows:
   Found: 602,1779
   Calculated: 602,1769
6) Ultraviolet absorption spectrum: ultraviolet absorption spectrum measured in water exhibits the following maximum absorption:
   244 nm (ε 14,000)
7) Optical rotation: optical rotation measured in water exhibits the following value:
   $[\alpha]_D^{20}$: +58° (c 0.39, H$_2$O)
8) Infrared absorption spectrum: Infrared absorption spectrum as measured by the potassium bromide (KBr) disk method exhibits the following absorption maxima:
   3390, 2937, 1683, 1510, 1461, 1432, 1411, 1344, 1268, 1206, 1179, 1135, 1071, 1023 cm$^{-1}$.
9) $^1$H nuclear magnetic resonance spectrum was measured in deuterium oxide with the signal of water as 4.75 ppm. $^1$H nuclear magnetic resonance spectrum is as follows:
   1.30(3H,d,J=6.8 Hz), 2.63(2H,m), 2.76(1H,dd,J=2.9,14.4 Hz), 2.84(1H,dd,J=8.8,14.4 Hz), 3.28(3H,s), 3.73(1H,dd,J=5.0,6.5 Hz), 3.98(1H,m), 4.19(1H,ddd,J=1.5,3.5,4.4 Hz), 4.38(1H,dd,J=3.2,5.0 Hz), 4.47(1H,dd,J=2.6,6.5 Hz), 4.50 (1H,dd,2.6,4.4 Hz), 4.73(1H,d,J=2.6 Hz), 5.02(1H,dd,J=2.9, 8.8 Hz), 5.39(1H,d,J=3.5 Hz), 5.75(1H,d,J=3.2 Hz), 5.85 (1H,d,J=8.1 Hz), 6.03(1H,dd,J=1.5,2.6 Hz), 7.74(1H,d,J= 8.1 Hz) ppm.
10) $^{13}$C nuclear magnetic resonance spectrum was measured in deuterium oxide with 1,4-dioxane (67.4 ppm) as an internal standard. $^{13}$C nuclear magnetic resonance spectrum is as follows:
    21.3(q), 30.0(t), 36.3(t),53.2(d), 55.9(d), 58.6(q), 62.7(d), 65.7(d), 72.7(d), 76.5(d), 78.9(d), 82.4(d), 91.1(d), 100.3(d), 102.7(d), 110.6(d), 141.9(d), 142.3(s), 152.1(s), 162.3(s), 166.9(s), 173.8(s), 174.5(s) ppm.

11) High performance liquid chromatography

Column: "Senshu Pak ODS-H-2151", 6φ×150 mm (product of Senshu Scientific Co., Ltd.)

Solvent: 8% acetonitrile—0.04% aqueous trifluoroacetic acid

Flow rate: 1.5 ml/min

Detection: UV 210 nm

Retention time: 14.4 minutes

In the below-described Examples, Me, TBS, THF, TBAF, DMAP and WSC stand for a methyl group, a tert-butyldimethylsilyl group, tetrahydrofuran, tetrabutylammonium fluoride, 4-(dimethylamino)pyridine and 1-ethyl-3-(3-dimethylaminopropyl)carbodiimide hydrochloride, respectively.

EXAMPLE 8
(Exemp. Compound No. 135)

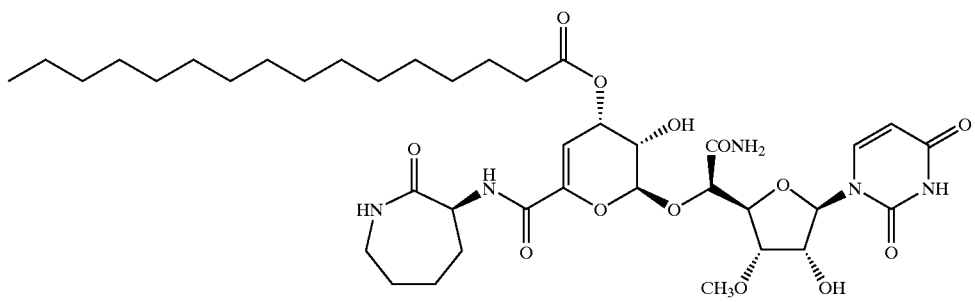

(8-1)

Capuramycin (2 g) was dried by azeotropy twice with pyridine and dissolved in 34 mL of pyridine. To the resulting solution, 1.59 g of tert-butyldimethylsilyl chloride was added, followed by stirring at room temperature. Three days later, the solvent was distilled off under reduced pressure. The residue was dissolved in 200 mL of ethyl acetate. The resulting solution was washed with 200 mL of saturated saline and dried over anhydrous magnesium sulfate. The residue obtained by distilling off the solvent under reduced pressure was charged on a silica gel column (300 g), which was developed with methylene chloride—methanol (concentration gradient from 97:3 to 90:10, which will hereinafter be described as "97:3 to 90:10"), whereby 474.6 mg of the below-described compound was obtained.

1) $^1$H nuclear magnetic resonance spectrum was measured in deuterated methanol with tetramethylsilane as an internal standard substance. $^1$H nuclear magnetic resonance spectrum is as follows:

δ=7.99 (d, J=8.1 Hz, 1H), 6.02 (d, J=3.7 Hz, 1H), 5.88 (d, J=5.1 Hz, 1H), 5.74 (d, J=8.1 Hz, 1H), 5.23 (d, J=5.8 Hz, 1H), 4.69 (s, 1H), 4.61 (d, J=2.2 Hz, 1H), 4.51 (d, J=11 Hz, 1H), 4.41 (t, J=4.7 Hz, 1H), 4.36 (t, J=4.6 Hz, 1H), 3.90 (m, 1H), 3.85 (m, 1H), 3.47 (s, 3H), 3.30–3.20 (m, 2H), 2.02 (m, 2H), 1.84 (m, 2H), 1.54–1.28 (m, 2H), 0.86 (s, 9H), 0.05 (s, 6H) ppm.

2) Infrared absorption spectrum: The infrared absorption spectrum as measured by the potassium bromide (KBr) disk method exhibits absorption maxima as follows:

3368, 2931, 2858, 1687, 1510, 1473, 1463, 1436, 1385, 1334, 1266, 1145, 1101, 1064 cm$^{-1}$.

(8-2)

In 3 mL of pyridine were dissolved 100 mg of the compound obtained in (8-1) and 2 mg of DMAP. To the resulting solution was added 145 mg of palmitic anhydride, followed by stirring at room temperature. Forty minutes later, the solvent was distilled off under reduced pressure, and the residue dissolved in 20 mL of ethyl acetate. The resulting solution was washed with 20 mL of saturated aqueous sodium bicarbonate and dried over anhydrous magnesium sulfate. The residue obtained by distilling off the solvent under reduced pressure was charged on a silica gel column (14 g), which was developed with methylene chloride—methanol (98:2 to 95:5), whereby 42.7 mg of the following compound was obtained.

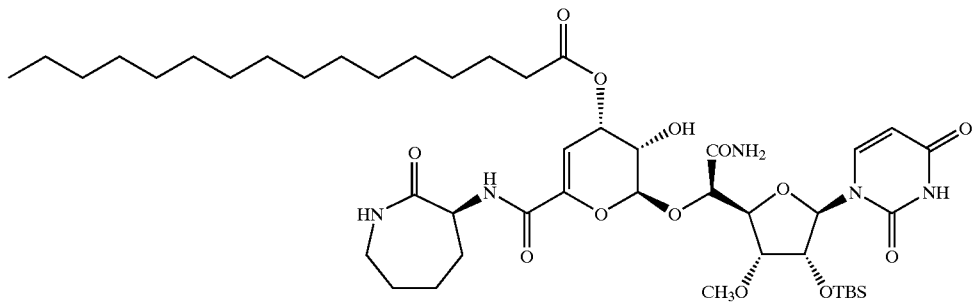

1) ¹H nuclear magnetic resonance spectrum was measured in deuterated chloroform with tetramnethylsilane as an internal standard substance. ¹H nuclear magnetic resonance spectrum is as follows:

δ=9.17 (br s, 1H), 7.88 (m, 2H), 7.47 (br s, 1H), 6.58 (br s, 1H), 6.04 (m, 2H), 5.78 (m, 2H), 5.58 (m, 1H), 5.12 (d, J=7.7 Hz, 1H), 4.64 (m, 1H), 4.60 (m, 1 H), 4.50 (m, 2H), 4.06 (m, 1H), 3.88 (m, 1H), 3.46 (s, 3H), 3.27 (m, 3H), 2.37 (m, 2H), 2.16–1.10 (m, 32H), 0.88 (m, 12H), 0.06 (s, 6H) ppm.

(8-3)

In 53 μL of THF were dissolved 41 mg of the compound obtained in (8-2). A 53 μL THF solution containing 1M of TBAF was added to the resulting solution and the mixture stirred at room temperature. Four hours later, the solvent was distilled off under reduced pressure. The residue was charged on a silica gel column (6 g), which was developed with methylene chloride—methanol (96:4 to 94:6), whereby 16.3 mg of the below-described compound was obtained as a desired compound of Example 8.

EXAMPLE 9

(Exemp. Compound No. 280)

(9-1)

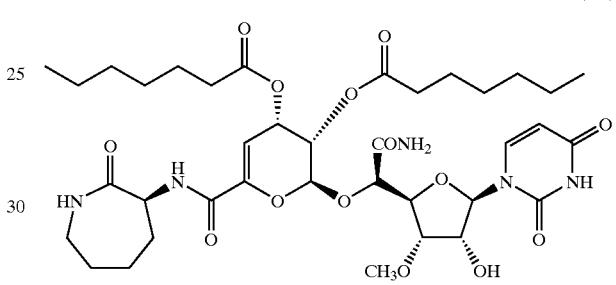

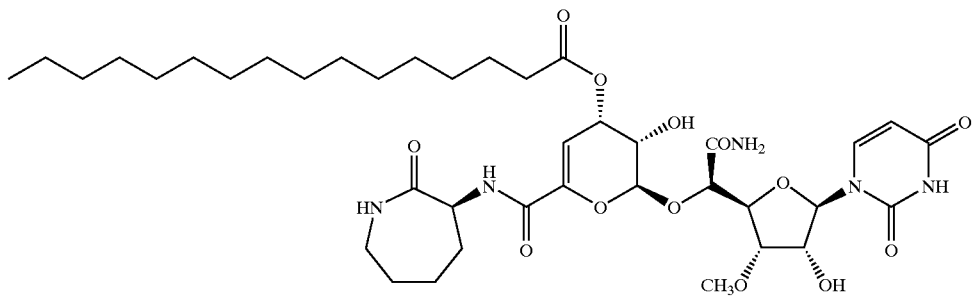

1) ¹H nuclear magnetic resonance spectrum was measured in deuterated methanol with tetramethylsilane as an internal standard substance. ¹H nuclear magnetic resonance spectrum is as follows:

δ=7.76 (d, J=8.1 Hz, 1H), 5.88 (d, J=3.7 Hz, 1H), 5.79 (d, J=5.1 Hz, 1H), 5.72 (d, J=8.1 Hz, 1H), 5.42 (m, 1H), 5.21 (d, J=4.7 Hz, 1H), 4.61 (d, J=2.2 Hz, 1H), 4.54–4.46 (m, 2H), 4.17 (m, 2H), 3.71 (t, J=4.8 Hz, 1H), 3.32 (s, 3H), 3.18 (m, 2H), 2.33 (t, J=7.3 Hz, 2H), 1.98–0.79 (m, 35H) ppm.

2) Infrared absorption spectrum: The infrared absorption spectrum as measured by the potassium bromide (KBr) disk method exhibits absorption maxima as follows:

3379, 2925, 2855, 1690, 1507, 1462, 1384, 1334, 1262, 1115 cm⁻¹.

(1-1)

In 4.5 mL of pyridine were dissolved 150 mg of the compound obtained in Example (8-1), 69 μL of heptanoic anhydride and 3 mg of DMAP. In a similar manner to that described in Example (8-2), the resulting solution was reacted, whereby 286 mg of the following compound was obtained.

(9-2)

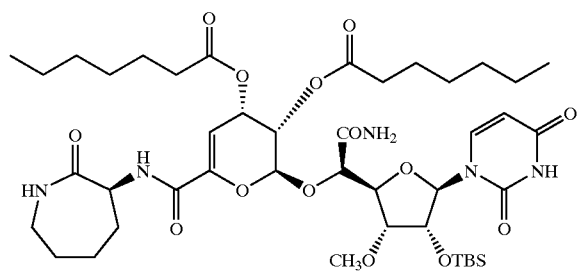

In 250 μL of THF was dissolved 286 mg of the compound obtained in Example (9-1). To the resulting solution was added 250 μL of a THF solution containing 1M of TBAF. The resulting mixture was reacted in a similar manner to that described in Example (8-3), whereby 96.3 mg of the below-described compound was obtained as the desired compound of Example 9.

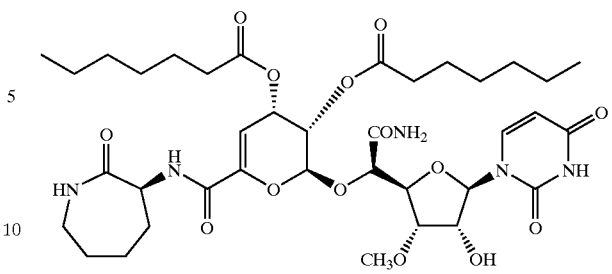

1) $^1$H nuclear magnetic resonance spectrum was measured in deuterated methanol with tetramethylsilane as an internal standard substance. $^1$H nuclear magnetic resonance spectrum is as follows:
δ=7.72 (d, J=8.1 Hz, 1H), 5.99 (m, 1H), 5.87 (d, J=8.1 Hz, 1H), 5.81 (d, J=4.6 Hz, 1H), 5.72 (m, 1H), 5.63 (m, 1H), 5.45 (d, J=3.2 Hz, 1H), 4.68 (d, J=2.2 Hz, 1H), 4.59 (m, 1H), 4.46 (m, 1H), 4.18 (t, J=4.8 Hz, 1H), 3.65 (t, J=5.1 Hz, 1H), 3.34 (s, 3H), 3.25 (m, 2H), 2.40–2.25 (m, 4H), 2.03 (m, 2H), 1.85 (m, 2H), 1.70–1.50 (m, 6H), 1.45–1.25 (m, 12H), 0.90 (m, 6H) ppm.

2) Infrared absorption spectrum: The infrared absorption spectrum as measured by the potassium bromide (KBr) disk method exhibits absorption maxima as follows:
3342, 2931, 2859, 1748, 1693, 1508, 1460, 1383, 1334, 1270, 1236, 1142, 1115, 1068, 990 cm$^{-1}$.

EXAMPLE 10

(Exemp. Compound No. 53)

(10-1)

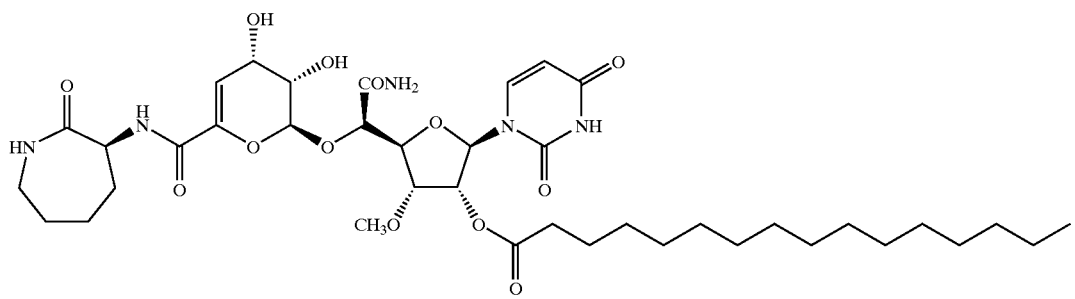

The compound shown above was synthesized in accordance with the process described in Japanese Patent Application Kokai Hei 5-148293. Described specifically, 1 g of capuramycin was dissolved in 175 mL of acetone. To the resulting solution were added 9.2 mL of 2,2-dimethoxypropane and 253 mg of "Amberlyst 15 (H$^+$)". The resulting mixture was stirred at room temperature. Two days later, the "Amberlyst 15 (H$^+$)" evaporated and the solvent was distilled off under reduced pressure. The residue was dissolved in 7 mL of chloroform, followed by the addition of 30 mL of hexane. White crystals thus precipitated were collected by filtration, and charged on a silica gel column (40 g), which was developed with methylene chloride—methanol (92:8), whereby 582.7 mg of the following compound was obtained.

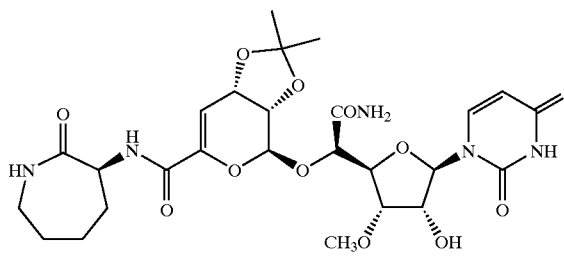

1) ¹H nuclear magnetic resonance spectrum was measured in deuterated chloroform with tetramethylsilane as an internal standard substance. ¹H nuclear magnetic resonance spectrum is as follows:

δ=9.69 (br s, 1H), 7.93 (d, J=6.0 Hz, 1H), 7.74 (d, J=8.2 Hz, 1H), 7.30 (br s, 1H), 7.03 (m, 1H), 6.34 (d, J=4.4 Hz, 1H), 6.12 (br s, 1H), 5.92 (d, J=6.4 Hz, 1H), 5.73 (d, J=8.2 Hz, 1H), 4.82 (d, J=7.2 Hz, 1H), 4.74 (m, 1H), 4.69 (m, 1H), 4.60 (m, 1H), 4.53 (m, 1H), 4.32 (m, 1H), 4.13 (t, J=6.5 Hz, 1H), 4.02 (m, 1H), 3.69 (m, 1H), 3.50 (s, 3H), 3.28 (m, 2H), 2.18–1.70 (m, 6H), 1.49 (s, 3H), 1.45 (s, 3H) ppm.

(10-2)

In 3 mL of pyridine were dissolved 100 mg of the compound obtained in (10-1), 243 mg of palmitic anhydride and 2 mg of DMAP. The resulting solution was stirred at room temperature. One hour later, 1 mL of methanol was added to terminate the reaction. The solvent was then distilled off under reduced pressure. The residue was dissolved in 100 mL of ethyl acetate. After washing with 100 mL of saturated aqueous sodium bicarbonate, drying was conducted over anhydrous sodium sulfate. The solvent was distilled off under reduced pressure. From the residue, pyridine was removed by azeotropy with toluene, whereby a mixture containing the below-described compound was obtained. The mixture was provided for the subsequent reaction (10-3) without purification.

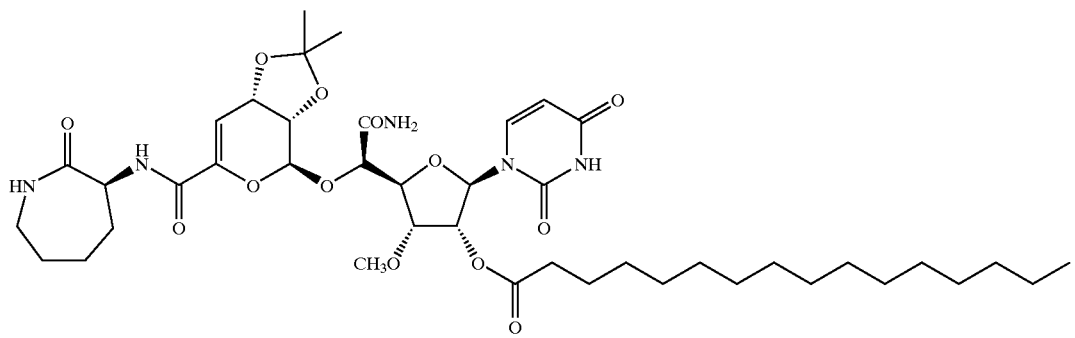

(10-3)

In 10 mL of methanol was dissolved the whole amount of the mixture obtained in (10-2). To the resulting solution was added 100 mg of "Amberlyst 15 (H⁺)", and the mixture was stirred for 47 hours at room temperature and for 4 hours at 80° C. After filtration through Celite, the solvent was distilled off under reduced pressure. The residue was charged on a silica gel column (5 g), which was developed with methylene chloride—methanol (95:5 to 93:7), whereby 84.9 mg of the below-described compound was obtained as the desired compound of Example 10.

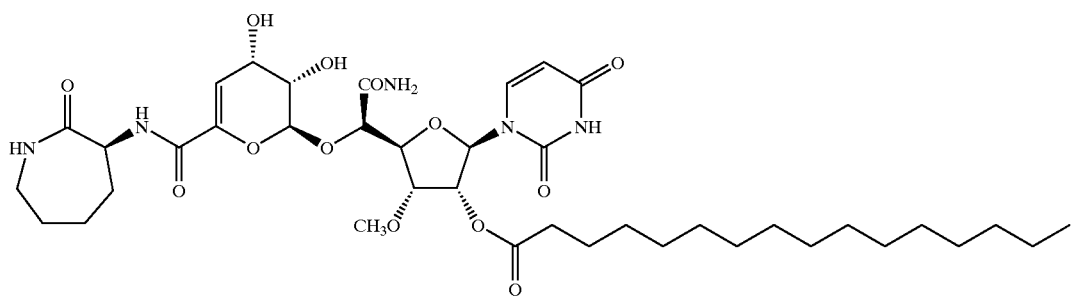

1) ¹H nuclear magnetic resonance spectrum was measured in deuterated methanol with tetramethylsilane as an internal standard substance. ¹H nuclear magnetic resonance spectrum is as follows:

δ=7.94 (d, J=8.2 Hz, 1H), 6.01 (d, J=3.5 Hz, 1H), 5.98 (d, J=4.8 Hz, 1 Hz, 1H), 5.72 (d, J=8.2 Hz, 1H), 5.42 (t, J=4.8 Hz, 1H), 5.24 (d, J=5.5 Hz, 1H), 4.68 (d, J=1.8 Hz, 1H), 4.55 (m, 2H), 4.42 (t, J=4.1 Hz, 1H), 4.05 (t, J=4.8 Hz, 1H), 3.98 (t, J=4.7 Hz, 1H), 3.38 (s, 3H), 3.25 (m, 2H), 2.37 (t, J=7.3 Hz, 2H), 2.01 (m, 2), 1.84 (m, 2H), 1.63–1.15 (m, 28H), 0.90 (t, J=6.8 Hz, 3H) ppm.

2) Infrared absorption spectrum: The infrared absorption spectrum as measured by the potassium bromide (KBr) disk method exhibits absorption maxima as follows:

3380, 2925, 1854, 1686, 1509, 1466, 1384, 1334, 1270, 1146, 1112, 1062 cm$^{-1}$.

EXAMPLE 11

(Exemp. Compound No. 21)

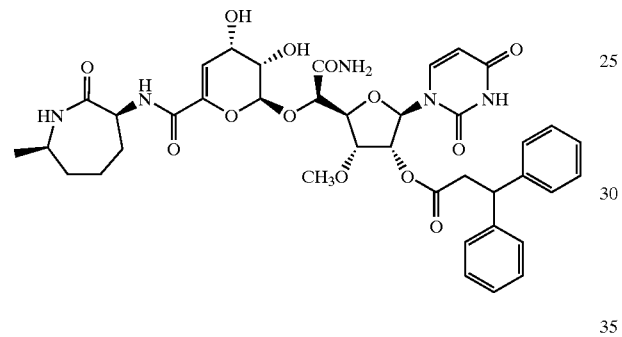

(11-1)

In 1.5 L of acetone was dissolved 8.5 g of A-500359A. To the resulting solution were added 72.7 mL of 2,2-dimethoxypropane and 2 g of "Amberlyst 15 (H⁺)". The resulting solution was stirred at room temperature. Three days later, the "Amberlyst 15 (H⁺)" was filtered off and the solvent distilled off under reduced pressure. The residue was dissolved in 50 mL of chloroform, followed by the addition of 200 mL of hexane. White crystals thus precipitated were collected by filtration and charged on a silica gel column (400 g) which was developed with methylene chloride—methanol (91:9), whereby 8.83 g of the following compound was obtained.

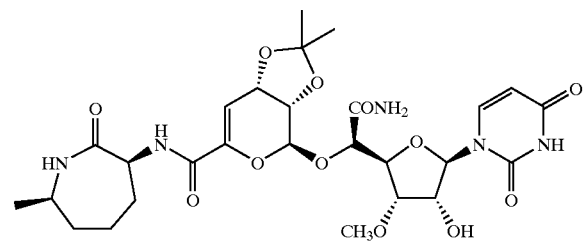

1) ¹H nuclear magnetic resonance spectrum was measured in deuterated chloroform with tetramethylsilane as an internal standard substance. ¹H nuclear magnetic resonance spectrum is as follows:

δ=9.90 (br s, 1H), 7.93 (d, J=6.2 Hz, 1H), 7.75 (d, J=8.1 Hz, 1H), 7.30 (br s, 1H), 6.63 (m, 1H), 6.33 (d, J=4.0 Hz, 1H), 6.14 (br s, 1H), 5.93 (d, J=6.2 Hz, 1H), 5.73 (d, J=8.2 Hz, 1H), 4.83 (d, J=7.1 Hz, 1H), 4.70 (m, 2H), 4.61 (m, 1H), 4.53 (m, 1H), 4.32 (m, 1H), 4.12 (t, J=6.6 Hz, 1H), 4.00 (m, 1H), 3.55 (m, 1H), 3.50 (s, 3H), 2.18–1.20 (m, 15H) ppm.

2) Infrared absorption spectrum: The infrared absorption spectrum as measured by the potassium bromide (KBr) disk method exhibits absorption maxima as follows:

3389, 2986, 2935, 1692, 1509, 1458, 1432, 1383, 1338, 1269. 1252, 1219, 1167, 1118, 1080, 1064, 1012 cm$^{-1}$.

(11-2)

In 2 mL of THF were dissolved 125 mg of the compound obtained in (11-1), 68 mg of 3,3-diphenylpropionic acid, 6 mg of DMAP and 58 mg of WSC. The resulting solution was stirred at room temperature. Two hours later, the solvent was distilled off under reduced pressure. The residue was dissolved in 20 ml of methylene chloride. The resulting solution was washed successively with 20 mL of aqueous sodium bicarbonate and 20 mL of 0.01N aqueous hydrochloric acid, and then dried over anhydrous sodium sulfate. The solvent was distilled off under reduced pressure, whereby a mixture containing the below-described compound was obtained. The resulting mixture was provided for the subsequent reaction (11-3) without purification.

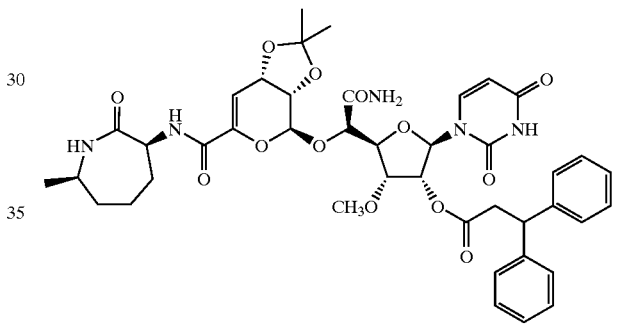

(11-3)

In 5 mL of methanol was dissolved the whole amount of the mixture obtained in (11-2). To the resulting solution was added 120 mg of "Amberlyst 15 (H⁺)" and the resulting mixture was stirred at 80° C. for 3 hours. After filtration through Celite, the solvent was distilled off under reduced pressure. The residue was charged on a silica gel column (15 g) which was developed with methylene chloride—methanol (94:6 to 92:8), whereby 107 mg of the below-described compound was obtained as the desired compound of Example 11.

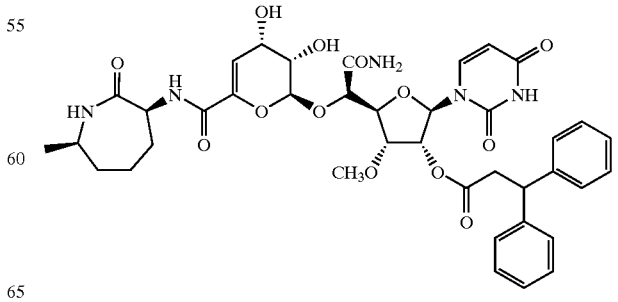

1) ¹H nuclear magnetic resonance spectrum was measured in deuterated methanol with tetramethylsilane as an internal standard substance. ¹H nuclear magnetic resonance spectrum is as follows:

δ=7.77 (d, J=8.1 Hz, 1H), 7.24 (m, 8H), 7.14 (m, 2H), 6.00 (d, J=4.0 Hz, 1H), 5.90 (d, J=5.4 Hz, 1H), 5.65 (d, J=8.1 Hz, 1H), 5.27 (t, J=5.2 Hz, 1H), 5.20 (d, J=5.4 Hz, 1H), 4.65 (d, J=2.1 Hz, 1H), 4.50 (m, 3H), 4.38 (t, J=4.0 Hz, 1H), 4.00 (t, J=4.6 Hz, 1H), 3.93 (t, J=4.9 Hz, 1H), 3.58 (m, 1H), 3.18 (s, 3H), 3.14 (d, J=8.1 Hz, 2H), 2.05–1.75 (m, 4H), 1.48 (m, 1H), 1.25 (m, 1H), 1.22 (d, J=6.6 Hz, 3H) ppm.

2) Infrared absorption spectrum: The infrared absorption spectrum as measured by the potassium bromide (KBr) disk method exhibits absorption maxima as follows:

3380, 2930, 1690, 1510, 1455, 1431, 1384, 1336, 1267, 1149, 1108, 1081, 1062 cm⁻¹.

EXAMPLE 12
(Exemp. Compound No. 22)

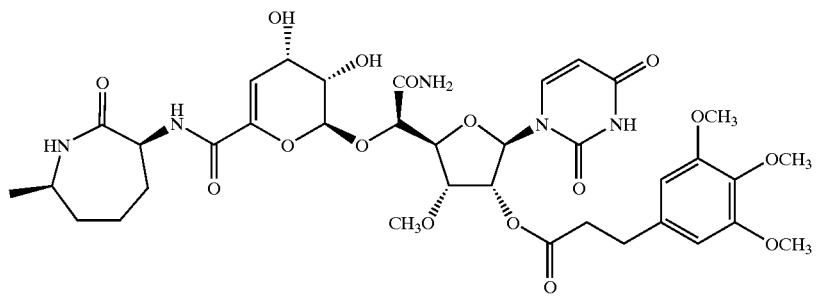

The reaction was conducted in a similar manner to that described in Example 11 by using 125 mg of the compound obtained in Example (11-1) and 72 mg of 3-(3,4,5-trimethoxyphenyl)propionic acid, whereby 113.6 mg of the below-described compound was obtained as the desired compound of Example 12.

1) ¹H nuclear magnetic resonance spectrum was measured in deuterated methanol with tetramethylsilane as an internal standard substance. ¹H nuclear magnetic resonance spectrum is as follows:

δ=7.92 (d, J=8.1 Hz, 1H), 6.53 (s, 2H), 6.01 (d, J=3.8 Hz, 1H), 5.91 (d, J=4.5 Hz, 1H), 5.71 (d, J=8.1 Hz, 1H), 5.45 (t, J=4.8 Hz, 1H), 5.24 (d, J=5.6 Hz, 1H), 4.67 (d, J=2.0 Hz, 1H), 4.52 (m, 2H), 4.42 (t, J=4.1 Hz, 1H), 4.01 (t, J=4.9 Hz, 1H), 3.97 (t, J=4.9 Hz, 1H), 3.81 (s, 6H), 3.71 (s, 3H), 3.57 (m, 1H), 3.29 (s, 3H), 2.87 (t, J=7.3 Hz, 2H), 2.72 (t, J=7.3 Hz, 2H), 2.05–1.75 (m, 4H), 1.48 (m, 1H), 1.25 (m, 1H), 1.21 (d, J=6.6 Hz, 3H) ppm.

2) Infrared absorption spectrum: The infrared absorption spectrum as measured by the potassium bromide (KBr) disk method exhibits absorption maxima as follows:

3388, 2933, 1692, 1591, 1509, 1458, 1424, 1384, 1335, 1268, 1239, 1127 cm⁻¹.

EXAMPLE 13

(Exemp. Compound No. 23)

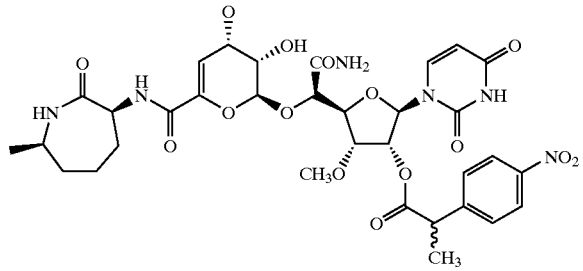

The reaction was conducted in a similar manner to that described in Example 11 by using 125 mg of the compound obtained in Example (11-1) and 59 mg of 2-(4-nitrophenyl) propionic acid, whereby 121.4 mg of the below-described compound was obtained as the desired compound of Example 13.

1) ¹H nuclear magnetic resonance spectrum was measured in deuterated methanol with tetramethylsilane as an internal standard substance. ¹H nuclear magnetic resonance spectrum is as follows:

δ=8.22 (m, 2H), 7.92 (m, 1H), 7.55 (d, J=8.6 Hz, 2H), 5.97 (m, 2H), 5.72 (m, 1H), 5.43 (m, 1H), 5.22 (m, 1H), 4.68–4.38 (m, 4H), 4.08–3.90 (m, 3H), 3.57 (m, 1H), 3.33 (m, 1.5H), 3.12 (s, 1.5H), 2.05–1.75 (m, 4H), 1.48 (m, 4H), 1.30 (m, 1H), 1.22 (d, J=6.6 Hz, 3H) ppm.

2) Infrared absorption spectrum: The infrared absorption spectrum as measured by the potassium bromide (KBr) disk method exhibits absorption maxima as follows:

3383, 2931, 1691, 1606, 1521, 1458, 1431, 1384, 1348, 1269, 1237, 1205, 1151, 1108, 1077, 1020 cm⁻¹.

EXAMPLE 14
(Exemp. Compound No. 10)

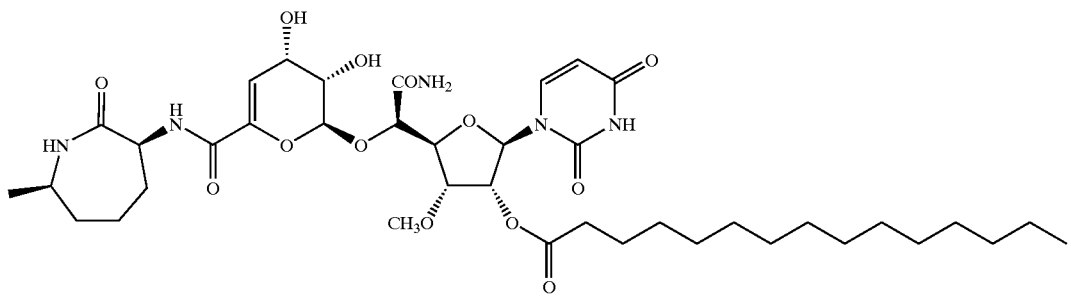

The reaction was conducted in a similar manner to that described in Example 11 by using 125 mg of the compound obtained in Example (1-1), 145 mg of pentadecanoic acid, 12 mg of DMAP and 116 mg of WSC, whereby 103.2 mg of the below-described compound was obtained as the desired compound of Example 14.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.01 (d, J=3.8 Hz, 1H), 5.97 (d, J=4.9 Hz, 1H), 5.72 (d, J=8.1 Hz, 1H), 5.44 (t, J=4.8 Hz, 1H), 5.24 (d, J=5.7 Hz, 1H), 4.68 (d, J=1.9 Hz, 1H), 4.55 (m, 2H), 4.42 (t, J=4.1 Hz, 1H), 4.06 (t, J=4.7 Hz, 1H), 3.97 (t, J=5.0 Hz, 1H), 3.57 (m, 1H), 3.38 (s, 3H), 2.37 (t, J=7.4 Hz, 2H), 2.05–1.75 (m, 4H), 1.63–1.15 (m, 29H), 0.90 (t, J=6.8 Hz, 3H) ppm.

2) Infrared absorption spectrum: The infrared absorption spectrum as measured by the potassium bromide (KBr) disk method exhibits absorption maxima as follows:
3391, 2925, 2854, 1686, 1510, 1460, 1430, 1384, 1337, 1270, 1235, 1146, 1109, 1061, 1021, 978 cm$^{-1}$.

EXAMPLE 15
(Exemp. Compound No. 46)

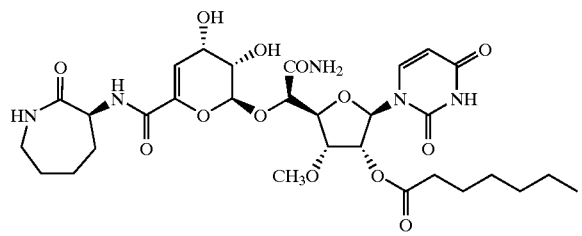

The reaction was conducted in a similar manner to that described in Example 10 by using 100 mg of the compound obtained in Example (10-1) and 129 μL of heptanoic anhydride, whereby 63.7 mg of the compound shown above was obtained as the desired compound of Example 15.

1) $^1$H nuclear magnetic resonance spectrum was measured in deuterated methanol with tetramethylsilane as an internal standard substance. $^1$H nuclear magnetic resonance spectrum is as follows:

δ=7.94 (d, J=8.2 Hz, 1H), 6.01 (d, J=3.6 Hz, 1H), 5.97 (d, J=4.9 Hz, 1H), 5.72 (d, J=8.2 Hz, 1H), 5.42 (t, J=4.9 Hz, 1H), 5.24 (d, J=5.5 Hz, 1H), 4.68 (d, J=2.0 Hz, 1H), 4.55 (m, 2H), 4.42 (t, J=4.2 Hz, 1H), 4.04 (t, J=4.8 Hz, 1H), 3.98 (t, J=4.9 Hz, 1H), 3.37 (s, 3H), 3.25 (m, 2H), 2.37 (t, J=7.3 Hz, 2H), 2.00 (m, 2H), 1.83 (m, 2H), 1.63–1.25 (m, 10H), 0.90 (t, J=6.8 Hz, 3H) ppm.

2) Infrared absorption spectrum: The infrared absorption spectrum as measured by the potassium bromide (KBr) disk method exhibits absorption maxima as follows:
3382, 2930, 2858, 1687, 1510, 1462, 1384, 1334, 1269, 1236, 1156, 1109, 1062 cm$^{-1}$.

EXAMPLE 16
(Exemp. Compound No. 11)

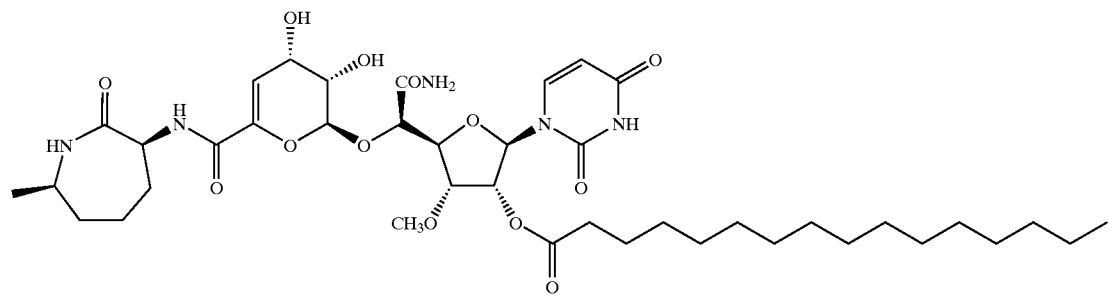

The reaction was conducted in a similar manner to that described in Example 10 by using 100 mg of the compound obtained in Example (11-1), 158 mg of palmitic anhydride and 2 mg of DMAP, whereby 93.4 mg of the compound shown above was obtained as the desired compound of Example 16.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.01 (d, J=3.7 Hz, 1H), 5.98 (d, J=4.9 Hz, 1H), 5.72 (d, J=8.1 Hz, 1H), 5.44 (t, J=4.9 Hz, 1H), 5.24 (d, J=5.6 Hz, 1H), 4.68 (d, J=1.7 Hz, 1H), 4.55 (m, 2H), 4.41 (t, J=4.2 Hz, 1H), 4.06 (t, J=4.8 Hz, 1H), 1H), 3.97 (t, J=4.7 Hz, 1H), 3.58 (m, 1H), 3.38 (s, 3H), 2.37 (t, J=7.3 Hz, 2H), 2.05–1.75 (m, 4H), 1.63–1.20 (m, 31H),0.90 (t, J=6.9 Hz, 3H) ppm.

2) Infrared absorption spectrum: The infrared absorption spectrum as measured by the potassium bromide (KBr) disk method exhibits absorption maxima as follows:
3390, 2925, 2854, 1744, 1689, 1509, 1459, 1432, 1384, 1337, 1269, 1235, 1147, 1111, 1062, 1021 cm$^{-1}$.

EXAMPLE 17
(Exemp. Compound No. 7)

The reaction was conducted in a similar manner to that described in Example 10 by using 100 mg of the compound obtained in Example (11-1) and 177 μL of decanoic anhydride, whereby 62.2 mg of the compound shown above was obtained as the desired compound of Example 17.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.01 (d, J=3.8 Hz, 1H), 5.97 (d, J=4.7 Hz, 1H), 5.72 (d, J=8.1 Hz, 1H), 5.44 (t, J=4.9 Hz, 1H), 5.24 (d, J=5.4 Hz, 1H), 4.68 (d, J=1.7 Hz, 1H), 4.55 (m, 2H), 4.41 (t, J=4.1 Hz, 1H), 4.06 (t, J=4.8 Hz, 1H), 3.97 (t, J=5.0 Hz, 1H), 3.58 (m, 1H), 3.38 (s, 3H), 2.37 (t, J=7.4 Hz, 2H), 2.05–1.75 (m, 4H), 1.63–1.20 (m, 19H), 0.90 (t, J=6.8 Hz, 3H) ppm.

2) Infrared absorption spectrum: The infrared absorption spectrum as measured by the potassium bromide (KBr) disk method exhibits absorption maxima as follows:
3390, 2927, 2855, 1689, 1510, 1459, 1430, 1384, 1336, 1269, 1151, 1109, 1062, 1022 cm$^{-1}$.

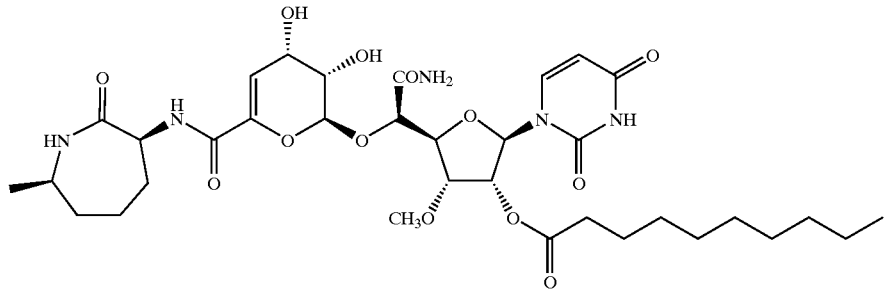

EXAMPLE 18
(Exemp. Compound No. 6)

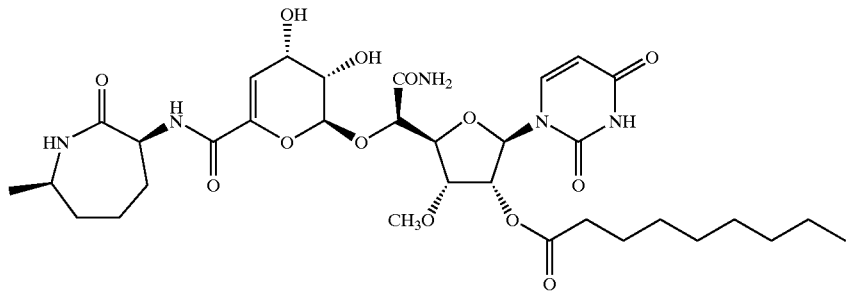

The reaction was conducted in a similar manner to that described in Example 10 by using 100 mg of the compound obtained in Example (11-1) and 160 μL of decanoic anhydride, whereby 59.9 mg of the desired compound shown above was obtained.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.01 (d, J=3.8 Hz, 1H), 5.97 (d, J=4.7 Hz, 1H), 5.7 (d, J=8.1 Hz, 1H), 5.44 (t, J=4.9 Hz, 1H), 5.24 (d, J=5.6 Hz, 1H), 4.68 (d, J=1.6 Hz, 1H), 4.55 (m, 2H), 4.42 (t, J=4.1 Hz, 1H), 4.06 (t, J=4.8 Hz, 1H), 3.97 (t, J=4.9 Hz, 1H), 3.58 (m, 1H), 3.38 (s, 3H), 2.37 (t, J=7.3 Hz, 2H), 2.05–1.75 (m, 4H), 1.63–1.20 (m, 17H), 0.90 (t, J=6.6 Hz, 3H) ppm.

2) Infrared absorption spectrum: The infrared absorption spectrum as measured by the potassium bromide (KBr) disk method exhibits absorption maxima as follows:
3389, 2928, 2856, 1688, 1510, 1459, 1384, 1336, 1269, 1153, 1108, 1061, 1023 cm$^{-1}$.

EXAMPLE 19
(Exemp. Compound No. 9)

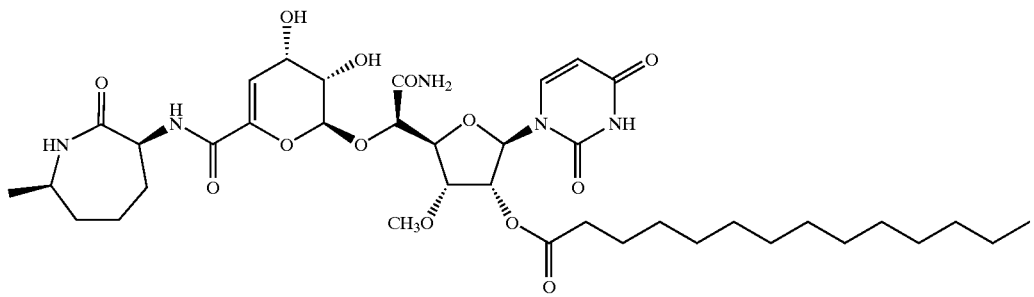

The reaction was conducted in a similar manner to that described in Example 10 by using 100 mg of the compound obtained in Example (11-1) and 105 mg of myristic anhydride, whereby 81.6 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.01 (d, J=3.9 Hz, 1H), 5.97 (d, J=4.8 Hz, 1H), 5.72 (d, J=8.1 Hz, 1H), 5.44 (t, J=4.9 Hz, 1H), 5.24 (d, J=5.6 Hz, 1H), 4.68 (d, J=1.8 Hz, 1H), 4.55 (m, 2H), 4.42 (t, J=4.1 Hz, 1H), 4.06 (t, J=4.8 Hz, 1H), 3.97 (t, J=4.9 Hz, 1H), 3.58 (m, 1H), 3.38 (s, 3H), 2.37 (t, J=7.3 Hz, 2H), 2.05–1.75 (m, 4H), 1.63–1.20 (m, 27H), 0.90 (t, J=6.6 Hz, 3H) ppm.

2) Infrared absorption spectrum: The infrared absorption spectrum as measured by the potassium bromide (KBr) disk method exhibits absorption maxima as follows:
3389, 2925, 2854, 1689, 1509, 1459, 1384, 1337, 1269, 1148, 1110, 1062, 1022 cm$^{-1}$.

EXAMPLE 20
(Exemp. Compound No. 8)

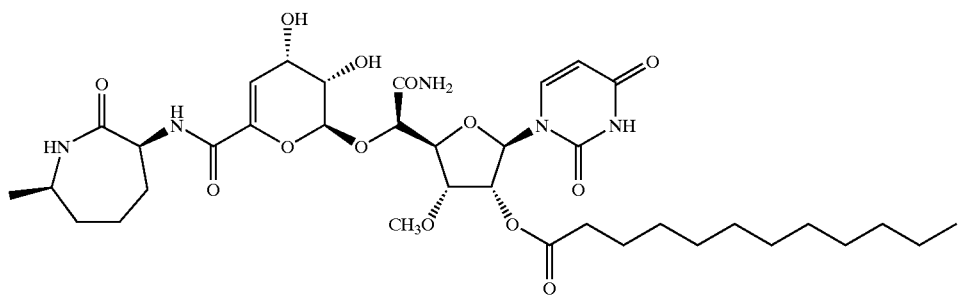

The reaction was conducted in a similar manner to that described in Example 10 by using 100 mg of the compound obtained in Example (11-1) and 91.8 mg of lauric anhydride, whereby 69.7 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.2 Hz, 1H), 6.01 (d, J=3.9 Hz, 1H), 5.97 (d, J=4.7 Hz, 1H), 5.72 (d, J=8.2 Hz, 1H), 5.44 (t, J=4.9 Hz, 1H), 5.24 (d, J=5.7 Hz, 1H), 4.69 (d, J=1.6 Hz, 1H), 4.55 (m, 2H), 4.42 (t, J=4.1 Hz, 1H), 4.07 (t, J=4.8 Hz, 1H), 3.97 (t, J=4.7 Hz, 1H), 3.58 (m, 1H), 3.38 (s, 3H), 2.37 (t, J=7.3 Hz, 2H), 2.05–1.75 (m, 4H), 1.63–1.20 (m, 23H), 0.90 (t, J=7.0 Hz, 3H) ppm.

2) Infrared absorption spectrutm: The infrared absorption spectrum as measured by the potassium bromide (KBr) disk method exhibits absorption maxima as follows:
3389, 2926, 2855, 1689, 1509, 1459, 1384, 1336, 1269, 1149, 1110, 1062, 1022 cm$^{-1}$.

EXAMPLE 21
(Exemp. Compound No. 16)

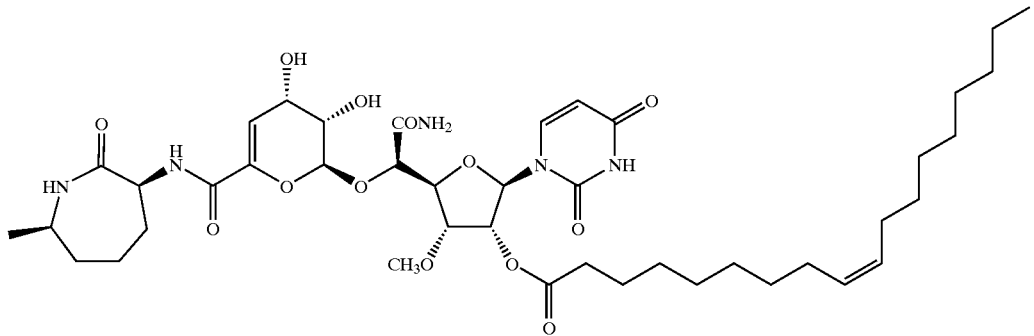

The reaction was conducted in a similar manner to that described in Example 11 by using 100 mg of the compound obtained in Example (11-1) and 92.2 ml of oleic acid, whereby 70.9 mg of the compound shown above was obtained.

1) 1H nuclear magnetic resonance spectrum was measured in deuterated methanol with tetramethylsilane as an internal standard substance. $^1$H nuclear magnetic resonance spectrum is as follows:
δ=7.95 (d, J=8.2 Hz, 1H), 6.01 (d, J=3.9 Hz, 1H), 5.97 (d, J=4.8 Hz, 1H), 5.72 (d, J=8.2 Hz, 1H), 5.44 (t, J=4.9 Hz, 1H), 5.34 (t, J=4.8 Hz, 2H), 5.24 (d, J=5.7 Hz, 1H), 4.68 (d, J=1.9 Hz, 1H), 4.55 (m, 2H), 4.42 (t, J=4.1 Hz, 1H), 4.07 (t, J=4.8 Hz, 1H), 3.97 (t, J=4.7 Hz, 1H), 3.58 (m, 1H), 3.38 (s, 3H), 2.37 (t, J=7.4 Hz, 2H), 2.05–1.75 (m, 8H), 1.60 (m, 2H), 1.49 (m, 1H), 1.33 (m, 21H), 1.22 (d, J=6.7 Hz, 3H), 0.89 (t, J=7.0 Hz, 3H) ppm.

2) Infrared absorption spectrum: The infrared absorption spectrum as measured by the potassium bromide (KBr) disk method exhibits absorption maxima as follows:
3391, 2926, 2855, 1688, 1509, 1459, 1431, 1384, 1336, 1269, 1145, 1109, 1061, 1022 cm$^{-1}$.

EXAMPLE 22
(Exemp. Compound No. 18)

The reaction was conducted in a similar manner to that described in Example 10 by using 100 mg of the compound obtained in Example (11-1) and 259 mg of linolenic acid anhydride, whereby 65 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:
δ=7.95 (d, J=8.0 Hz, 1H), 6.01 (d, J=3.8 Hz, 1H), 5.97 (d, J=4.8 Hz, 1H), 5.72 (d, J=8.0 Hz, 1H), 5.45 (t, J=4.9 Hz, 1H), 5.34 (m, 6H), 5.24 (d, J=5.7 Hz, 1H), 4.68 (d, J=1.9 Hz, 1H), 4.55 (m, 2H), 4.41 (t, J=4.2 Hz, 1H), 4.07 (t,J=4.8 Hz, 1H), 3.97 (t, J=4.8 Hz, 1H), 3.58 (m, 1H), 3.38 (s, 3H), 2.81 (t, J=5.9 Hz, 4H), 2.38 (t, J=7.3 Hz, 2H), 2.10–1.75 (m, 8H), 1.60 (m, 2H), 1.49 (m, 1H), 1.32 (m, 9H), 1.22 (d, J=6.7 Hz, 3H), 0.97 (t, J=7.5 Hz, 3H) ppm.

2) Infrared absorption spectrum: The infrared absorption spectrum as measured by the potassium bromide (KBr) disk method exhibits absorption maxima as follows:
3389, 3011, 2928, 2855, 1688, 1509, 1459, 1430, 1385, 1337, 1269, 1144, 1108, 1061, 1022 cm$^{-1}$.

EXAMPLE 23
(Exemp. Compound No. 17)

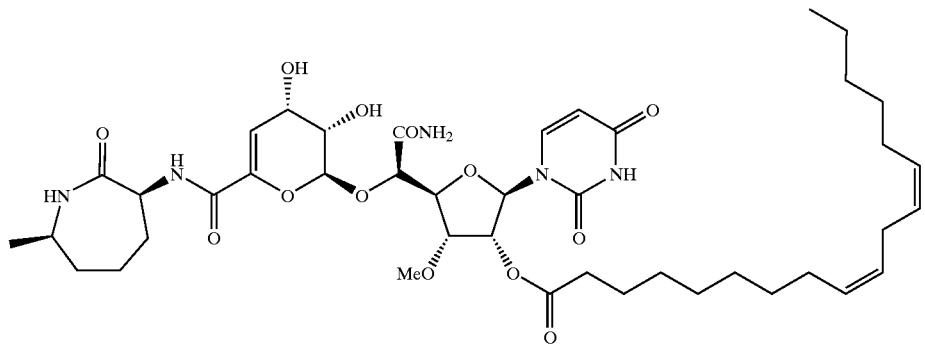

The reaction was conducted in a similar manner to that described in Example 10 by using 150 mg of the compound obtained in Example (11-1) and 326 mg of linoleic anhydride, whereby 80.5 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.01 (d, J=3.9 Hz, 1H), 5.97 (d, J=4.8 Hz, 1H), 5.72 (d J=8.1 Hz, 1H), 5.45 (t J=4.9 Hz, 1H), 5.35 (m, 4H), 5.24 (d, J=5.7 Hz, 1H), 4.68 (d, J=1.9 Hz, 1H), 4.55 (m, 2H), 4.41 (t, J=4.2 Hz, 1H), 4.07 (t, J=4.8 Hz, 1H), 3.97 (t, J=5.0 Hz, 1H), 3.58 (m, 1H), 3.38 (s, 3H), 2.77 (t, J=6.3 Hz, 2H), 2.38 (t, J=7.3 Hz, 2H), 2.10–1.75 (m, 8H), 1.60 (m, 2H), 1.49 (m, 1H), 1.32 (m, 15H), 1.22 (d, J=6.7 Hz, 3H), 0.97 (t, J=6.9 Hz, 3H) ppm.

2) Infrared absorption spectrum: The infrared absorption spectrum as measured by the potassium bromide (KBr) disk method exhibits absorption maxima as follows:
3388, 3009, 2928, 2856, 1687, 1510, 1459, 1430, 1384, 1337, 1270, 1144, 1108, 1061, 1021 cm$^{-1}$.

EXAMPLE 24
(Exemp. Compound No. 50)

The reaction was conducted in a similar manner to that described in Example 10 by using 100 mg of the compound obtained in Example (10-1) and 125.5 mg of lauric anhydride, whereby 78.3 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:

δ7.95 (d, J=8.1 Hz, 1H), 6.01 (d, J=3.9 Hz, 1H), 5.97 (d, J=4.8 Hz, 1 H), 5.72 (d, J=8.1 Hz, 1H), 5.42 (t, J=4.9 Hz, 1H), 5.24 (d, J=5.7 Hz, 1H), 4.68 (d, J=1.6 Hz, 1H), 4.55 (m, 2H), 4.42 (t, J=4.1 Hz, 1H), 4.04 (t, J=4.8 Hz, 1H), 3.98 (t, J=4.8 Hz, 1H), 3.37 (s, 3H), 3.25 (m, 2H), 2.37 (t, J=7.3 Hz, 2H), 2.00 (m, 2H), 1.84 (m, 2H), 1.64–1.25 (m, 20H), 0.90 (t, J=6.8 Hz, 3H) ppm.

2) Infrared absorption spectrum: The infrared absorption spectrum as measured by the potassium bromide (KBr) disk method exhibits absorption maxima as follows:
3381, 2926, 2855, 1689, 1509, 1462, 1436, 1383, 1333, 1269, 1149, 1111, 1063 cm$^{-1}$.

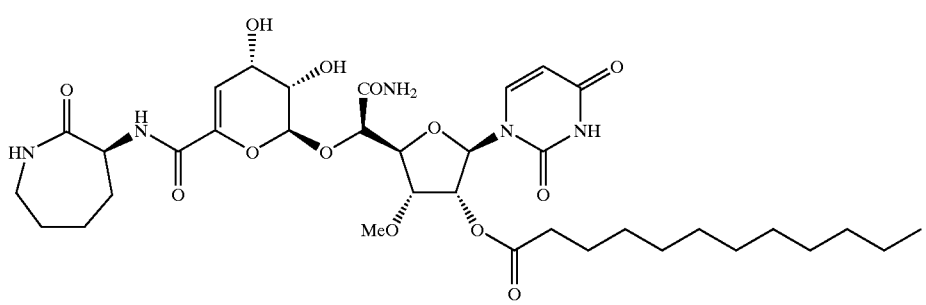

EXAMPLE 25
(Exemp. Compound No. 49)

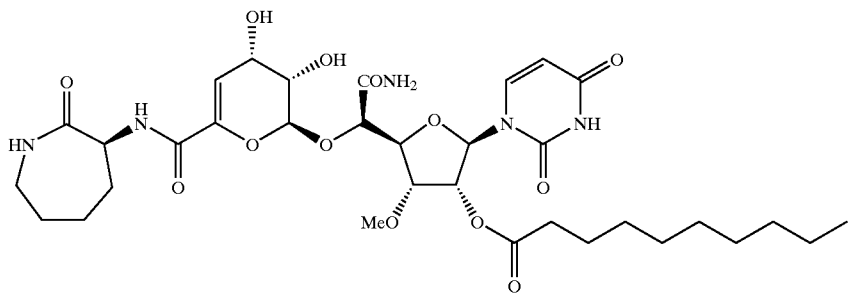

The reaction was conducted in a similar manner to that described in Example 10 by using 150 mg of the compound obtained in Example (10-1) and 181 μl of decanoic anhydride, whereby 124.3 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:

δ=7.94 (d, J=8.1 Hz, 1H), 6.01 (d, J=3.9 Hz, 1H), 5.97 (d, J=4.9 Hz, 1H), 5.72 (d, J=8.1 Hz, 1H), 5.42 (t, J=4.8 Hz, 1H), 5.24 (d, J=5.6 Hz, 1H), 4.68 (d, J=1.7 Hz, 1H), 4.55 (m, 2H), 4.42 (t, J=4.2 Hz, 1H), 4.04 (t, J=4.8 Hz, 1H), 3.98 (t, J=4.8 Hz, 1H), 3.37 (s, 3H), 3.25 (m, 2H), 2.37 (t, J=7.3 Hz, 2H), 2.00 (m, 2H), 1.84 (m, 2H), 1.64–1.25 (m, 16H), 0.90 (t, J=6.8 Hz, 3H) ppm.

2) Infrared absorption spectrum: The infrared absorption spectrum as measured by the potassium bromide (KBr) disk method exhibits absorption maxima as follows:
3378, 2927, 2856, 1689, 1509, 1462, 1436, 1383, 1333, 1270, 1151, 1111, 1063 cm$^{-1}$.

EXAMPLE 26
(Exemp. Compound No. 51)

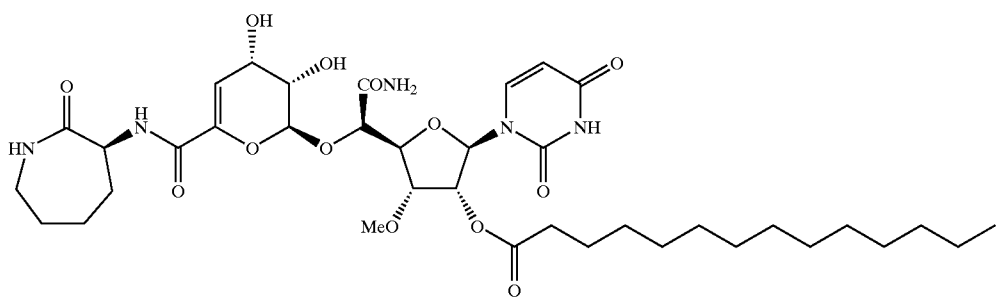

The reaction was conducted in a similar manner to that described in Example 10 by using 100 mg of the compound obtained in Example (10-1) and 181 mg of myristic anhydride, whereby 67.5 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:

δ=7.94 (d, J=8.1 Hz, 1H), 6.01 (d, J=3.9 Hz, 1H), 5.97 (d, J=4.8 Hz, 1H), 5.72 (d, J=8.1 Hz, 1H), 5.42 (t, J=5.0 Hz, 1H), 5.24 (d, J=5.6 Hz, 1H), 4.68 (d, J=1.6 Hz, 1H), 4.55 (m, 2H), 4.42 (t, J=4.1 Hz, 1H), 4.04 (t, J=4.8 Hz, 1H), 3.98 (t, J=4.9 Hz, 1H), 3.37 (s, 3H), 3.25 (m, 2H), 2.37 (t, J=7.3 Hz, 2H), 2.00 (m, 2H), 1.84 (m, 2H), 1.64–1.25 (m, 24H), 0.90 (t, J=6.8 Hz, 3H) ppm.

2) Infrared absorption spectrum: The infrared absorption spectrum as measured by the potassium bromide (KBr) disk method exhibits absorption maxima as follows:
3378, 2926, 2855, 1689, 1509, 1464, 1435, 1383, 1333, 1269, 1147, 1111, 1063 cm$^{-1}$.

EXAMPLE 27
(Exemp. Compound No. 48)

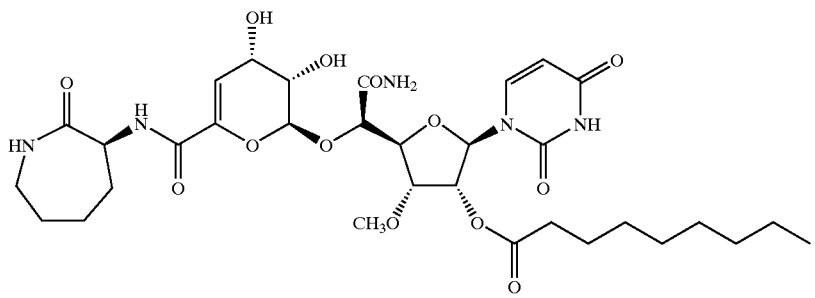

The reaction was conducted in a similar manner to that described in Example 10 by using 150 mg of the compound obtained in Example (10-1) and 163 μl of pelargonic acid anhydride, whereby 93.5 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:
   δ=7.94 (d, J=8.1 Hz, 1H), 6.01 (d, J=3.8 Hz, 1H), 5.97 (d, J=5.0 Hz, 1H), 5.72 (d, J=8.1 Hz, 1H), 5.42 (t, J=4.8 Hz, 1H), 5.24 (d, J=5.4 Hz, 1H), 4.68 (d, J=1.8 Hz, 1H), 4.55 (m, 2H), 4.42 (t, J=4.2 Hz, 1H), 4.04 (t, J=4.8 Hz, 1H), 3.98 (t, J=4.9 Hz, 1H), 3.37 (s, 3H), 3.25 (m, 2H), 2.37 (t, J=7.3 Hz, 2H), 2.00 (m, 2H), 1.84 (m, 2H), 1.64–1.25 (m, 14H), 0.90 (t, J=6.8 Hz, 3H) ppm.
2) Infrared absorption spectrum: The infrared absorption spectrum as measured by the potassium bromide (KBr) disk method exhibits absorption maxima as follows:
   3376, 2927, 2856, 1690, 1509, 1461, 1436, 1379, 1334, 1264, 1150, 1108, 1064 cm$^{-1}$.

EXAMPLE 28
(Exemp. Compound No. 282)

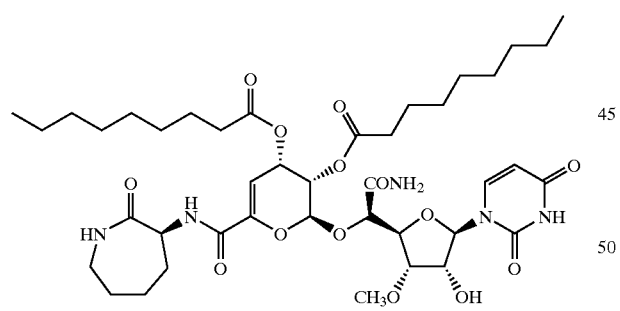

The reaction was conducted in a similar manner to that described in Example 9 by using 243 mg of the compound obtained in Example (8-1) and 130 μl of pelargonic acid anhydride, whereby 145.5 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:
   <
   δ7.72 (d, J=8.1 Hz, 1H), 5.99 (t, J=2.5 Hz, 1H), 5.88 (d, J=8.1 Hz, 1H), 5.81 (d, J=4.5 Hz, 1H), 5.72 (m, 1H), 5.64 (m, 1H), 5.45 (d, J=3.3 Hz, 1H), 4.68 (d, J=2.2 J=4.8 Hz, 1H), 3.65 (t, J=5.2 Hz, 1H), 3.34 (s, 3H), 3.25 (m, 2H), 2.37 (m, 4H), 2.03 (m, 2H), 1.85 (m, 2H), 1.62 (m, 5H), 1.32 (m, 21H), 0.90 (m, 6H) ppm.

2) Infrared absorption spectrum: The infrared absorption spectrum as measured by the potassium bromide (KBr) disk method exhibits absorption maxima as follows:
   3369, 2927, 2856, 1749, 1693, 1508, 1461, 1380, 1335, 1270, 1258, 1143, 1115, 1067 cm$^{-1}$.

EXAMPLE 29

(Exemp. Compound No. 52)

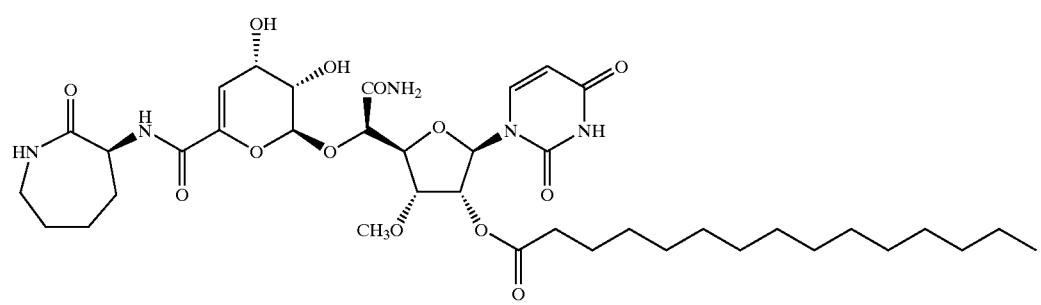

The reaction was conducted in a similar manner to that described in Example 11 by using 153.7 mg of the compound obtained in Example (10-1) and 122.2 mg of pentadecanoic acid, whereby 102.8 mg of the compound shown above was obtained.

1) $^1$H nuclear magnetic resonance spectrum was measured in deuterated methanol with tetramethylsilane as an internal standard substance. $^1$H nuclear magnetic resonance spectrum is as follows:

δ=7.94 (d, J=8.1 Hz, 1H), 6.01 (d, J=3.7 Hz, 1H), 5.97 (d, J=5.0 Hz, 1H), 5.72 (d, J=8.1 Hz, 1H), 5.42 (t, J=4.9 Hz, 1H), 5.24 (d, J=5.6 Hz, 1H), 4.68 (d, J=2.0 Hz, 1H), 4.55 (m, 2H), 4.42 (t, J=4.1 Hz, 1H), 4.04 (t, J=4.8 Hz, 1H), 3.98 (t, J=4.8 Hz, 1H), 3.37 (s, 3H), 3.25 (m, 2H), 2.37 (t, J=7.3 Hz, 2H), 2.00 (m, 2H), 1.84 (m, 2H), 1.64–1.25 (m, 26H), 0.90 (t, J=6.8 Hz, 3H) ppm.

2) Infrared absorption spectrum: The infrared absorption spectrum as measured by the potassium bromide (KBr) disk method exhibits absorption maxima as follows:

3383, 2925, 2854, 1688, 1509, 1465, 1436, 1384, 1334, 1270, 1147, 1112, 1063 cm$^{-1}$.

EXAMPLE 30
(Exemp. Compound No. 283)

The reaction was conducted in a similar manner to that described in Example 9 by using decanoic acid anhydride instead of heptanoic acid anhydride whereby 40.6 mg of the desired compound was obtained.

1) $^1$H nuclear magnetic resonance spectrum was measured in deuterated methanol with tetramethylsilane as an internal standard substance. $^1$H nuclear magnetic resonance spectrum is as follows:

δ=7.72 (d, J=8.1 Hz, 1H), 5.99 (m, 1H), 5.87 (d, J=8.1 Hz, 1H), 5.81 (d, J=4.4 Hz, 1H), 5.72 (m, 1H), 5.64 (m, 1H), 5.45 (d, J=3.1 Hz, 1H), 4.68 (d, J=2.2 Hz, 1H), 4.57 (m, 1H), 4.46 (dd, J=2.1 and 5.4 Hz, 1H), 4.18 (t, J=5.0 Hz, 1H), 3.65 (t, J=5.0 Hz, 1H), 3.33 (s, 3H), 3.25 (m, 2H), 2.36 (m, 4H), 2.02 (m, 2H), 1.85 (m, 2H), 1.70–1.25 (m, 30H), 0.90 (t, J=6.3 Hz, 6H) ppm.

2) Infrared absorption spectrum: The infrared absorption spectrum as measured by the potassium bromide (KBr) disk method exhibits absorption maxima as follows:

3375, 2926, 2854, 1747, 1691, 1507, 1463, 1380, 1334, 1267, 1247, 1142, 1115, 1066 cm$^{-1}$.

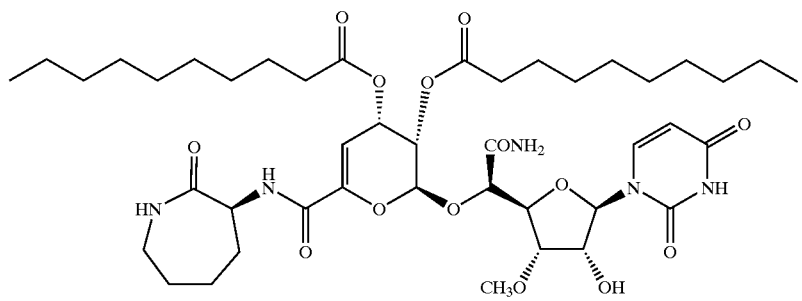

EXAMPLE 31
(Exemp. Compound No. 5)

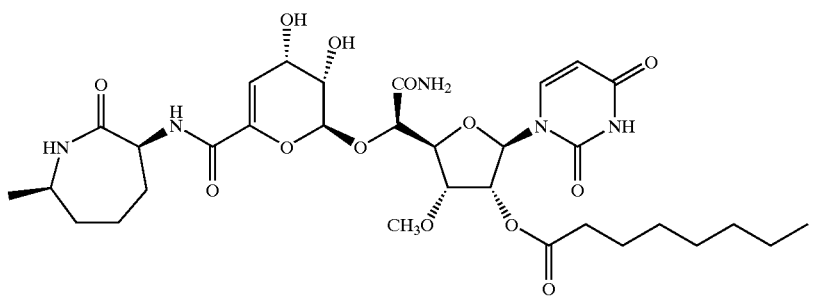

The reaction was conducted in a similar manner to that described in Example 10 by using 187 mg of the compound obtained in Example (11-1) and 267 μl of octanoic acid anhydride, whereby 115 mg of the desired compound shown above was obtained.

1) $^1$H nuclear magnetic resonance spectrum was measured in deuterated methanol with tetramethylsilane as an internal standard substance. $^1$H nuclear magnetic resonance spectrum is as follows:

67 =7.95 (d, J=8.1 Hz, 1H), 6.01 (d, J=3.9 Hz, 1H), 5.97 (d, J=4.9 Hz, 1H), 5.72 (d, J=8.1 Hz, 1H), 5.44 (t, J=4.9 Hz, 1H), 5.23 (d, J=5.5 Hz, 1H), 4.68 (d, J=2.0 Hz, 1H), 4.56 (m, 1H), 4.52 (m, 1H), 4.42 (t, J=4.1 Hz, 1H), 4.06 (t, J=4.7 Hz, 1H), 3.97 (t, J=5.1 Hz, 1H), 3.57 (m, 1H), 3.38 (s, 3H), 2.37 (t, J=7.3 Hz, 2H), 2.05–1.75 (m, 4H), 1.60 (m, 2H), 1.48 (m, 1H), 1.32 (m, 9H), 1.21 (d, J=6.6 Hz, 3H), 0.90 (t, J=6.6 Hz, 3H) ppm.

2) Infrared absorption spectrum: The infrared absorption spectrum as measured by the potassium bromide (KBr) disk method exhibits absorption maxima as follows:
3399, 2930, 2857, 1686, 1511, 1459, 1430, 1385, 1335, 1268, 1231, 1152, 1107, 1061, 1022 cm$^{-1}$.

EXAMPLE 32
(Exemp. Compound No. 540)

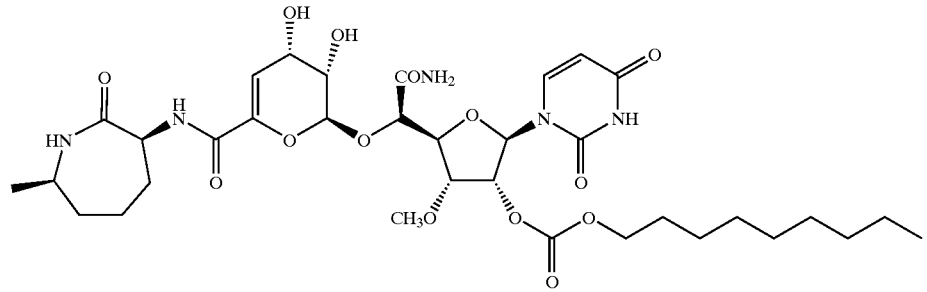

In 3 mL of pyridine were dissolved 125 mg of the compound obtained in Example (11-1), 170 μl of nonyl chloroformate, 147 mg of dimethylaminopyridine and 3 mg of 4-pyridylpyridine. The resulting solution was stirred at room temperature. Three hours later, the solvent was distilled off under reduced pressure. The residue was then dissolved in 60 mL of ethyl acetate. After washing with 60 mL of each of saturated aqueous NaHCO$_3$ and saturated saline, drying was conducted over anhydrous sodium sulfate. The solvent was distilled off under reduced pressure and the residue was dissolved in 4 mL of methanol. To the resulting solution was added 200 mg of "Amberlyst 15", followed by heating under reflux. Three hours later, the insoluble matter was filtered off and the solvent was distilled off under reduced pressure. The residue was subjected to a silica gel column (8 g) and eluted with 5% methanol—methylene chloride, whereby 108 mg of the desired compound was obtained.

1) $^1$H nuclear magnetic resonance spectrum was measured in deuterated methanol with tetramethylsilane as an internal standard substance. $^1$H nuclear magnetic resonance spectrum is as follows:
δ=7.94 (d, J=8.2 Hz, 1H), 6.01 (d, J=4.0 Hz, 1H), 5.98 (d, J=4.6 Hz 1H), 5.71 (d, J=8.2 Hz, 1H), 5.32 (t, J=4.8 Hz, 1H), 5.23 (d, J=5.7 Hz, 1H), 4.68 (d, J=2.0 Hz, 1H), 4.56 (m, 1H), 4.52 (m, 1H), 4.41 (t, J=4.2 Hz, 1H), 4.13 (m, 3H), 3.97 (t, J=5.0 Hz, 1H), 3.57 (m, 1H), 3.40 (s, 3H), 2.05–1.75 (m, 4H), 1.65 (m, 2H), 1.48 (m, 1H), 1.32 (m, 13H), 1.22 (d, J=6.6 Hz, 3H), 0.90 (t, J=6.6 Hz, 3H) ppm.

2) Infrared absorption spectrum: The infrared absorption spectrum as measured by the potassium bromide (KBr) disk method exhibits absorption maxima as follows:
3385, 2929, 2855, 1753, 1691, 1510, 1458, 1431, 1393, 1259, 1144, 1101, 1076, 1021

EXAMPLE 33
(Exemp. Compound No. 539)

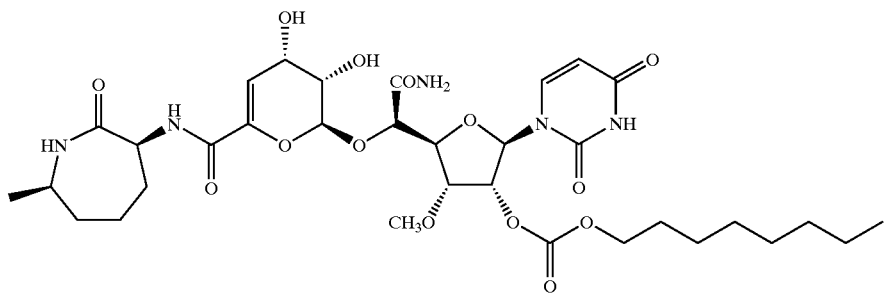

The reaction was conducted in a similar manner to that described in Example 32 except for the use of 157 μl of octyl chloroformate instead of nonyl chloroformate, whereby 91 mg of the desired compound was obtained.

1) $_1$H nuclear magnetic resonance spectrum was measured in deuterated methanol with tetramethylsilane as an internal standard substance. $^1$H nuclear magnetic resonance spectrum is as follows:
δ=7.94 (d, J=8.1 Hz, 1H), 6.01 (d, J=3.9 Hz, 1H), 5.98 (d, J=4.4 Hz, 1H), 5.71 (d, J=8.1 Hz, 1H), 5.32 (t, J=4.6 Hz, 1H), 5.24 (d, J=5.6 Hz, 1H), 4.69 (d, J=2.0 Hz, 1H), 4.56 (m, 1H), 4.52 (m, 1H), 4.41 (t, J=4.0 Hz, 1H), 4.13 (m, 3H), 3.97 (t, J=5.0 Hz, 1H), 3.57 (m, 1H), 3.40 (s, 3H), 2.05–1.75 (m, 4H), 1.65 (m, 2H), 1.48 (m, 1H), 1.32 (m, 11H), 1.22 (d, J=6.6 Hz, 3H), 0.90 (t, J=6.6 Hz, 3H) ppm.

2) Infrared absorption spectrum: The infrared absorption spectrum as measured by the potassium bromide (KBr) disk method exhibits absorption maxima as follows:
3387, 2929, 2856, 1752, 1689, 1510, 1458, 1431, 1392, 1335, 1260, 1143, 1101, 1073, 1021 cm$^{-1}$.

EXAMPLE 34
(Exemp. Compound No. 594)

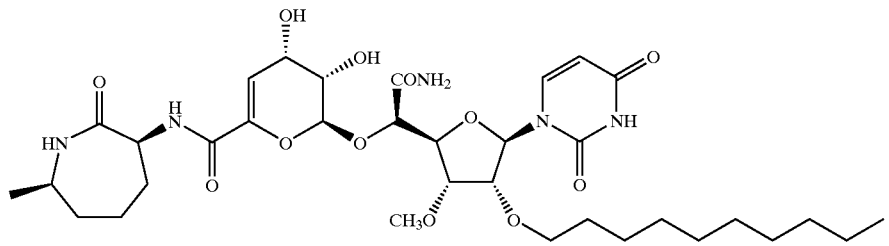

(34-1)

In 50 mL of dimethylformamide (DMF) were dissolved 4.57 g of the compound obtained in Example (11-1) and 2.2 mL of 1,8-diazabicyclo[5.4.0]-7-undecene (DBU). To the resulting solution was added a solution obtained by dissolving 2.45 g of 4-methoxybenzyl chloromethyl ether in 50 mL of DMF. The resulting mixture was stirred at room temperature. After 2.5 hours, the solvent was distilled off under reduced pressure. The residue was dissolved in 300 mL of methylene chloride. The resulting solution was washed successively with 300 mL each of 0.1N aqueous hydrochloric acid, saturated aqueous sodium bicarbonate and saturated saline, and then dried over anhydrous magnesium sulfate. The solvent was distilled off under reduced pressure and then charged on a silica gel column (200 g), which was developed with 3% methanol in methylene chloride, whereby 4.80 g of the desired compound was obtained.

1) $^1$H nuclear magnetic resonance spectrum was measured in deuterated chloroform with tetramethylsilane as an internal standard substance. $^1$H nuclear magnetic resonance spectrum is as follows:
δ=7.85 (m, 1H), 7.69 (d, J=8.2 Hz, 1H), 7.32 (m, 2H), 7.15 (m, 2H), 6.85 (d, J=8.7 Hz, 2H), 6.37 (d, J=4.3 Hz, 1H), 6.06 (d, J=6.2 Hz, 1H), 5.82 (m, 1H), 5.75 (d, J=8.2 Hz, 1H), 5.70 (m, 1H), 5.44 (m, 2H), 4.73 (m, 3H), 4.61 (s, 2H), 4.57 (s, 1H), 4.45 (m, 1H) 4.25 (m, 1H), 4.03 (m, 2H), 3.79 (s, 3H), 3.56 (s, 3H), 3.53 (m, 1H), 3.28 (d, J=7.8 Hz, 1H), 2.35 (s, 2H), 2.15 (m, 1H), 2.02–1.75 (m, 4H), 1.49 (s, 3H), 1.42 (s, 3H), 1.30 (m, 2H), 1.23 (d, J=6.6 Hz, 3H) ppm.

2) Infrared absorption spectrum: The infrared absorption spectrum as measured by the potassium bromide (KBr) disk method exhibits absorption maxima as follows:
3387, 3105, 2984, 2935, 1669, 1612, 1514, 1457, 1383, 1361, 1300, 1248, 1219, 1169, 1114, 1079, 1064, 1012 cm$^{-1}$.

(34-2)

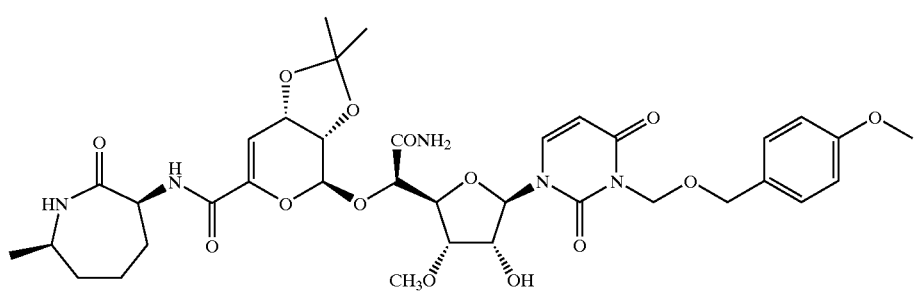

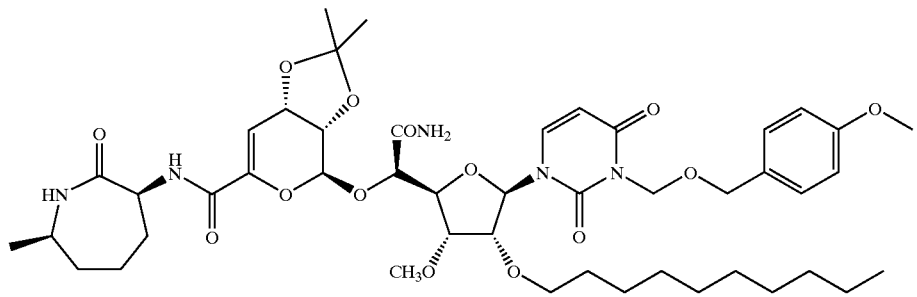

In 5 mL of DMF was dissolved 773 mg of the compound obtained in Example (34-1). The resulting solution was stirred at 0° C. under a nitrogen gas stream. To the reaction mixture was added 60 mg of NaH (about 60%). Two minutes later, 2.13 mL of 1-iododecane was added. Five minutes later, the temperature was allowed to rise back to room temperature, at which stirring was conducted for further 25 minutes. The reaction mixture was then distilled under reduced pressure to remove the solvent. The residue was dissolved in 250 mL of methylene chloride. The resulting solution was washed successively with 300 mL each of 0.01N aqueous hydrochloric acid, saturated aqueous sodium bicarbonate and saturated saline, and then dried over anhydrous magnesium sulfate. The solvent was distilled off under reduced pressure and the residue charged on a silica gel column (200 g) which was developed with 2% methanol in methylene chloride, whereby 395 mg of the desired compound was obtained.

1) $^1$H nuclear magnetic resonance spectrum was measured in deuterated chloroform with tetramethylsilane as an internal standard substance. $^1$H nuclear magnetic resonance spectrum is as follows:

δ=7.89 (d, J=8.1 Hz, 1H), 7.75 (d, J=5.9 Hz, 1H), 7.31 (d, J=8.8 Hz, 2H), 7.13 (br s, 1H), 6.86 (d, J=8.8 Hz, 2H), 6.37 (m, 1H), 5.95 (s, 1H), 5.75 (br s, 1H), 5.70 (d, J=8.1 Hz, 1H), 5.57 (m, 1H), 5.45 (s, 2H), 4.78 (d, J=8.1 Hz, 1H), 4.74 (m, 2H), 4.63 (s, 2H), 4.55 (s, 1H), 4.46 (m, 1H), 4.05 (m, 2H), 3.95 (m, 1H), 3.79 (s, 3H), 3.62 (m, 1H), 3.51 (m, 1H), 3.43 (s, 3H), 4.09 (m, 1H), 1.98 (m, 1H), 1.86 (m, 1H), 1.77 (m, 1H), 1.49 (s, 3H), 1.44 (s,, 3H), 1.40–1.20 (m, 18H), 1.19 (d, J=6.6 Hz, 3H), 0.88 (t, J=6.6 Hz, 3H) ppm.

2) Infrared absorption spectrum: The infrared absorption spectrum as measured by the potassium bromide (KBr) disk method exhibits absorption maxima as follows:

3386, 3102, 2928, 2855, 1713, 1670, 1613, 1587, 1514, 1456, 1382, 1359, 1338, 1300, 1271, 1248, 1220, 1167, 1112, 1066, 1013 cm$^{-1}$.

(34-3)

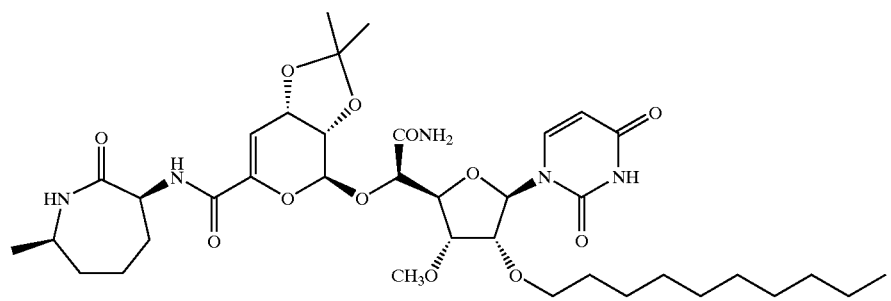

In 5 mL of methylene chloride was dissolved 390 mg of the compound obtained in Example (34-2). To the resulting solution were added 276 μL of water and 484 mg of 2,3-dichloro-5,6-dicyano-1,4-benzoquinone and the resulting mixture was stirred at room temperature. After 75 minutes, the insoluble matter was filtered off. The filtrate was diluted with 200 mL of methylene chloride, followed by successive washing with 200 mL each of saturated aqueous sodium bicarbonate and saturated saline, and then dried over anhydrous magnesium sulfate. The solvent was distilled off under reduced pressure and the residue was charged on a silica gel column (50 g) which was developed with 5% methanol in methylene chloride. whereby 278 mg of the desired compound was obtained.

1) $^1$H nuclear magnetic resonance spectrum was measured in deuterated chloroform with tetramethylsilane as an internal standard substance. $^1$H nuclear magnetic resonance spectrum is as follows:

δ=9.30 (br s, 1H), 7.99 (d, J=7.3 Hz, 1H), 7.70 (d, J=8.1 Hz, 1H), 7.19 (br s, 1H), 6.36 (d, J=4.4 Hz, 1H), 5.98 (br s, 1H), 5.85 (br s, 1H), 5.81 (d, J=5.1 Hz, 1H), 5.69 (dd, J=2.2 and 8.1 Hz, 1H), 4.74 (m, 2H), 4.60 (m, 2H), 4.28 (t, J=4.7 Hz, 1H), 4.12 (t, J=6.2 Hz, 1H), 4.07 (t, J=4.7 Hz, 1H), 3.59 (m, 3H), 4.43 (s, 3H), 2.10–1.73 (m, 4H), 1.60 (m, 2H), 1.48 (s, 3H), 1.42 (s, 3H), 1.23 (m, 19H), 0.88 (t, J=6.6 Hz, 3H) ppm.

2) Infrared absorption spectrum: The infrared absorption spectrum as measured by the potassium bromide (KBr) disk method exhibits absorption maxima as follows:

3387, 3227, 3098, 2928, 2855, 1692, 1506, 1457, 1431, 1382, 1337, 1296, 1268, 1250, 1235, 1220, 1166, 1121, 1082, 1065, 1013 cm$^{-1}$.

(34-4)

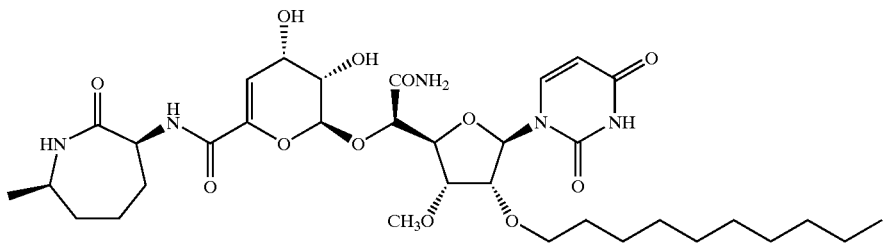

In 15 mL of methanol was dissolved 273 mg of the compound obtained in Example (34-3). To the resulting solution was added 260 mg of "Amberlyst 15" and the resulting mixture was stirred at 80° C. After 4 hours and 20 minutes, the insoluble matter was filtered off. The filtrate was distilled under reduced pressure, and the residue was charged on a silica gel column (15 g) which was developed with 5% methanol in methylene chloride, whereby 176 mg of the desired compound was obtained.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.02 (d, J=3.6 Hz, 1H), 5.92 (d, J=4.5 Hz, 1H), 5.72 (d, J=8.1 Hz, 1H), 5.23 (d, J=5.3 Hz, 1H), 4.67 (s, 1H), 4.59 (m, 1H), 4.52 (m, 1H), 4.38 (t, J=4.2 Hz, 1H), 4.08 (t, J=4.6 Hz, 1H), 3.98 (t, J=4.7 Hz, 1H), 3.94 (t, J=4.7 Hz, 1H), 3.58 (m, 3H), 3.40 (s, 3H), 2.05–1.75 (m, 4H), 1.52 (m, 3H), 1.25 (m, 18H), 0.89 (t, J=6.6 Hz, 3H) ppm.

2) Infrared absorption spectrum: The infrared absorption spectrum as measured by the potassium bromide (KBr) disk method exhibits absorption maxima as follows:
3391, 3099, 2927, 2854, 1686, 1509, 1458, 1431, 1385, 1335, 1269, 1132, 1099, 1063, 1020 cm$^{-1}$.

EXAMPLE 35
(Exemp. Compound No. 590)

In a similar manner to that described in Example (34-2) except for the use of 1.48 mL of 1-iodohexane instead of 1-iododecane, 460 mg of the desired compound was obtained.

1) $^1$H nuclear magnetic resonance spectrum was measured in deuterated methanol with tetramethylsilane as an internal standard substance. $^1$H nuclear magnetic resonance spectrum is as follows:

δ=7.91 (d, J=8.3 Hz, 1H), 7.24 (d, J=8.6 Hz, 2H), 6.85 (d, J=8.6 Hz, 2H), 6.18 (d, J=4.1 Hz, 1H), 5.92 (d, J=4.0 Hz, 1H), 5.74 (d, J=8.3 Hz, 1H), 5.42 (s, 2H), 5.11 (d, J=5.4 Hz, 1H), 4.80 (m, 1H), 4.70 (m, 1H), 4.55 (m, 3H), 4.37 (t, J=5.8 Hz, 1H), 4.08 (t, J=4.3 Hz, 1H), 3.94 (t, J=5.2 Hz, 1H), 3.76 (s, 3H), 3.60 (m, 3H), 3.41 (s, 3H), 2.05–1.75 (m, 4H), 1.55 (m, 3H), 1.43 (s, 6H), 1.25 (m, 8H), 1.19 (d, J=6.6 Hz, 3H), 0.88 (t, J=6.6 Hz, 3H) ppm.

2) Infrared absorption spectrum: The infrared absorption spectrum as measured by the potassium bromide (KBr) disk method exhibits absorption maxima as follows:
3381, 3103, 2933, 2871, 2859, 1670, 1613, 1587, 1514, 1455, 1383, 1359, 1300, 1271, 1249, 1220, 1167, 1130, 1112, 1066, 1013cm$^{-1}$.

(35-2)

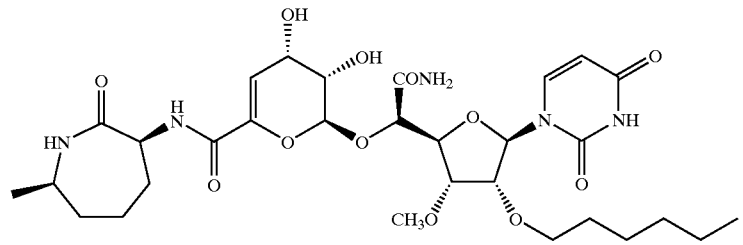

(35-1)

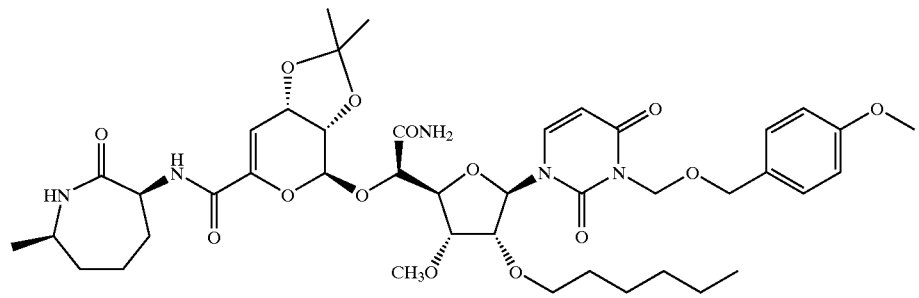

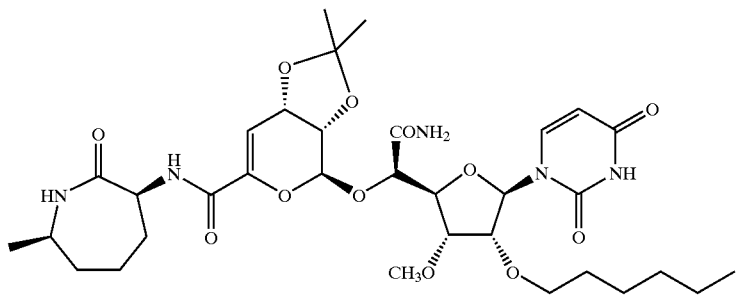

The reaction was conducted in a similar manner to that described in Example (34-3) using 458 mg of the compound obtained in Example (35-1), 313 mg of the desired compound was obtained.

1) $^1$H nuclear magnetic resonance spectrum was measured in deuterated chloroform with tetramethylsilane as an internal standard substance. $^1$H nuclear magnetic resonance spectrum is as follows:

δ=9.28 (br s, 1H), 7.99 (d, J=6.6 Hz, 1H), 7.71 (d, J=8.1 Hz, 1H), 7.19 (br s, 1H), 6.36 (d, J=4.4 Hz, 1H), 5.98 (br s, 1H), 5.85 (br s, 1H), 5.81 (d, J=5.1 Hz, 1H), 5.69 (dd, J=2.2 and 8.1 Hz, 1H), 4.74 (m, 2H), 4.60 (m, 3H), 4.28 (t, J=4.7 Hz, 1H), 4.12 (t, J=6.9 Hz, 1H), 4.07 (t, J=4.7 Hz, 1H), 3.59 (m, 3H), 4.42 (s, 3H), 2.10–1.73 (m, 4H), 1.60 (m, 2H), 1.48 (s, 3H), 1.42 (s, 3H), 1.23 (m, 11H), 0.87 (t, J=6.6 Hz, 3H) ppm.

2) Infrared absorption spectrum: The infrared absorption spectrum as measured by the potassium bromide (KBr) disk method exhibits absorption maxima as follows: 3386, 3097, 2933, 2872, 2859, 1692, 1507, 1457, 1432, 1383, 1337, 1268, 1235, 1220, 1166, 1129, 1082, 1065, 1012 cm$^{-1}$.

(35-3)

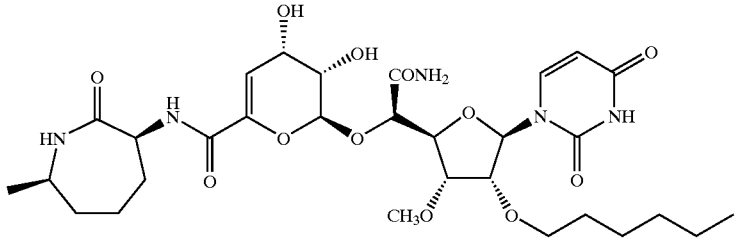

In 15 mL of methanol was dissolved 273 mg of the compound obtained in Example (35-2). To the resulting solution was added 260 mg of "Amberlyst 15". The resulting mixture was stirred at 80° C. After 4 hours and 20 minutes, the insoluble matter was filtered off. The filtrate was distilled under reduced pressure. The residue was subjected to a silica gel column (15 g) and then eluted with 5% methanol in methylene chloride, whereby 176 mg of the desired compound was obtained.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.01 (d, J=3.9 Hz, 1H), 5.92 (d, J=4.5 Hz, 1H), 5.72 (d, J=8.1 Hz, 1H), 5.23 (d, J=5.6 Hz,

1H), 4.66 (d, J=2.0 Hz, 1H), 4.59 (m, 1H), 4.50 (m, 1H), 4.38 (t, J=3.9 Hz, 1H), 4.08 (t, J=4.7 Hz, 1H), 3.99 (t, J=4.9 Hz, 1H), 3.93 (t, J=4.7 Hz, 1H), 3.58 (m, 3H), 3.40 (s, 3H), 2.05–1.75 (m, 4H), 1.52 (m, 3H), 1.25 (m, 7H), 1.22 (d, J=6.6 Hz, 3H), 0.89 (t, J=6.6 Hz, 3H) ppm.

2) Infrared absorption spectrum: The infrared absorption spectrum as measured by the potassium bromide (KBr) disk method exhibits absorption maxima as follows:
3387, 3098, 2931, 2859, 1687, 1509, 1458, 1431, 1385, 1335, 1268, 1131, 1098, 1063, 1020 cm$^{-1}$.

EXAMPLE 36
(Exemp. Compound No. 891)

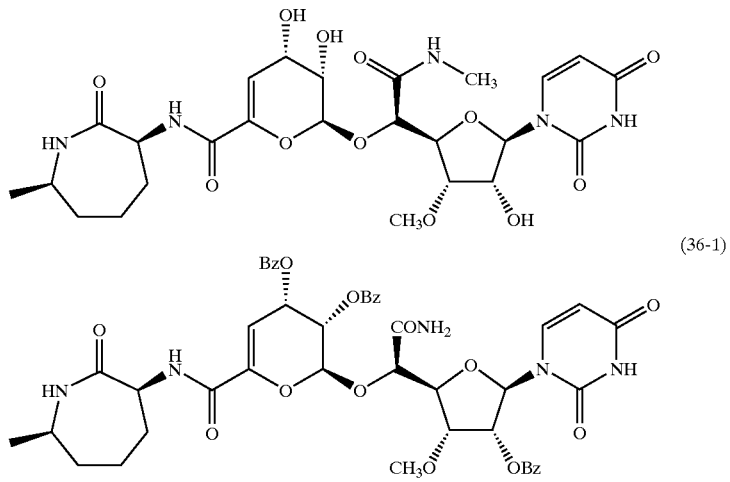

(36-1)

In pyridine was dissolved 300 mg of Compound A-500359A. To the resulting solution were added 696 mg of benzoic anhydride and 6.4 mg of dimethylaminopyridine. The resulting mixture was stirred at room temperature. Four hours later, the solvent was distilled off under reduced pressure and the residue dissolved in 200 mL of ethyl acetate. The resulting solution was washed successively with 200 mL each of saturated aqueous sodium bicarbonate and saturated and then dried over anhydrous sodium sulfate. The solvent was distilled off under reduced pressure and the residue was charged on a silica gel column (50 g), which was developed with 3% methanol in methylene chloride, whereby 423 mg of the desired compound was obtained.

1) $^1$H nuclear magnetic resonance spectrum was measured in deuterated chloroform with tetramethylsilane as an internal standard substance. $^1$H nuclear magnetic resonance spectrum is as follows:
δ=9.40 (br s, 1H), 8.06 (m, 4H), 7.92 (m, 4H), 7.55 (m, 5H), 7.40 (m, 5H), 7.15 (br s, 1H), 6.45 (br s, 1H), 6.32 (d, J=3.7 Hz, 1H), 6.13 (m, 1H), 6.09 (br s, 1H), 5.96 (d, J=3.7 Hz, 1H), 5.83 (m, 2H), 5.62 (m, 2H), 4.69 (m, 1H), 4.61 (m, 1 H), 4.56 (m, 1H), 4.36 (t, J=5.9 Hz, 1H), 3.54 (m, 1H), 3.34 (s, 3H), 2.12 (m, 1H), 2.00–1.50 (m, 4H), 1.32 (m, 1H), 1.24 (d, J=6.6 Hz, 3H) ppm.

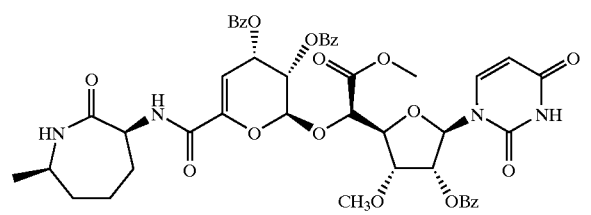

(36-2)

In 6.3 mL of methylene chloride was dissolved 418 mg of the compound obtained in Example (36-1). To the resulting solution was added 5 mL of water, followed by stirring at room temperature. To the reaction mixture, 4.74 g of nitrosylsulfuric acid was gradually added over 30 minutes. After stirring for a further 10 minutes, the resulting mixture was diluted with 30 mL of methylene chloride. The organic layer separated was washed with 10 mL each of water and saturated saline and the solvent was then distilled off under reduced pressure. The residue was dissolved in 10 mL of methylene chloride. To the resulting solution was added an ether solution of diazomethane prepared by mixing 144 mg of N-methyl-N-nitrosourea, 90 mg of potassium hydroxide, 2.8 mL of ether and 2.8 mL of water and the resulting mixture was stirred at room temperature. One hour later, the solvent was distilled off under reduced pressure. The residue was charged on a silica gel column (20 g) which was developed with 1.5% methanol in methylene chloride, whereby 99 mg of the desired compound was obtained.

1) $^1$H nuclear magnetic resonance spectrum was measured in deuterated chloroform with tetramethylsilane as an internal standard substance. $^1$H nuclear magnetic resonance spectrum is as follows:
δ=8.28 (s, 1H), 8.06 (d, J=7.3 Hz, 2H), 7.99 (d, J=7.3 Hz, 2H), 7.95 (m, 3H), 7.60–7.32 (m, 11H), 6.33 (s, 1H), 6.20 (t, J=3.6 Hz, 1H), 6.06 (d, J=4.4 Hz 1 H), 5.94 (d, J=5.9 Hz, 1H), 5.88 (t J=4.0 Hz, 1H), 5.70 (d, J=3.7 Hz, 1H), 5.54 (m, 2H), 4.79 (m, 1H), 4.63 (m, 1H), 4.17 (t, J=5.5 Hz, 1H), 3.83 (s, 3H), 3.80 (m, 1 H), 3.72 (m, 1H), 3.35 (m, 1H), 3.30 (s, 3H), 2.19 (m, 1H), 2.02–1.75 (m, 3H), 1.52 (m, 1H), 1.32 (m, 1H), 1.24 (d, J=6.6 Hz, 3H) ppm.

2) Infrared absorption spectrum: The infrared absorption spectrum as measured by the potassium bromide (KBr) disk method exhibits absorption maxima as follows:
3388, 3093, 3069, 2933, 2855, 1729, 1697, 1658, 1602, 1584, 1551, 1509, 1452, 1383, 1336, 1315, 1270, 1177, 1115, 1070, 1026 cm$^{-1}$.

(36-3)

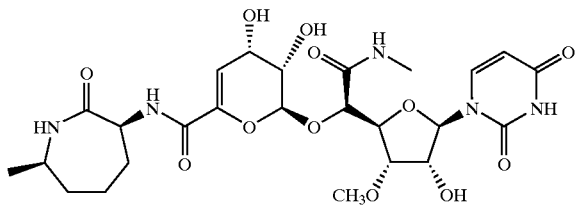

In 2 mL of a 40% methylamine—methanol solution was dissolved 98 mg of the compound obtained in Example (36-2). The resulting solution was hermetically sealed and then stirred. Forty-five minutes later, the solvent was distilled off under reduced pressure. The residue was subjected to reverse-phase preparative HPLC (Inertsil Prep-ODS), followed by elution with 16% acetonitrile—water, whereby 30 mg of the desired compound was obtained.

compound obtained in Example (36-2), 0.4 mL of n-propylamine and 2 mL of methanol, whereby 16 mg of the desired compound was obtained.

1) $^1$H nuclear magnetic resonance spectrum was measured in deuterated methanol with tetramethylsilane as an internal standard substance. $^1$H nuclear magnetic resonance spectrum is as follows:
δ=7.91 (d, J=8.1 Hz, 1H), 6.02 (d, J=4.2 Hz, 1H), 5.89 (d, J=5.5 Hz, 1H), 5.72 (d, J=8.1 Hz, 1H), 5.16 (d, J=6.4 Hz, 1H), 4.67 (d, J=2.0 Hz, 1H), 4.55 (m, 2H), 4.37 (t, J=4.3 Hz, 1H), 4.33 (t, J=5.2 Hz, 1H), 3.92 (m, 2H), 3.60 (m, 1H), 3.45 (s, 3H), 3.25 (m, 2H), 2.05–1.75 (m, 4H), 1.53 (m, 3H), 1.25 (m, 1H), 1.22 (d, J=6.6 Hz, 3H), 0.91 (t, J=7.5 Hz, 3H) ppm.

2) Infrared absorption spectrum: The infrared absorption spectrum as measured by the potassium bromide (KBr) disk method exhibits absorption maxima as follows:
3369, 3098, 2964, 2934, 2878, 1683, 1515, 1459, 1432, 1385, 1335, 1269, 1140, 1080, 1062, 1022, 981 cm$^{-1}$.

EXAMPLE 38

(Exemp. Compound No. 1091)

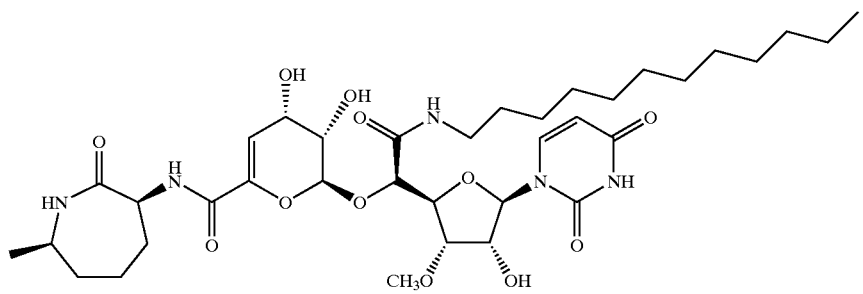

1) $^1$H nuclear magnetic resonance spectrum was measured in deuterated methanol with tetramethylsilane as an internal standard substance. $^1$H nuclear magnetic resonance spectrum is as follows:
δ=7.86 (d, J=8.0 Hz, 1H), 5.98 (m, 1H), 5.83 (m, 1H), 5.74 (dd, J=2.9 and 8.1 Hz, 1H), 5.24 (d, J=4.9 Hz, 1H), 4.73 (dd, J=2.1 and 10.9 Hz, 1H), 4.50 (m, 2H), 4.38 (t, J=4.0 Hz, 1H), 4.25 (m, 1H), 4.04 (m, 2H), 3.75 (m, 1H), 3.39 (d, J=2.8 Hz, 3H), 2.74 (d, J=2.4 Hz, 3H), 1.65 (m, 1H), 1.25 (m, 2H), 1.00 (m, 3H), 0.92 (m, 1H), 0.75 (m, 2H) ppm.

EXAMPLE 37
(Exemp. Compound No. 991)

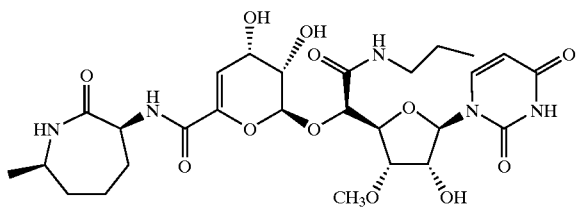

The reaction was conducted in a similar manner to that described in Example (36-3) by using 120 mg of the The reaction was conducted in a similar manner to that described in Example (36-3) using 270 mg of the compound obtained in Example (36-2), 1.92 g of dodecylamine and 6.9 mL of methanol, whereby 15 mg of the desired compound was obtained.

1) $^1$H nuclear magnetic resonance spectrum was measured in deuterated methanol with tetramethylsilane as an internal standard substance. $^1$H nuclear magnetic resonance spectrum is as follows:
δ=7.92 (d, J=8.1 Hz, 1H), 6.02 (d, J=4.4 Hz, 1H), 5.91 (d, J=5.9 Hz, 1H), 5.73 (d, J=8.1 Hz, 1H), 5.15 (d, J=5.9 Hz, 1H), 4.67 (d, J=2.2 Hz, 1H), 4.55 (m, 2H), 4.36 (t, J=4.4 Hz, 1H), 4.32 (t, J=5.5 Hz, 1H), 3.92 (m, 2H), 3.60 (m, 1H), 3.47 (s, 3H), 3.35 (m, 1H), 3.20 (m, 1H), 2.05–1.75 (m, 4H), 1.50 (m, 3H), 1.28 (m, 19H), 1.22 (d, J=6.6 Hz, 3H), 0.89 (t, J=6.6 Hz, 3H) ppm.

2) Infrared absorption spectrum: The infrared absorption spectrum as measured by the potassium bromide (KBr) disk method exhibits absorption maxima as follows:
3351, 3098, 2926, 2854, 1685, 1512, 1459, 1432, 1385, 1335, 1264, 1139, 1090, 1063, 1022, 993 cm$^{-1}$.

EXAMPLE 39
(Exemp. Compound No. 548)

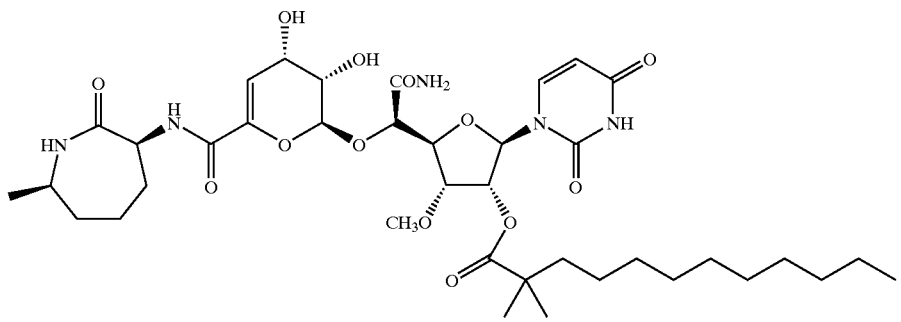

(39-1)

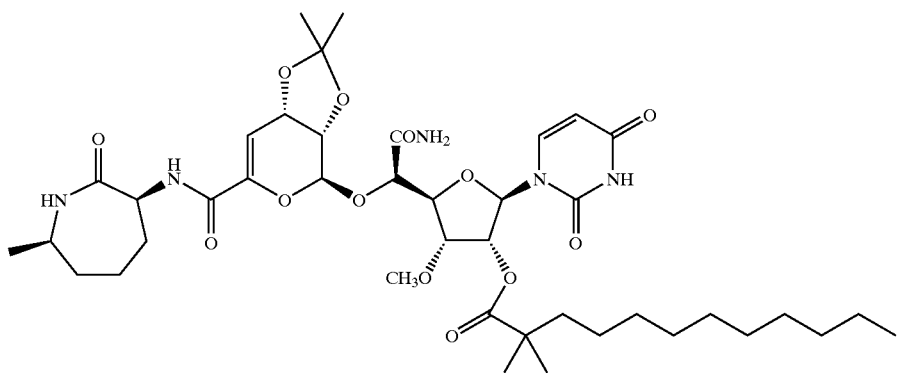

In 4 mL of pyridine was dissolved 125 mg of the compound obtained in Example (11-1). Under a nitrogen gas stream, 147 mg of dimethylaminopyridine and 3.9 mg of 4-pyrrolidinopyridine were added to the solution. After cooling to 0° C. 209.1 mg of 2,2-dimethyldodecanoyl chloride (B. D. Roth, et al, Journal of Medicinal Chemistry, 35, 1609–1617 (1992)) was added. The resulting mixture was stirred at room temperature for 28 hours. After cooling to 0° C. 2 mL of methanol was added to the reaction mixture. The resulting mixture was stirred for 10 minutes followed by concentration under reduced pressure. To the residue were added 20 mL of 0.02N hydrochloric acid and 20 mL of methylene chloride to separate it into layers. The organic layer thus obtained was washed three times with saturated saline, dried over anhydrous sodium sulfate and concentrated under reduced pressure, whereby 307 mg of a crude product was obtained. The product was purified by Lobar's silica gel column (eluted first with a 3:7 mixture of hexane and ethyl acetate, followed by ethyl acetate), whereby 132 mg of the desired compound was obtained as a white powder.

1) $^1$H nuclear magnetic resonance spectrum was measured in deuterated methanol with tetramethylsilane as an internal standard substance. $^1$H nuclear magnetic resonance spectrum is as follows:

δ=7.90 (d, J=8.1 Hz, 1H), 6.16 (d, J=3.7 Hz, 1H), 6.03 (d, J=5.4 Hz, 1H), 5.72 (d, J=8.1 Hz, 1H), 5.32 (t, J=5.2 Hz, 1H), 5.14 (d, J=5.3 Hz, 1H), 4.90 (m, 1H), 4.75 (d, J=2.1 Hz, 1H), 4.59–4.55 (m, 2H), 4.38 (t, J=5.8 Hz, 1H), 4.05 (t, J=4.4 Hz, 1H), 3.64–3.55 (m, 1H), 3.40 (s, 3H), 2.01–1.77 (m, 4H), 1.59–1.47 (m, 3H), 1.45 (s, 6H), 1.34–1.10 (m, 26H), 0.89 (t, J=6.7 Hz, 3H) ppm.

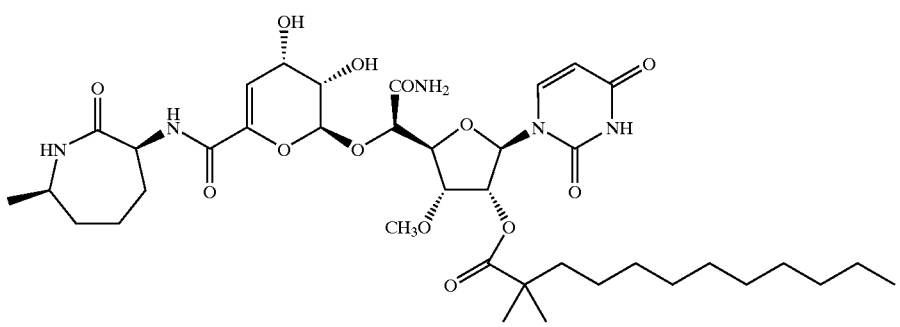

(39-2)

To 125 mg of the compound obtained in Example (39-1) was added 50 mL of a 5% trifluoroacetic acid—methylene chloride solution, and the resulting mixture was stirred at room temperature for 5 hours. Concentration of the reaction mixture and azeotropy with toluene yielded 147 mg of a crude product. The resulting product was purified by thin-layer chromatography (elution with a 8% methanol in methylene chloride mixture), whereby 64.8 mg of the desired compound was obtained as a white powder.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.02 (d, J=3.9 Hz, 1H), 5.98 (d, J=4.8 Hz, 1H), 5.71 (d, J=8.1 Hz, 1H), 5.39 (t, J=4.8 Hz, 1H), 5.24 (d, J=5.4 Hz, 1H), 4.69 (d, J=2.1 Hz, 1H), 4.57–4.56 (m, 1H), 4.54–4.50 (m, 1H), 4.42 (t, J=4.1 Hz, 1H), 4.06 (t, J=4.8 Hz, 1H), 3.98 (t, J=4.9 Hz, 1H), 3.61–3.53 (m, 1H), 3.37 (s, 3H), 2.04–1.76 (m, 4H), 1.56–1.43 (m, 2H), 1.33–1.16 (m, 27H), 0.89 (t, J=6.8 Hz, 3H) ppm.

2) Infrared absorption spectrum: The infrared absorption spectrum as measured by the potassium bromide (KBr) disk method exhibits absorption maxima as follows:
3390, 2927, 2854, 1688, 1510, 1459, 1387, 1336, 1269, 1144, 1108, 1062 cm$^{-1}$.

EXAMPLE 40
(Exemp. Compound No. 574)

1) $^1$H nuclear magnetic resonance spectrum was measured in deuterated methanol with tetramethylsilane as an internal standard substance. $^1$H nuclear magnetic resonance spectrum is as follows:

δ=7.90 (d, J=8.1 Hz, 1H) 6.16 (d, J=3.7 Hz, 1H), 6.03 (d J=5.7 Hz, 1H), 5.72 (d, J=8.1 Hz, 1H), 5.30 (t, J=5.3 Hz, 1H), 5.15 (d, J=5.4 Hz, 1H), 4.90 (m, 1H), 4.75 (d, J=2.1 Hz, 1H), 4.59–4.57 (m, 2H), 4.39 (t, J=5.9 Hz, 1H), 4.03 (t, J=4.4 Hz, 1H), 3.39 (s, 3H), 3.31–3.28 (m, 2H), 2.02 (d, J=11 Hz, 2H), 1.87–1.77 (m, 2H) 1.60–1.49 (m, 2H), 1.44 (s, 6H), 1.40–1.20 (m, 18H), 1.17 (s, 6H), 0.89 (t, J=6.9 Hz, 3H) ppm.

2) Infrared absorption spectrum: The infrared absorption spectrum as measured by the potassium bromide (KBr) disk method exhibits absorption maxima as follows:

3377, 2929, 2856, 1695, 1507, 1459, 1382, 1334, 1269, 1140, 1116, 1064 cm$^{-1}$.

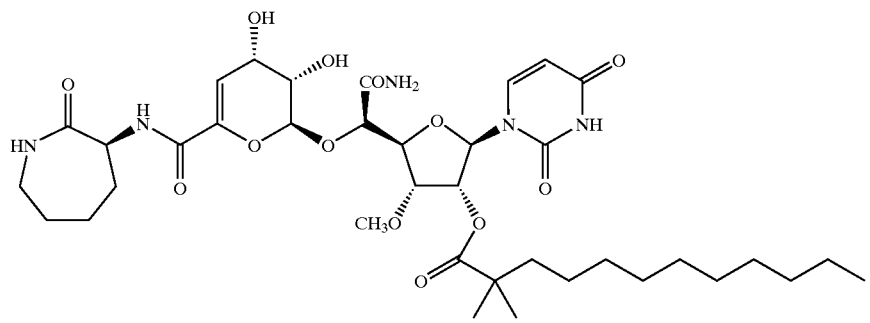

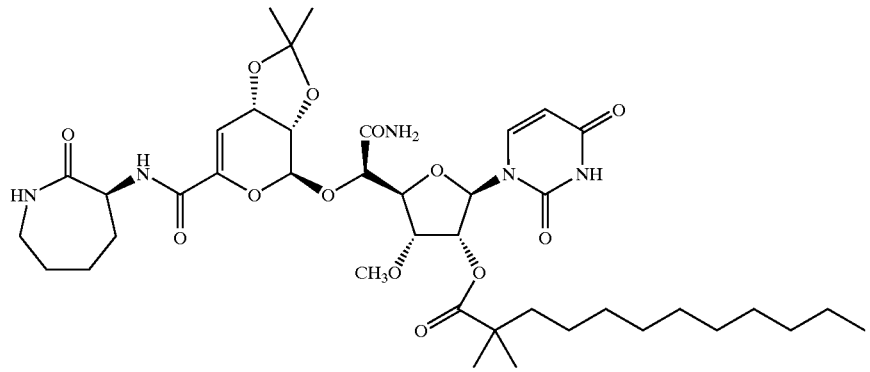

(40-1)

In a similar manner to that described in Example (39-1) except for the use of 122 mg of the compound obtained in Example (10-1) instead of the compound obtained in Example (11-1), the reaction was conducted, whereby 126.9 mg of the desired compound was obtained as a white powder.

(40-2)

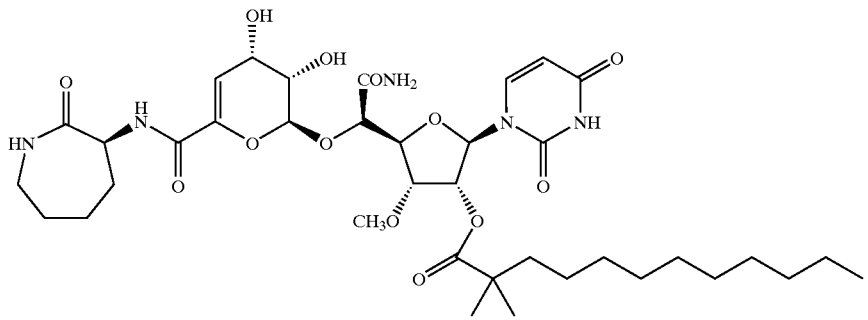

In a similar manner to that described in Example (39-2) except for the use of 95.3 mg of the compound obtained in Example (40-1) instead of the compound obtained in Example (39-1), whereby 72.4 mg of the desired compound was obtained as a white powder.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.2 Hz, 1H), 6.02 (d, J=3.8 Hz, 1H), 5.98 (d, J=4.8 Hz, 1H), 5.72 (d, J=8.2 Hz, 1H), 5.37 (t, J=5.0 Hz, 1H), 5.24 (d, J=5.4 Hz, 1H), 4.68 (d, J=2.1 Hz, 1H), 4.57–4.52 (m, 2H), 4.42 (t, J=4.1 Hz, 1H), 4.04 (t, J=4.9 Hz, 1 H), 3.98 (t, J=4.8 Hz, 1H), 3.37 (s, 3H), 3.27–3.22 (m, 2H), 2.04–1.89 (m, 2H), 1.86–1.77 (m, 2H), 1.58–1.46 (m, 2H), 1.43–1.19 (m, 18H), 1.16 (d, J=6.2 Hz, 6H), 0.89 (t, J=6.9 Hz, 3H) ppm.

2) Infrared absorption spectrum: The infrared absorption spectrum as measured by the potassium bromide (KBr) tablet method exhibits absorption maxima as follows: 3369, 2927, 2854, 1689, 1509, 1463, 1389, 1332, 1269, 1143, 1110, 1062 cm$^{-1}$.

EXAMPLE 41
(Exemp. Compound No. 545)

(1992)] instead of 2,2-dimethyldodecanoyl chloride, 82.5 mg of the desired compound was obtained as a white powder.

1) $^1$H nuclear magnetic resonance spectrum was measured in deuterated methanol with tetramethylsilane as an internal standard substance. $^1$H nuclear magnetic resonance spectrum is as follows:

δ=7.96 (d, J=8.1 Hz, 1H), 6.01 (d, J=4.0 Hz, 1H), 5.98 (dd, J=4.5 and 3.4 Hz, 1H), 5.71 (d, J=8.1 Hz, 1H), 5.46–5.43 (m, 1H), 5.24 (d, J=5.5 Hz, 1H), 4.68 (d, J=1.9 Hz, 1H), 4.57 (dd, J=4.8 and 1.7 Hz, 1H) 4.52 (dd, J=11 and 1.5 Hz, 1H), 4.42 (t, J=4.1 Hz, 1H), 4.08–4.05 (m, 1H), 3.97 (t, J=5.0 Hz, 1H), 3.61–3.54 (m, 1H), 3.38 (s, 3H), 2.53–2.48 (m, 1H), 2.04–1.37 (m, 6H), 1.28 (s, 18H), 1.22 (d, J=6.6 Hz, 3H), 1.15–1.13 (m, 3H), 0.89 (t, J=6.8 Hz, 3H) ppm.

2) Infrared absorption spectrum: The infrared absorption spectrum as measured by the potassium bromide (KBr) disk method exhibits absorption maxima as follows: 3389, 2927, 2854, 1689, 1510, 1459, 1384, 1335, 1269, 1145, 1108, 1061 cm$^{-1}$.

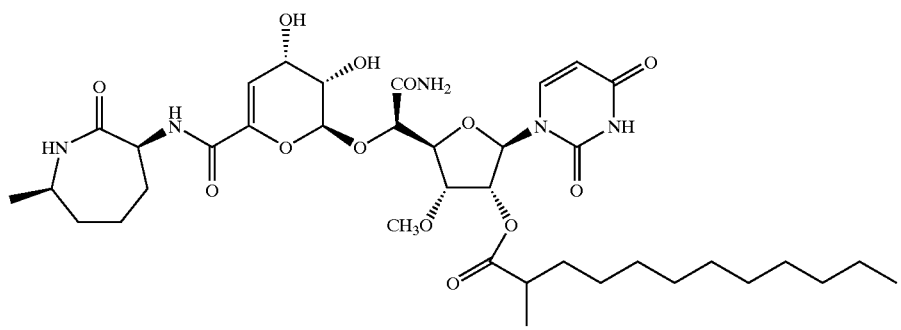

In a similar manner to that described in Example 25 except for the use of 2-methyldodecanoyl chloride [synthesized by chlorinating 2-methyldodecanoic acid which was synthesized by the process described in Organic Synthesis, 4,616, by the method as described in B. D. Roth. et al., Journal of Medicinal Chemistry, 35, 1609–1617

EXAMPLE 42
(Exemp. Compound No. 571)

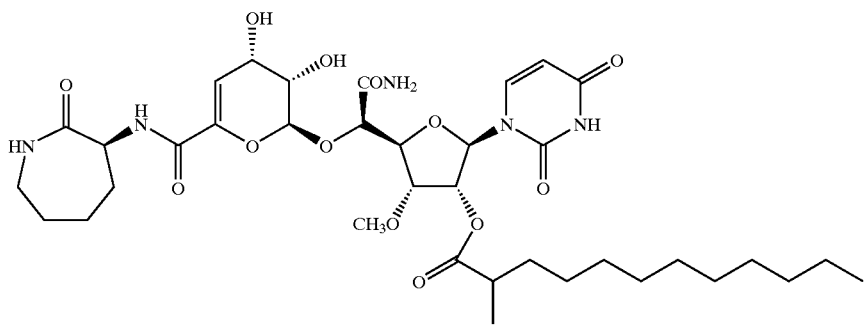

In a similar manner to that described in Example 40 except for the use of 2-methyldodecanoyl chloride instead of 2,2-dimethyldodecanoyl chloride. 77.5 mg of the desired compound was obtained as a white powder.

1) $^1$H nuclear magnetic resonance spectrum was measured in deuterated methanol with tetramethylsilane as an internal standard substance. $^1$H nuclear magnetic resonance spectrum is as follows:

δ=7.95 (d, J=8.1 Hz, 1H), 6.01 (d, J=3.7 Hz, 1H), 5.98 (dd, J=4.5 and 3.6 Hz, 1H), 5.72 (d, J=8.1 Hz, 1H), 5.44–5.40 (m, 1H), 5.24 (d, J=5.5 Hz, 1H), 4.68 (d, J=1.8 Hz, 1H), 4.57–4.52 (m, 2H), 4.42 (t, J=4.1 Hz, 1H), 4.04 (t, J=4.8 Hz, 1H), 3.98 (t, J=5.0 Hz, 1H), 3.37 (s, 3H), 3.29–3.23 (m, 2H), 2.23–2.48 (m, 1H), 2.03–1.99 (m, 2H), 1.89–1.76 (m, 2H), 1.67–1.32 (m, 2H), 1.28 (s, 18H), 1.15–1.13 (m, 3H), 0.89 (t, J=6.8 Hz, 3H) ppm.

2) Infrared absorption spectrum: The infrared absorption spectrum as measured by the potassium bromide (KBr) disk method exhibits absorption maxima as follows:
3369, 2927, 2854, 1689, 1509, 1461, 1382, 1333, 1269, 1144, 1110, 1062 cm$^{-1}$.

EXAMPLE 43
Cultivation of *Streptomyces griseus* Strain SANK60196 (FERM BP-5420)

Into each of four 2 L Erlenmeyer flasks (seed flasks), each containing 500 ml of the seed culture medium described below, were inoculated aseptically four loopfuls of Strain SANK60196 followed by shaking in a rotary shaker at 23° C. and 210 rpm, and the seed culture was thus conducted for 3 days.

Medium for seed culture: containing the following components in 1000 ml of tap water:

| | |
|---|---|
| Maltose | 30 g |
| Meat extract | 5 g |
| Polypeptone | 5 g |
| Sodium chloride | 5 g |
| Calcium carbonate | 3 g |
| Antifoamer "CB442" (product of NOF Corporation) | 50 mg |

After adjustment of pH to 7.4, sterilization was conducted at 121° C. for 30 minutes.

Cultivation was conducted as described below. Described specifically, the seed culture was inoculated at 3% (volume/volume: which will hereinafter be abbreviated as "v/v") into two 30 L jar fermenters, each containing 15 L of a cultivation medium. Six hours later after the initiation of cultivation at 23° C., filter-sterilized S-(2-aminoethyl)-L-cysteine hydrochloride was added to give a final concentration of 10 mM, followed by cultivation with aeration and agitation for 6 days.

Medium for cultivation: containing the following components in 1000 ml of tap water:

| | |
|---|---|
| Maltose | 30 g |
| Yeast extract (product of Difco Laboratories) | 5 g |
| Meat extract | 5 g |
| Polypeptone | 5 g |
| Sodium chloride | 5 g |
| Calcium carbonate | 3 g |
| Antifoamer "CB442" (product of NOF Corporation) | 50 mg |

After adjustment of pH to 7.4, sterilization was conducted at 125° C. for 30 minutes.

EXAMPLE 44
Purification of Compound A-500359E

The cultured broth (30 L) obtained in Example 43 was filtered with the aid of "Celite 545" (product of Celite Corporation).

Upon purification as described later, the active fraction was monitored by HPLC using the column and analytical conditions described below.

Column: "Senshu Pak ODS-H-2151" 6φ×150 mm (product of Senshu Scientific Co., Ltd.)

Solvent: 0.04% aqueous trifluoroacetic acid containing 4% acetonitrile

Flow rate: 1.0 ml/min

Detection: UV 210 nm

Retention time: 21.2 minutes

30 L of the resulting filtrate was charged on a column (6 L) packed with "Diaion HP-20" (product of Mitsubishi Chemical). After washing the column with 12 L of deionised water, the non-adsorbed fraction and washing fraction were combined (the combined fraction will hereinafter be called "non-adsorbed.washing fraction"). The adsorbed substance was eluted with 12 L of 10% aqueous acetone. The eluate was concentrated to remove acetone and lyophilized, whereby 39 g of a crude powdery product was obtained.

The resulting crude powdery product was dissolved in 200 mL of deionised water and charged on a column (2 L) packed with "Diaion CHP-20P" (product of Mitsubishi Chemical). The column was then washed with 4 L of deionised water and 4 L of 10% aqueous methanol, while the adsorbed substance was eluted with 4 L of 15% aqueous methanol and 4 L of 20% aqueous methanol. A 2 to 4 L portion of the 15% aqueous methanol eluate and the 20% aqueous methanol eluate were combined, followed by concentration. After removal of methanol by distillation, the residue was lyophilized to give 8.9 g of a powder.

The resulting powder was dissolved in 200 ml of deionised water and the resulting solution was charged on a column (1 L) packed with "Toyopearl HW40F" (product of TOSOH Corporation), followed by development of the column with deionised water. As a result of fractionation of the eluate into portions of 100 ml each, the active substance having a retention time of 21.2 minutes upon the above-described HPLC was eluted in Fraction Nos. 5 to 10. The resulting fractions were concentrated and lyophilized to give 2.7 g of a powder.

The resulting powder was dissolved in 200 ml of deionised water and charged on an HPLC column ("YMC-Pack ODS-1050-20-SR": 100φ×500 mm; product of YMC) equilibrated with 0.04% aqueous trifluoroacetic acid containing 4% acetonitrile. The column was developed at a flow rate of 208 ml/min with 0.04% aqueous trifluoroacetic acid containing 4% acetonitrile. As a result of fractionation of the eluate into portions of 1 L each, the active substance was eluted in Fraction Nos. 6 and 7.

These fractions were combined, followed by concentration to 200 ml by "Evapor" (product of Okawara Seisakujo) and lyophilization, whereby 99 mg of a powder was obtained. The resulting powder was suspended in 5 ml of distilled water and insoluble matter was then filtered off. The filtrate was concentrated to 2 ml by a rotary evaporator, followed by lyophilization, whereby 87 mg of Compound A-500359E was obtained as a pure product.

The compound A-500359E has the following physico-chemical properties:
1) Appearance of the substance: white powder
2) Solubility: soluble in water, slightly soluble in methanol, insoluble in normal hexane and chloroform
3) Molecular formula: $C_{18}H_{23}N_3O_{12}$
4) Molecular weight: 473 (as measured by FAB mass spectrometry)
5) Accurate mass, $[M+H]^+$, as measured by high-resolution FAB mass spectrometry is as follows:
Found: 474.1349.
Calculated: 474.1359.
6) Ultraviolet absorption spectrum: ultraviolet absorption spectrum measured in water exhibits the following maximum absorption:
251 nm (ε10,000)
7) Optical rotation: optical rotation measured in water exhibits the following value:
$[\alpha]_D^{20}$: +115° (c 0.28)
8) Infrared absorption spectrum: Infrared absorption spectrum as measured by the potassium bromide (KBr) disk method exhibits the following absorption maxima:
3410, 2955, 1683, 1464, 1441, 1396, 1309, 1267, 1206, 1138, 1115, 1088, 1062, 1023 $cm^{-1}$.
9) $^1H$ nuclear magnetic resonance spectrum was measured in deuterated dimethyl sulfoxide with tetramethylsilane as an internal standard substance. $^1H$ nuclear magnetic resonance spectrum is as follows:
3.24 (3H, s), 3.52 (1H, dd, J=4.5, 6.1 Hz), 3.72 (3H, s), 3.98 (1H, m), 4.10 (1H, m), 4.25 (1H, m), 4.29 (1H, d, J=2.0 Hz), 4.33 (1H, dd, J=2.0, 6.1 Hz), 5.05 (1H, d, J=3.9 Hz), 5.16 (1H, d, J=6.8 Hz), 5.45 (1H, d, J=4.2 Hz), 5.54 (1H, d, J=5.9 Hz), 5.61 (1H, d, J=3.3 Hz), 5.61 (1H, d, J=8.1 Hz), 5.93 (1H, dd, J=1.3, 2.9 Hz), 7.56 (1H, br, s); 7.69 (1H, br, s), 7.74 (1H, d, J=8.1 Hz) ppm.
10) $^{13}C$ nuclear magnetic resonance spectrum was measured in deuterated dimethyl sulfoxide with tetramethylsilane as an internal standard substance. $^{13}C$-nuclear magnetic resonance spectrum is as follows:
52.0 (q), 57.3 (q), 61.5 (d), 64.9 (d), 72.1 (d), 75.4 (d), 78.2 (d), 81.3 (d), 89.0 (d), 99.2 (d), 101.2 (d), 114.2 (d), 139.2 (s), 139.8 (d), 150.3 (s), 161.8 (s), 163.1 (s), 170.1 (s) ppm.
11) High performance liquid chromatography (which will hereinafter be abbreviated as "HPLC") analysis:
Column: "Senshu Pack ODS-H-2151"
6φ×150 mn (product of Senshu Scientific Co., Ltd.)
Solvent: 0.04% aqueous trifluoroacetic acid containing 4% acetonitrile
Flow rate: 1.0 ml/min
Detection: UV 210 nm
Retention time: 21 minutes

EXAMPLE 45

Purification of Compounds A-500359F and A-500359H

In the purification described below, the active fraction was monitored by HPLC using the following column and analytical conditions.
Column: "Senshu Pak ODS-H-2151" 6φ×150 mm (product of Senshu Scientific Co., Ltd.)
Solvent: 0.04% aqueous trifluoroacetic acid
Flow rate: 1.5 ml/min
Detection: UV 210 nm
Retention time:
8 minutes (Compound A-500359H)
18 minutes (Compound A-500359F)

After 42 L of non-adsorbed.washing fraction obtained in Example 44 was adjusted to pH 9 with 6N sodium hydroxide, this fraction was charged on a column (8.5 L) packed with "Diaion PA3 16 (Cl')" (product of Mitsubishi Chemical). The column was washed with 27 L of deionised water and the adsorbed substance was then eluted with 27 L of 0.1N hydrochloric acid.

The eluate was adjusted to pH 7 with 6N sodium hydroxide and then charged on an activated charcoal column (2 L). The column was washed with 8 L of deionised water and the active substance was then eluted with 8 L of 0.5N aqueous ammonia containing 10% acetone. Concentration and lyophilization of the resulting eluate yielded 28 g of a powder.

The resulting powder was dissolved in 400 ml of distilled water. After adjustment to pH 3.0, the resulting solution was charged on a column (2 L) which had been adjusted with water and packed with "Diaion CHP-20P" (product of Mitsubishi Chemical). The non-adsorbed liquid and washing fractions were collected, concentrated and lyophilized, whereby 12 g of a viscous substance was obtained.

This viscous substance was dissolved in 200 ml of distilled water. After adjustment to pH 3.3 with trifluoroacetic acid, the resulting solution was then charged on a column (1 L) equilibrated with 0.04% aqueous trifluoroacetic acid and packed with "Diaion CHP-20P" (product of Mitsubishi Chemical). After development of the column with 2 L of 0.04% aqueous trifluoroacetic acid and pooling of the fraction (Fraction H) eluted between 0.8 and 1.4 L, the eluting solution was changed to 2 L of distilled water. Concentration and lyophilization of 2 L of the fraction (Fraction F) eluted with distilled water yielded 605 mg of a powder.

600 ml of Fraction H was diluted with distilled water to 1 L and its pH adjusted to 2.8 with trifluoroacetic acid, and the resulting solution was then charged again on a column (1 L) packed with "Diaion CHP-20P" (product of Mitsubishi Chemical) equilibrated with 0.04% aqueous trifluoroacetic acid. The column was eluted with 2.2 L of 0.04% aqueous trifluoroacetic acid. Fractions 8 to 11 obtained by fractionation of the eluate in portions of 200 ml each were concentrated and lyophilized, whereby 233 mg of a powder was obtained.

A 100 mg portion of the resulting powder was dissolved in 5 ml of water and 1 ml portions of the resulting solution were charged on an HPLC column ("Senshu Pak ODS-H-5251": 20φ×250 mm; product of Senshu Scientific) equilibrated with 0.04% aqueous trifluoroacetic acid. The column was developed at a flow rate of 10 ml/min. The ultraviolet absorption of the active fraction at 210 nm was detected and a peak eluted during a retention time of 14 to 16 minutes was collected. the process being carried out 5 times. The fractions thus obtained were concentrated by a rotary evaporator, followed by lyophilization, whereby 23 mg of Compound A-500359H was obtained as a pure product.

In 15 ml of water were dissolved 605 mg of lyophilized powder of Fraction F and 1 ml portions of the resulting solution were charged on an HPLC column ("Senshu Pak ODS-H-525": 20φ×250 mm: product of Senshu Scientific) equilibrated with 0.04% aqueous trifluoroacetic acid. The column was developed at a flow rate of 10 ml/min. The absorption of the active fraction at the ultraviolet portion of 210 nm was detected and a peak eluted during a retention time of 29 to 31 minutes was collected 15 times by fractionation. The fractions thus obtained were concentrated by a rotary evaporator, followed by lyophilization, whereby 134 mg of Compound A-500359F was obtained as a pure product.

The compound A-500359F has the following physicochemical properties:
1) Appearance of the substance: white powder
2) Solubility: soluble in water, slightly soluble in methanol, insoluble in normal hexane and chloroform
3) Molecular formula: $C_{17}H_{21}N_3O_{12}$
4) Molecular weight: 459 (as measured by FAB mass spectrometry)
5) Accurate mass, $[M+H]^+$, as measured by high-resolution FAB mass spectrometry is as follows:
   Found: 460.1201.
   Calculated: 460.1203.
6) Ultraviolet absorption spectrum: ultraviolet absorption spectrum measured in water exhibits the following maximum absorption:
   262 nm ($\epsilon$7,000)
7) Optical rotation: optical rotation measured in water exhibits the following value:
   $[\alpha]_D^{20}$: +111° (c 0.41)
8) Infrared absorption spectrum: Infrared absorption spectrum as measured by the potassium bromide (KBr) disk method exhibits the following absorption maxima:
   3391, 2941, 1684, 1466, 1400 1333, 1269, 1205, 1137, 1115, 1062, 1020 cm$^{-1}$.
9) $^1$H nuclear magnetic resonance spectrum was measured in deuterium oxide with the signal of water as 4.75 ppm. $^1$H nuclear magnetic resonance spectrum is as follows:
   3.37 (3H, s), 3.79 (1H, dd J=5.1, 6.4 Hz), 4.17 (1H, ddd, J=1.6, 3.4, 4.6 Hz), 4.38 (1H, dd, J=3.5, 5.1 Hz), 4.48 (1H, dd, J=2.4, 6.4 Hz), 4.49 (1H, ddd, J=0.6, 2.7, 4.6 Hz), 4.69 (1H, d, J=2.4 Hz), 5.32 (1H, dd, J=0.6, 3.4 Hz), 5.77 (1H, d, J=3.5 Hz), 5.90 (1H, d, J=8.1 Hz), 6.11 (1H, dd, J=1.6, 2.7 Hz), 7.75 (1H, d, J=8.1 Hz) ppm.
10) $^{13}$C nuclear magnetic resonance spectrum was measured in deuterium oxide with 1,4-dioxane (67.4 ppm) as an internal standard substance. $^{13}$C nuclear magnetic resonance spectrum is as follows:
    58.6 (q), 62.7 (d), 65.5 (d), 72.7 (d), 76.3 (d), 78.8 (d), 91.2 (d), 100.0 (d), 102.7 (d), 114.8 (d), 140.7 (s), 141.9 (d), 152.1 (s), 165.4(s), 167.0 (s), 173.9 (s) ppm.
11) HPLC analysis:
    Column: "Senshu Pak ODS-H-2151"
    6φ×150 mm (product of Senshu Scientific Co., Ltd.)
    Solvent: 0.04% aqueous trifluoroacetic acid
    Flow rate: 1.5 ml/min
    Detection: UV 210 nm
    Retention time: 18 minutes Compound A-500359H has the following physicochemical properties:
1) Appearance of the substance: white powder
2) Solubility: soluble in water, slightly soluble in methanol, insoluble in normal hexane and chloroform
3) Molecular formula: $C_{16}H_{19}N_3O_{12}$
4) Molecular weight: 445
5) Accurate mass, $[M+H]^+$, as measured by high-resolution FAB spectrometry is as follows:
   Found: 446.1025.
   Calculated: 446.1047.
6) Ultraviolet absorption spectrum: ultraviolet absorption spectrum measured in water exhibits the following maximum absorption:
   262 nm ($\epsilon$7,400)
7) Optical rotation: optical rotation measured in water exhibits the following value:
   $[\alpha]_D^{20}$: +115° (c 0.33)
8) Infrared absorption spectrum: Infrared absorption spectrum as measured by the potassium bromide (KBr) disk method exhibits the following absorption maxima:
   3361, 2934, 1683, 1467, 1403, 1336, 1270, 1206, 1114, 1090, 1058, 1021 cm$^{-1}$.
9) $^1$H nuclear magnetic resonance spectrum was measured in deuterium oxide with the signal of water as 4.75 ppm. $^1$H nuclear magnetic resonance spectrum is as follows:
   4.13 (br, t, J=5.4 Hz), 4.15–4.19 (2H), 4.43 (1H, dd, J=2.5, 5.8 Hz), 4.48 (1H, dd, J=2.9, 4.7 Hz), 4.72 (1H, d, J=2.5 Hz), 5.31 (1H, d, J=4.0 Hz), 5.80 (1H, d, J=4.0 Hz), 5.89 (1H, d, J=8.3 Hz), 6.12 (1H, dd, J=1.4, 2.9 Hz), 7.75 (1H, d, J=8.3 Hz) ppm.
10) $^{13}$C nuclear magnetic resonance spectrum was measured in deuterium oxide with 1,4-dioxane (67.4 ppm) as an internal standard substance. $^{13}$C nuclear magnetic resonance spectrum is as follows:
    62.8 (d), 65.8 (d), 70.3 (d), 74.6 (d), 77.0 (d), 84.2 (d), 90.3 (d), 100.3 (d), 102.9 (d), 113.9 (d), 141.2 (s), 141.9 (d), 152.2 (s), 165.9 (s), 167.0 (s), 174.2 (s) ppm.
11) HPLC analysis:
    Column: "Senshu Pak ODS-H-2151"
    6φ×150 mm (product of Senshu Scientific Co., Ltd.)
    Solvent: 0.04% aqueous trifluoroacetic acid
    Flow rate: 1.5 ml/min
    Detection: UV 210 nm
    Retention time: 8 minutes

EXAMPLE 46

Cultivation of *Streptomyces griseus* Strain SANK 60196 (FERM BP-5420)

Into each of three 2 L Erlenmeyer flasks, each containing 500 ml of the seed culture medium having the composition described below were aseptically inoculated four loopfuls of Strain SANK60196. These flasks were shaken on a rotary shaker at 23° C. and 210 rpm and thus, the initial seed culture was conducted for 3 days.

The seed culture medium contains the following components in 1000 ml of tap water.

| | |
|---|---|
| Glucose | 20 g |
| Soluble starch | 10 g |
| Pressed yeast | 9 g |
| Meat extract | 5 g |
| Polypeptone | 5 g |
| Sodium chloride | 5 g |
| Calcium carbonate | 3 g |
| Antifoamer "CB442" (product of NOF Corporation) | 50 mg |

After adjustment of pH to 7.4, sterilization was conducted at 121° C. for 20 minutes.

The first seed culture thus obtained was inoculated at 3% into a 60 L tank containing 30 L of the same preculture medium, and the second seed culture was carried out with aeration and agitation at 23° C. for 24 hours.

Cultivation was conducted as described below. Described specifically, the second seed culture broth was inoculated at 3% (v/v) into two 600 L tanks, each containing 400 L of the below-described cultivation medium and cultivation was then carried out with aeration and agitation at 23° C. for 6 days.

The medium for cultivation: containing the following components in 1000 ml of tap water.

| | |
|---|---|
| Glucose | 20 g |
| Soluble starch | 10 g |
| Pressed yeast | 9 g |
| Meat extract | 5 g |
| Polypeptone | 5 g |
| Sodium chloride | 5 g |
| Calcium carbonate | 3 g |
| Antifoamer "CB442" (product of NOF Corporation) | 50 mg |

After adjustment to pH 7.4, 3 g of calcium carbonate was added and the mixture was sterilized at 125° C. for 20 minutes.

EXAMPLE 47
Purification of Compound A-500359E

The cultured broth (810 L) obtained in Example 46 was filtered with the aid of "Celite 545" (product of Celite Corporation).

Upon subsequent purification. the active fraction was monitored by HPLC using the following column and analytical conditions.

Column: "YMC-Pak ODS-A A-312" 6φ×150 mm (product of YMC)

Solvent: 0.04% aqueous trifluoroacetic acid containing 4% acetonitrile

Flow rate: 1.0 ml/min

Detection: WV 210 nm

Retention time: 19.8 minutes

The resulting filtrate (800 L) was charged on a column (160 L) packed with "Diaion HP-20P" (product of Mitsubishi Chemical). The column was washed with 640 L of deionised water and the non-adsorbed fraction and washing fraction were then combined (non-adsorbed.washing fraction). The adsorbed substance was eluted with 348 L of 10% aqueous acetone.

After concentration of the eluted fraction to 10 L, the residue was charged on a column (45 L) packed with "Diaion CHP-20P" (product of Mitsubishi Chemical). The column was then washed with 90 L of deionised water, 100 L of 10% aqueous methanol and 100 L of 15% aqueous methanol. The adsorbed substance was eluted with 100 L of 20% aqueous methanol.

After concentration of the 20% aqueous methanol fraction to 5 L, the concentrate was charged on a column (22 L) packed with "Toyopearl HW40F" (product of TOSOH Corporation). The column was developed with deionised water and the eluate was collected by fractionation in portions of 5 L each. The active substance having a retention time of 19.8 minutes upon the above-described HPLC was eluted in Fractions Nos. 3 to 6. These fractions were concentrated to 5.8 L and lyophilized to yield 55.8 g of a powder.

The resulting powder was dissolved in 1.2 L of deionised water. A 200 ml portion of the resulting solution was charged on an HPLC column ("YMC-Pak ODS-1050-20-SR"; 100φ×500 mm; product of YMC) equilibrated with 0.04% aqueous trifluoroacetic acid containing 4% acetonitrile. The column was developed at a flow rate of 200 ml/min with 0.04% aqueous trifluoroacetic acid containing 4% acetonitrile. The active substance had a retention time of 105 to 124 minutes. That operation was repeated 6 times. The fractions thus obtained were combined, concentrated to 5 L by "Evapor" and then lyophilized, whereby 24.2 g of Compound A-500359E was obtained as a pure product.

EXAMPLE 48
Purification of Compounds A-500359F and A-500359H

Upon subsequent purification, the active fraction was monitored by HPLC using the following column and analytical conditions.

Column: "YMC-Pak ODS-A A-312" 6φ150 mm (product of YMC)

Solvent: 0.04% aqueous trifluoroacetic acid

Flow rate: 1.5 ml/min

Detection: UV 210 nm

Retention time:
7.7 minutes (Compound A-500359H)
16.6 minutes (Compound A-500359F)

The non-adsorbed.washing fraction (1370 L) obtained in Example 47 was charged on an activated charcoal column (65 L). After the column was washed with 260 L of deionised water, the active substance was eluted with 270 L of 0.5N aqueous ammonia containing 10% acetone. After concentration of the eluate to 40 L and adjustment of the concentrate to pH 2.4 with trifluoroacetic acid, it was charged on a column (45 L) packed with "Diaion CHP-20P" (product of Mitsubishi Chemical) equilibrated with 0.04% aqueous trifluoroacetic acid. The column was developed with 0.04% aqueous trifluoroacetic acid to yield a fraction (Fraction H) eluted in 0 to 47 L and another fraction (Fraction F) eluted in 47 to 91 L. Fraction H was concentrated to 1.5 L, while Fraction F was obtained as 287 g of a powder after concentration and lyophilization.

The concentrate of Fraction H was diluted with deionised water to 3.2 L. A 160 ml portion of it was charged on an HPLC column ("YMC-Pack ODS-1050-20-SR": 100φ×500 mm; product of YMC) equilibrated with 0.04% aqueous trifluoroacetic acid, followed by development at a flow rate of 200 ml/min. Ultraviolet absorption of the active fraction at 210 nm was detected and a peak eluted at a retention time of 67 to 72 minutes was collected by fractionation. This operation was repeated 20 times. The fractions thus obtained were concentrated by "Evapor" (product of Okawara Seisakujo) and lyophilized to yield 5.9 g of Compound A-500359H as a pure product.

A 277 g portion of Fraction F in powder form was dissolved in 50 L of deionised water and the resulting solution was adjusted to pH 2.2 with trifluoroacetic acid. The solution was charged again on a column (45 L) packed with "Diaion CHP-20P" (product of Mitsubishi Chemical) equilibrated with 0.04% aqueous trifluoroacetic acid. After washing the column with 97 L of 0.04% aqueous trifluoroacetic acid, the active substance was eluted with 120 L of deionised water. The deionised water eluted fraction was concentrated and lyophilized, whereby 75.6 g of Fraction F was obtained as a lyophilized powder.

The resulting lyophilized powder of Fraction F was dissolved in 4 L of water. A 150 ml portion of the solution was charged on an HPLC column ("YMC-Pak ODS-1050-20-SR", 100ϕ×500 mm: product of YMC) equilibrated with a mixture of 0.5% acetonitrile and 0.04% aqueous trifluoroacetic acid, followed by development with the same solvent system at a flow rate of 200 ml/min. The absorption of the active fraction at the ultraviolet portion of 210 nm was detected and a peak eluted at a retention time of 88 to 97 minutes was collected by fractionation. This operation was repeated 27 times. The fractions thus obtained were concentrated and lyophilized, whereby 19.2 g of Compound A-500359F was obtained as a pure product.

EXAMPLE 49

Preparation Process of Each of Compound A-500359F and the Amide Derivative of Compound A-500359F (Chemical Conversion of Compound A-500359E by Aqueous Ammonia)

Compound A-500359E (75 mg) obtained in Example 44 was dissolved in 2 ml of 0.5N aqueous ammonia. The resulting solution was allowed to stand at room temperature for 2 hours. After completion of the reaction, the reaction mixture was lyophilized to yield 78 mg of a powder.

The resulting powder was dissolved in 1 mL of 0.04% aqueous TFA. A 100 µl portion of the resulting solution was charged on an HPLC column ("Capcellpak UG 120 Å", 20ϕ×250 mm; product of Shiseido) equilibrated with 0.04% aqueous trifluoroacetic acid, followed by elution with 0.04% aqueous trifluoroacetic acid at a flow rate of 10 ml/min. The ultraviolet absorption of the active fraction at 210 nm was detected and peaks eluted at a retention time of 21 to 22 minutes and at a retention time of 31 to 33 minutes were collected by fractionation, the process being carried out 10 times.

The fractions eluted at a retention time of 21 to 22 minutes were concentrated by a rotary evaporator and lyophilized, whereby 14 mg of the amide derivative of compound A-500359F was obtained in pure form.

The fractions eluted at a retention time of 31 to 33 minutes were concentrated by a rotary evaporator and lyophilized, whereby 50 mg of Compound A-500359F was obtained in pure form.

The amide derivative of compound A-500359F has the following physico-chemical properties:

1) Appearance of the substance: white powder
2) Solubility: soluble in water, slightly soluble in methanol, insoluble in normal hexane and chloroform
3) Molecular formula: $C_{17}H_{22}N_4O_{11}$
4) Molecular weight: 458 (as measured by FAB mass spectrometry)
5) Accurate mass, $[M+H]^+$, as measured by high-resolution FAB mass spectrometry is as follows:
   Found: 459.1328.
   Calculated: 459.1364.
6) Ultraviolet absorption spectrum: ultraviolet absorption spectrum measured in water exhibits the following maximum absorption:
   258 nm (ϵ7,500)
7) Optical rotation: optical rotation measured in water exhibits the following value:
   $[\alpha]_D^{25}$: +119° (c 0.87)
8) Infrared absorption spectrum: Infrared absorption spectrum as measured by the potassium bromide (KBr) disk method exhibits the following absorption maxima:
   3339, 2943, 1686, 1598, 1495, 1402, 1337, 1272, 1205, 1136, 1115, 1060, 1019 $cm^{-1}$.
9) $^1H$ nuclear magnetic resonance spectrum was measured in deuterium oxide with the signal of water as 4.75 ppm. $^1H$ nuclear magnetic resonance spectrum is as follows:
   3.30 (3H, s) 3.67 (1H, dd, J=5.0, 6.8 Hz), 4.17 (1H, ddd, J=1.8, 2.9, 4.4 Hz), 4.35 (1H, dd, J=3.2, 5.0 Hz), 4.43 (1H, dd, J=2.3, 6.8 Hz), 4.45 (1H, dd, J=2.4, 4.4 Hz), 4.66 (1H, d, J=2.3 Hz), 5.35 (1H, d, J=2.9 Hz), 5.71 (1H, d, J=3.2 Hz), 5.85 (1H, d, J=8.1 Hz), 5.97 (1H, dd, J=1.8, 2.4 Hz), 7.71 (1H, d, J=8.1 Hz) ppm.
10) $^{13}C$ nuclear magnetic resonance spectrum was measured in deuterium oxide with 1,4-dioxane (67.4 ppm) as an internal standard substance. $^{13}C$ nuclear magnetic resonance spectrum is as follows:
    58.6 (q), 62.7 (d), 65.3 (d), 72.6 (d), 75.7 (d), 78.7 (d), 82.3 (d), 91.3 (d), 99.8 (d), 102.7 (d), 110.8 (d), 141.9 (d), 142.3 (s), 152.1 (s), 166.0 (s), 167.0 (s) ppm.
11) HPLC analysis:
    Column: "Senshu Pack ODS-H-2151", 6ϕ×150 mm (product of Senshu Scientific Co., Ltd.)
    Solvent: 0.04% aqueous trifluoroacetic acid
    Flow rate: 1.5 ml/min
    Detection: UV 210 nm
    Retention time: 11 minutes

EXAMPLE 50

Preparation of Compound A-500359F (Hydrolysis of Compound A-500359E by Sodium Hydroxide)

Compound A-500359E (4.4 mg) obtained in Example 44 was dissolved in 0.5 ml of distilled water. After the dropwise addition of 0.5 ml of 0.02N aqueous sodium hydroxide, 1 ml of 0.1N aqueous sodium hydroxide was added dropwise. The resulting mixture was allowed to stand at room temperature for 50 minutes. The reaction mixture was neutralized with 1N hydrochloric acid and then charged on 2 ml of an activated charcoal column. The column was washed with 8 ml of distilled water and the reaction substance was then eluted with 8 ml of 0.5N aqueous ammonia containing 10% acetone.

After concentration of the eluate to 700 µl, the concentrate was charged on an HPLC column ("Senshu Pak ODS-H4251"; 10ϕ×250 mm; product of Senshu Scientific) equilibrated with 0.04% aqueous trifluoroacetic acid, followed by elution at a flow rate of 4 ml/min. The ultraviolet absorption of the active substance at 210 nm was detected and a peak eluted at a retention time of 25 to 30 minutes was collected by fractionation. This operation was repeated three times. The fractions thus obtained were concentrated in a rotary evaporator and lyophilized, whereby 2.6 mg of Compound A-500359F was obtained in pure form.

EXAMPLE 51

Cultivation of *Streptomyces griseus* Strain SANK60196 (FERM BP-5420)

One loopful of strain SANK60196 was sterilised before being inoculated into a 500 ml Erlenmeyer flask (seed flask) containing 100 ml of a medium having the composition described below. Seed culture was conducted for 3 days by shaking the flask in a rotary shaker at 23° C. and 210 rpm.

Seed culture medium containing the following components in 1000 ml of tap water.

| | |
|---|---|
| Maltose | 30 g |
| Meat extract | 5 g |
| Polypeptone | 5 g |
| Sodium chloride | 5 g |
| Calcium carbonate | 3 g |
| "Antifoamer CB442" | 50 mg |

After adjustment to pH 7.4, sterilization was conducted at 121° C. for 30 minutes.

Cultivation was conducted as described below. Described specifically, the seed culture was inoculated at 3% (VNV) into each of ten 500 ml Erlenmeyer flasks. each containing 100 ml of a sterilized medium having the composition described below. Cultivation was conducted for 11 days by shaking the flasks in a rotary shaker at 23° C. and 210 rpm.

Cultivation medium: containing the following components in 1000 ml of tap water.

| | |
|---|---|
| Glucose | 50 g |
| Meat extract | 4 g |
| Polypeptone | 3 g |
| Skimmed milk | 10 g |
| Corn steep liquor | 10 g |
| Sodium chloride | 5 g |
| "Antifoamer CB442" | 50 mg |

After adjustment to pH 7.4, sterilization was conducted at 125° C. for 30 minutes.

EXAMPLE 52

Purification of Compound A-500359J

Upon subsequent purification, the active fraction was monitored by HPLC using the following column and analytical conditions.

Column: "Pegasil ODS", 6φ×150 mm (product of Senshu Scientific Co., Ltd.)

Solvent: 0.04% aqueous trifluoroacetic acid

Flow rate: 1.0 ml/min

Detection: UV 260 nm

Retention time: 5.57 minutes

The cultured broth obtained in Example 51 was filtered with the aid of "Celite 545" added at 5% (W/V). The filtrate (1 L) thus obtained was charged on a column (200 ml) of "Diaion HP-20". The column was then washed with distilled water (500 ml). After adjustment of the pH of 1.5 L of non-adsorbed.washing fraction to 9 with 6N sodium hydroxide, the fraction was charged on a column (100 ml) of "Dowex SBR-P (OH')". The column was washed with distilled water (300 ml) and the adsorbed substance was eluted with 300 ml of 1N aqueous hydrochloric acid. After adjustment of pH after elution to 7 with sodium hydroxide, the eluate was charged on an active charcoal column (50 ml). The column was washed with distilled water (100 ml) and the active substance was diluted with 60% aqueous acetone (200 ml). Concentration and lyophilization of the eluate yielded 558 mg of a powder. The powder was dissolved in 5 ml of distilled water and 500 µl portions of the resulting solution were charged on an HPLC column ("Senshu Pack Pegasil ODS"; 20φ×250 mm; product of Senshu Scientific) equilibrated with 0.05% aqueous trifluoroacetic acid. They were developed at a flow rate of 10.0 ml/min. The ultraviolet absorption of the active substance at 260 nm was detected and a peak eluted at a retention time of 11.1 minutes was collected by fractionation, the process being carried out 10 times. The resulting fractions were concentrated by a rotary evaporator and then lyophilized, whereby 16.2 mg of Substance A-500359J was obtained in pure form.

The compound A-500359J has the following physico-chemical properties:

1) Appearance of the substance: white powder
2) Solubility: soluble in water, slightly soluble in methanol, insoluble in normal hexane and chloroform
3) Molecular formula: $C_{16}H_{21}N_3O_{13}$
4) Molecular weight: 463 (as measured by FAB mass spectrometry)
5) Accurate mass, $[M+H]^+$, as measured by high-resolution FAB mass spectrometry is as follows:

Found: 462.0996.

Calculated: 462.1006.

6) Ultraviolet absorption spectrum: ultraviolet absorption spectrum measured in water exhibits the following maximum absorption:

194 (ε8800), 262 (ε10000) nm

7) Optical rotation: optical rotation measured in water exhibits the following value:

$[\alpha]_D^{28}$: +83° (c 0.1, $H_2O$)

8) Infrared absorption spectrum: Infrared absorption spectrum as measured by the potassium bromide (KBr) disk method exhibits the following absorption maxima:

3372, 2931, 1684, 1467, 1407, 1273, 1204, 1107, 1058 $cm^{-1}$.

9) $^1H$ nuclear magnetic resonance spectrum was measured in deuterium oxide with 1,4-dioxane (3.53 ppm) as an internal standard substance. $^1H$ nuclear magnetic resonance spectrum is as follows:

3.75 (1H, t, J=3.4 Hz), 3.83 (1H, ddd, J=1.4, 1.9, 3.4 Hz), 4.02 (1H, ddd, J=1.4, 1.7, 3.4 Hz), 4.05 (1H, dd, J=5.3, 5.6 Hz), 4.11 (1H, t, J=5.6 Hz), 4.13 (1H, dd, J=3.1, 5.6 Hz), 4.30 (1H, d, J=5.3 Hz), 4.33 (1H, d, J=1.7 Hz), 4.90 (1H, d, J=1.9 Hz), 5.50 (1H, d, J=3.1 Hz), 5.7 (1H,d, J=8.2 Hz), 7.6 (1H, d, J=8.2 Hz) ppm.

10) $^{13}C$ nuclear magnetic resonance spectrum was measured in deuterium oxide with 1,4-dioxane (67.4 ppm) as an internal standard substance. $^{13}C$ nuclear magnetic resonance spectrum is as follows:

64.4 (d), 68.8 (d), 68.9 (d), 69.7 (d), 71.4 (d), 73.0 (d), 75.4 (d), 82.8 (d), 90.7 (d), 99.2 (d), 101.7 (d), 141.6 (d), 151.0 (s), 165.9 (s), 171.9 (s), 172.6 (s) ppm.

11) HPLC analysis:

Column: "Senshu Pak ODS-H-2151", 6φ×150 mm (product of Senshu Scientific Co., Ltd.)

Solvent: 0.05% aqueous trifluoroacetic acid

Flow rate: 1.0 ml/min

Detection: UV 260 nm

Retention time: 5.57 minutes

EXAMPLE 53

Cultivation of *Streptomyces griseus* Strain SANK 60196 (FERM BP-5420)

One loopful of strain SANK60196 was sterilised prior to inoculation in a 500 ml Erlenmeyer flask (seed flask) containing 100 ml of a medium having the composition described below. Preculture was conducted for 3 days by shaking the flask in a rotary shaker at 23° C. and 210 rpm.

Medium for preculture: containing the following components in 1000 ml of tap water.

| | |
|---|---|
| Maltose | 30 g |
| Meat extract | 5 g |
| Polypeptone | 5 g |
| Sodium chloride | 5 g |
| Calcium carbonate | 3 g |
| "Antifoamer CB442" | 50 mg |

After adjustment to pH 7.4, sterilization was conducted at 121° C. for 30 minutes.

Cultivation was conducted as described below. Described specifically the preculture broth was inoculated at 3% (V/V) into each of ten 500 ml Erlenmeyer flasks, each containing 100 ml of a sterilized medium having the composition described below. Cultivation was conducted by shaking the flasks in a rotary shaker at 23° C. and 210 rpm. Six hours after initiation of the cultivation, filter-sterilized S-(2-aminoethyl)-L-cysteine hydrochloride and L-allylglycine were added to give a final concentration of 10 mM. Cultivation was then continued for 7 days.

Cultivation medium: containing the following components in 1000 ml of tap water.

| | |
|---|---|
| Maltose | 30 g |
| Yeast extract (product of Difco Laboratories) | 5 g |
| Meat extract | 5 g |
| Polypeptone | 5 g |
| Sodium chloride | 5 g |
| Calcium carbonate | 3 g |
| "Antifoamer CB442" | 50 mg |

After adjustment to pH 7.4, sterilization was conducted at 125° C. for 30 minutes.

EXAMPLE 54

Purification of Substance A-500359M-3

The cultured broth (1 L) obtained in Example 53 was centrifuged at 3000 rpm for 20 minutes and the resulting supernatant was purified.

Upon subsequent purification, the active fraction was monitored by HPLC using the following column and analytical conditions.

Column: "Pegasil ODS" 6φ×150 mm (product of Senshu Scientific)

Solvent: 7.2% acetonitrile—0.05% aqueous trifluoroacetic acid

Flow rate: 1.0 ml/min

Detection: UV 260 nm

Retention time: 10.1 minutes

After adjustment of the supernatant to pH 3 with trifluoroacetic acid, the resulting solution (1 L) was charged on a "Diaion HP-20" column (200 ml) equilibrated with 0.05% aqueous trifluorocetic acid. The column was washed with 0.05% aqueous trifluoroacetic acid (500 ml), followed by elution with distilled water (500 ml). The distilled water eluate (500 ml) thus obtained was concentrated and lyophilized to yield 230 mg of a crude powdery product.

The crude powdery product was dissolved in 2 ml of distilled water and a 500 µl portion of the resulting solution was charged on an HPLC column ("Pegasil ODS", trade name; 20φ×250 mm; product of Senshu Scientific) equilibrated with 0.05% aqueous trifluoroacetic acid containing 7% acetonitrile.

The column was developed with the same solvent at a flow rate of 10.0 ml/min and the ultraviolet absorption at 210 nm was monitored, resulting in elution of the active substance at a retention time of 28.0 minutes. This operation was repeated four times and the eluates were combined, concentrated and lyophilized, whereby 11.1 mg of Substance A-500359M-3 was obtained in pure form.

The compound A-500359M-3 has the following physicochemical properties:

1) Appearance of the substance: white powder
2) Solubility: soluble in water and methanol, insoluble in normal hexane and chloroform
3) Molecular formula: $C_{22}H_{28}N_4O_{13}$
4) Molecular weight: 556 (as measured by FAB mass spectrometry)
5) Accurate mass, $[M+H]^+$, as measured by high-resolution FAB mass spectrometry is as follows:
   Found: 557.1754.
   Calculated: 557.1731.
6) Ultraviolet absorption spectrum: ultraviolet absorption spectrum measured in water exhibits the following maximum absorption:
   236 nm (ε10,000)
7) Optical rotation: optical rotation measured in water exhibits the following value:
   $[\alpha]_D^{26}$: +92° (c 0.1, $H_2O$)
8) Infrared absorption spectrum: Infrared absorption spectrum as measured by the potassium bromide (KBr) disk method exhibits the following absorption maxima:
   3407, 2938, 1684, 1524, 1465, 1399, 1385, 1335, 1268, 1205, 1139, 1118, 1095, 1063, 1021 $cm^{-1}$.
9) $^1H$ nuclear magnetic resonance spectrum was measured in deuterium oxide with 1,4-dioxane (3.53 ppm) as an internal standard substance. $^1H$ nuclear magnetic resonance spectrum is as follows:
   2.44 (1H, ddd, J=4.3, 7.3, 13.3 Hz), 2.52 (1H, ddd, J=4.3, 7.5, 13.3 Hz), 3.27 (3H, s), 3.66 (1H, t, J=5.5 Hz), 4.17 (1H, ddd, J=1.1, 2.5, 3.1 Hz), 4.32 (1H, dd, J=3.7, 5.5 Hz), 4.33 (1H, t, J=4.3 Hz), 4.45 (1H, m), 4.46 (1H, m), 4.73 (1H overlapped with HDO), 5.07 (1H, d, J=10.2 Hz), 5.36 (1H, d, J=3.1 Hz), 5.51 (1H, d, J=17.1 Hz), 5.58 (1H, d, J=8.1 Hz), 5.73 (1H, m), 5.74 (1H, d, J=3.7 Hz), 5.95 (1H, dd, J=1.1, 1.9 Hz), 7.72 (1H, d, J=8.1 Hz) ppm.
10) $^{13}C$ nuclear magnetic resonance spectrum was measured in deuterium oxide with 1,4-dioxane (67.4 ppm) as an internal standard substance. $^{13}C$ nuclear magnetic resonance spectrum is as follows:
    37.1 (t), 55.4 (d), 58.6 (q), 62.6 (d), 65.3 (d), 72.6 (d), 75.7 (d), 78.9 (d), 82.4 (d), 90 (d), 99.8 (d), 102.6 (d), 109.9 (d), 119.0 (t), 134.0 (d), 141.7 (d), 142.2 (s), 152.0 (s), 162.3 (s), 166.8 (s), 173.6 (s), 177.6 (s) ppm.
11) HPLC analysis:
    Column: "Pegasil ODS" 6φ×150 mm (product of Senshu Scientific Co., Ltd.)
    Solvent: 7.2% acetonitrile—0.05% aqueous trifluoroacetic acid
    Flow rate: 1.0 ml/min
    Detection: UV 260 nm
    Retention time: 10.1 minutes Test 1. Antibacterial Activity (1) Minimum Inhibitory Concentration The minimum inhibitory concentration of preferred compounds of the invention against *Mycobacterium smegmatis* Strain SANK 75075 was determined in accordance with the process described below. The concentration of the compound to be tested was set at four stages by four-fold dilution starting from 1000 µg/ml (1000 µg/ml, 250 µg/ml, 62 µg/ml and 15 µg/ml). A 1 ml portion of the diluted sample of each stage was poured into a Petri dish ("Terumo Petri dish", 90×20 mm). A nutrient agar medium (9 ml, product of Eiken Chemical) containing 5% glycerol was added and they were mixed to prepare a plate medium. A test microorganism *Mycobacterium smegmatis* SANK 75075 was precultured overnight at 37° C. on a trypto-soy broth (T.S.B) medium (product of Eiken Chemical) containing 5% glycerol. On the testing day, the microorganism solution was diluted 100-fold with T.S.B. and one loopful of the diluted culture was streaked onto the plate medium. After cultivation at 37° C. for 18 hours, the minimum concentration (MIC) of the test substance inhibiting the growth of the microorganism was determined. The results are shown in Table 6.

TABLE 6

Antibacterial activities again *Mycobacterium smegmatis* SANK 75075

| Exemp. Compound No. | Minimum inhibitory concentration (µg/ml) |
|---|---|
| 1 | 6.2 |
| 7 | 6.2 |
| 8 | 1.5 |
| 9 | 3.1 |
| 10 | 6.2 |
| 11 | 6.2 |
| 16 | 6.2 |
| 17 | 6.2 |
| 18 | 3.1 |
| 50 | 3.1 |
| 51 | 1.5 |
| 52 | 3.1 |
| 53 | 1.5 |
| 135 | 1.5 |
| 282 | 6.2 |
| 548 | 6.2 |
| 891 | 6.2 |
| 1091 | 6.2 |
| Capuramycin | 12.5 |

The minimum inhibitory concentration of preferred compounds of the invention of the formula (Ia) against *Mycobacterium avium* Strain NIHJ1605 was determined. Described specifically, Tween 80 (0.1%) was added to Middleblook 7H9 broth. After autoclave sterilization, Middleblook ADC enrichment was added (20%). Into each of micro-test tubes was poured a 0.8 ml portion of the resulting mixture. To each of the test tubes was added a 0.1 ml portion of each of the compounds of the invention diluted two-fold (which will hereinafter be abbreviated as "medicament-containing medium"). On the side, a colony obtained by preculturing *Mycobacterium avium* NIHJ 1605 on a Tween egg medium for 10 to 14 days was charged in a test tube containing Tween 80 and glass beads. After sufficient mixing, Middleblook 7H9 broth was added to form a uniform microorganism solution. The microorganism solution was adjusted to $OD_{625\ nm}$=0.10 (viable cell count: about $1\times10^8$ CFU/ml). followed by 100-fold dilution. A 0.1 ml portion of the resulting microorganism solution was inoculated into the above-described medicament-containing medium (final viable cell count: about $1\times10^5$ CFU/ml), followed by aerobic culture at 37° C. for 6 days. The minimum medicament amount at which no colony having a diameter of 1 mm or greater was recognized on the bottom of the test tube was determined as MIC (µg/ml). The results are shown in Table 7.

TABLE 7

Antibacterial activities against *Mycobacterium avium* NIHJ 1605

| Exemp. Compound No. | Minimum inhibitory concentration (µg/ml) |
|---|---|
| 539 | 0.25 |
| 571 | 1 |
| 594 | 1 |
| Capuramycin | 8 |

(2) Disk Assay

So-called disk assay was conducted using 40 µg of a test substance per paper disk of 8 mm. Compound A-500359M-2 (Exemp. compound No. 396) exhibited an inhibitory zone of 14 mm in diameter against *Bacillus subtilis* PCI 219, that of 30 mm in diameter against *Mycobacterium smegmatis* SANK 75075 and that of 25 mm in diameter against *Klebsiella pneumoniae* PCI 602.

So-called Disk assay ("Experimental Agricultural Chemistry". ed. by Agricultural Chemistry Class/Agriculture Dept./Tokyo Univ., 3rd edition, Volume II, published by Asakura Shoten in 1978) was conducted using 40 µg of a test substance per paper disk of 8 mm. Compound A-500359E exhibited an inhibitory circle of 12 mm in diameter against *Mycobacterium smegmatis* SANK 75075, the amide derivative of compound A-500359F exhibited an inhibitory circle of 12 mm in diameter and Compound A-500359M-3 also exhibited an inhibitory circle of 12 mm in diameter.

Preparation Example 1

Capsules

| A-500359A or C | 100 mg |
|---|---|
| Lactose | 100 mg |
| Corn starch | 148.8 mg |
| Magnesium stearate | 1.2 mg |
| Total amount | 350 mg |

A capsule was obtained by mixing powders in accordance with the above-described formulation, sieving the resulting mixture through a 60-mesh sieve, and then charging the resulting powder in a gelatin capsule.

Preparation Example 2

Capsules were each obtained by mixing 100 mg of Compound A-500359E, Compound A-500359F, the amide derivative of compound A-500359F, Compound A-500359H, Compound A-500359J or Compound A-500359M-3, 100 mg of lactose respectively, 148.8 mg of corn starch and 1.2 mg of magnesium stearate (totally, 350 mg) in the powdery form, sieving the resulting mixture through a 60-mesh sieve and charging the powder in a gelatin capsule.

Toxicity Test

The invention compound A-500359A exhibited no toxicity when intravenously administered to a mouse in an amount of 500 mg/kg.

The results described above show that the compounds of the invention represented by the formulae (I), (XI), (XII), (XIII), (XIV), (XV) and (XVI) respectively, various derivatives of the compound represented by the formula (Ia), and pharmacologically acceptable salts thereof exhibit excellent antibacterial activities against various bacteria including Mycobacteria so that they are useful in the prevention or treatment of infectious diseases caused by such bacteria. *Streptomyces griseus* SANK60196 (FERM BP-5420) is useful as a bacterium producing the compound represented by the formula (I), (XI), (XII), (XIV), (XV) or (XVI). The compounds of the invention represented by the formulae (I), (XI), (XIII), (XIV), (XV) or (XVI) are also useful as a starting material for the synthesis of a derivative for the preparation of a prevention or treatment of various infectious diseases by organic chemical or microbiological conversion.

What is claimed is:

1. A compound of formula (I) or a pharmaceutically acceptable salt thereof:

(I)

wherein:
$R^1$ is a methyl group, $R^2$ is a methyl group, $R^4$ is a hydroxy group, and X is a methylene group;
$R^1$ is a methyl group, $R^2$ is a hydrogen atom, $R^4$ is a hydroxy group, and X is a methylene group;
$R^1$ is a methyl group, $R^2$ is a methyl group, $R^4$ is a hydrogen atom, and X is a methylene group;
$R^1$ is a hydrogen atom, $R^2$ is a hydrogen atom, $R^4$ is a hydroxy group, and X is a methylene group; or
$R^1$ is a methyl group, $R^2$ is a methyl group, $R^4$ is a hydroxy group, and X is a sulfur atom.

2. A compound according to claim 1 or a pharmaceutically acceptable salt thereof, wherein $R^1$ is a methyl group, $R^2$ s a methyl group, $R^4$ is a hydroxy group, and X is a methylene group.

3. A pharmaceutically acceptable ester, ether, or an N-carbamoyl selected from the group consisting of an N-alkylcarbamoyl, an N-alkenylcarbamoyl and an N-alkynylcarbamoyl of a compound of formula (Ia), or a pharmaceutically acceptable salt thereof:

(Ia)

wherein:
$R^1$ is a hydrogen atom or a methyl group;
$R^2_a$ is a hydrogen atom, a protecting group for a hydroxy group, or a methyl group;
$R^3$ is a hydrogen atom or a protecting group for a hydroxy group;
$R^4_a$ is a hydrogen atom, a hydroxy group or a protected hydroxy group;
$R^5$ is a hydrogen atom or a protecting group for a hydroxy group; and X is a methylene group or a sulfur atom,
PROVIDED THAT:
when
X is a sulfur atom,
$R^1$ is a methyl group, $R^2_a$ is a methyl group, and $R^4_a$ is a hydroxy group or a protected hydroxy group;
when
X is a methylene group, $R^1$ is a methyl group, and $R^2_a$ is a hydrogen atom,
$R^4_a$ is a hydroxy group or a protected hydroxy group; or
when
X is a methylene group, and $R^1$ is a hydrogen atom, $R^2_a$ is a methyl group, and $R^4_a$ is a hydroxy group or a protected hydroxy group;
AND THAT:
when X is a methylene group, $R^1$ is a hydrogen atom, $R^2_a$ is a methyl group, and $R^3$ is a hydrogen atom or a phenoxythiocarbonyl group, $R^4_a$ may not be a hydroxy group when $R^1$ is a hydrogen atom, and $R^4_a$ and $R^5$ may not together represent an oxyalkylene group; AND THAT the compound wherein X is a methylene group, $R^1$ is a hydrogen atom, $R^2_a$ is a methyl group, $R^3$ is a pivaloyl group, $R^4_a$ is an acetoxy group and $R^5$ is an acetyl group is excluded.

4. A compound of formula (Ia) according to claim 3 wherein the protecting group for a hydroxy group is selected from the group consisting of tetrahydropyranyl, tetrahydrothiopyranyl, silyl, aralkyl, aralkyloxycarbonyl, 1-(aliphatic acyloxy)-(lower alkyl), 1-(cycloalkylcarbonyloxy)-(lower alkyl), 1-(lower alkoxycarbonyloxy)-(lower alkyl), 1-(cycloalkyloxycarbonyloxy)-(lower alkyl), phthalidyl and oxodioxolenylmethyl groups.

5. A compound of formula (Ia) according to claim 3 wherein the protecting group for a hydroxy group is selected from the group consisting of tetrahydropyran-2-yl, 4-methoxytetrahydropyran-4-yl, tetrahydrothiopyran-2-yl, trimethylsilyl, triethylsilyl, tert-butyldimethylsilyl, di(tert-butyl)methylsilyl, diphenylmethylsilyl, benzyl, diphenylmethyl, triphenylmethyl, 4-methylbenzyl, 4-methoxybenzyl, 2-nitrobenzyl, 4-nitrobenzyl, 4-chlorobenzyl, benzyloxycarbonyl, 4-methoxybenzyloxycarbonyl, 2-nitrobenzyloxycarbonyl, 4-nitrobenzyloxycarbonyl, acetoxymethyl, propionyloxymethyl, butyryloxymethyl, pivaloyloxymethyl, valeryloxymethyl, 1-acetoxyethyl, butyryloxyethyl, 1-pivaloyloxyethyl, cyclopentylcarbonyloxymethyl, cyclohexylcarbonyloxymethyl, 1-cyclopentylcarbonyloxyethyl, 1-cyclohexylcarbonyloxyethyl, methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-(methoxycarbonyloxy)ethyl, 1-(ethoxycarbonyloxy)ethyl, 1-(isopropoxycarbonyloxy)ethyl, cyclopentyloxycarbonyloxymethyl, cyclohexyloxycarbonyloxymethyl, 1-(cyclopentyloxycarbonyloxy)ethyl, 1-(cyclohexyloxycarbonyloxy)ethyl, phthalidyl, (5-phenyl-2-oxo-1,3-dioxolen-4-yl)methyl, [5-(4-methylphenyl)-2-oxo-1,3-dioxolen-4-yl]methyl, (5-methyl-2-oxo-1,3-dioxolen-4-yl)methyl and (5-ethyl-2-oxo-1,3-dioxolen-4-yl)methyl groups.

6. A compound of formula (Ia) according to claim 3 wherein the protecting group for a hydroxy group is selected from the group consisting of trimethylsilyl, tert-butyldimethylsilyl, triphenylmethyl, benzyl, 4-methoxybenzyl, acetoxymethyl, propionyloxymethyl, butyryloxymethyl, pivaloyloxymethyl, valeryloxymethyl, cyclopentylcarbonyloxymethyl, cyclohexylcarbonyloxymethyl, methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, cyclopentyloxycarbonyloxymethyl, cyclohexyloxycarbonyloxymethyl, (5-phenyl-2-oxo-1,3-dioxolen-4-yl)methyl, [5-(4-methylphenyl)-2-oxo-1,3-dioxolen-4-yl]methyl, (5-methyl-2-oxo-1,3-dioxolen-4-yl) methyl and (5-ethyl-2-oxo-1,3-dioxolen-4-yl)methyl groups.

7. An ester derivative of compound (Ia) according to claim 3 in which the ester residue is a group $R^6CO—$ or $R^6OCO—$ wherein $R^6$ is selected from the group consisting of hydrogen; a $C_1–C_{21}$ alkyl group; a $C_2–C_{21}$ alkenyl or alkynyl group having 1 to 3 double or triple bonds; a $C_1–C_{21}$ alkyl group substituted with 1 to 4 substituents selected from the group consisting of lower alkoxy, halogen and nitro groups; a $C_1–C_{21}$ alkyl group substituted with 1 to 3 $C_6–C_{10}$ aryl groups which are optionally substituted with 1 to 4 substituents selected from the group consisting of lower alkyl, lower alkoxy, halo and nitro groups; and a $C_6–C_{10}$ aryl group which is optionally substituted with 1 to 4 substituents selected from the group consisting of lower alkyl, lower alkoxy, halo and nitro groups.

8. An ester derivative of compound (Ia) according to claim 3 in which the ester residue is a group $R^6CO—$ or $R^6OCO—$ wherein $R^6$ is selected from the group consisting of hydrogen; a $C_1–C_{21}$ alkyl group; a $C_2–C_{21}$ alkenyl group having 1 to 3 double bonds; a $C_2–C_6$ alkynyl group having one triple bond; a $C_1–C_6$ alkyl group substituted with 1 to 4 substituents selected from the group consisting of $C_1–C_4$ alkoxy, halo and nitro groups; a $C_1–C_6$ alkyl group substituted with 1 to 3 $C_6–C_{10}$ aryl groups which are optionally substituted with 1 to 3 substituents selected from the group consisting of $C_1–C_4$ alkyl, $C_1–C_4$ alkoxy, halo and nitro groups; and a $C_6–C_{10}$ aryl group which is optionally substituted with 1 to 3 substituents selected from the group consisting of $C_1–C_4$ alkyl, $C_1–C_4$ alkoxy, halo and nitro groups.

9. An ester derivative of compound (Ia) according to claim 3 in which the ester residue is a group $R^6CO—$ or $R^6OCO—$ wherein $R^6$ is selected from the group consisting of a $C_1–C_{21}$ alkyl group; a $C_6–C_{20}$ alkenyl group having 1 to 3 double bonds; a $C_2–C_6$ alkynyl group having one triple bond; a $C_1–C_6$ alkyl group substituted with one substituent selected from the group consisting of $C_1–C_4$ alkoxy and nitro groups; a $C_1–C_6$ alkyl group substituted with 1 to 3 substituents selected from the group consisting of halogen; a $C_1–C_4$ alkyl group substituted with 1 to 3 phenyl or naphthyl groups which are optionally substituted with 1 to 3 substituents selected from the group consisting of $C_1–C_4$ alkyl, $C_1–C_4$ alkoxy, halo and nitro groups; and a phenyl or naphthyl group which is optionally substituted with 1 to 3 substituents selected from the group consisting of $C_1–C_4$ alkyl, $C_1–C_4$ alkoxy, halo and nitro groups.

10. An ester derivative of compound (Ia) according to claim 3 in which the ester residue is a group $R^6CO—$ or $R^6OCO—$ wherein $R^6$ is selected from the group consisting of a $C_6–C_{20}$ alkyl group; a $C_{10}–C_{20}$ alkenyl group having 1 to 3 double bonds; a $C_3–C_5$ alkynyl group having one triple bond; a $C_1–C_4$ alkyl group substituted with one substituent selected from the group consisting of $C_1–C_4$ alkoxy and nitro groups; a $C_1–C_4$ alkyl group substituted with 1 to 3 substituents selected from the group consisting of fluoro and chloro groups; a $C_1–C_4$ alkyl group substituted with 1 to 3 phenyl groups which are optionally substituted with 1 or 2 substituents selected from the group consisting of $C_1–C_2$ alkyl, $C_1–C_4$ alkoxy, fluoro and chloro groups; and a phenyl group which is optionally substituted with 1 to 3 substituents selected from the group consisting of $C_1–C_2$ alkyl, $C_1–C_4$ alkoxy, fluoro and chloro groups.

11. An ester derivative of compound (Ia) according to claim 3 in which the ester residue is a group $R^6CO—$ or $R^6OCO—$ wherein $R^6$ is selected from the group consisting of a $C_6–C_{20}$ alkyl group; a $C_{10}–C_{20}$ alkenyl group having 1 to 3 double bonds; a $C_3–C_5$ alkynyl group having one triple bond; a $C_1–C_4$ alkyl group substituted with one substituent selected from the group consisting of $C_1–C_4$ alkoxy, fluoro, chloro and nitro groups; a $C_1–C_4$ alkyl group substituted with 1 to 3 phenyl groups which are optionally substituted with 1 or 2 substituents selected from the group consisting of $C_1–C_2$ alkyl, $C_1–C_4$ alkoxy, fluoro and chloro groups; and a phenyl group which is optionally substituted with 1 to 3 substituents selected from the group consisting of $C_1–C_2$ alkyl, $C_1–C_4$ alkoxy, fluoro and chloro groups.

12. An ester derivative of compound (Ia) according to claim 3 in which the ester residue is a group $R^6CO—$ or $R^6OCO—$ wherein $R^6$ is selected from the group consisting of a $C_6–C_{20}$ alkyl group; a $C_{10}–C_{20}$ alkenyl group having 1 to 3 double bonds; a $C_3–C_5$ alkynyl group having one triple bond; a $C_1–C_4$ alkyl group substituted with one substituent selected from the group consisting of $C_1–C_4$ alkoxy groups; and a $C_1–C_4$ alkyl group substituted with 1 or 2 phenyl groups which are optionally substituted with 1 or 2 substituents selected from the group consisting of $C_1–C_2$ alkyl, $C_1–C_4$ alkoxy, fluoro and chloro groups.

13. An ester derivative of compound (Ia) according to claim 3 in which the ester residue is a group $R^6CO—$ or $R^6OCO—$ wherein $R^6$ is selected from the group consisting of a $C_6–C_{20}$ alkyl group and a $C_{10}–C_{20}$ alkenyl group having 1 to 3 double bonds.

14. An ether derivative of compound (Ia) according to claim 3 wherein the ether residue is selected from the group consisting of a $C_1–C_{21}$ alkyl group; a $C_2–C_{21}$ alkenyl or alkynyl group having 1 to 3 double or triple bonds; a $C_1–C_{21}$ alkyl group which has 1 to 4 substituents selected from the group consisting of lower alkoxy, halo and nitro groups; a $C_1–C_{21}$ alkyl group which has 1 to 3 $C_6–C_{10}$ aryl groups which are optionally substituted with 1 to 4 substituents selected from the group consisting of lower alkyl, lower alkoxy, halo and nitro groups; and a $C_6–C_{10}$ aryl group which is optionally substituted with 1 to 4 substituents selected from the group consisting of lower alkyl, lower alkoxy, halo and nitro groups.

15. An ether derivative of compound (Ia) according to claim 3 wherein the ether residue is selected from the group consisting of a $C_1–C_{21}$ alkyl group; a $C_2–C_{21}$ alkenyl group having 1 to 3 double bonds; a $C_2–C_6$ alkynyl group having one triple bond; a $C_1–C_6$ alkyl group which has 1 to 4 substituents selected from the group consisting of $C_1–C_4$ alkoxy, halo and nitro groups; a $C_1–C_6$ alkyl group which has 1 to 3 $C_6–C_{10}$ aryl groups which are optionally substituted with 1 to 3 substituents selected from the group consisting of $C_1–C_4$ alkyl, $C_1–C_4$ alkoxy, halo and nitro groups; and a $C_6–C_{10}$ aryl group which is optionally substituted with 1 to 3 substituents selected from the group consisting of $C_1–C_4$ alkyl, $C_1–C_4$ alkoxy, halo and nitro groups.

16. An ether derivative of compound (Ia) according to claim 3 wherein the ether residue is selected from the group consisting of a $C_1$–$C_{21}$ alkyl group; a $C_6$–$C_{20}$ alkenyl group having 1 to 3 double bonds; a $C_2$–$C_6$ alkynyl group having one triple bond; a $C_1$–$C_6$ alkyl group which has one substituent selected from the group consisting of $C_1$–$C_4$ alkoxy and nitro groups; a $C_1$–$C_6$ alkyl group which has 1 to 3 substituents selected from the group consisting of halo groups; a $C_1$–$C_4$ alkyl group which has 1 to 3 phenyl or naphthyl groups which are optionally substituted with 1 to 3 substituents selected from the group consisting of $C_1$–$C_4$ alkyl, $C_1$–$C_4$ alkoxy, halo and nitro groups; and a phenyl or naphthyl group which is optionally substituted with 1 to 3 substituents selected from the group consisting of $C_1$–$C_4$ alkyl, $C_1$–$C_4$ alkoxy, halo and nitro groups.

17. An ether derivative of compound (Ia) according to claim 3 wherein the ether residue is selected from the group consisting of a $C_6$–$C_{20}$ alkyl group; a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy and nitro groups; a $C_1$–$C_4$ alkyl group which has 1 to 3 substituents selected from the group consisting of fluoro and chloro groups; a $C_1$–$C_4$ alkyl group which has 1 to 3 phenyl groups which are optionally substituted with 1 or 2 substituents selected from the group consisting of $C_1$–$C_2$ alkyl, $C_1$–$C_4$ alkoxy, fluoro and chloro groups; and a phenyl group which is optionally substituted with 1 to 3 substituents selected from the group consisting of $C_1$–$C_2$ alkyl, $C_1$–$C_4$ alkoxy, fluoro and chloro groups.

18. An ether derivative of compound (Ia) according to claim 3 wherein the ether residue is selected from the group consisting of a $C_6$–$C_{20}$ alkyl group; a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy, fluoro, chloro and nitro groups; a $C_1$–$C_4$ alkyl group which has 1 to 3 phenyl groups which are optionally substituted with 1 or 2 substituents selected from the group consisting of $C_1$–$C_2$ alkyl, $C_1$–$C_4$ alkoxy, fluoro and chloro groups; and a phenyl group which is optionally substituted with 1 to 3 substituents selected from the group consisting of $C_1$–$C_2$ alkyl, $C_1$–$C_4$ alkoxy, fluoro and chloro groups.

19. An ether derivative of compound (Ia) according to claim 3 wherein the ether residue is selected from the group consisting of a $C_6$–$C_{20}$ alkyl group; a $C_{10}$–$C_{20}$ alkenyl group having 1 to 3 double bonds; a $C_3$–$C_5$ alkynyl group having one triple bond; a $C_1$–$C_4$ alkyl group which has one substituent selected from the group consisting of $C_1$–$C_4$ alkoxy groups; and a $C_1$–$C_4$ alkyl group which has 1 or 2 phenyl groups optionally substituted with 1 or 2 substituents selected from the group consisting of $C_1$–$C_2$ alkyl, $C_1$–$C_4$ alkoxy, fluoro and chloro groups.

20. An ether derivative of compound (Ia) according to claim 3 wherein the ether residue is selected from the group consisting of a $C_6$–$C_{20}$ alkyl group and a $C_{10}$–$C_{20}$ alkenyl group having 1 to 3 double bonds.

21. An N-alkylcarbamoyl of compound (Ia) according to claim 3 wherein the alkyl moiety thereof is selected from the group consisting of an unsubstituted $C_1$–$C_{21}$ alkyl group; a $C_1$–$C_{21}$ alkyl group which is substituted with substituents selected from the group consisting of lower alkoxy, halo and nitro groups; and a $C_1$–$C_{21}$ alkyl group which has 1 to 3 $C_6$–$C_{10}$ aryl groups which are unsubstituted or substituted with 1 to 4 substituents selected from the group consisting of lower alkyl, lower alkoxy, halo and nitro groups.

22. An N-alkylcarbamoyl derivative of compound (Ia) according to claim 3 wherein the alkyl moitey thereof is selected from the group consisting of a $C_1$–$C_{21}$ alkyl group which is substituted with 1 to 4 substituents selected from the group consisting of $C_1$–$C_4$ alkoxy, halo and nitro groups; and a $C_1$–$C_6$ alkyl group which has 1 to 3 $C_6$–$C_{10}$ aryl groups which are unsubstituted or substituted with 1 to 3 substituents selected from the group consisting of $C_1$–$C_4$ alkyl, $C_1$–$C_4$ alkoxy, halo and nitro groups.

23. An N-alkylcarbamoyl of compound (Ia) according to claim 3 wherein the alkyl moiety thereof is selected from the group consisting of a $C_1$–$C_{21}$ alkyl group; a $C_1$–$C_6$ alkyl group which is substituted with one substituent selected from the group. consisting of $C_1$–$C_4$ alkoxy and nitro groups; a $C_1$–$C_6$ alkyl group which is substituted with 1 to 3 substituents selected from the group consisting of halo groups; and a $C_1$–$C_4$ alkyl group which has 1 to 3 phenyl or naphthyl groups which are unsubstituted or substituted with 1 to 3 substituents selected from the group consisting of $C_1$–$C_4$ alkoxy, $C_1$–$C_4$ alkoxy, halo and nitro groups.

24. An N-alkylcarbamoyl of compound (Ia) according to claim 3 wherein the alkyl moitey thereof is selected from the group consisting of a $C_6$–$C_{20}$ alkyl group; a $C_1$–$C_4$ alkyl group which is substituted with one substituent selected from the group consisting of $C_1$–$C_4$ alkoxy, nitro groups; and a $C_1$–$C_4$ alkyl group which is substituted with 1 to 3 sustituents selected from the group consisting of fluoro and chloro groups; and a $C_1$–$C_4$ alkyl group which has 1 to 3 phenyl groups which are unsubstituted or substituted with 1 or 2 sustituents selected from the group consisting of $C_1$–$C_2$ alkyl, $C_1$–$C_4$ alkoxy, fluoro and chloro groups.

25. An N-alkylcarbamoyl of compound (Ia) according to claim 3 wherein the alkyl moiety thereof is selected from the group consisting of a $C_6$–$C_{20}$ alkyl group; a $C_1$–$C_4$ alkyl group which is substituted with one substituent selected from the group consisting of $C_1$–$C_4$ alkoxy, fluoro, chloro and nitro groups; and a $C_1$–$C_4$ alkyl group which has 1 to 3 phenyl groups which are unsubstituted or substituted with 1 or 2 substituents selected from the group consisting of $C_1$–$C_2$ alkyl, $C_1$–$C_4$ alkoxy, fluoro and chloro group.

26. An N-alkylcarbamoyl of compound (Ia) according to claim 3 wherein the alkyl moiety thereof is selected from the group consisting of $C_6$–$C_{20}$ alkyl group; a $C_1$–$C_4$ alkyl group which is substituted with one substituent selected from the group consisting of $C_1$–$C_4$ alkoxy groups; and a $C_1$–$C_4$ alkyl group which has 1 or 2 phenyl groups which are unsubstituted or substituted with 1 or 2 substituents selected from the group consisting of $C_1$–$C_2$ alkyl, $C_1$–$C_4$ alkoxy, fluoro and chloro groups.

27. An N-alkylcarbamoyl of compound (Ia) according to claim 3 wherein the alkyl moiety thereof is a $C_6$–$C_{20}$ alkyl group.

28. A compound of formula (Ib) selected from the compound group consisting of the following compounds, or a pharmaceutically acceptable salt thereof.

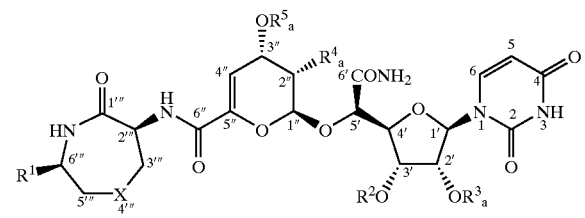

(Ib)

a compound wherein $R^1$ is a methyl group, $R^2$ is a methyl group, $R^3_a$ is a hydrogen atom, $R^4_a$ is a hydroxy group, $R^5_a$ is a hydrogen atom and X is a methylene group;

a compound wherein $R^1$ is a methyl group, $R^2$ is a hydrogen atom, $R^3_a$ is a hydrogen atom, $R^4_a$ is a hydroxy group, $R^5_a$ is a hydrogen atom and X is a methylene group;

a compound wherein $R^1$ is a methyl group, $R^2$ is a methyl group, $R^3_a$ is a hydrogen atom, $R^4_a$ is a hydrogen atom, $R^5_a$ is a hydrogen atom and X is a methylene group;

a compound wherein $R^1$ is a methyl group, $R^2$ is a methyl group, $R^3_a$ is a decanoyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a lauroyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a myristoyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a pentadecanoyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a palmitoyl group, $R^4_a$ is a hydroxy group, $R^5_a$ is a hydrogen atom and X is a methylene group;

a compound wherein $R^1$ is a hydrogen atom, $R^2$ is a hydrogen atom, $R^3_a$ is a hydrogen atom, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a decanoyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a lauroyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a myristoyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a pentadecanoyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a palmitoyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a hydrogen atom, $R^4_a$ is a hydroxy group, $R^5_a$ is a decanoyl group and X is a methylene group;

a compound wherein $R^1$ is a methyl group, $R^2$ is a methyl group, $R^3_a$ is a hydrogen atom, $R^4_a$ is a hydroxy group, $R^5_a$ is a lauroyl group and X is a methylene group;

a compound wherein $R^1$ is a methyl group, $R^2$ is a methyl group, $R^3_a$ is a hydrogen atom, $R^4_a$ is a hydroxy group, $R^5_a$ is a myristoyl group and X is a methylene group;

a compound wherein $R^1$ is a methyl group, $R^2$ is a methyl group, $R^3_a$ is a hydrogen atom, $R^4_a$ is a hydroxy group, $R^5_a$ is a pentadecanoyl group and X is a methylene group;

a compound wherein $R^1$ is a methyl group, $R^2$ is a methyl group, $R^3_a$ is a hydrogen atom, $R^4_a$ is a hydroxy group, $R^5_a$ is a palmitoyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a decanoyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a lauroyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a myristoyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a pentadecanoyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a palmitoyl group and X is a methylene group;

a compound wherein $R^1$ is a methyl group, $R^2$ is a methyl group, $R^3_a$ is a hexyloxycarbonyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a heptyloxycarbonyl group, $R^4_a$ is a hydroxy group, $R^5_a$ is a hydrogen atom and X is a methylene group;

a compound wherein $R^1$ is a methyl group, $R^2$ is a methyl group, $R^3_a$ is an octyloxycarbonyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a nonyloxycarbonyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a decyloxycarbonyl group, $R^4_a$ is a hydroxy group, $R^5_a$ is a hydrogen atom and X is a methylene group;

a compound wherein $R^1$ is a methyl group, $R^2$ is a methyl group, $R^3_a$ is an undecyloxycarbonyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a dodecyloxycarbonyl group, $R^4_a$ is a hydroxy group, $R^5_a$ is a hydrogen atom and X is a methylene group;

a compound wherein $R^1$ is a methyl group, $R^2$ is a methyl group, $R^3_a$ is a hydrogen atom, $R^4_a$ is a hydroxy group, $R^5_a$ is a hexyloxycarbonyl group and X is a methylene group;

a compound wherein $R^1$ is a methyl group, $R^2$ is a methyl group, $R^3_a$ is a hydrogen atom, $R^4_a$ is a hydroxy group, $R^5_a$ is a heptyloxycarbonyl group and X is a methylene group;

a compound wherein $R^1$ is a methyl group, $R^2$ is a methyl group, $R^3_a$ is a hydrogen atom, $R^4_a$ is a hydroxy group, $R^5_a$ is an octyloxycarbonyl group and X is a methylene group;

a compound wherein $R^1$ is a methyl group, $R^2$ is a methyl group, $R^3_a$ is a hydrogen atom, $R^4_a$ is a hydroxy group, $R^5_a$ is a nonyloxycarbonyl group and X is a methylene group;

a compound wherein $R^1$ is a methyl group, $R^2$ is a methyl group, $R^3_a$ is a hydrogen atom, $R^4_a$ is a hydroxy group, $R^5_a$ is a decyloxycarbonyl group and X is a methylene group;

a compound wherein $R^1$ is a methyl group, $R^2$ is a methyl group, $R^3_a$ is a hydrogen atom, $R^4_a$ is a hydroxy group, $R^5_a$ is an undecyloxycarbonyl group and X is a methylene group;

a compound wherein $R^1$ is a methyl group, $R^2$ is a methyl group, $R^3_a$ is a hydrogen atom, $R^4_a$ is a hydroxy group, $R^5_a$ is a dodecyloxycarbonyl group and X is a methylene group;

a compound wherein $R^1$ is a hydrogen atom, $R^2$ is a methyl group, $R^3_a$ is a hexyloxycarbonyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a heptyloxycarbonyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is an octyloxycarbonyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a nonyloxycarbonyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a decyloxycarbonyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is an undecyloxycarbonyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a dodecyloxycarbonyl group, $R^4_a$ is a hydroxy group, $R^5_a$ is a hydrogen atom and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a hexyloxycarbonyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a heptyloxycarbonyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is an octyloxycarbonyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a nonyloxycarbonyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is a decyloxycarbonyl group and X is a methylene group;

a compound wherein $R^1$ is a hydrogen atom, $R^2$ is a methyl group, $R^3_a$ is a hydrogen atom, $R^4_a$ is a hydroxy group, $R^5_a$ is an undecyloxycarbonyl group and X is a methylene group;

a compound wherein $R^1$ is a hydrogen atom, $R^2$ is a methyl group, $R^3_a$ is a hydrogen aton, $R^4_a$ is a hydroxy group, $R^5_a$ is a dodecyloxycarbonyl group and X is a methylene group;

a compound wherein $R^1$ is a methyl group, $R^2$ is a methyl group, $R^3_a$ is a decyl group, $R^4_a$ is a hydroxy group, $R^5_a$ is a hydrogen atom and X is a methylene group; and a compound wherein $R^1$ is a hydrogen atom, $R^2$ is a methyl group, $R^3_a$ is a decyl group, $R^4_a$ is a hydroxy group, $R^5_a$ is a hydrogen atom and X is a methylene group.

29. A compound of formula (Ik) selected from the compound group consisting of the following compounds, or a pharmaceutically acceptable salt thereof:

(Ik)

a compound wherein $R^1$ is a methyl group, $R^{11}$ is a methyl group, $R^3$ is a hydrogen atom and $R^5$ is a hydrogen atom;

a compound wherein $R^1$ is a methyl group, $R^{11}$ is a methyl group, $R^3$ is a decanoyl group and $R^5$ is a hydrogen atom;

a compound wherein $R^1$ is a methyl group, $R^{11}$ is a methyl group, $R^3$ is a hydrogen atom and $R^5$ is a decanoyl group;

a compound wherein $R^1$ is a methyl group, $R^{11}$ is a dodecyl group, $R^3$ is a hydrogen atom and $R^5$ is a hydrogen atom;

a compound wherein $R^1$ is a hydrogen atom, $R^{11}$ is a methyl group, $R^3$ is a hydrogen atom and $R^5$ is a hydrogen atom;

a compound wherein $R^1$ is a hydrogen atom, $R^{11}$ is a methyl group, $R^3$ is a decanoyl group and $R^5$ is a hydrogen atom;

a compound wherein $R^1$ is a hydrogen atom, $R^{11}$ is a methyl group, $R^3$ is a hydrogen atom and $R^5$ is a decanoyl group; and a compound wherein $R^1$ is a hydrogen atom, $R^{11}$ is a dodecyl group, $R^3$ is a hydrogen atom and $R^5$ is a hydrogen atom.

30. A pharmaceutical composition comprising an effective amount of a pharmacologically active compound together with a carrier therefor, wherein said pharmacologically active compound is a compound according to claim 1 or claim 2 or a pharmaceutically acceptable salt thereof.

31. A pharmaceutical composition comprising an effective amount of a pharmacologically active compound together with a carrier therefor, wherein said pharmacologically active compound is a compound according to any one of claims 3 to 27 or a pharmaceutically acceptable salt thereof.

32. A pharmaceutical composition comprising an effective amount of a pharmacologically active compound together with a carrier therefor, wherein said pharmacologically active compound is a compound according to claim 28 or a pharmaceutically acceptable salt thereof.

33. A pharmaceutical composition comprising an effective amount of a pharmacologically active compound together with a carrier therefor, wherein said pharmacologically active compound is a compound according to claim 29 or a pharmaceutically acceptable salt thereof.

34. A method for the treatment or prevention of a bacterial infection in a human, which comprises administering to a human in need of such treatment an effective amount of a compound according to claim 1 or claim 2 or a pharmaceutically acceptable salt thereof.

35. A method for the treatment or prevention of a bacterial infection in a mammal, which comprises administering to a mammal in need of such treatment an effective amount of a compound according to any one of claims 3 to 27 or a pharmaceutically acceptable salt thereof.

36. A method for the treatment or prevention of a bacterial infection in a human, which comprises administering to a human in need of such treatment an effective amount of a compound according to claim 28 or a pharmaceutically acceptable salt thereof.

37. A method for the treatment or prevention of a bacterial infection in a human, which comprises administering to a human in need of such treatment an effective amount of a compound according to claim 29 or a pharmaceutically acceptable salt thereof.

38. A compound of formula (XI) or a salt thereof (XI)

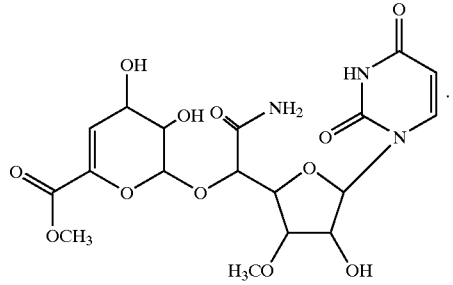

39. A compound of formula (XII) or a salt thereof (XII)

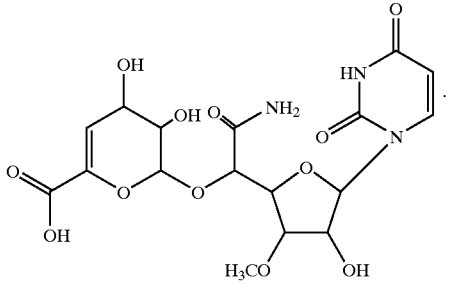

40. An amide compound of formula (XIII) or a salt thereof (XIII)

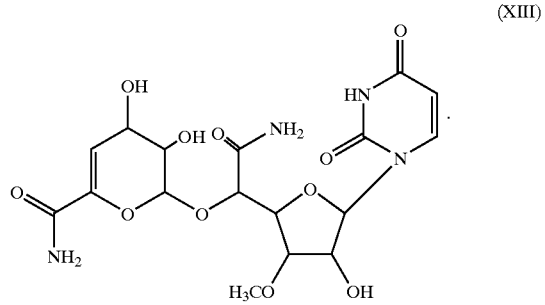

41. A compound of formula (XIV) or a salt thereof (XIV)

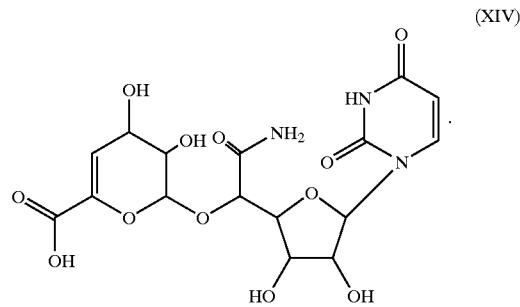

42. A compound of formula (XV) or a salt thereof (XV)

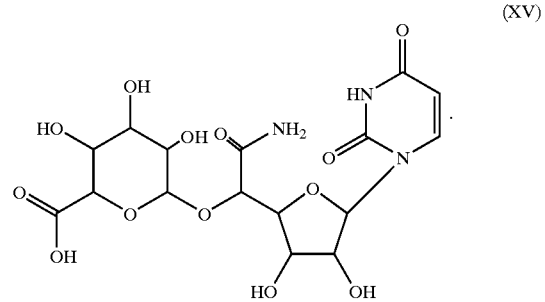

43. A compound of formula (XVI) or a salt thereof (XVI)

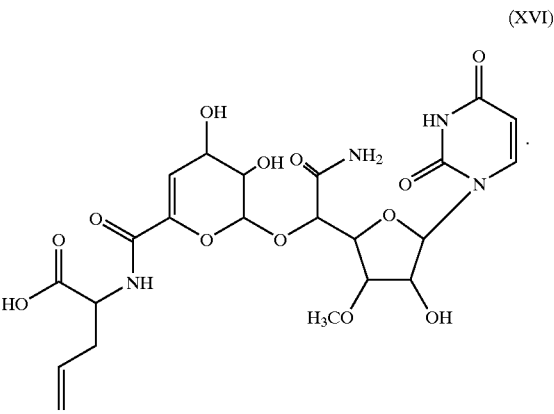

44. A pharmaceutical composition comprising an effective amount of a pharmacologically active compound together with a carrier therefor, wherein said pharmacologically active compound is a compound according to claim 38 or a pharmaceutically acceptable salt thereof.

45. A pharmaceutical composition comprising an effective amount of a pharmacologically active compound together with a carrier therefor, wherein said pharmacologically active compound is a compound according to claim 39 or a pharmaceutically acceptable salt thereof.

46. A pharmaceutical composition comprising an effective amount of a pharmacologically active compound together with a carrier therefor, wherein said pharmacologically active compound is a compound according to claim 40 or a pharmaceutically acceptable salt thereof.

47. A pharmaceutical composition comprising an effective amount of a pharmacologically active compound together with a carrier therefor, wherein said pharmacologically active compound is a compound according to claim 41 or a pharmaceutically acceptable salt thereof.

48. A pharmaceutical composition comprising an effective amount of a pharmacologically active compound together with a carrier therefor, wherein said pharmacologically active compound is a compound according to claim 42 or pharmaceutically acceptable salt thereof.

49. A pharmaceutical composition comprising an effective amount of a pharmacologically active compound together with a carrier therefor, wherein said pharmacologically active compound is a compound according to claim 43 or a pharmaceutically acceptable salt thereof.

50. A method for the treatment or prevention of a bacterial infection in a human, which comprises administering to a human in need of such treatment an effective amount of a compound according to claim 38 or a pharmaceutically acceptable salt thereof.

51. A method for the treatment or prevention of a bacterial infection in a human, which comprises administering to a human in need of such treatment an effective amount of a compound according to claim 39 or a pharmaceutically acceptable salt thereof.

52. A method for the treatment or prevention of a bacterial infection in a human, which comprises administering to a human in need of such treatment an effective amount of a compound according to claim 40 or a pharmaceutically acceptable salt thereof.

53. A method for the treatment or prevention of a bacterial infection in a human, which comprises administering to a human in need of such treatment an effective amount of a compound according to claim 41 or a pharmaceutically acceptable salt thereof.

54. A method for the treatment or prevention of a bacterial infection in a human, which comprises administering to a human in need of such treatment an effective amount of a compound according to claim 42 or a pharmaceutically acceptable salt thereof.

55. A method for the treatment or prevention of a bacterial infection in a human, which comprises administering to a human in need of such treatment an effective amount of a compound according to claim 43 or a pharmaceutically acceptable salt thereof.

56. An N-alkenylcarbamoyl of a compound (Ia) according to claim 3 wherein the alkenyl moiety thereof is a $C_2$–$C_{21}$ alkenyl group having 1 to 3 double bonds.

57. An N-alkenylcarbamoyl of a compound (Ia) according to claim 3 wherein the alkenyl moiety thereof is a $C_6$–$C_{20}$ alkenyl group having 1 to 3 double bonds.

58. An N-alkenylcarbamoyl of a compound (Ia) according to claim 3 wherein the alkenyl moiety thereof is a $C_{10}$–$C_{20}$ alkenyl group having 1 to 3 double bonds.

59. An N-alkynylcarbamoyl of a compound (Ia) according to claim 3 wherein the alkynyl moiety thereof has 1 to 3 triple bonds.

60. An N-alkynylcarbamoyl of a compound (Ia) according to claim 3 wherein the alkynyl moiety thereof is a $C_2$–$C_6$ alkynyl group having one triple bond.

61. An N-alkynylcarbamoyl of a compound (Ia) according to claim 3 wherein the alkynyl moiety thereof is a $C_3$–$C_5$ alkynyl group having one triple bond.

62. A pharmaceutical composition comprising a pharmaceutically effective amount of a compound according to claim 56 in combination with a pharmaceutically acceptable carrier.

63. A pharmaceutical composition comprising a pharmaceutically effective amount of a compound according to claim 57 in combination with a pharmaceutically acceptable carrier.

64. A pharmaceutical composition comprising a pharmaceutically effective amount of a compound according to claim 58 in combination with a pharmaceutically acceptable carrier.

65. A pharmaceutical composition comprising a pharmaceutically effective amount of a compound according to claim 59 in combination with a pharmaceutically acceptable carrier.

66. A pharmaceutical composition comprising a pharmaceutically effective amount of a compound according to claim 60 in combination with a pharmaceutically acceptable carrier.

67. A pharmaceutical composition comprising a pharmaceutically effective amount of a compound according to claim 61 in combination with a pharmaceutically acceptable carrier.

68. A method for the treatment or prevention of a bacterial infection in a mammal which comprises administering to a mammal in need thereof a pharmaceutically effective amount of a compound according to claim 56, either alone or in combination with a pharmaceutically acceptable carrier.

69. A method for the treatment or prevention of a bacterial infection in a mammal which comprises administering to a mammal in need thereof a pharmaceutically effective amount of a compound according to claim 57, either alone or in combination with a pharmaceutically acceptable carrier.

70. A method for the treatment or prevention of a bacterial infection in a mammal which comprises administering to a mammal in need thereof a pharmaceutically effective amount of a compound according to claim 58, either alone or in combination with a pharmaceutically acceptable carrier.

71. A method for the treatment or prevention of a bacterial infection in a mammal which comprises administering to a mammal in need thereof a pharmaceutically effective amount of a compound according to claim 59, either alone or in combination with a pharmaceutically acceptable carrier.

72. A method for the treatment or prevention of a bacterial infection in a mammal which comprises administering to a mammal in need thereof a pharmaceutically effective amount of a compound according to claim 60, either alone or in combination with a pharmaceutically acceptable carrier.

73. A method for the treatment or prevention of a bacterial infection in a mammal which comprises administering to a mammal in need thereof a pharmaceutically effective amount of a compound according to claim 61, either alone or in combination with a pharmaceutically acceptable carrier.

74. A method according to claim 34 wherein the bacterial infection is caused by a bacteria of Mycobacterium.

75. A method according to claim 35 wherein the bacterial infection is caused by a bacteria of Mycobacterium.

76. A method according to claim 36 wherein the bacterial infection is caused by a bacteria of Mycobacterium.

77. A method according to claim 37 wherein the bacterial infection is caused by a bacteria of Mycobacterium.

78. A method according to claim 69 wherein the bacterial infection is caused by a bacteria of Mycobacterium.

79. A method according to claim 70 wherein the bacterial infection is caused by a bacteria of Mycobacterium.

80. A method according to claim 71 wherein the bacterial infection is caused by a bacteria of Mycobacterium.

81. A method according to claim 72 wherein the bacterial infection is caused by a bacteria of Mycobacterium.

82. A method according to claim 73 wherein the bacterial infection is caused by a bacteria of Mycobacterium.

83. A method according to claim 34 wherein the bacterial infection is caused by *Mycobacterium tuberculosis*.

84. A method according to claim 35 wherein the bacterial infection is caused by *Mycobacterium tuberculosis*.

85. A method according to claim 36 wherein the bacterial infection is caused by *Mycobacterium tuberculosis*.

86. A method according to claim 37 wherein the bacterial infection is caused by *Mycobacterium tuberculosis*.

87. A method according to claim 69 wherein the bacterial infection is caused by *Mycobacterium tuberculosis*.

88. A method according to claim 70 wherein the bacterial infection is caused by *Mycobacterium tuberculosis*.

89. A method according to claim 71 wherein the bacterial infection is caused by *Mycobacterium tuberculosis*.

90. A method according to claim 72 wherein the bacterial infection is caused by *Mycobacterium tuberculosis*.

91. A method according to claim 73 wherein the bacterial infection is caused by *Mycobacterium tuberculosis*.

92. A method for the treatment or prevention of a bacterial infection in a mammal caused by *Mycobacterium tuberculosis* comprising administering to a mammal in need thereof a pharmaceutically effective amount of capuramycin.

93. A method according to claim 92 wherein the mammal is a human.

* * * * *

UNITED STATES PATENT AND TRADEMARK OFFICE
CERTIFICATE OF CORRECTION

PATENT NO. : 6,472,384 B1
DATED : October 29, 2002
INVENTOR(S) : Inukai et al.

It is certified that error appears in the above-identified patent and that said Letters Patent is hereby corrected as shown below:

Column 2,
Line 65, before "term" delete "the" and insert -- The --.

Column 53,
Line 40, after "D-glucose" delete "-" and insert -- + --.
Line 42, after "D-xylose" delete "-" and insert -- + --.

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,472,384 B1
DATED : October 29, 2002
INVENTOR(S) : Masatoshi Inukai et al.

It is certified that error appears in the above-identified patent and that said Letters Patent is hereby corrected as shown below:

<u>Column 162,</u>
Line 20, following "when", replace "$R^1$" with -- $R^5$ --.

Signed and Sealed this

First Day of March, 2005

JON W. DUDAS
*Director of the United States Patent and Trademark Office*